US009850203B2

(12) United States Patent
Hutchinson et al.

(10) Patent No.: US 9,850,203 B2
(45) Date of Patent: Dec. 26, 2017

(54) AUTOTAXIN INHIBITOR COMPOUNDS

(71) Applicant: PharmAkea, Inc., San Diego, CA (US)

(72) Inventors: John Howard Hutchinson, San Diego, CA (US); David Lonergan, San Marcos, CA (US); Fei Huang, La Mesa, CA (US); Martin Rowbottom, San Diego, CA (US); Imelda Calderon, San Diego, CA (US)

(73) Assignee: PHARMAKEA, INC., San Diego, CA (US)

( * ) Notice: Subject to any disclaimer, the term of this patent is extended or adjusted under 35 U.S.C. 154(b) by 0 days.

(21) Appl. No.: 15/023,465

(22) PCT Filed: Sep. 25, 2014

(86) PCT No.: PCT/US2014/057477
§ 371 (c)(1),
(2) Date: Mar. 21, 2016

(87) PCT Pub. No.: WO2015/048301
PCT Pub. Date: Apr. 2, 2015

(65) Prior Publication Data
US 2016/0214935 A1  Jul. 28, 2016

Related U.S. Application Data

(60) Provisional application No. 61/883,026, filed on Sep. 26, 2013, provisional application No. 62/038,052, filed on Aug. 15, 2014.

(51) Int. Cl.
| | |
|---|---|
| *C07D 209/30* | (2006.01) |
| *C07D 401/06* | (2006.01) |
| *C07D 403/06* | (2006.01) |
| *C07D 403/12* | (2006.01) |
| *C07D 413/12* | (2006.01) |
| *C07D 417/14* | (2006.01) |
| *C07D 471/10* | (2006.01) |
| *C07D 491/107* | (2006.01) |
| *C07D 498/10* | (2006.01) |
| *C07D 401/14* | (2006.01) |
| *C07D 413/14* | (2006.01) |
| *C07D 403/14* | (2006.01) |
| *C07D 487/10* | (2006.01) |
| *C07D 491/10* | (2006.01) |
| *A61K 9/00* | (2006.01) |
| *A61K 47/02* | (2006.01) |
| *A61K 9/06* | (2006.01) |
| *A61K 9/08* | (2006.01) |
| *A61K 47/38* | (2006.01) |
| *A61K 9/20* | (2006.01) |
| *A61K 9/48* | (2006.01) |

(52) U.S. Cl.
CPC .......... *C07D 209/30* (2013.01); *A61K 9/0014* (2013.01); *A61K 9/0019* (2013.01); *A61K 9/06* (2013.01); *A61K 9/08* (2013.01); *A61K 9/2054* (2013.01); *A61K 9/4866* (2013.01); *A61K 47/02* (2013.01); *A61K 47/38* (2013.01); *C07D 401/06* (2013.01); *C07D 401/14* (2013.01); *C07D 403/06* (2013.01); *C07D 403/12* (2013.01); *C07D 403/14* (2013.01); *C07D 413/12* (2013.01); *C07D 413/14* (2013.01); *C07D 417/14* (2013.01); *C07D 471/10* (2013.01); *C07D 487/10* (2013.01); *C07D 491/10* (2013.01); *C07D 491/107* (2013.01); *C07D 498/10* (2013.01)

(58) Field of Classification Search
CPC .. C07D 209/30; C07D 401/06; C07D 403/06; C07D 403/12; C07D 413/12; C07D 417/14; C07D 471/10; C07D 491/107; C07D 498/10
USPC ........ 514/212.02, 228.2, 235.2, 254.09, 278, 514/300, 307, 314, 323, 333, 339, 380, 514/397, 407, 409, 414, 418; 540/543; 544/58.5, 143, 373; 546/16, 17, 19, 113, 546/146, 165, 194, 201, 277.7; 548/245, 548/364.7, 407, 409, 410, 411, 455, 465, 548/484
See application file for complete search history.

(56) References Cited

U.S. PATENT DOCUMENTS

| | | | |
|---|---|---|---|
| 5,641,800 | A | 6/1997 | Bach et al. |
| 7,060,697 | B2 | 6/2006 | Marsilje et al. |
| 7,417,063 | B2 | 8/2008 | Smallheer et al. |
| 8,022,239 | B2 | 9/2011 | Parrill-Baker et al. |
| 8,268,891 | B1 | 9/2012 | Parrill-Baker et al. |

(Continued)

FOREIGN PATENT DOCUMENTS

| | | |
|---|---|---|
| CA | 2264020 A1 | 3/1998 |
| EP | 2246326 A1 | 11/2010 |

(Continued)

OTHER PUBLICATIONS

Albers et al. Boronic acid-based inhibitor of autotaxin reveals rapid turnover of LPA in the circulation. PNAS USA 107:7257-7262 (2010).

(Continued)

*Primary Examiner* — Brenda Coleman
(74) *Attorney, Agent, or Firm* — Wilson Sonsini Goodrich & Rosati

(57) ABSTRACT

Described herein are compounds that are autotaxin inhibitors, methods of making such compounds, pharmaceutical compositions and medicaments comprising such compounds, and methods of using such compounds in the treatment of conditions, diseases, or disorders associated with autotaxin activity.

20 Claims, No Drawings

(56) References Cited

U.S. PATENT DOCUMENTS

| | | |
|---|---|---|
| 8,329,907 B2 | 12/2012 | Schultz et al. |
| 8,343,934 B2 | 1/2013 | Parrill-Baker et al. |
| 8,378,100 B2 | 2/2013 | Lynch et al. |
| 8,497,371 B2 | 7/2013 | Parrill-Baker et al. |
| 8,673,882 B2 | 3/2014 | Gupte et al. |
| 9,000,025 B2 | 4/2015 | Roppe et al. |
| 9,051,320 B1 | 6/2015 | Evans |
| 2003/0232787 A1 | 12/2003 | Dooley |
| 2005/0228000 A1 | 10/2005 | Smallheer et al. |
| 2006/0270634 A1 | 11/2006 | Miller et al. |
| 2007/0203209 A1 | 8/2007 | Bartolini et al. |
| 2010/0016258 A1 | 1/2010 | Lynch et al. |
| 2010/0136650 A1 | 6/2010 | Parrill-Baker et al. |
| 2010/0222341 A1 | 9/2010 | Schiemann et al. |
| 2011/0110886 A1 | 5/2011 | Braddock |
| 2011/0118478 A1 | 5/2011 | Ford et al. |
| 2011/0160148 A1 | 6/2011 | Parrill-Baker et al. |
| 2011/0230471 A1 | 9/2011 | Staehle et al. |
| 2011/0237583 A1 | 9/2011 | Schiemann et al. |
| 2012/0015959 A1 | 1/2012 | Staehle et al. |
| 2012/0015976 A1 | 1/2012 | Schultz et al. |
| 2012/0059016 A1 | 3/2012 | Schiemann et al. |
| 2012/0100592 A1 | 4/2012 | Parrill-Baker et al. |
| 2012/0115852 A1 | 5/2012 | Schultz et al. |
| 2012/0190650 A1 | 7/2012 | Gupte et al. |
| 2012/0202827 A1 | 8/2012 | Schiemann et al. |
| 2012/0316162 A1 | 12/2012 | Schiemann et al. |
| 2013/0012505 A1 | 1/2013 | Staehle et al. |
| 2013/0023556 A1 | 1/2013 | Schultz et al. |
| 2013/0029948 A1 | 1/2013 | Roppe et al. |
| 2013/0150326 A1 | 6/2013 | Roppe et al. |
| 2014/0171403 A1 | 6/2014 | Legrand et al. |
| 2014/0171404 A1 | 6/2014 | Furminger et al. |
| 2016/0046614 A1 | 2/2016 | Hutchinson et al. |

FOREIGN PATENT DOCUMENTS

| | | |
|---|---|---|
| EP | 2424835 A1 | 3/2012 |
| WO | WO-9603376 A1 | 2/1996 |
| WO | WO-9808818 A1 | 3/1998 |
| WO | WO-9943672 A1 | 9/1999 |
| WO | WO-0130343 A1 | 5/2001 |
| WO | WO-0144182 A2 | 6/2001 |
| WO | WO-0191736 A2 | 12/2001 |
| WO | WO-02083126 A1 | 10/2002 |
| WO | WO-03029212 A1 | 4/2003 |
| WO | WO-2004019869 A2 | 3/2004 |
| WO | WO-2004020408 A1 | 3/2004 |
| WO | WO-2004020409 A1 | 3/2004 |
| WO | WO-2005061455 A1 | 7/2005 |
| WO | WO-2005099709 A2 | 10/2005 |
| WO | WO-2006041961 A1 | 4/2006 |
| WO | WO-2006050236 A2 | 5/2006 |
| WO | WO-2006134499 A2 | 12/2006 |
| WO | WO-2007022501 A2 | 2/2007 |
| WO | WO-2007134169 A2 | 11/2007 |
| WO | WO-2009075250 A1 | 6/2009 |
| WO | WO-2009151644 A2 | 12/2009 |
| WO | WO-2010040080 A1 | 4/2010 |
| WO | WO-2010060532 A1 | 6/2010 |
| WO | WO-2010063352 A1 | 6/2010 |
| WO | WO-2010112116 A1 | 10/2010 |
| WO | WO-2010112124 A1 | 10/2010 |
| WO | WO-2010115491 A2 | 10/2010 |
| WO | WO-2010127786 A1 | 11/2010 |
| WO | WO-2011002918 A1 | 1/2011 |
| WO | WO-2011006569 A1 | 1/2011 |
| WO | WO-2011053597 A1 | 5/2011 |
| WO | WO-2011116867 A1 | 9/2011 |
| WO | WO-2012024620 A2 | 2/2012 |
| WO | WO-2012028162 A1 | 3/2012 |
| WO | WO-2012100018 A1 | 7/2012 |
| WO | WO-2012166415 A1 | 12/2012 |
| WO | WO-2013054185 A1 | 4/2013 |
| WO | WO-2014097151 A2 | 6/2014 |
| WO | WO-2015042052 A1 | 3/2015 |
| WO | WO-2015042053 A1 | 3/2015 |
| WO | WO-2015048301 A1 | 4/2015 |
| WO | WO-2015077502 A1 | 5/2015 |
| WO | WO-2015077503 A1 | 5/2015 |

OTHER PUBLICATIONS

Albers et al. Chemical evolution of autotaxin inhibitors. Chem. Rev. 112:2593-2603 (2012).

Albers et al. Discovery and optimization of boronic acid based inhibitors of autotaxin. J. Med. Chem. 53:4958-4967 (2010).

Albers et al. Structure-based design of novel boronic acid-based inhibitors of autotaxin. J. Med. Chem. 54:4619-4626 (2011).

Baker et al. Carba analogs of cyclic phosphatidic acid are selective inhibitors of autotaxin and cancer cell invasion and metastasis. J. Biol. Chem. 281:22786-22793 (2006).

Barbayianni et al. Autotaxin inhibitors: a patent review. Expert Opin Ther Pat. 23(9)1123-1132 (2013).

Cui et al. alpha- and beta-substituted phosphonate analogs of LPA as autotaxin inhibitors. Bioorg. Med. Chem. 16:2212-2225 (2008).

Cui et al. Synthesis and biological evaluation of phosphonate derivatives as autotaxin (ATX) inhibitors. Bioorg. Med. Chem. Lett. 17:1634-1640 (2007).

Durgam et al. Synthesis and pharmacological evaluation of second-generation phosphatidic acid derivatives as lysophosphatidic acid receptor ligands. Bioorg. Med. Chem. Lett. 16:633-640 (2006).

Durgam et al. Synthesis, structure-activity relationships, and biological evaluation of fatty alcohol phosphates as lysophosphatidic acid receptor ligands, activators of PPARgamma, and inhibitors of autotaxin. J. Med. Chem. 48:4919-4930 (2005).

East et al. Synthesis and structure-activity relationships of tyrosine-based inhibitors of autotaxin (ATX). Bioorg. Med. Chem. Lett. 20:7132-7136 (2010).

Federico et al. Therapeutic potential of autotaxin/lysophospholipase d inhibitors. Curr Drug Targets 9(8):698-708 (2008).

Ferry et al. S32826, A Nanomolar Inhibitor of Autotaxin: Discovery, Synthesis and Applications as a Pharmacological Tool. J. Pharmacol. Exp. Ther. 327:809-819 (2008).

Gajewak et al. Synthesis, pharmacology, and cell biology of sn-2-aminooxy analogues of lysophosphatidic acid. Org. Lett. 10:1111-1114 (2008).

Gendaszewska-Darmach et al. The chemical synthesis of metabolically stabilized 2-OMe-LPA analogues and preliminary studies of their inhibitory activity toward autotaxin. Bioorg. Med. Chem. Lett. 22:2698-2700 (2012).

Gierse et al. A novel autotaxin inhibitor reduces lysophosphatidic acid levels in plasma and the site of inflammation. J. Pharmacol. Exp. 334:310-317 (2010).

Gududuru et al. Identification of Darmstoff analogs as selective agonists and antagonists of lysophosphatidic acid receptors. Bioorg. Med. Chem. Lett. 16:451-456 (2006).

Gupte et al. Benzyl and naphthalene methylphosphonic acid inhibitors of autotaxin with anti-invasive and anti-metastatic activity. ChemMedChem 6:922-935 (2011).

Gupte et al. Synthesis and pharmacological evaluation of the stereoisomers of 3-carba cyclic-phosphatidic acid. Bioorg. Med. Chem. Lett. 20:7525-7528 (2010).

Higazi et al. Immunomodulatory effects of plasminogen activators on hepatic fibrogenesis. Clin Exp Immunol 152(1):163-173 (2008).

Hoeglund et al. Characterization of non-lipid autotaxin inhibitors. Bioorg. Med. Chem. 18:769-776 (2010).

Hoeglund et al. Optimization of a pipemidic acid autotaxin inhibitor. J. Med. Chem. 53:1056-1066 (2010).

Jiang et al. Alpha-substituted phosphonate analogues of lysophosphatidic acid (LPA) selectively inhibit production and action of LPA. ChemMedChem 2:679-690 (2007).

Jiang et al. Aromatic phosphonates inhibit the lysophospholipase D activity of autotaxin. Bioorg. Med. Chem. Lett. 21:5098-5101 (2011).

(56) References Cited

OTHER PUBLICATIONS

Kano et al. LPA and its analogs—attractive tools for elucidation of LPA biology and drug development. Curr. Med. Chem. 15:2122-2131 (2008).

Moulharat et al. Molecular pharmacology of adipocyte-secreted autotaxin. Chem.-Biol. Interact. 172:115-124 (2008).

North et al. Pharmacophore development and application toward the identification of novel, small-molecule autotaxin inhibitors. J. Med. Chem. 53:3095-3105 (2010).

Parrill et al. Autotaxin Inhibitors: A Persepctive on Initial Medicinal Chemisty Efforts. Expert Opin Ther Pat 20(12):1619-1625 (2010).

Parrill et al. Virtual screening approaches for the identification of non-lipid autotaxin inhibitors. Bioorg. Med. Chem. 16:1784-1795 (2008).

PCT/US2014/057477international Search Report and Written Opinion dated Jan. 7, 2015.

PCT/US2014/057477 International Preliminary Report on Patentability dated Apr. 7, 2016.

Saunders et al. Identification of small-molecule inhibitors of autotaxin that inhibit melanoma cell migration and invasion. Mol. Cancer Ther. 7:3352-3362 (2008).

Tanaka et al. Efficient synthesis of 3-O-thia-cPA and preliminary analysis of its biological activity toward autotaxin. Bioorg. Med. Chem. Lett. 21:4180-4182 (2011).

Van Meeteren et al. Anticancer activity of FTY720: phosphorylated FTY720 inhibits autotaxin, a metastasis-enhancing and angiogenic lysophospholipase D. Cancer Lett. 266:203-208 (2008).

Van Meeteren et al. Inhibition of autotaxin by lysophosphatidic acid and sphingosine 1-phosphate. J. Biol. Chem. 280:21155-21161 (2005).

Zhang et al. Dual activity lysophosphatidic acid receptor pan-antagonist/autotaxin inhibitor reduces breast cancer cell migration in vitro and causes tumor regression in vivo. Cancer Res 69:5441-5449 (2009).

AUTOTAXIN INHIBITOR COMPOUNDS

RELATED APPLICATIONS

This application is filed pursuant to 35 U.S.C. §371 as a U.S. National Phase Application of International Application No. PCT/US2014/057477 entitled "AUTOTAXIN INHIBITOR COMPOUNDS" filed Sep. 25, 2014, which claims the benefit of U.S. Provisional Application No. 61/883,026 entitled "AUTOTAXIN INHIBITOR COMPOUNDS" filed on Sep. 26, 2013, and U.S. Provisional Patent Application No. 62/038,052 entitled "AUTOTAXIN INHIBITOR COMPOUNDS" filed on Aug. 15, 2014, each incorporated herein by reference in its entirety.

FIELD OF THE INVENTION

Described herein are compounds that are autotaxin inhibitors, methods of making such compounds, pharmaceutical compositions and medicaments comprising such compounds, and methods of using such compounds in the treatment of conditions, diseases, or disorders associated with autotaxin activity.

BACKGROUND OF THE INVENTION

Lysophosphatidic acid (LPA) is a lipid mediator that functions, for example, as a mitogen, chemoattractant, and survival factor for many cell types. LPA signaling is implicated in, for example, cancer, angiogenesis, chronic inflammation, autoimmune diseases, fibrotic diseases, neurodegenerative diseases, reperfusion injury post stroke or myocardial ischemia, reproduction and tumor progression.

SUMMARY OF THE INVENTION

Compounds described herein are autotaxin (ATX) inhibitors. In some embodiments, the autotaxin inhibitors described herein are useful as agents for the treatment or prevention of diseases or conditions in which ATX and/or LPA participates, is involved in the etiology or pathology of the disease, or is otherwise associated with at least one symptom of the disease. Inhibition of the physiological activity of ATX and/or LPA is useful in a variety of diseases or conditions. The ATX-LPA signaling pathway has been implicated in fibrotic diseases, cancer, pruritus, angiogenesis, inflammation, autoimmune diseases, reproduction and tumor progression.

Compounds described herein are used in the treatment of diseases or conditions in which autotaxin activity contributes to the symptomology or progression of the disease, disorder or condition. These diseases, disorders, or conditions may arise from one or more of a genetic, iatrogenic, immunological, infectious, metabolic, ontological, toxic, surgical, and/or traumatic etiology. In one aspect, the methods, compounds, pharmaceutical compositions, and medicaments described herein comprise autotaxin inhibitors.

In one aspect, the compounds described herein are useful for the treatment of diseases or conditions such as, but not limited to, fibrosis, cell proliferative disease, inflammatory disease, autoimmune diseases, reproductive diseases, abnormal angiogenesis-associated diseases, scleroderma, brain or heart reperfusion injury, neurodegenerative diseases, neuropathic pain, peripheral neuropathy, ocular disease, diabetic retinopathy, proliferative vitreoretinopathy, cicatricial pemphigoid, and glaucoma.

In one aspect, described herein is a compound of Formula (I), or a pharmaceutically acceptable salt, or solvate thereof:

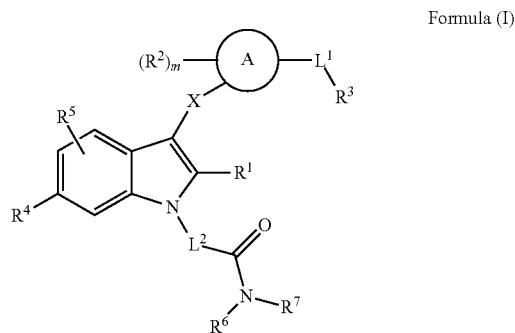

Formula (I)

wherein, $R^1$ is H, D, halogen, —CN, —C(=O)H, —NH$_2$, $C_1$-$C_4$alkyl, $C_3$-$C_6$cycloalkyl, $C_1$-$C_4$fluoroalkyl, —O $C_1$-$C_4$alkyl or $C_1$-$C_4$deuteroalkyl;

X is —O—, —S—, —S(=O)—, or —S(=O)$_2$—;

Ring A is a monocyclic aryl, bicyclic aryl, monocyclic heterocycloalkyl, monocyclic heteroaryl or bicyclic heteroaryl;

each $R^2$ is independently selected from H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, or substituted or unsubstituted monocyclic heteroaryl;

m is 0, 1, or 2;

$L^1$ is absent, $C_1$-$C_6$alkylene, $C_1$-$C_6$fluoroalkylene, or $C_3$-$C_6$cycloalkylene;

$R^3$ is —CO$_2$H, —CO$_2$($C_1$-$C_6$alkyl), —OH, —B(OH)$_2$, —C(=O)NHSO$_2$R$^9$, —C(=O)N(R$^{10}$)$_2$, —C(=O)NH— OH, —C(=O)NH—CN, —SO$_2$NHC(=O)R$^9$, —OP(=O) (OH)$_2$, —P(=O)(OH)$_2$, tetrazolyl, or carboxylic acid bioisostere;

$R^4$ is H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S (=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N (R$^{10}$)$_2$, —NHC(=O)R$^9$, —NHC(=O)OR$^9$, $C_1$-$C_4$alkyl, $C_1$-$C_4$fluoroalkyl, $C_1$-$C_4$deuteroalkyl, $C_1$-$C_4$hydroxyalkyl, $C_1$-$C_4$heteroalkyl, $C_3$-$C_6$cycloalkyl, substituted or unsubstituted phenyl, substituted or unsubstituted monocyclic heteroaryl;

$R^5$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, or $C_1$-$C_4$fluoroalkoxy;

$L^2$ is absent or $C_1$-$C_6$ alkylene;

$R^6$ is H, $C_1$-$C_6$alkyl, $C_1$-$C_6$fluoroalkyl, $C_1$-$C_6$deuteroalkyl, or $C_3$-$C_8$cycloalkyl;

$R^7$ is $C_1$-$C_6$alkyl, $C_1$-$C_6$fluoroalkyl, $C_1$-$C_6$deuteroalkyl, substituted or unsubstituted cycloalkyl, substituted or unsubstituted heterocycloalkyl, substituted or unsubstituted aryl, substituted or unsubstituted heteroaryl, —C(=O)R$^9$, or —S(=O)$_2$R$^9$, wherein if $R^7$ is substituted, then $R^7$ is substituted with 1 to 4 $R^8$ groups;

or $R^6$ and $R^7$ are taken together with the nitrogen atom to which they are attached to form an unsubstituted N-containing heterocycle or a substituted N-containing heterocycle that is substituted with 1-4 $R^8$ and 0 or 1 $R^{12}$ groups;

each $R^8$ and $R^{12}$ substituent is independently selected from the group consisting of H, halogen, OH, —CN, —$NO_2$, $C_1$-$C_6$alkyl, $C_1$-$C_6$fluoroalkyl, $C_1$-$C_6$deuteroalkyl, $C_1$-$C_6$heteroalkyl, $C_3$-$C_8$cycloalkyl, $C_1$-$C_6$alkoxy, $C_2$-$C_{10}$heterocycloalkyl, —C(=O)$R^9$, —S(=O)$_2R^9$, S(=O)$R^9$, $SR^9$, —S(=O)$_2$N($R^{10}$)$_2$, —$NR^{10}$S(=O)$_2R^9$, —OC(=O)$R^9$, —$CO_2R^{10}$, —$OCO_2R^9$, —N($R^{10}$)$_2$, —C(=O)N($R^{10}$)$_2$, —OC(=O)N($R^{10}$)$_2$, —NHC(=O)$R^9$, —NHC(=O)$OR^9$, substituted or unsubstituted aryl, $C_1$-$C_6$alkylene-substituted or unsubstituted aryl, —Y—$C_1$-$C_6$alkylene-substituted or unsubstituted aryl, substituted or unsubstituted heteroaryl, $C_1$-$C_6$alkylene-substituted or unsubstituted heteroaryl, and —Y—$C_1$-$C_6$alkylene-substituted or unsubstituted heteroaryl; Y is O or S;

or two $R^8$ substituents on the same carbon atom are taken together to form =O, or two $R^8$ substituents on the same or different carbon atoms are taken together to form to form a substituted or unsubstituted ring containing 0, 1, 2, or 3 heteroatoms in the ring selected from —$NR^{11}$—, —S(=O)$_n$—, and —O—;

n is 0, 1, or 2;

$R^9$ is $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, $C_1$-$C_4$alkylene-substituted or unsubstituted phenyl, a substituted or unsubstituted monocyclic heteroaryl, $C_1$-$C_4$alkylene-substituted or unsubstituted monocyclic heteroaryl, a substituted or unsubstituted bicyclic heteroaryl, or a $C_1$-$C_4$alkylene-substituted or unsubstituted bicyclic heteroaryl;

each $R^{10}$ is independently selected from H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, $C_1$-$C_4$alkylene-substituted or unsubstituted phenyl, a substituted or unsubstituted monocyclic heteroaryl, $C_1$-$C_4$alkylene-substituted or unsubstituted monocyclic heteroaryl, a substituted or unsubstituted bicyclic heteroaryl, or a $C_1$-$C_4$alkylene-substituted or unsubstituted bicyclic heteroaryl; or two $R^{10}$ groups attached to the same N atom are taken together with the N atom to which they are attached to form a substituted or unsubstituted heterocycle; and $R^{11}$ is H, $C_1$-$C_6$alkyl, $C_1$-$C_6$fluoroalkyl, $C_1$-$C_6$deuteroalkyl, $C_3$-$C_8$cycloalkyl, —C(=O)$R^9$, —S(=O)$_2R^9$, —$CO_2R^9$, —C(=O)N($R^{10}$)$_2$, substituted or unsubstituted aryl, $C_1$-$C_4$alkylene-substituted or unsubstituted aryl, substituted or unsubstituted heteroaryl, or $C_1$-$C_4$alkylene-substituted or unsubstituted heteroaryl.

For any and all of the embodiments, substituents are selected from among a subset of the listed alternatives. For example, in some embodiments, X is —O—, —S—, —S(=O)—, or —S(=O)$_2$—. In other embodiments, X is —O— or —S—. In other embodiments, X is —S—, —S(=O)—, or —S(=O)$_2$—. In some embodiments, X is —S—.

In some embodiments, $R^6$ and $R^7$ are taken together with the nitrogen atom to which they are attached to form a ring B that is an unsubstituted N-containing heterocycle or a substituted N-containing heterocycle that is substituted with 1-4 $R^8$ and 0 or 1 $R^{12}$ groups. In some embodiments, the compound has the structure of Formula (II), or a pharmaceutically acceptable salt, or solvate thereof:

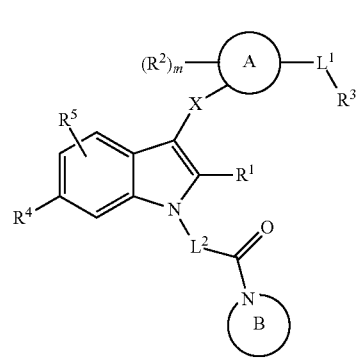

Formula (II)

wherein,

Ring B is an N-containing monocyclic or bicyclic heterocycle that is unsubstituted or substituted with 1-4 $R^8$ and 0 or 1 $R^{12}$ groups;

each $R^8$ substituent is independently H, halogen, OH, —CN, —$NO_2$, $C_1$-$C_6$alkyl, $C_1$-$C_6$fluoroalkyl, $C_1$-$C_6$deuteroalkyl, $C_1$-$C_6$heteroalkyl, $C_3$-$C_8$cycloalkyl, $C_1$-$C_6$alkoxy, $C_2$-$C_{10}$heterocycloalkyl, —C(=O)$R^9$, —S(=O)$_2R^9$, —S(=O)$R^9$, —$SR^9$, —S(=O)$_2$N($R^{10}$)$_2$, —$NR^{10}$S(=O)$_2R^9$, —OC(=O)$R^9$, —$CO_2R^{10}$, —$OCO_2R^9$, —N($R^{10}$)$_2$, —C(=O)N($R^{10}$)$_2$, —OC(=O)N($R^{10}$)$_2$, —NHC(=O)$R^9$, —NHC(=O)$OR^9$, substituted or unsubstituted aryl, $C_1$-$C_6$alkylene-substituted or unsubstituted aryl, —Y—$C_1$-$C_6$alkylene-substituted or unsubstituted aryl, substituted or unsubstituted heteroaryl, $C_1$-$C_6$alkylene-substituted or unsubstituted heteroaryl, or —Y—$C_1$-$C_6$alkylene-substituted or unsubstituted heteroaryl; Y is O or S;

or two $R^8$ substituents on the same carbon atom are taken together to form =O, or two $R^8$ substituents on the same or different carbon atoms are taken together to form to form a substituted or unsubstituted ring containing 0, 1, 2, or 3 heteroatoms in the ring selected from —$NR^{11}$—, —S(=O)$_n$—, and —O—;

n is 0, 1, or 2.

In some embodiments, Ring B is aziridinyl, azetidinyl, pyrrolidinyl, piperidinyl, azepanyl, morpholinyl, thiomorpholinyl, piperzinyl, indolinyl, azaindolinyl, isoindolinyl, azaisoindolinyl, indolinonyl, azaindolinonyl, tetrahydroquinolinyl, azatetrahydroquinolinyl, tetrahydroisoquinolinyl, or azatetrahydroisoquinolinyl, where ring B is unsubstituted or substituted with 1-4 $R^8$ and 0 or 1 $R^{12}$ groups. In some embodiments, Ring B is aziridinyl, azetidinyl, pyrrolidinyl, piperidinyl, azepanyl, morpholinyl, thiomorpholinyl, or piperzinyl, where ring B is unsubstituted or substituted with 1-4 $R^8$ and 0 or 1 $R^{12}$ groups.

In some embodiments,

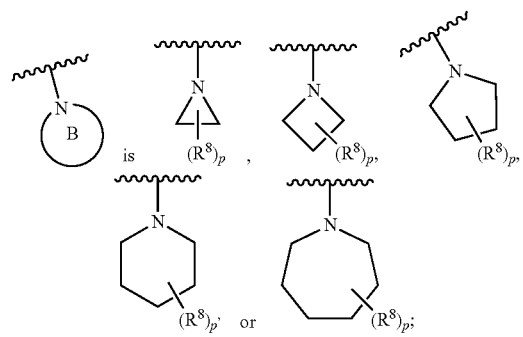

p is 1, 2, 3, or 4.

In some embodiments,

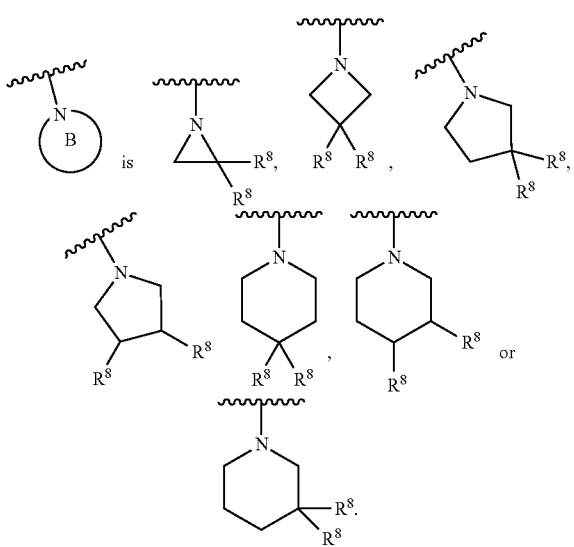

is

In some embodiments, the compound has the structure of Formula (III):

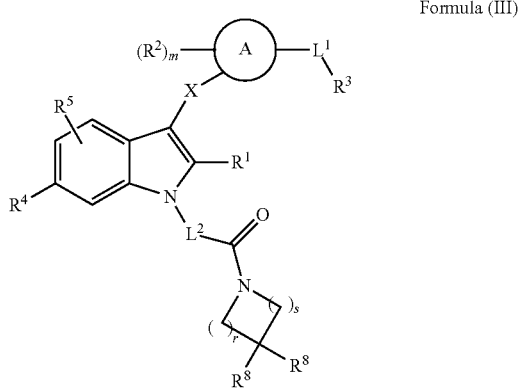

Formula (III)

wherein,
r is 1, 2, 3, or 4;
s is 0, 1, or 2.

In some embodiments, X is —S—.

In some embodiments, Ring A is phenyl, naphthyl, monocyclic heterocycloalkyl containing 1-2 N atoms and 0-1 O or S atoms, monocyclic heteroaryl containing 1-4 N atoms and 0 or 1 O or S atoms, monocyclic heteroaryl containing 0-4 N atoms and 1 O or S atoms, bicyclic heteroaryl containing 1-4 N atoms and 0 or 1 O or S atoms, or bicyclic heteroaryl containing 0-4 N atoms and 1 O or S atoms. In some embodiments, Ring A is phenyl, naphthyl, indanyl, indenyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl. In some embodiments, Ring A is phenyl, naphthyl indanyl, or indenyl. In some embodiments, Ring A is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl.

In some embodiments, Ring A is pyridinyl, pyrimidinyl, pyrazinyl, pyridazinyl, or triazinyl.

In some embodiments, Ring A is phenyl, pyridinyl, pyrimidinyl, pyrazinyl, pyridazinyl, or triazinyl. In some embodiments, Ring A is phenyl, or pyridinyl. In some embodiments, Ring A is phenyl. Tn some embodiments, Ring A is pyridinyl.

In some embodiments, the compound has the following structure of Formula (IV):

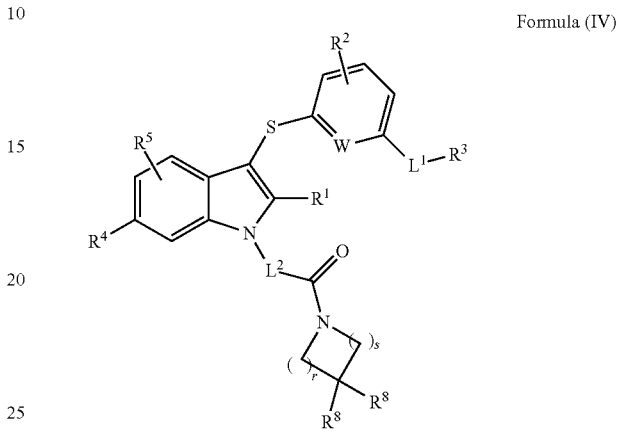

Formula (IV)

wherein,
W is CH, CF or N;
or a pharmaceutically acceptable salt, or solvate thereof.

In some embodiments, Ring A is furanyl, pyrrolyl, oxazolyl, thiazolyl, imidazolyl, pyrazolyl, triazolyl, tetrazolyl, isoxazolyl, isothiazolyl, oxadiazolyl, or thiadiazolyl.

In some embodiments, Ring A is quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, $L^2$ is absent or $C_1$-$C_4$ alkylene. In some embodiments, $L^2$ is absent, —CH$_2$—, —CH(CH$_3$)—, —C(CH$_3$)$_2$—, or —(CH$_2$)$_2$—.

In some embodiments, $R^1$ is H, halogen, —CN, —C(=O)H, $C_1$-$C_4$alkyl, $C_3$-$C_6$cycloalkyl, or $C_1$-$C_4$fluoroalkyl. In some embodiments, $R^1$ is halogen, $C_1$-$C_4$alkyl, $C_3$-$C_6$cycloalkyl, or $C_1$-$C_4$fluoroalkyl. Tn some embodiments, $R^1$ is Cl, —CH$_3$, —CH$_2$CH$_3$, cyclopropyl, or —CF$_3$. Tn some embodiments, $R^1$ is Cl, —CH$_3$, cyclopropyl, or —CF$_3$. In some embodiments, $R^1$ is —CH$_3$.

In some embodiments, the compound has the following structure of Formula (V):

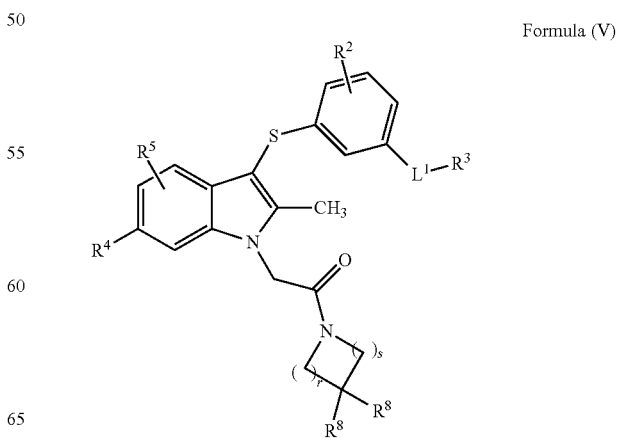

Formula (V)

or a pharmaceutically acceptable salt, or solvate thereof.

In some embodiments, the two $R^8$ substituents are joined together to form a substituted or unsubstituted cycloalkyl or substituted or unsubstituted heterocycloalkyl.

In some embodiments, the two $R^8$ substituents are joined together to form a substituted or unsubstituted $C_3$-$C_8$cycloalkyl. In some embodiments, the two $R^8$ substituents are joined together to form a substituted or unsubstituted $C_3$-$C_8$cycloalkyl or a substituted or unsubstituted $C_2$-$C_8$ heterocycloalkyl containing 1, 2, or 3 heteroatoms selected from —$NR^{11}$— or —O—.

In some embodiments, the two $R^8$ substituents are joined together to form a substituted or unsubstituted $C_3$-$C_8$cycloalkyl. In some embodiments, the two $R^8$ substituents are joined together to form a substituted or unsubstituted $C_3$-$C_6$cycloalkyl.

In some embodiments, the two $R^8$ substituents are joined together to form a substituted or unsubstituted $C_2$-$C_8$ heterocycloalkyl containing 1, 2, or 3 heteroatoms selected from —$NR^{11}$— or —O—. In some embodiments, the two $R^8$ substituents are joined together to form a substituted or unsubstituted 4-membered, 5-membered or 6-membered heterocycloalkyl containing 1, 2, or 3 heteroatoms selected from —$NR^{11}$— or —O—. In some embodiments, the two $R^8$ substituents are joined together to form a substituted or unsubstituted 5-membered heterocycloalkyl containing 1, 2, or 3 heteroatoms selected from —$NR^{11}$— or —O—.

In some embodiments, the two $R^8$ substituents are joined together to form =O.

In some embodiments, each $R^8$ substituent is independently H, $C_1$-$C_6$alkyl, —CN, substituted or unsubstituted aryl, $C_1$-$C_6$alkylene-substituted or unsubstituted aryl, —O—$C_1$-$C_6$alkylene-substituted or unsubstituted aryl, substituted or unsubstituted heteroaryl, $C_1$-$C_6$alkylene-substituted or unsubstituted heteroaryl, or O—$C_1$-$C_6$alkylene-substituted or unsubstituted heteroaryl. In some embodiments, each $R^8$ substituent is independently H, halogen, OH, —CN, $C_1$-$C_6$alkyl, $C_1$-$C_6$fluoroalkyl, $C_1$-$C_6$heteroalkyl, $C_3$-$C_8$cycloalkyl, or $C_1$-$C_6$alkoxy.

In some embodiments, each $R^8$ substituent is H.

In some embodiments,

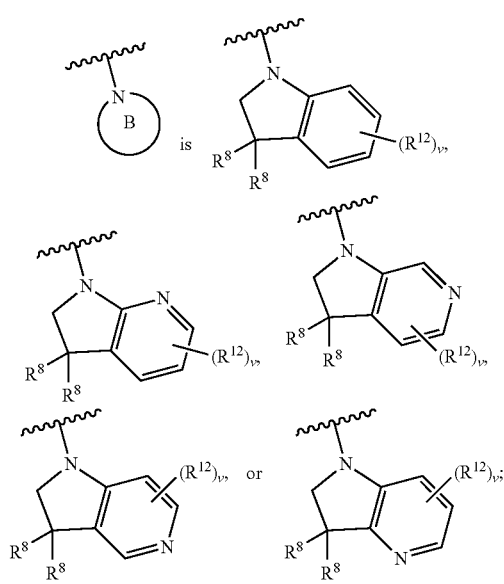

and v is 0 or 1. In some embodiments,

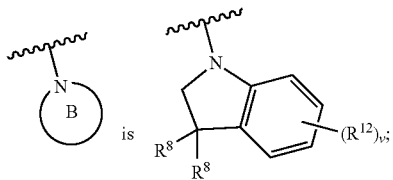

and v is 0 or 1.

In some embodiments,

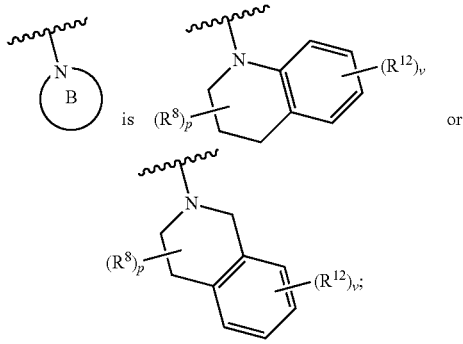

p is 0, 1, 2, 3, or 4; v is 0 or 1.

In some embodiments, the compound has the following structure of Formula (VI):

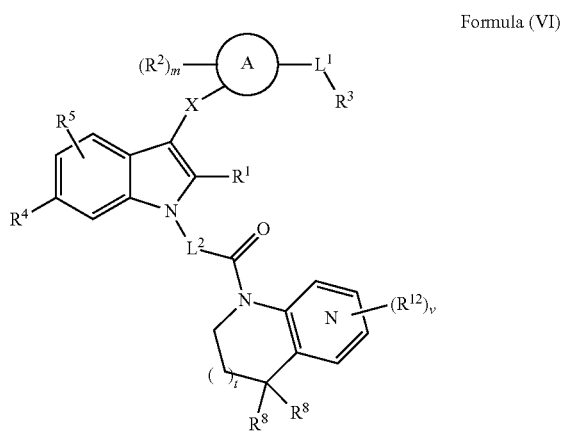

Formula (VI)

wherein, ring N is phenyl or a 6-membered heteroaryl containing 1 or 2 nitrogen atoms;

each $R^8$ substituent is independently H, halogen, OH, —CN, —$NO_2$, $C_1$-$C_6$alkyl, $C_1$-$C_6$fluoroalkyl, $C_1$-$C_6$deuteroalkyl, $C_1$-$C_6$heteroalkyl, $C_3$-$C_8$cycloalkyl, $C_1$-$C_6$alkoxy, $C_2$-$C_{10}$heterocycloalkyl, —C(=O)$R^9$, —S(=O)$_2R^9$, S(=O)$R^9$, $SR^9$, —S(=O)$_2$N($R^{10}$)$_2$, —$NR^{10}$S(=O)$_2R^9$, —OC(=O)$R^9$, —$CO_2R^{10}$, —$OCO_2R^9$, —N($R^{10}$)$_2$, —C(=O)N($R^{10}$)$_2$, —OC(=O)N($R^{10}$)$_2$, —NHC(=O)$R^9$, —NHC(=O)O$R^9$, substituted or unsubstituted aryl, $C_1$-$C_6$alkylene-substituted or unsubstituted aryl, —Y—$C_1$-$C_6$alkylene-substituted or unsubstituted aryl, substituted or unsubstituted heteroaryl, $C_1$-$C_6$alkylene-substituted or unsubstituted heteroaryl, or —Y—$C_1$-$C_6$alkylene-substituted or unsubstituted heteroaryl;

Y is O or S;

or two $R^8$ substituents are taken together to form to form a substituted or unsubstituted ring containing 0, 1, 2, or 3 heteroatoms in the ring selected from —$NR^{11}$—, —S(=O)$_n$—, and —O—;

n is 0, 1, or 2;
t is 0 or 1;
each $R^{12}$ is independently selected from H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, C$_1$-C$_6$alkyl, C$_1$-C$_6$fluoroalkyl, C$_1$-C$_6$deuteroalkyl, C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted phenyl, or substituted or unsubstituted monocyclic heteroaryl; and
v is 0 or 1.

In some embodiments, X is —S—.
In some embodiments, Ring A is phenyl, naphthyl, monocyclic heterocycloalkyl containing 1-2 N atoms and 0-1 O or S atoms, monocyclic heteroaryl containing 1-4 N atoms and 0 or 1 O or S atoms, monocyclic heteroaryl containing 0-4 N atoms and 1 O or S atoms, bicyclic heteroaryl containing 1-4 N atoms and 0 or 1 O or S atoms, or bicyclic heteroaryl containing 0-4 N atoms and 1 O or S atoms. In some embodiments, Ring A is phenyl, naphthyl, indanyl, indenyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl. In some embodiments, Ring A is phenyl, naphthyl, indanyl, or indenyl. In some embodiments, Ring A is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl. In some embodiments, Ring A is pyridinyl, pyrimidinyl, pyrazinyl, pyridazinyl, or triazinyl.

In some embodiments, Ring A is phenyl, pyridinyl, pyrimidinyl, pyrazinyl, pyridazinyl, or triazinyl; X is —S—. In some embodiments, Ring A is phenyl, or pyridinyl; X is —S—. In some embodiments, Ring A is phenyl; X is —S—. In some embodiments, Ring A is pyridinyl; X is —S—.

In some embodiments, t is 0. In some embodiments, t is 1.

In some embodiments, the compound has the following structure of Formula (VII):

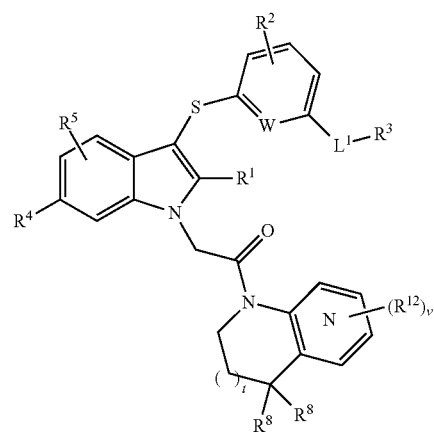

Formula (VII)

wherein,
W is CH, CF or N;
or a pharmaceutically acceptable salt, or solvate thereof.

In some embodiments, Ring A is furanyl, pyrrolyl, oxazolyl, thiazolyl, imidazolyl, pyrazolyl, triazolyl, tetrazolyl, isoxazolyl, isothiazolyl, oxadiazolyl, or thiadiazolyl.

In some embodiments, Ring A is quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, L$_2$ is absent or C$_1$-C$_4$ alkylene.
In some embodiments, L$_2$ is absent, —CH$_2$—, —CH(CH$_3$)—, —C(CH$_3$)$_2$—, or —(CH$_2$)$_2$—.
In some embodiments, R$^1$ is H, halogen, —CN, —C(=O)H, C$_1$-C$_4$alkyl, C$_3$-C$_6$cycloalkyl, or C$_1$-C$_4$fluoroalkyl. In some embodiments, R$^1$ is halogen, C$_1$-C$_4$alkyl, C$_3$-C$_6$cycloalkyl, or C$_1$-C$_4$fluoroalkyl. In some embodiments, R$^1$ is Cl, —CH$_3$, —CH$_2$CH$_3$, cyclopropyl, or —CF$_3$. In some embodiments, R$^1$ is Cl, —CH$_3$, cyclopropyl, or —CF$_3$. In some embodiments, R$^1$ is Cl, —CH$_3$, or cyclopropyl. In some embodiments, R$^1$ is —CH$_3$.

In some embodiments, the compound has the following structure of Formula (VIII):

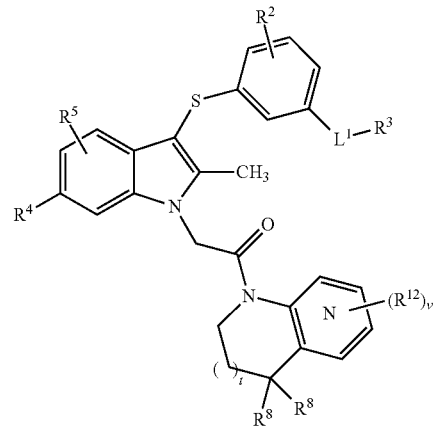

Formula (VIII)

or a pharmaceutically acceptable salt, or solvate thereof.

In some embodiments, the two R$^8$ substituents are joined together to form a substituted or unsubstituted cycloalkyl or substituted or unsubstituted heterocycloalkyl.

In some embodiments, the two R$^8$ substituents are joined together to form a substituted or unsubstituted C$_3$-C$_8$cycloalkyl. In some embodiments, the two R$^8$ substituents are joined together to form a cyclopropyl, cyclobutyl, cyclopentyl, or cyclohexyl. In some embodiments, the two R$^8$ substituents are joined together to form a cyclopropyl, cyclobutyl, or cyclopentyl. In some embodiments, the two R$^8$ substituents are joined together to form a cyclopropyl, or cyclobutyl. In some embodiments, the two R$^8$ substituents are joined together to form a cyclopropyl.

In some embodiments, the two R$^8$ substituents are joined together to form a substituted or unsubstituted C$_2$-C$_8$heterocycloalkyl containing 1, 2, or 3 heteroatoms selected from NR$^{11}$ or O.

In some embodiments, each R$^8$ substituent is independently H, C$_1$-C$_6$alkyl, —CN, substituted or unsubstituted aryl, C$_1$-C$_6$alkylene-substituted or unsubstituted aryl, —O—C$_1$-C$_6$alkylene-substituted or unsubstituted aryl, substituted or unsubstituted heteroaryl, C$_1$-C$_6$alkylene-substituted or unsubstituted heteroaryl, or O—C$_1$-C$_6$alkylene-substituted or unsubstituted heteroaryl.

In some embodiments, each R$^8$ substituent is H.
In some embodiments, R$^6$ is H, C$_1$-C$_6$alkyl, C$_1$-C$_6$fluoroalkyl, C$_1$-C$_6$deuteroalkyl, or C$_3$-C$_8$cycloalkyl; R$^7$ is C$_1$-C$_6$alkyl, C$_1$-C$_6$fluoroalkyl, C$_1$-C$_6$deuteroalkyl, substituted or unsubstituted cycloalkyl, substituted or unsubstituted heterocycloalkyl, substituted or unsubstituted aryl, substituted or unsubstituted heteroaryl, —C(O)R$^9$, N(R$^{10}$)$_2$, —S(O)$_2$R$^9$, or S(O)R$^9$; wherein if R$^7$ is substituted, then R$^7$ is substituted with 1 to 4 R$^8$ groups; and each R$^8$ substituent is independently H, halogen, OH, —CN, —NO$_2$, C$_1$-C$_6$alkyl, C$_1$-C$_6$fluoroalkyl, C$_1$-C$_6$deuteroalkyl, C$_1$-C$_6$heteroalkyl, C$_3$-C$_8$cycloalkyl, C$_1$-C$_6$alkoxy, C$_2$-C$_{10}$heterocycloalkyl, —C(=O)R$^9$, —S(=O)$_2$R$^9$, S(=O)R$^9$, SR$^9$, —S(=O)$_2$N(R$^{10}$)$_2$, —NR$^{10}$S(=O)$_2$R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, substituted or unsubstituted aryl, C$_1$-C$_6$alkylene-substituted or unsubstituted aryl, —Y—C$_1$-C$_6$alkylene-substituted or unsubstituted aryl, substituted or unsubstituted heteroaryl, C$_1$-C$_6$alkylene-substituted or unsubstituted heteroaryl, or —Y—C$_1$-C$_6$alkylene-substituted or unsubstituted heteroaryl; Y is O or S; or two R$^8$ substituents on the same carbon atom are taken together to form =O, or two R$^8$ substituents on the same or different carbon atoms are taken together to form to form a substituted or unsubstituted ring containing 0, 1, 2, or 3 heteroatoms in the ring selected from —NR$^{11}$—, —S(=O)$_n$—, and —O—; n is 0, 1, or 2.

In some embodiments, X is —S—.

In some embodiments, Ring A is phenyl, naphthyl, indanyl, indenyl, monocyclic heterocycloalkyl containing 1-2 N atoms and 0-1 O or S atoms, monocyclic heteroaryl containing 1-4 N atoms and 0 or 1 O or S atoms, monocyclic heteroaryl containing 0-4 N atoms and 1 O or S atoms, bicyclic heteroaryl containing 1-4 N atoms and 0 or 1 O or S atoms, or bicyclic heteroaryl containing 0-4 N atoms and 1 O or S atoms. In some embodiments, Ring A is phenyl, naphthyl, indanyl, indenyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl. In some embodiments, Ring A is phenyl, naphthyl, indanyl, or indenyl. In some embodiments, Ring A is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl. In some embodiments, Ring A is pyridinyl, pyrimidinyl, pyrazinyl, pyridazinyl, or triazinyl.

In some embodiments, the compound has the following structure of Formula (IX):

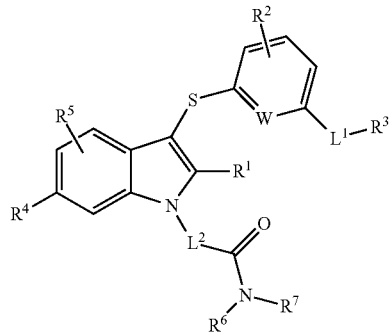

Formula (IX)

wherein,
W is CH, CF or N;
or a pharmaceutically acceptable salt, or solvate thereof.

In some embodiments, Ring A is furanyl, pyrrolyl, oxazolyl, thiazolyl, imidazolyl, pyrazolyl, triazolyl, tetrazolyl, isoxazolyl, isothiazolyl, oxadiazolyl, or thiadiazolyl.

In some embodiments, Ring A is quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, L$_2$ is absent or C$_1$-C$_4$ alkylene. In some embodiments, L$_2$ is absent, —CH$_2$—, —CH(CH$_3$)—, —C(CH$_3$)$_2$—, or —(CH$_2$)$_2$—.

In some embodiments, R$^1$ is H, halogen, —CN, —C(=O)H, C$_1$-C$_4$alkyl, C$_3$-C$_6$cycloalkyl, or C$_1$-C$_4$fluoroalkyl. In some embodiments, R$^1$ is halogen, C$_1$-C$_4$alkyl, C$_3$-C$_6$cycloalkyl, or C$_1$-C$_4$fluoroalkyl. In some embodiments, R$^1$ is Cl, —CH$_3$, —CH$_2$CH$_3$, cyclopropyl, or —CF$_3$.

In some embodiments, the compound has the following structure of Formula (X):

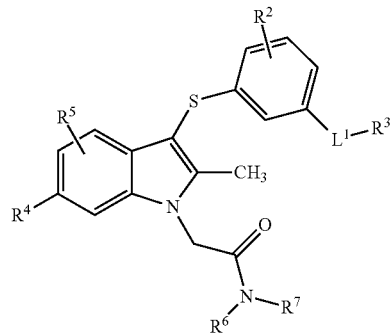

Formula (X)

or a pharmaceutically acceptable salt, or solvate thereof.

In some embodiments, R$^6$ is H, C$_1$-C$_6$alkyl, or C$_1$-C$_6$fluoroalkyl. In some embodiments, R$^6$ is H or C$_1$-C$_4$alkyl. In some embodiments, R$^6$ is H or —CH$_3$.

In some embodiments, R$^7$ is C$_1$-C$_6$alkyl, C$_1$-C$_6$fluoroalkyl, substituted or unsubstituted C$_3$-C$_{10}$cycloalkyl, substituted or unsubstituted C$_2$-C$_{10}$heterocycloalkyl, substituted or unsubstituted aryl, substituted or unsubstituted heteroaryl, C(O)R$^9$, or —S(O)$_2$R$^9$.

In some embodiments, R$^7$ is substituted or unsubstituted phenyl, substituted or unsubstituted naphthyl, substituted or unsubstituted furanyl, substituted or unsubstituted substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted triazolyl, substituted or unsubstituted tetrazolyl, substituted or unsubstituted isoxazolyl, substituted or unsubstituted isothiazolyl, substituted or unsubstituted oxadiazolyl, substituted or unsubstituted thiadiazolyl, substituted or unsubstituted pyridinyl, substituted or unsubstituted pyrimidinyl, substituted or unsubstituted pyrazinyl, substituted or unsubstituted pyridazinyl, substituted or unsubstituted triazinyl, substituted or unsubstituted quinolinyl, substituted or unsubstituted isoquinolinyl, substituted or unsubstituted quinazolinyl, substituted or unsubstituted quinoxalinyl, substituted or unsubstituted naphthyridinyl, substituted or unsubstituted indolyl, substituted or unsubstituted indolinyl, substituted or unsubstituted indazolyl, substituted or unsubstituted benzoxazolyl, substituted or unsubstituted benzisoxazolyl, substituted or unsubstituted benzofuranyl, substituted or unsubstituted benzothienyl, substituted or unsubstituted benzothiazolyl, substituted or unsubstituted benzimidazolyl, substituted or unsubstituted purinyl, substituted or unsubstituted cinnolinyl, substituted or unsubstituted phthalazinyl, substituted or unsubstituted pteridinyl, substituted or unsubstituted pyridopyrimidinyl, substituted or unsubstituted pyrazolopyrimidinyl, or substituted or unsubstituted azaindolyl.

In some embodiments, $R^7$ is substituted or unsubstituted phenyl, substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted triazolyl, substituted or unsubstituted isoxazolyl, substituted or unsubstituted isothiazolyl, substituted or unsubstituted oxadiazolyl, substituted or unsubstituted thiadiazolyl, substituted or unsubstituted pyridinyl, substituted or unsubstituted pyrimidinyl, substituted or unsubstituted indolyl, substituted or unsubstituted indolinyl, or substituted or unsubstituted indazolyl.

In some embodiments, $R^7$ is $C_1$-$C_4$alkyl, $C_1$-$C_4$fluoroalkyl, substituted or unsubstituted cyclohexyl, substituted or unsubstituted cyclopentyl, substituted or unsubstituted cyclobutyl, substituted or unsubstituted cyclopropyl, C(O)Me, or S(O)$_2$Me.

In some embodiments, $R^7$ is substituted with two $R^8$ groups on the same carbon, wherein the two $R^8$ groups are joined together to form a substituted or unsubstituted $C_3$-$C_8$cycloalkyl.

In some embodiments, $R^7$ is substituted with two $R^8$ groups on the same carbon, wherein the two $R^8$ groups are joined together to form a substituted or unsubstituted $C_2$-$C_8$heterocycloalkyl containing 1 or 2 heteroatoms selected from $NR^{11}$ or O.

In some embodiments, $R^2$ and $R^5$ are each independently H, halogen, —CN, —OH, $C_1$-$C_4$alkyl, $C_1$-$C_4$alkoxy, $C_1$-$C_4$fluoroalkoxy, or $C_1$-$C_4$fluoroalkyl.

In some embodiments, $R^2$ is H, F, Cl, —CN, —CH$_3$, —OCH$_3$, —CF$_3$, or —OCF$_3$.

In some embodiments, $R^5$ is H, F, Cl, —CN, —OH, —CH$_3$, —OCH$_3$, —CF$_3$, or —OCF$_3$. In some embodiments, $R^5$ is H, F, or Cl.

In some embodiments, $L^1$ is absent, $C_1$-$C_6$alkylene, or $C_3$-$C_6$cycloalkylene. In some embodiments, $L^1$ is absent, —CH$_2$—, —CH(CH$_3$)—, —C(CH$_3$)$_2$—, or —CH$_2$CH$_2$—. In some embodiments, $L^1$ is absent or —CH$_2$—. In some embodiments, $L^1$ is —CH$_2$—. In some embodiments, $L^1$ is absent.

In some embodiments, $R^3$ is —CO$_2$H, —CO$_2$(C$_1$-C$_6$alkyl), —B(OH)$_2$, —C(=O)NHSO$_2$R$^9$, —SO$_2$NHC(=O)R$^9$, tetrazolyl, —OP(=O)(OH)$_2$, —P(=O)(OH)$_2$, or carboxylic acid bioisostere. In some embodiments, $R^3$ is —CO$_2$H, —CO$_2$(C$_1$-C$_6$alkyl), or C(=O)NHSO$_2$R$^9$. In some embodiments, $R^3$ is —CO$_2$H or —CO$_2$(C$_1$-C$_6$alkyl). In some embodiments, $R^3$ is —CO$_2$H.

In some embodiments, $R^4$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, or $C_1$-$C_4$hydroxyalkyl.

In some embodiments, $R^4$ is halogen, —CN, —OH, $C_1$-$C_4$alkyl, $C_1$-$C_4$alkoxy, —S—$C_1$-$C_4$alkyl, $C_1$-$C_4$fluoroalkyl, or $C_1$-$C_4$fluoroalkoxy. In some embodiments, $R^4$ is F, Cl, Br, I, —CN, —OH, —CH$_3$, —CH$_2$CH$_3$, —CH(CH$_3$)$_2$, —OCH$_3$, —OCH$_2$CH$_3$, —CF$_3$, —OCF$_3$, or —S—CH$_3$. In some embodiments, $R^4$ is F, Cl, Br, or I. In some embodiments, $R^4$ is F or Cl.

In some embodiments, $R^2$ is H, F, Cl, —CN, —OH, —CH$_3$, —OCH$_3$, —CF$_3$, or —OCF$_3$; $L^1$ is absent, $C_1$-$C_6$alkylene, or $C_3$-$C_6$cycloalkylene; $R^3$ is —CO$_2$H, —CO$_2$(C$_1$-$C_6$alkyl), —B(OH)$_2$, or C(=O)NHSO$_2$R$^9$; $R^4$ is F, Cl, Br, I, —CN, —OH, —CH$_3$, —CH$_2$CH$_3$, —CH(CH$_3$)$_2$, —OCH$_3$, —OCH$_2$CH$_3$, —CF$_3$, —OCF$_3$, —S—CH$_3$, or —S(O)$_2$—CH$_3$; and $R^5$ is H, F, Cl, —CN, —OH, —CH$_3$, —OCH$_3$, —CF$_3$, or —OCF$_3$.

In some embodiments, $R^2$ is H, F, Cl, —CN, —OH, —CH$_3$, —OCH$_3$, —CF$_3$, or —OCF$_3$; $L^1$ is absent, —CH$_2$—, —CH(CH$_3$)—, or —CH$_2$CH$_2$—; $R^3$ is —CO$_2$H or —CO$_2$(C$_1$-$C_6$alkyl); $R^4$ is F, Cl, Br, —CN, —OCH$_3$, or —CF$_3$; and $R^5$ is H, F, Cl, —CN, —CH$_3$, —OCH$_3$, —CF$_3$, or —OCF$_3$.

In some embodiments, $R^2$ is H, F, Cl, —CH$_3$, —OCH$_3$, —CF$_3$, or —OCF$_3$; $L^1$ is absent or —CH$_2$—; $R^3$ is —CO$_2$H; $R^4$ is F or Cl; and $R^5$ is H, F, or Cl.

Any combination of the groups described above for the various variables is contemplated herein. Throughout the specification, groups and substituents thereof are chosen by one skilled in the field to provide stable moieties and compounds.

In one aspect, described herein is a pharmaceutical composition comprising a compound described herein, or a pharmaceutically acceptable salt, or solvate thereof, and at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is in the form of a tablet, a pill, a capsule, a liquid, a suspension, a gel, a dispersion, a solution, an emulsion, an ointment, or a lotion.

In one aspect, described herein is a method of treating or preventing any one of the diseases or conditions described herein comprising administering a therapeutically effective amount of a compound described herein, or a pharmaceutically acceptable salt, or solvate thereof, to a mammal in need thereof.

In another aspect, described herein is a method for treating or preventing cancer, fibrosis, pruritis, an inflammatory disease or condition, an airway disease or condition, an autoimmune disease or condition, obesity, intraocular pressure, neuropathic pain, or combinations thereof in a mammal comprising administering a therapeutically effective amount of a compound described herein, or a pharmaceutically acceptable salt, or solvate thereof, to the mammal in need thereof.

In one aspect, described herein is a method for treating or preventing cancer in a mammal comprising administering a therapeutically effective amount of a compound described herein, or a pharmaceutically acceptable salt, or solvate thereof, to the mammal in need thereof. In some embodiments, the cancer is a solid tumor. In other embodiments, the cancer is bladder cancer, colon cancer, brain cancer, breast cancer, endometrial cancer, heart cancer, kidney cancer, lung cancer, liver cancer, uterine cancer, blood and lymphatic cancer, ovarian cancer, pancreatic cancer, prostate cancer, thyroid cancer, or skin cancer. In yet other embodiments, the cancer is a sarcoma, carcinoma, or lymphoma. In some embodiments, the cancer is amenable to treatment with an autotaxin inhibitor. In some embodiments, the method further comprises administering a second therapeutic agent to the mammal in addition to the compound described herein, or a pharmaceutically acceptable salt, or solvate thereof.

In one aspect, described herein is a method for the treatment or prevention of fibrosis in a mammal comprising administering a therapeutically effective amount of a compound described herein, or a pharmaceutically acceptable salt, or solvate thereof, to the mammal in need thereof. In some embodiments, the fibrosis comprises lung fibrosis, liver fibrosis, kidney fibrosis, ocular fibrosis or cutaneous fibrosis. In other embodiments, the fibrosis is amenable to treatment with an autotaxin inhibitor. In some embodiments, the method further comprises administering a second therapeutic agent to the mammal in addition to the compound described herein, or a pharmaceutically acceptable salt, or solvate thereof.

In one aspect, described herein is a method of reducing or inhibiting angiogenesis in a mammal comprising administering a therapeutically effective amount of a compound described herein, or a pharmaceutically acceptable salt, or solvate thereof, to the mammal in need thereof. In some embodiments, reducing or inhibiting angiogenesis in the mammal treats atherosclerosis, hypertension, tumor growth, inflammation, rheumatoid arthritis, wet-form macular degeneration, choroidal neovascularization, retinal neovascularization, or diabetic retinopathy.

In another aspect, described herein is a method of treating or preventing an inflammatory disease or condition in a mammal comprising administering a therapeutically effective amount of a compound described herein, or a pharmaceutically acceptable salt, or solvate thereof, to the mammal in need thereof. In some embodiments, the inflammatory disease or condition is psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, eczema, lupus erythematosus, dermatomyositis, Sjogren's syndrome, thyroiditis, myasthenia gravis, autoimmune hemolytic anemia, multiple sclerosis, cystic fibrosis, chronic relapsing hepatitis, primary biliary cirrhosis, primary sclerosing cholangitis, allergic conjunctivitis or atopic dermatitis.

In one aspect, described herein is a method for treating or preventing pruritis in a mammal comprising administering a therapeutically effective amount of a compound described herein, or a pharmaceutically acceptable salt, or solvate thereof, to the mammal in need thereof. In some embodiments, the pruritus is associated with dermatitis herpetiformis, dermatomyositis, pemphigoid, Sjögren's syndrome, Darier's disease, Hailey-Hailey disease, Ichthyoses, Sjögren-Larsson syndrome, dermatophytosis, folliculitis, impetigo and other bacterial infections, insect bites, pediculosis, scabies, viral infection, asteatosis, atopic eczema, contact dermatitis, drug reaction, lichen planus, lichen simplex chronicus, mastocytosis (urticaria pigmentosa), miliaria, psoriasis, scar(s), urticaria, cutaneous T-cell lymphoma or mycosis fungoides, cutaneous B-cell lymphoma, leukemia cutis, pemphigoid gestationis, polymorphic eruption of pregnancy or prurigo gestationis.

In another aspect, described herein is a method for treating or preventing cholestatic pruritus in a mammal comprising administering a therapeutically effective amount of a compound described herein, or a pharmaceutically acceptable salt, or solvate thereof, to the mammal in need thereof.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by inhalation; and/or (e) administered by nasal administration; or and/or (f) administered by injection to the mammal; and/or (g) administered topically to the mammal; and/or (h) administered by ophthalmic administration; and/or (i) administered rectally to the mammal; and/or (j) adminstered non-systemically or locally to the mammal.

In any of the aforementioned aspects are further embodiments comprising single administrations of the effective amount of the compound, including further embodiments in which the compound is administered once a day to the mammal or the compound is administered to the mammal multiple times over the span of one day. In some embodiments, the compound is administered on a continuous dosing schedule. Tn some embodiments, the compound is administered on a continuous daily dosing schedule.

In any of the aforementioned aspects involving the treatment of ATX dependent diseases or conditions are further embodiments comprising administering at least one additional agent in addition to the administration of a compound described herein, or a pharmaceutically acceptable salt thereof. In various embodiments, each agent is administered in any order, including simultaneously.

In any of the embodiments disclosed herein, the mammal is a human.

In some embodiments, compounds provided herein are administered to a human.

In some embodiments, compounds provided herein are orally administered.

Articles of manufacture, which include packaging material, a compound described herein, or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for inhibiting the activity of autotaxin, or for the treatment, prevention or amelioration of one or more symptoms of a disease or condition that would benefit from inhibition of the activity of autotaxin, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Autotaxin and LPA

Autotaxin (ATX, NPP2, or E-NPP2), an approximately 120 kDa glycoprotein, is a secreted nucleotide pyrophosphatase/phosphodiesterase (NPP) with lysophospholipase D activity that converts extracellular lysophosphatidylcholine (LPC) and other lysophospholipids to lysophosphatidic acid (LPA). ATX is considered to be responsible for the majority of circulating LPA production.

LPA acts through sets of specific G protein-coupled receptors (GPCRs), such as LPA1, LPA2, LPA3, LPA4, LPA5, LPA6, LPA7, LPA8, in an autocrine and paracrine fashion to produce a variety of biological responses. For example, lysophospholipids, such as lysophosphatidic acid (LPA), are known to affect such biological functions as cellular proliferation, differentiation, survival, migration, adhesion, invasion, and morphogenesis. In addition, LPA is known to play a role in such processes as platelet activation, smooth muscle contraction, actin stress fiber formation, and cell migration.

ATX and LPA have been detected in various biological fluids such as serum, plasma, cerebrospinal fluid, seminal fluid, urine, and saliva, both in animals and humans, suggesting that they are potential biomarkers to predict certain diseases. For example, serum ATX concentration and activity is elevated in patients with chronic liver diseases and in pregnant women. In addition, ATX concentration has been found to be lower in postoperative cancer patients as a result of postoperative damage or poor nutritional state. In addition, ATX is known to be essential for normal development. For example, ATX-deficient mice die at embryonic day 9.5 with profound vascular defects in both the yolk sac and the embryo. Furthermore, at embryonic day 8.5 ATX-deficient embryos were found to have malformed allantois, neural tube defects, and asymmetric headfolds.

Cancer

ATX has been demonstrated to increase cell motility, neovascularization, proliferation and aggressiveness of tumors. It is upregulated in numerous tumor lineages, such as breast, renal, liver, glioblastoma, ovarian and prostate cancer.

In some embodiments, disclosed herein are methods of treating cancer with a compound disclosed herein.

ATX is a prometastatic enzyme initially isolated from the conditioned medium of human melanoma cells. In addition, ATX overexpression is frequently observed in malignant tumor tissues such as breast cancer, renal cancer, Hodgkin lymphoma, hepatocellular carcinoma, pancreatic cancer and glioblastoma. LPA also contributes to tumorigenesis by increasing motility and invasiveness of cells.

The term "cancer" as used herein, refers to an abnormal growth of cells that tend to proliferate in an uncontrolled way and, in some cases, to metastasize (spread). Types of cancer include, but are not limited to, solid tumors (such as those of the bladder, bowel, brain, breast, endometrium, heart, kidney, lung, liver, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, desmoid tumors, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, Hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Sezary syndrome, skin cancer, small cell lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglubulinemia, and Wilms tumor.

In some embodiments, a compound disclosed herein, or a pharmaceutically acceptable salt thereof, is used in the treatment of ovarian cancer, prostate cancer, breast cancer, lung cancer, melanoma, head and neck cancer, bowel cancer (colorectal cancer), thyroid cancer, glioblastoma, follicular lymphoma, renal cancer, Hodgkin lymphoma, hepatocellular carcinoma, pancreatic cancer or melanoma.

In some embodiments, a compound disclosed herein, or a pharmaceutically acceptable salt thereof, is used in the treatment of bone metastases.

In some embodiments, a compound disclosed herein, or a pharmaceutically acceptable salt thereof, is used in the treatment of oral cancer, prostate cancer, rectal cancer, non-small cell lung cancer, lip and oral cavity cancer, liver cancer, lung cancer, anal cancer, kidney cancer, vulvar cancer, breast cancer, oropharyngeal cancer, nasal cavity and paranasal sinus cancer, nasopharyngeal cancer, urethra cancer, small intestine cancer, bile duct cancer, bladder cancer, ovarian cancer, laryngeal cancer, hypopharyngeal cancer, gallbladder cancer, colon cancer, colorectal cancer, head and neck cancer, parathyroid cancer, penile cancer, vaginal cancer, thyroid cancer, pancreatic cancer, esophageal cancer, Hodgkin's lymphoma, leukemia-related disorders, mycosis fungoides, or myelodysplastic syndrome.

In some embodiments, a compound disclosed herein, or a pharmaceutically acceptable salt thereof, is used in the treatment of non-small cell lung cancer, pancreatic cancer, breast cancer, ovarian cancer, colorectal cancer, or head and neck cancer.

In some embodiments, a compound disclosed herein, or a pharmaceutically acceptable salt thereof, is used in the treatment of a carcinoma, a tumor, a neoplasm, a lymphoma, a melanoma, a glioma, a sarcoma, or a blastoma.

In some embodiments, the carcinoma is selected from the group consisting of: carcinoma, adenocarcinoma, adenoid cystic carcinoma, adenosquamous carcinoma, adrenocortical carcinoma, well differentiated carcinoma, squamous cell carcinoma, serous carcinoma, small cell carcinoma, invasive squamous cell carcinoma, large cell carcinoma, islet cell carcinoma, oat cell carcinoma, squamous carcinoma, undifferentiatied carcinoma, verrucous carcinoma, renal cell carcinoma, papillary serous adenocarcinoma, merkel cell carcinoma, hepatocellular carcinoma, soft tissue carcinomas, bronchial gland carcinomas, capillary carcinoma, bartholin gland carcinoma, basal cell carcinoma, carcinosarcoma, papilloma/carcinoma, clear cell carcinoma, endometrioid adenocarcinoma, mesothelial, metastatic carcinoma, mucoepidermoid carcinoma, cholangiocarcinoma, actinic keratoses, cystadenoma, and hepatic adenomatosis.

In some embodiments, the tumor is selected from the group consisting of: astrocytic tumors, malignant mesothelial tumors, ovarian germ cell tumor, supratentorial primitive neuroectodermal tumors, Wilm's tumor, pituitary tumors, extragonadal germ cell tumor, gastrinoma, germ cell tumors, gestational trophoblastic tumor, brain tumors, pineal and supratentorial primitive neuroectodermal tumors, pituitary tumor, somatostatin-secreting tumor, endodermal sinus tumor, carcinoids, central cerebral astrocytoma, glucagonoma, hepatic adenoma, insulinoma, medulloepithelioma, plasmacytoma, vipoma, and pheochromocytoma.

In some embodiments, the neoplasm is selected from the group consisting of: intaepithelial neoplasia, multiple myeloma/plasma cell neoplasm, plasma cell neoplasm, interepithelial squamous cell neoplasia, endometrial hyperplasia, focal nodular hyperplasia, hemangioendothelioma, lymphangioleio myomatosis and malignant thymoma.

In some embodiments, the lymphoma is selected from the group consisting of: nervous system lymphoma, AIDS-related lymphoma, cutaneous T-cell lymphoma, non-Hodgkin's lymphoma, mantle cell lymphoma, follicular lymphoma and Waldenstrom's macroglobulinemia.

In some embodiments, the melanoma is selected from the group consisting of: acral lentiginous melanoma, superficial spreading melanoma, uveal melanoma, lentigo maligna melanomas, melanoma, intraocular melanoma, adenocarcinoma nodular melanoma, and hemangioma.

In some embodiments, the sarcoma is selected from the group consisting of: adenomas, adenosarcoma, chondosarcoma, endometrial stromal sarcoma, Ewing's sarcoma, Kaposi's sarcoma, leiomyosarcoma, rhabdomyosarcoma, sarcoma, uterine sarcoma, osteosarcoma, and pseudosarcoma.

In some embodiments, the glioma is selected from the group consisting of: glioma, brain stem glioma, and hypothalamic and visual pathway glioma.

In some embodiments, the blastoma is selected from the group consisting of: pulmonary blastoma, pleuropulmonary blastoma, retinoblastoma, neuroblastoma, medulloblastoma, glioblastoma, and hemangiblastomas.

Fibrosis

In some embodiments, disclosed herein are methods of treating fibrosis with a compound disclosed herein.

"Fibrosis," as used herein, refers to the accumulation of extracellular matrix constituents that occurs following trauma, inflammation, tissue repair, immunological reactions, cellular hyperplasia, and neoplasia. Examples of tissue fibrosis include, but are not limited to, pulmonary fibrosis, renal fibrosis, cardiac fibrosis, cirrhosis and fibrosis of the liver, skin scars and keloids, adhesions, fibromatosis, atherosclerosis, and amyloidosis.

In some embodiments, disclosed herein is a method of reducing fibrosis in a tissue comprising contacting a fibrotic cell or tissue with a compound disclosed herein, in an amount sufficient to decrease or inhibit the fibrosis. In some embodiments, the fibrosis includes a fibrotic condition.

In some embodiments, reducing fibrosis, or treatment of a fibrotic condition, includes reducing or inhibiting one or more of: formation or deposition of extracellular matrix proteins; the number of pro-fibrotic cell types (e.g., fibroblast or immune cell numbers); cellular collagen or hydroxyproline content within a fibrotic lesion; expression or activity of a fibrogenic protein; or reducing fibrosis associated with an inflammatory response.

In some embodiments, the fibrotic condition is primary fibrosis. In some embodiments, the fibrotic condition is idiopathic. In some embodiments, the fibrotic condition is associated with (e.g., is secondary to) a disease (e.g., an infectious disease, an inflammatory disease, an autoimmune disease, a malignant or cancerous disease, and/or a connective disease); a toxin; an insult (e.g., an environmental hazard (e.g., asbestos, coal dust, polycyclic aromatic hydrocarbons), cigarette smoking, a wound); a medical treatment (e.g., surgical incision, chemotherapy or radiation), or a combination thereof.

In some embodiments, the fibrotic condition is a fibrotic condition of the lung, a fibrotic condition of the liver, a fibrotic condition of the heart or vasculature, a fibrotic condition of the kidney, a fibrotic condition of the skin, a fibrotic condition of the gastrointestinal tract, a fibrotic condition of the bone marrow or a hematopoietic tissue, a fibrotic condition of the nervous system, or a combination thereof.

In some embodiments, the fibrotic condition affects a tissue chosen from one or more of muscle, tendon, cartilage, skin (e.g., skin epidermis or endodermis), cardiac tissue, vascular tissue (e.g., artery, vein), pancreatic tissue, lung tissue, liver tissue, kidney tissue, uterine tissue, ovarian tissue, neural tissue, testicular tissue, peritoneal tissue, colon, small intestine, biliary tract, gut, bone marrow, or hematopoietic tissue.

In some embodiments, the fibrotic condition is a fibrotic condition of the lung. In some embodiments, the fibrotic condition of the lung is chosen from one or more of: pulmonary fibrosis, idiopathic pulmonary fibrosis (IPF), usual interstitial pneumonitis (UIP), interstitial lung disease, cryptogenic fibrosing alveolitis (CFA), bronchiolitis obliterans, or bronchiectasis. In some embodiments, the fibrosis of the lung is secondary to a disease, a toxin, an insult, a medical treatment, or a combination thereof. In some embodiments, fibrosis of the lung is associated with one or more of: a disease process such as asbestosis and silicosis; an occupational hazard; an environmental pollutant; cigarette smoking; an autoimmune connective tissue disorders (e.g., rheumatoid arthritis, scleroderma and systemic lupus erythematosus (SLE)); a connective tissue disorder such as sarcoidosis; an infectious disease, e.g., infection, particularly chronic infection; a medical treatment, including but not limited to, radiation therapy, and drug therapy, e.g., chemotherapy (e.g., treatment with as bleomycin, methotrexate, amiodarone, busulfan, and/or nitrofurantoin). In some embodiments, the fibrotic condition of the lung treated with the methods of the invention is associated with (e.g., secondary to) a cancer treatment, e.g., treatment of a cancer (e.g. squamous cell carcinoma, testicular cancer, Hodgkin's disease with bleomycin).

In some embodiments, the fibrotic condition is a fibrotic condition of the liver. In certain embodiments, the fibrotic condition of the liver is chosen from one or more of: fatty liver disease, steatosis (e.g., nonalcoholic steatohepatitis (NASH), cholestatic liver disease (e.g., primary biliary cirrhosis (PBC), cirrhosis, alcohol-induced liver fibrosis, biliary duct injury, biliary fibrosis, cholestasis or cholangiopathies. In some embodiments, hepatic or liver fibrosis includes, but is not limited to, hepatic fibrosis associated with alcoholism, viral infection, e.g., hepatitis (e.g., hepatitis C, B or D), autoimmune hepatitis, non-alcoholic fatty liver disease (NAFLD), progressive massive fibrosis, exposure to toxins or irritants (e.g., alcohol, pharmaceutical drugs and environmental toxins).

In some embodiments, the fibrotic condition is a fibrotic condition of the heart. In certain embodiments, the fibrotic condition of the heart is myocardial fibrosis (e.g., myocardial fibrosis associated with radiation myocarditis, a surgical procedure complication (e.g., myocardial post-operative fibrosis), infectious diseases (e.g., Chagas disease, bacterial, trichinosis or fungal myocarditis)); granulomatous, metabolic storage disorders (e.g., cardiomyopathy, hemochromatosis); developmental disorders (e.g., endocardial fibroelastosis); arteriosclerotic, or exposure to toxins or irritants (e.g., drug induced cardiomyopathy, drug induced cardiotoxicity, alcoholic cardiomyopathy, cobalt poisoning or exposure). In some embodiments, the myocardial fibrosis is associated with an inflammatory disorder of cardiac tissue (e.g., myocardial sarcoidosis).

In some embodiments, the fibrotic condition is a fibrotic condition of the kidney. In some embodiments, the fibrotic condition of the kidney is chosen from one or more of: renal fibrosis (e.g., chronic kidney fibrosis), nephropathies associated with injury/fibrosis (e.g., chronic nephropathies associated with diabetes (e.g., diabetic nephropathy)), lupus, scleroderma of the kidney, glomerular nephritis, focal segmental glomerular sclerosis, IgA nephropathyrenal fibrosis associated with human chronic kidney disease (CKD), chronic progressive nephropathy (CPN), tubulointerstitial fibrosis, ureteral obstruction, chronic uremia, chronic interstitial nephritis, radiation nephropathy, glomerulosclerosis, progressive glomerulonephrosis (PGN), endothelial/thrombotic microangiopathy injury, HIV-associated nephropathy, or fibrosis associated with exposure to a toxin, an irritant, or a chemotherapeutic agent.

In some embodiments, the fibrotic condition is a fibrotic condition of the skin. In some embodiments, the fibrotic condition of the skin is chosen from one or more of: skin fibrosis, scleroderma, nephrogenic systemic fibrosis (e.g., resulting after exposure to gadolinium which is frequently used as a contrast substance for MRIs in patients with severe kidney failure), scarring and keloid.

In some embodiments, the fibrotic condition is a fibrotic condition of the gastrointestinal tract. Tn some embodiments, the fibrotic condition is chosen from one or more of fibrosis associated with scleroderma; radiation induced gut fibrosis; fibrosis associated with a foregut inflammatory disorder such as Barrett's esophagus and chronic gastritis, and/or fibrosis associated with a hindgut inflammatory disorder, such as inflammatory bowel disease (IBD), ulcerative colitis and Crohn's disease.

In some embodiments, the fibrotic condition is adhesions. In some embodiments, the adhesions are chosen from one or more of: abdominal adhesions, peritoneal adhesions, pelvic adhesions, pericardial adhesions, peridural adhesions, peritendinous or adhesive capsulitis.

In some embodiments, the fibrotic condition is a fibrotic condition of the eye. In some embodiments, the fibrotic condition of the eye involves diseases of the anterior segment of the eye such as glaucoma and corneal opacification; in some embodiments, the fibrotic condition of the eye involves disease of the posterior segment of the eye such as age-related macular degeneration, diabetic retinopathy, retinopathy of prematurity and neovascular glaucoma; in some embodiments, the fibrotic condition of the eye results from fibrosis following ocular surgery.

In some embodiments, the fibrotic condition is a fibrotic condition of the bone marrow or a hematopoietic tissue. In some embodiments, the fibrotic condition of the bone marrow is an intrinsic feature of a chronic myeloproliferative neoplasm of the bone marrow, such as primary myelofibrosis (also referred to herein as agnogenic myeloid metaplasia or chronic idiopathic myelofibrosis). In some embodiments, the bone marrow fibrosis is associated with (e.g., is secondary to) a malignant condition or a condition caused by a clonal proliferative disease. In some embodiments, the bone marrow fibrosis is associated with a hematologic disorder (e.g., a hematologic disorder chosen from one or more of polycythemia vera, essential thrombocythemia, myelodysplasia, hairy cell leukemia, lymphoma (e.g., Hodgkin or non-Hodgkin lymphoma), multiple myeloma or chronic myelogeneous leukemia (CML)). In some embodiments, the bone marrow fibrosis is associated with (e.g., secondary to) a non-hematologic disorder (e.g., a non-hematologic disorder chosen from solid tumor metastasis to bone marrow, an autoimmune disorder (e.g., systemic lupus erythematosus, scleroderma, mixed connective tissue disorder, or polymyositis), an infection (e.g., tuberculosis), or secondary hyperparathyroidism associated with vitamin D deficiency.

Pruritis

In some embodiments, disclosed herein are methods of treating pruritis with a compound disclosed herein.

Pruritus is a condition involving localized or general itching that is a common and distressing symptom in a variety of diseases. Although usually occurring in the skin, pruritus can also occur in non-cutaneous sites such as mucous membranes. Pruritus is a frequent manifestation of localized skin disorders caused by hypersensitivity reactions such as allergic reactions to insect bites or to environmental allergens, urticaria, dermatoses of fungal and bacterial origins, ectoparasite infections, and hemorrhoids. In some embodiments, disclosed herein are method of treating pruritus caused by systemic diseases, including, for example, hypothyroidism, thyrotoxicosis, mucocandiasis in diabetes mellitus, and Hodgkin's disease. In some embodiments, disclosed herein are methods of treating bouts of persistent or recurrent pruritus associated with many systemic diseases and skin disorders.

In some embodiments, disclosed herein are methods of treating pruritus associated with liver diseases and intrahepatic or posthepatic cholestasis. Hepatic diseases leading to pruritus include primary biliary cirrhosis, B and C viral hepatitis, primary sclerosing cholangitis, carcinoma of bile ducts, alcoholic cirrhosis, autoimmune hepatitis and others.

In some embodiments, disclosed herein are method of treating pruritus arising from a variety of causes such as xerosis, skin conditions (such as psoriasis, eczema, sunburn, athlete's foot), insect bites, poisonous plants (such as poison ivy, poison oak, poison sumac), Hodgkin's disease, jaundice, polycythemia, scabies, lice, worms, thyroid illness, diabetes mellitus, dandruff, iron deficiency anemia, parasitic infections, medications, cholestasis, pruritus related to pregnancy, HIV infection or other causes of itching or pruritus.

Inflammation

In some embodiments, disclosed herein are methods of treating an inflammatory condition, disease, or disorder with a compound disclosed herein.

As used in the present disclosure, "inflammation" refers to the well known localized response to various types of injury or infection, which is characterized by redness, heat, swelling, and pain, and often also including dysfunction or reduced mobility.

Airway Diseases

Inflammatory conditions, diseases, and disorders, which can be treated with a compound disclosed herein, include airway diseases comprising pulmonary inflammation, such as chronic obstructive pulmonary disease (COPD), cystic fibrosis, and asthma. COPD is comprised primarily of two related diseases: chronic bronchitis and emphysema. In both diseases, there is chronic obstruction of the flow of air through the airways and out of the lungs, and the obstruction generally is permanent and progressive over time Asthma is a chronic disease of the airways of the lungs, characterized by inflammation and paradoxical narrowing of the bronchi. Asthma includes asthmatic conditions mediated via T-cell action, including extrinsic asthma (allergic asthma), intrinsic asthma (non-allergic asthma), mixed asthma (extrinsic and intrinsic asthma), occupational asthma induced by agents such as toluene diisocyanate, polyvinyl chloride, phthalic anhydride, trimellitic anhydride, plicatic acid (Western Red Cedar trees) or metal salts such as platinum or nickel), drug-induced asthma (including aspirin-induced asthma or asthma induced by non-steroidal anti-inflammatory drugs (NSATDs)), exercise-induced asthma, and cough variant asthma. In some embodiments, the asthma is an allergic or non-allergic asthmatic condition mediated by T-cell function.

In some embodiments, disclosed herein is a method of treating asthma with a compound disclosed herein. In an asthmatic individual, the release of normal repair mediators, including LPA, is exaggerated or the actions of the repair mediators are inappropriately prolonged leading to inappropriate airway remodeling. Major structural features of the remodeled airway observed in asthma include a thickened lamina reticularis (the basement membrane-like structure just beneath the airway epithelial cells), increased numbers and activation of myofibroblasts, thickening of the smooth muscle layer, increased numbers of mucus glands and mucus secretions, and alterations in the connective tissue and capillary bed throughout the airway wall. In some embodiments, ATX and/or LPA contribute to these structural changes in the airway. In some embodiments, ATX and/or LPA are involved in acute airway hyperresponsiveness in asthma. The lumen of the remodeled asthmatic airway is narrower due to the thickening of the airway wall, thus decreasing airflow. In some embodiments, LPA contributes to the long-term structural remodeling and the acute hyper-responsiveness of the asthmatic airway. In some embodiments, LPA contributes to the hyper-responsiveness that is a primary feature of acute exacerbations of asthma.

In some embodiments, disclosed herein is a method of treating or preventing COPD with a compound disclosed herein. The term "chronic obstructive pulmonary disease (COPD)" refers to a group of lung diseases, including chronic bronchitis, emphysema and obliterative bronchiolitis. The most common of these diseases are chronic bronchitis and emphysema. Although a person with COPD may have either chronic bronchitis or emphysema, he or she will often have a mixture of the symptoms of these two conditions. Although emphysema usually results from damage to the lungs caused by environmental insult, usually as a result of long-term smoking, emphysema may also be caused by congenital absence of al-antitrypsin in the lungs; this type of emphysema is usually inherited.

In some embodiments, disclosed herein is a method of treating chronic bronchitis with a compound disclosed herein. Chronic bronchitis (CB) is inflammation of one or more bronchi, usually secondary to infection, and is characterized by excessive production of mucus in the bronchi, accompanied by a recurrent cough which persists for at least three months of the year during at least two successive years. CB is the major non-asthmatic disease of the lung. Many different factors initiate CB, including cigarette smoking, environmental pollution, chronic infections and various genetic abnormalities. Of these factors, cigarette smoking is the most prevalent. Pathological changes in the lung include: (1) hypertrophy and hyperplasia of mucus-secreting glands in the bronchi, (2) increase in goblet cells, (3) disappearance or damage of cilia, and (4) chronic inflammatory changes and narrowing of small airways.

In some embodiments, disclosed herein is a method of treating emphysema with a compound disclosed herein. Emphysema is a lung condition which results from damage to the alveolar sacs in the lungs, usually caused by long-term smoking. This damage leads to a pathological accumulation of air in the tissues.

Administration of LPA in vivo induces airway hyperresponsiveness, itch-scratch responses, infiltration and activation of eosinophils and neutrophils, vascular remodeling, and nociceptive flexor responses. LPA also induces histamine release from mouse and rat mast cells. In an acute allergic reaction, histamine induces various responses, such as contraction of smooth muscle, plasma exudation, and mucus production. Plasma exudation is important in the airway, because the leakage and subsequent airway-wall edema contribute to the development of airway hyperresponsiveness. In some embodiments, disclosed herein is a method of reducing plasma exudation due to an acute allergic reaction with a compound disclosed herein.

Autoimmune Diseases

The methods described herein, in some embodiments, include methods for the treatment, reduction of risk, and delaying of onset of an autoimmune disease or disorder with a compound disclosed herein. Examples of autoimmune diseases include, but are not limited to, Alopecia Areata, Lupus, Ankylosing Spondylitis, Meniere's Disease, Antiphospholipid Syndrome, Mixed Connective Tissue Disease, Autoimmune Addison's Disease, Autoimmune Hemolytic Anemia, Myasthenia Gravis, Autoimmune Hepatitis, Pemphigus Vulgaris, Behcet's Disease, Pernicious Anemia, Bullous Pemphigoid, Polyarthritis Nodosa, Cardiomyopathy, Polychondritis, Celiac Sprue-Dermatitis, Polyglandular Syndromes, Chronic Fatigue Syndrome (CFIDS), Polymyalgia Rheumatica, Chronic Inflammatory Demyelinating, Polymyositis and Dermatomyositis, Chronic Inflammatory Polyneuropathy, Primary Agammaglobulinemia, Churg-Strauss Syndrome, Primary Biliary Cirrhosis, Cicatricial Pemphigoid, Psoriasis, CREST Syndrome, Raynaud's Phenomenon, Cold Agglutinin Disease, Reiter's Syndrome, Crohn's Disease, Rheumatic Fever, Discoid Lupus, Rheumatoid Arthritis, Essential Mixed, Cryoglobulinemia Sarcoidosis, Fibromyalgia, Scleroderma, Grave's Disease, Sjögren's Syndrome, Guillain-Barre, Stiff-Man Syndrome, Hashimoto's Thyroiditis, Takayasu Arteritis, Idiopathic Pulmonary Fibrosis, Temporal Arteritis/Giant Cell Arteritis, Idiopathic Thrombocytopenia Purpura (ITP), Ulcerative Colitis, IgA Nephropathy, Uveitis, Insulin Dependent Diabetes (Type I), Diabetes (Type II), Vasculitis, Lichen Planus, and Vitiligo.

Other Inflammatory Disorders

The methods described herein, in some embodiments, include methods for the treatment, reduction of risk, and delaying onset of other inflammatory conditions or diseases with a compound disclosed herein, such as (a Ocular inflammation associated with corneal ulcers, giant papillary conjunctivitis, blepharitis, chelazion, uveitis, dry eye, post-surgical inflammation, and contact lens associated inflammation; (b) allergic diseases such as hay fever, rhinitis, seasonal allergic conjunctivitis, vernal conjunctivitis and other eosinophil-mediated conditions; (c) skin diseases such as psoriasis, contact dermatitis, eczema, infectious skin ulcers, open wounds, and cellulitis; (d) infectious diseases including sepsis, septic shock, encephalitis, infectious arthritis, endotoxic shock, gram negative shock, Jarisch-Herxheimer reaction, shingles, toxic shock, cerebral malaria, bacterial meningitis, acute respiratory distress syndrome (ARDS), lyme disease, and HIV infection, (e) wasting diseases such as cachexia secondary to cancer and HIV; (f) inflammation due to organ, tissue or cell transplantation (e.g., bone marrow, cornea, kidney, lung, liver, heart, skin, pancreatic islets) including transplant rejection, and graft versus host disease; (g) adverse effects from drug therapy, including adverse effects from amphotericin B treatment, adverse effects from immunosuppressive therapy, e.g., interleukin-2 treatment, adverse effects from OKT3 treatment, adverse effects from GM-CSF treatment, adverse effects of cyclosporine treatment, and adverse effects of aminoglycoside treatment, stomatitis, and mucositis due to immunosuppression; (h) cardiovascular conditions including circulatory diseases induced or exasperated by an inflammatory response, such as ischemia, atherosclerosis, peripheral vascular disease, restenosis following angioplasty, inflammatory aortic aneurysm, vasculitis, stroke, spinal cord injury, congestive heart failure, hemorrhagic shock, ischemia/reperfusion injury, vasospasm following subarachnoid hemorrhage, vasospasm following cerebrovascular accident, pleuritis, pericarditis, and the cardiovascular complications of diabetes; (i) dialysis, including pericarditis, due to peritoneal dialysis; (j) gout; and (k) chemical or thermal-induced inflammation due to burns, acid, alkali and the like.

Obesity

In some embodiments, disclosed herein are methods of treating obesity and/or diabetes with a compound disclosed herein.

ATX is responsible for the lysoPLD activity released by adipocytes and exerts a paracrine control on preadipocyte growth via an LPA-dependent mechanism. In addition, ATX is up-regulated during adipocyte differentiation and in genetic obesity. In certain instances, ATX mRNA is up-regulated in adipocytes from db/db mice suggesting that the up-regulation of ATX is related to the severe type 2 diabetes phenotype and adipocyte insulin resistance. In some instances, up-regulation of ATX in adipocytes is associated with type 2 diabetes.

"Obesity," as used herein, refers to a medical condition in which excess body fat has accumulated to the extent that it may have an adverse effect on health, leading to increased health problems. In some embodiments, "obesity" refers to a weight increase, which is at least 5% of the total body weight. In some embodiments, disclosed herein is a method of treating postmenopausal obesity and/or visceral obesity with a compound disclosed herein.

Intraocular Pressure

In some embodiments, disclosed herein are methods of treating elevated intraocular pressure associated with glaucoma.

Glaucoma is one of the leading causes of blindness and is characterized by elevated intraocular pressure (IOP). IOP is a primary risk factor for developing glaucoma and the risk of developing glaucoma decreases when IOP is reduced. Ocular hypotensive therapy is the mainstay of glaucoma treatment. Elevated IOP results from diminished aqueous humor (AH) drainage through the trabecular pathway and autotaxin activity is an abundant protein in human AH. Autotaxin is secreted by human trabecular meshwork cells and ATX activity is significantly elevated from glaucoma patients Inhibition of autotaxin activity in AH by topical and intracameral delivery of a small molecule inhibitor leads to decreased IOP in rabbits.

Neuropathic Pain

In some embodiments, disclosed herein are methods of treating neuropathic pain with a compound disclosed herein.

LPA induces neuropathic pain as well as demyelination and pain-related protein expression changes via LPA1. In some instances, ATX heterozygous knockout mice show about 50% recovery of nerve injury-induced neuropathic pain compared to wild type mice. Lysophosphatidylcholine (LPC), is known to induce neuropathic pain. In certain instances, LPC-induced neuropathic pain is partially reduced in ATX heterozygous knockout mice.

Neuropathic pain results from injury to a nerve. In contrast to immediate pain caused by tissue injury, in some embodiments, neuropathic pain develops days or months after a traumatic injury. In addition, neuropathic pain frequently is long-lasting or chronic and can occur spontaneously or as a result of stimulation that normally is not painful.

Compounds

Compounds described herein, including pharmaceutically acceptable salts, prodrugs, active metabolites and pharmaceutically acceptable solvates thereof, are autotaxin inhibitors.

In one aspect, described herein is a compound of Formula (I), or a pharmaceutically acceptable salt, or solvate thereof:

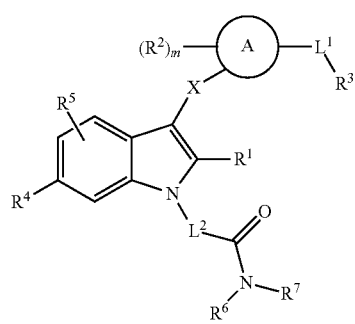

Formula (I)

wherein, $R^1$ is H, D, halogen, —CN, —C(=O)H, —NH$_2$, $C_1$-$C_4$alkyl, $C_3$-$C_6$cycloalkyl, $C_1$-$C_4$fluoroalkyl, —O $C_1$-$C_4$alkyl or $C_1$-$C_4$deuteroalkyl;

X is —O—, —S—, —S(=O)—, or —S(=O)$_2$—;

Ring A is a monocyclic aryl, bicyclic aryl, monocyclic heterocycloalkyl, monocyclic heteroaryl or bicyclic heteroaryl;

each $R^2$ is independently selected from H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, C$_1$-C$_6$alkyl, C$_1$-C$_6$fluoroalkyl, C$_1$-C$_6$deuteroalkyl, C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted phenyl, or substituted or unsubstituted monocyclic heteroaryl;

m is 0, 1, or 2;

L is absent, C$_1$-C$_6$alkylene, C$_1$-C$_6$fluoroalkylene, or C$_3$-C$_6$cycloalkylene;

$R^3$ is —CO$_2$H, —CO$_2$(C$_1$-C$_6$alkyl), —OH, —B(OH)$_2$, —C(=O)NHSO$_2$R$^9$, —C(=O)N(R$^{10}$)$_2$, —C(=O)NH—OH, —C(=O)NH—CN, —SO$_2$NHC(=O)R$^9$, —OP(=O)(OH)$_2$, —P(=O)(OH)$_2$, tetrazolyl, or carboxylic acid bioisostere;

$R^4$ is H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, C$_1$-C$_4$alkyl, C$_1$-C$_4$fluoroalkyl, C$_1$-C$_4$deuteroalkyl, C$_1$-C$_4$hydroxyalkyl, C$_1$-C$_4$heteroalkyl, C$_3$-C$_6$cycloalkyl, substituted or unsubstituted phenyl, substituted or unsubstituted monocyclic heteroaryl;

$R^5$ is H, halogen, —CN, —OH, C$_1$-C$_4$alkyl, C$_1$-C$_4$fluoroalkyl, C$_1$-C$_4$deuteroalkyl, C$_1$-C$_4$alkoxy, or C$_1$-C$_4$fluoroalkoxy;

$L^2$ is absent or C$_1$-C$_6$ alkylene;

$R^6$ is H, C$_1$-C$_6$alkyl, C$_1$-C$_6$fluoroalkyl, C$_1$-C$_6$deuteroalkyl, or C$_3$-C$_8$cycloalkyl;

$R^7$ is C$_1$-C$_6$alkyl, C$_1$-C$_6$fluoroalkyl, C$_1$-C$_6$deuteroalkyl, substituted or unsubstituted cycloalkyl, substituted or unsubstituted heterocycloalkyl, substituted or unsubstituted aryl, substituted or unsubstituted heteroaryl, —C(=O)R$^9$, or —S(=O)$_2$R$^9$, wherein if $R^7$ is substituted, then $R^7$ is substituted with 1 to 4 $R^8$ groups;

or $R^6$ and $R^7$ are taken together with the nitrogen atom to which they are attached to form an unsubstituted N-containing heterocycle or a substituted N-containing heterocycle that is substituted with 1-4 $R^8$ and 0 or 1 $R^{12}$ groups;

each $R^8$ and $R^{12}$ substituent is independently selected from the group consisting of H, halogen, OH, —CN, —NO$_2$, C$_1$-C$_6$alkyl, C$_1$-C$_6$fluoroalkyl, C$_1$-C$_6$deuteroalkyl, C$_1$-C$_6$heteroalkyl, C$_3$-C$_8$cycloalkyl, C$_1$-C$_6$alkoxy, C$_2$-C$_{10}$heterocycloalkyl, —C(=O)R$^9$, —S(=O)$_2$R$^9$, S(=O)R$^9$, SR$^9$, —S(=O)$_2$N(R$^{10}$)$_2$, —NR$^{10}$S(=O)$_2$R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, substituted or unsubstituted aryl, C$_1$-C$_6$alkylene-substituted or unsubstituted aryl, —Y—C$_1$-C$_6$alkylene-substituted or unsubstituted aryl, substituted or unsubstituted heteroaryl, C$_1$-C$_6$alkylene-substituted or unsubstituted heteroaryl, and —Y—C$_1$-C$_6$alkylene-substituted or unsubstituted heteroaryl; Y is O or S;

or two $R^8$ substituents on the same carbon atom are taken together to form =O, or two $R^8$ substituents on the same or different carbon atoms are taken together to form to form a substituted or unsubstituted ring containing 0, 1, 2, or 3 heteroatoms in the ring selected from —NR$^{11}$—, —S(=O)$_n$—, and —O—;

n is 0, 1, or 2;

$R^9$ is C$_1$-C$_6$alkyl, C$_1$-C$_6$fluoroalkyl, C$_1$-C$_6$deuteroalkyl, C$_3$-C$_6$cycloalkyl, a substituted or unsubstituted phenyl, C$_1$-C$_4$alkylene-substituted or unsubstituted phenyl, a substituted or unsubstituted monocyclic heteroaryl, C$_1$-C$_4$alkylene-substituted or unsubstituted monocyclic heteroaryl, a substituted or unsubstituted bicyclic heteroaryl, or a C$_1$-C$_4$alkylene-substituted or unsubstituted bicyclic heteroaryl;

each $R^{10}$ is independently selected from H, C$_1$-C$_6$alkyl, C$_1$-C$_6$fluoroalkyl, C$_1$-C$_6$deuteroalkyl, C$_3$-C$_6$cycloalkyl, a substituted or unsubstituted phenyl, C$_1$-C$_4$alkylene-substituted or unsubstituted phenyl, a substituted or unsubstituted monocyclic heteroaryl, C$_1$-C$_4$alkylene-substituted or unsubstituted monocyclic heteroaryl, a substituted or unsubstituted bicyclic heteroaryl, or a C$_1$-C$_4$alkylene-substituted or unsubstituted bicyclic heteroaryl; or two $R^{10}$ groups attached to the same N atom are taken together with the N atom to which they are attached to form a substituted or unsubstituted heterocycle; and $R^{11}$ is H, C$_1$-C$_6$alkyl, C$_1$-C$_6$fluoroalkyl, C$_1$-C$_6$deuteroalkyl, C$_3$-C$_8$cycloalkyl, —C(=O)R$^9$, —S(=O)$_2$R$^9$, —CO$_2$R$^9$, —C(=O)N(R$^{10}$)$_2$, substituted or unsubstituted aryl, C$_1$-C$_4$alkylene-substituted or unsubstituted aryl, substituted or unsubstituted heteroaryl, or C$_1$-C$_4$alkylene-substituted or unsubstituted heteroaryl.

For any and all of the embodiments, substituents are selected from among a subset of the listed alternatives. For example, in some embodiments, X is —O—, —S—, —S(=O)—, or —S(=O)$_2$—. In other embodiments, X is —O— or —S—. In other embodiments, X is —S—, —S(=O)—, or —S(=O)$_2$—. In some embodiments, X is —S—.

In some embodiments, $R^{11}$ is H, C$_1$-C$_6$alkyl, C$_1$-C$_6$fluoroalkyl, C$_1$-C$_6$deuteroalkyl, C$_3$-C$_8$cycloalkyl, —C(=O)R$^9$, —S(=O)$_2$R$^9$, —CO$_2$R$^9$, —C(=O)N(R$^{10}$)$_2$, substituted or unsubstituted aryl, C$_1$-C$_4$alkylene-substituted or unsubstituted aryl, substituted or unsubstituted heteroaryl, or C$_1$-C$_4$alkylene-substituted or unsubstituted heteroaryl. In some embodiments, $R^{11}$ is H, C$_1$-C$_6$alkyl, C$_1$-C$_6$fluoroalkyl, C$_1$-C$_6$deuteroalkyl, C$_3$-C$_8$cycloalkyl, —C(=O)R$^9$, —S(=O)$_2$R$^9$, —CO$_2$R$^9$, —C(=O)N(R$^{10}$)$_2$, substituted or unsubstituted phenyl, C$_1$-C$_4$alkylene-substituted or unsubstituted phenyl, substituted or unsubstituted monocyclic heteroaryl, or C$_1$-C$_4$alkylene-substituted or unsubstituted monocyclic heteroaryl. In some embodiments, $R^{11}$ is H, C$_1$-C$_6$alkyl, or C$_1$-C$_4$alkylene-substituted or unsubstituted phenyl. In some embodiments, $R^{11}$ is H or C$_1$-C$_6$alkyl.

In some embodiments, $R^6$ and $R^7$ are taken together with the nitrogen atom to which they are attached to form an aziridine, azetidine, pyrrolidne or piperidine, wherein the ring that is formed by taking $R^6$ and $R^7$ together with the nitrogen atom to which they are attached is unsubstituted or is substituted with 1-4 $R^8$ and 0 or 1 $R^{12}$ groups.

In some embodiments, $R^6$ and $R^7$ are taken together with the nitrogen atom to which they are attached to form a ring B that is an unsubstituted N-containing heterocycle or a substituted N-containing heterocycle that is substituted with 1-4 $R^8$ and 0 or 1 $R^{12}$ groups. In some embodiments, the compound has the structure of Formula (II), or a pharmaceutically acceptable salt, or solvate thereof:

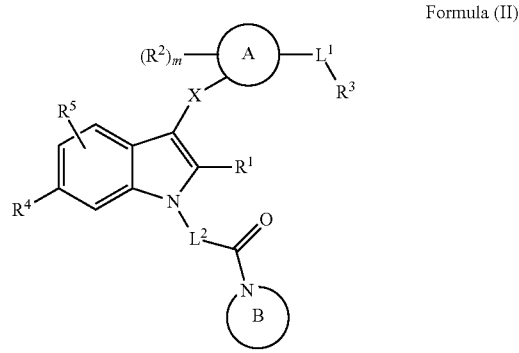

Formula (II)

wherein,

Ring B is an N-containing monocyclic or bicyclic heterocycle that is unsubstituted or substituted with 1-4 $R^8$ and 0 or 1 $R^{12}$ groups;

each $R^8$ substituent is independently H, halogen, OH, —CN, —NO$_2$, C$_1$-C$_6$alkyl, C$_1$-C$_6$fluoroalkyl, C$_1$-C$_6$deuteroalkyl, C$_1$-C$_6$heteroalkyl, C$_3$-C$_8$cycloalkyl, C$_1$-C$_6$alkoxy, C$_2$-C$_{10}$heterocycloalkyl, —C(=O)R$^9$, —S(=O)$_2$R$^9$, S(=O)R$^9$, SR$^9$, —S(=O)$_2$N(R$^{10}$)$_2$, —NR$^{10}$S(=O)$_2$R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, substituted or unsubstituted aryl, C$_1$-C$_6$alkylene-substituted or unsubstituted aryl, —Y—C$_1$-C$_6$alkylene-substituted or unsubstituted aryl, substituted or unsubstituted heteroaryl, C$_1$-C$_6$alkylene-substituted or unsubstituted heteroaryl, or —Y—C$_1$-C$_6$alkylene-substituted or unsubstituted heteroaryl; Y is O or S;

or two $R^8$ substituents on the same carbon atom are taken together to form =O, or two $R^8$ substituents on the same or different carbon atoms are taken together to form to form a substituted or unsubstituted ring containing 0, 1, 2, or 3 heteroatoms in the ring selected from —NR$^{11}$—, —S(=O)$_n$—, and —O—;

n is 0, 1, or 2.

In some embodiments, Ring B is aziridinyl, azetidinyl, pyrrolidinyl, piperidinyl, azepanyl, morpholinyl, thiomorpholinyl, piperzinyl, indolinyl, azaindolinyl, isoindolinyl, azaisoindolinyl, indolinonyl, azaindolinonyl, tetrahydroquinolinyl, azatetrahydroquinolinyl, tetrahydroisoquinolinyl, or azatetrahydroisoquinolinyl, where ring B is unsubstituted or substituted with 1-4 $R^8$ and 0 or 1 $R^{12}$ groups. In some embodiments, Ring B is aziridinyl, azetidinyl, pyrrolidinyl, piperidinyl, azepanyl, morpholinyl, thiomorpholinyl, or piperzinyl, where ring B is unsubstituted or substituted with 1-4 $R^8$ and 0 or 1 $R^{12}$ groups.

In some embodiments,

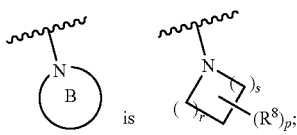

r is 1, 2, 3, or 4; s is 0, 1, or 2; p is 0, 1, 2, 3, or 4. In some embodiments,

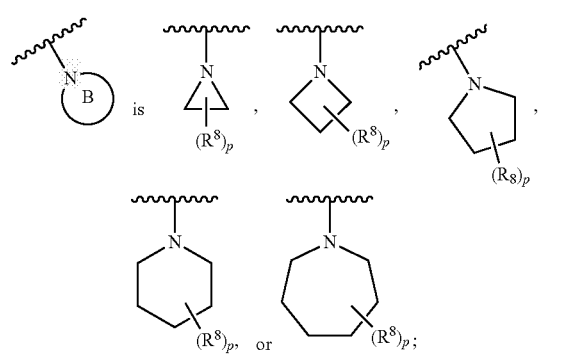

p is 0, 1, 2, 3, or 4. In some embodiments, p is 0, 1, or 2. In some embodiments, p is 1, or 2. In some embodiments, p is 2. In some embodiments, p is 1, 2, 3, or 4. In some embodiments,

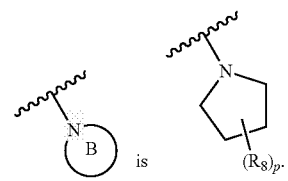

In some embodiments,

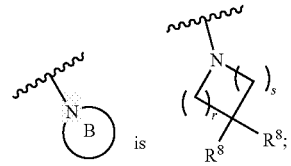

r is 1, 2, 3, or 4; s is 0, 1, or 2. In some embodiments,

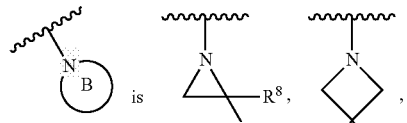

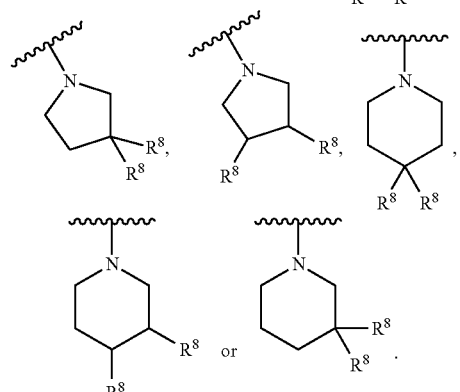

In some embodiments,

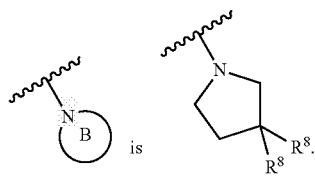

In some embodiments, the compound of Formula (II) has the structure:

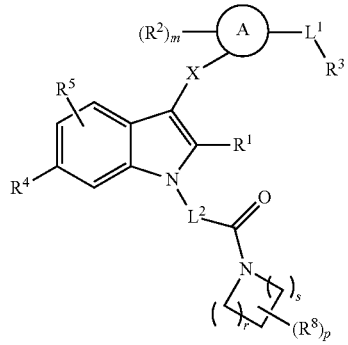

wherein,
p is 0, 1, 2, 3, or 4;
r is 1, 2, 3, or 4;
s is 0, 1, or 2.

In some embodiments,

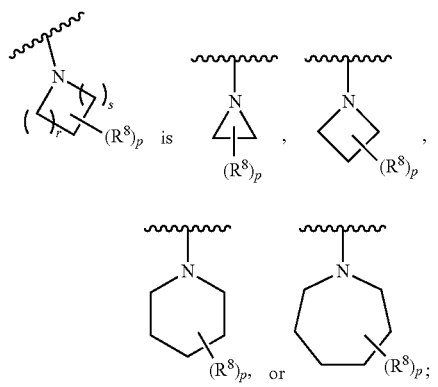

p is 0, 1, 2, 3, or 4. In some embodiments,

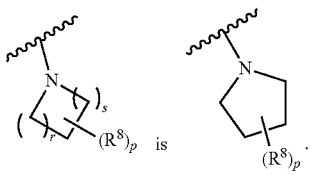

In some embodiments, p is 0, 1, or 2. In some embodiments, p is 2.

In some embodiments, the compound has the structure of Formula (III):

Formula (III)

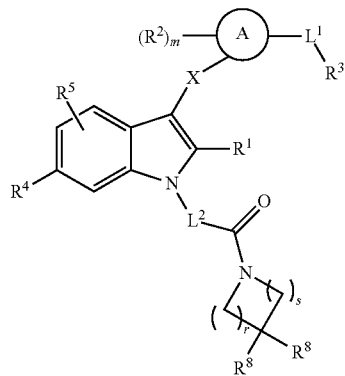

wherein,
r is 1, 2, 3, or 4;
s is 0, 1, or 2.

In some embodiments, the compound of Formula (III) has the structure:

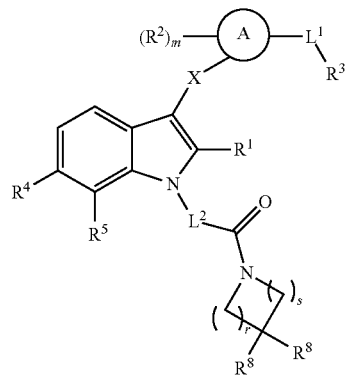

wherein,
r is 1, 2, 3, or 4;
s is 0, 1, or 2.

In some embodiments, X is —S—.

In some embodiments,

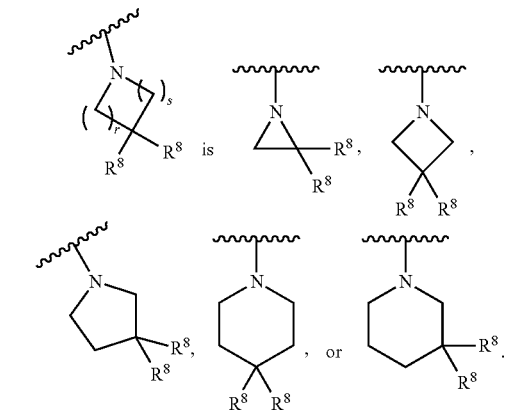

In some embodiments,

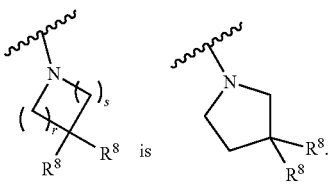

In some embodiments, Ring A is phenyl, naphthyl, monocyclic heterocycloalkyl containing 1-2 N atoms and 0-1 O or S atoms, monocyclic heteroaryl containing 1-4 N atoms and 0 or 1 O or S atoms, monocyclic heteroaryl containing 0-4 N atoms and 1 O or S atoms, bicyclic heteroaryl containing 1-4 N atoms and 0 or 1 O or S atoms, or bicyclic heteroaryl containing 0-4 N atoms and 1 O or S atoms. In some embodiments, Ring A is phenyl, naphthyl, indanyl, indenyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl. In some embodiments, Ring A is phenyl, naphthyl indanyl, or indenyl. In some embodiments, Ring A is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl. In some embodiments, Ring A is pyridinyl, pyrimidinyl, pyrazinyl, pyridazinyl, or triazinyl.

In some embodiments, Ring A is 1,3-phenylene or 2,6-pyridinylene. In some embodiments, Ring A is 1,3-phenylene. In some embodiments, Ring A is 2,6-pyridinylene.

In some embodiments, the compound has the following structure of Formula (IV):

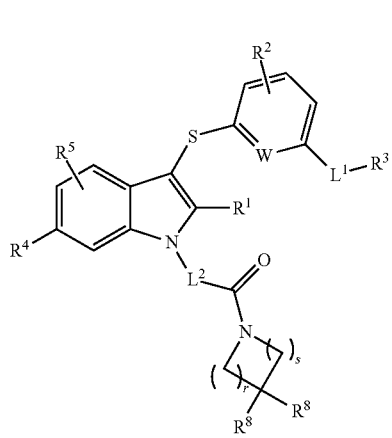

Formula (IV)

wherein,
W is CH, CF or N;
or a pharmaceutically acceptable salt, or solvate thereof.

In some embodiments, the compound of Formula (IV) has the following structure:

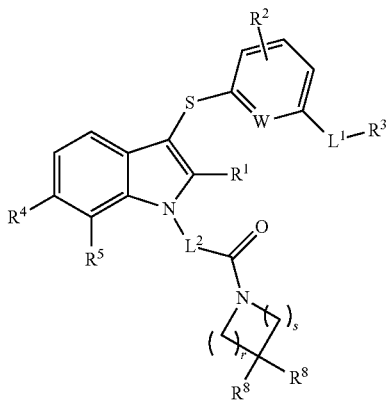

wherein,
W is CH, CF or N;
or a pharmaceutically acceptable salt, or solvate thereof.

In some embodiments, Ring A is furanyl, pyrrolyl, oxazolyl, thiazolyl, imidazolyl, pyrazolyl, triazolyl, tetrazolyl, isoxazolyl, isothiazolyl, oxadiazolyl, or thiadiazolyl.

In some embodiments, Ring A is quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, $L^2$ is absent or $C_1$-$C_4$ alkylene. In some embodiments, $L^2$ is absent, —$CH_2$—, —$CH(CH_3)$—, —$C(CH_3)_2$—, or $(CH_2)_2$—.

In some embodiments, $R^1$ is H, halogen, —CN, —C(=O)H, $C_1$-$C_4$alkyl, $C_3$-$C_6$cycloalkyl, or $C_1$-$C_4$fluoroalkyl. In some embodiments, $R^1$ is halogen, $C_1$-$C_4$alkyl, $C_3$-$C_6$cycloalkyl, or $C_1$-$C_4$fluoroalkyl. In some embodiments, $R^1$ is Cl, —$CH_3$, —$CH_2CH_3$, cyclopropyl, or —$CF_3$.

In some embodiments, the compound has the following structure of Formula (V):

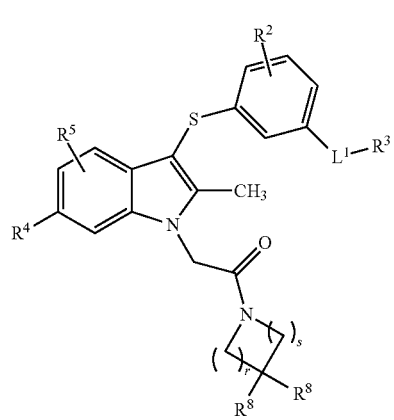

Formula (V)

or a pharmaceutically acceptable salt, or solvate thereof.

In some embodiments, the compound of Formula (V) has the following structure:

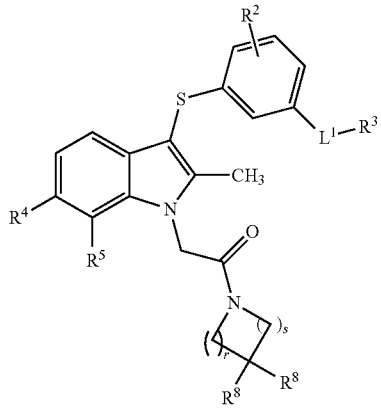

or a pharmaceutically acceptable salt, or solvate thereof.

In some embodiments, the two $R^8$ substituents are joined together to form a substituted or unsubstituted cycloalkyl or substituted or unsubstituted heterocycloalkyl.

In some embodiments, the two $R^8$ substituents are joined together to form a substituted or unsubstituted $C_3$-$C_8$cycloalkyl. In some embodiments, the two $R^8$ substituents are joined together to form an unsubstituted $C_3$-$C_8$cycloalkyl.

In some embodiments, the two $R^8$ substituents are joined together to form a substituted or unsubstituted $C_2$-$C_8$ heterocycloalkyl containing 1, 2, or 3 heteroatoms selected from —$NR^{11}$— or —O—.

In some embodiments, the two $R^8$ substituents are joined together to form =O.

In some embodiments, each $R^8$ substituent is independently selected from the group consisting of H, halogen, —OH, —CN, —$NO_2$, $C_1$-$C_6$alkyl, $C_1$-$C_6$fluoroalkyl, $C_1$-$C_6$deuteroalkyl, $C_1$-$C_6$heteroalkyl, $C_3$-$C_8$cycloalkyl, $C_1$-$C_6$alkoxy, substituted or unsubstituted aryl, —$C_1$-$C_6$alkylene-substituted or unsubstituted aryl, —O—$C_1$-$C_6$alkylene-substituted or unsubstituted aryl, substituted or unsubstituted heteroaryl, $C_1$-$C_6$alkylene-substituted or unsubstituted heteroaryl, or O—$C_1$-$C_6$alkylene-substituted or unsubstituted heteroaryl. In some embodiments, each $R^8$ substituent is independently selected from the group consisting of H, —OH, —CN, $C_1$-$C_6$alkyl, $C_1$-$C_6$fluoroalkyl, or $C_1$-$C_6$deuteroalkyl. In some embodiments, each $R^8$ substituent is independently selected from the group consisting of H, —OH, —CN, $C_1$-$C_6$alkyl, or $C_1$-$C_6$fluoroalkyl. In some embodiments, each $R^8$ substituent is independently selected from the group consisting of H, —OH, —CN, —$CH_3$, —$CH_2CH_3$, —$CH_2CH_2CH_3$, —$CH(CH_3)_2$, —$CH_2F$, —$CHF_2$, —$CF_3$, or —$CH_2CF_3$. In some embodiments, each $R^8$ substituent is independently selected from the group consisting of H, —OH, —CN, —$CH_3$, —$CH_2F$, —$CHF_2$, or —$CF_3$. In some embodiments, each $R^8$ substituent is independently selected from the group consisting of H, —OH, —CN, —$CH_3$, or —$CF_3$.

In some embodiments, $R^6$ and $R^7$ are taken together with the nitrogen atom to which they are attached to form a pyrrolidne, wherein the ring that is formed by taking $R^6$ and $R^7$ together with the nitrogen atom to which they are attached is substituted with 2 $R^8$ groups, wherein each $R^8$ substituent is independently selected from the group consisting of H, —OH, —CN, —$CH_3$, or —$CF_3$.

In some embodiments, each $R^8$ substituent is independently H, $C_1$-$C_6$alkyl, —CN, substituted or unsubstituted aryl, $C_1$-$C_6$alkylene-substituted or unsubstituted aryl, —O—$C_1$-$C_6$alkylene-substituted or unsubstituted aryl, substituted or unsubstituted heteroaryl, $C_1$-$C_6$alkylene-substituted or unsubstituted heteroaryl, or O—$C_1$-$C_6$alkylene-substituted or unsubstituted heteroaryl.

In some embodiments, each $R^8$ substituent is H.

In some embodiments, each $R^8$ substituent is different. In some embodiments, each $R^8$ substituent is the same.

In some embodiments, when the two $R^8$ substituents are joined together to form a ring, then the ring formed by taking the two $R^8$ joined together is unsubstituted or substituted with 1, 2, 3, or 4 substituents independently selected from oxo (=O), halogen, OH, —CN, —$NO_2$, $C_1$-$C_6$alkyl, $C_1$-$C_6$fluoroalkyl, $C_1$-$C_6$deuteroalkyl, $C_1$-$C_6$heteroalkyl, $C_3$-$C_8$cycloalkyl, $C_1$-$C_6$alkoxy, $C_2$-$C_{10}$heterocycloalkyl, —C(=O)$R^9$, —S(=O)$_2R^9$, S(=O)$R^9$, $SR^9$, —S(=O)$_2$N($R^{10}$)$_2$, —$NR^{10}$S(=O)$_2R^9$, —OC(=O)$R^9$, —$CO_2R^{10}$, —$OCO_2R^9$, —N($R^{10}$)$_2$, —C(=O)N($R^{10}$)$_2$, —OC(=O)N($R^{10}$)$_2$, —NHC(=O)$R^9$, —NHC(=O)$OR^9$, substituted or unsubstituted aryl, $C_1$-$C_6$alkylene-substituted or unsubstituted aryl, —Y—$C_1$-$C_6$alkylene-substituted or unsubstituted aryl, substituted or unsubstituted heteroaryl, $C_1$-$C_6$alkylene-substituted or unsubstituted heteroaryl, or —Y—$C_1$-$C_6$alkylene-substituted or unsubstituted heteroaryl; Y is O or S.

In some embodiments, when the two $R^8$ substituents are joined together to form a ring, then the ring formed by taking the two $R^8$ joined together is unsubstituted or substituted with 1 or 2 substituents independently selected from oxo (=O), halogen, OH, —CN, $C_1$-$C_6$alkyl, $C_1$-$C_6$fluoroalkyl, $C_1$-$C_6$deuteroalkyl, $C_1$-$C_6$heteroalkyl, $C_3$-$C_8$cycloalkyl, $C_1$-$C_6$alkoxy, $C_2$-$C_{10}$heterocycloalkyl, —C(=O)$R^9$, —S(=O)$_2R^9$, —S(=O)$R^9$, —$SR^9$, —S(=O)$_2$N($R^{10}$)$_2$, —$NR^{10}$S(=O)$_2R^9$, —OC(=O)$R^9$, —$CO_2R^{10}$, —$OCO_2R^9$, —N($R^{10}$)$_2$, —C(=O)N($R^{10}$)$_2$, —OC(=O)N($R^{10}$)$_2$, —NHC(=O)$R^9$, —NHC(=O)$OR^9$, substituted or unsubstituted aryl, $C_1$-$C_2$alkylene-substituted or unsubstituted aryl, —Y—$C_1$-$C_2$alkylene-substituted or unsubstituted aryl, substituted or unsubstituted heteroaryl, $C_1$-$C_2$alkylene-substituted or unsubstituted heteroaryl, or —Y—$C_1$-$C_2$alkylene-substituted or unsubstituted heteroaryl; Y is O or S.

In some embodiments, the two $R^8$ substituents are joined together to form =O.

In some embodiments,

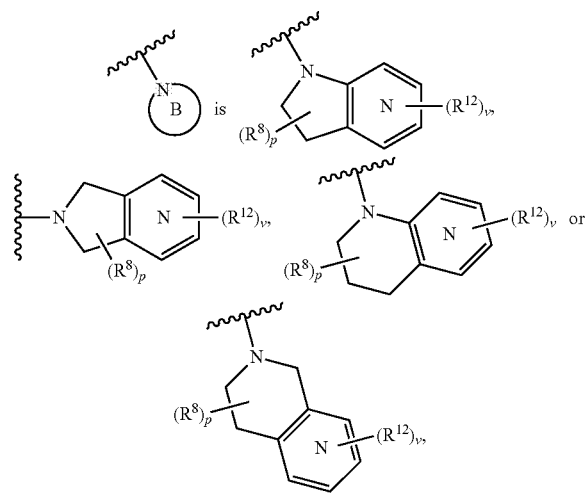

where ring N is phenyl or a 6-membered heteroaryl containing 1 or 2 nitrogen atoms; p is 0, 1, 2, 3, or 4; v is 0 or 1.

In some embodiments, ring N is phenyl or a 6-membered heteroaryl containing 1 or 2 nitrogen atoms. In some embodiments, ring N is phenyl or a 6-membered heteroaryl containing 1 nitrogen atom. In some embodiments, ring N is phenyl. In some embodiments, ring N is a 6-membered heteroaryl containing 1 nitrogen atom.

In some embodiments,

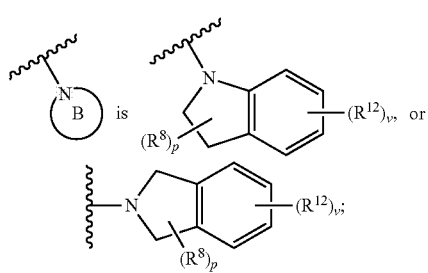

p is 0, 1, 2, 3, or 4; v is 0 or 1. In some embodiments,

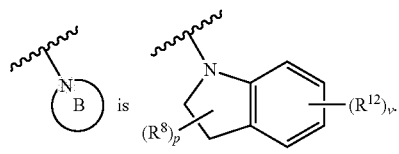

In some embodiments,

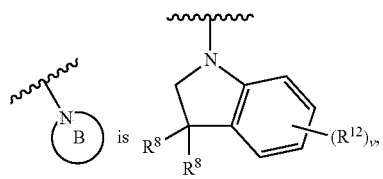

-continued

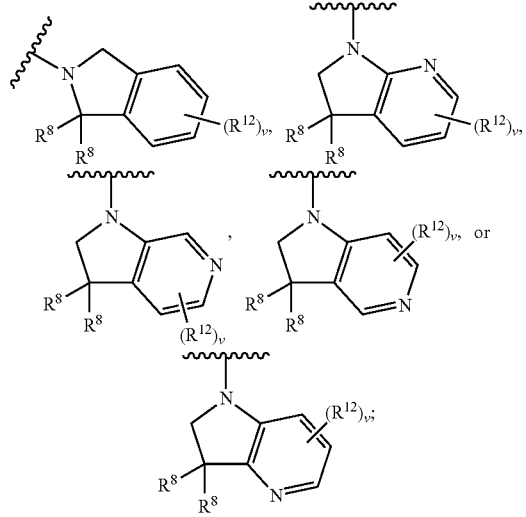

and v is 0 or 1.

In some embodiments,

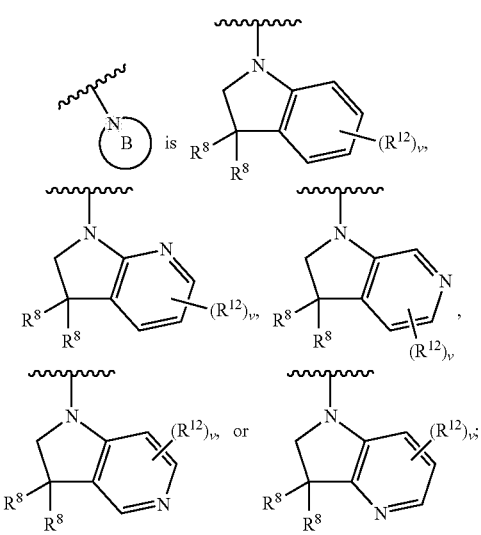

and v is 0 or 1. In some embodiments,

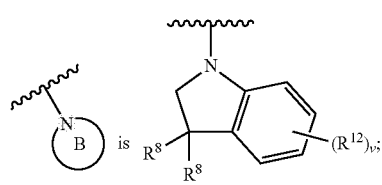

and v is 0 or 1.

In some embodiments,

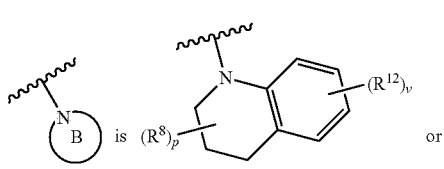

-continued

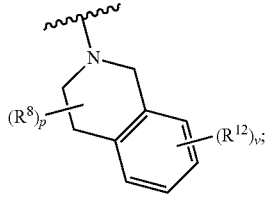

p is 0, 1, 2, 3, or 4; v is 0 or 1. In some embodiments,

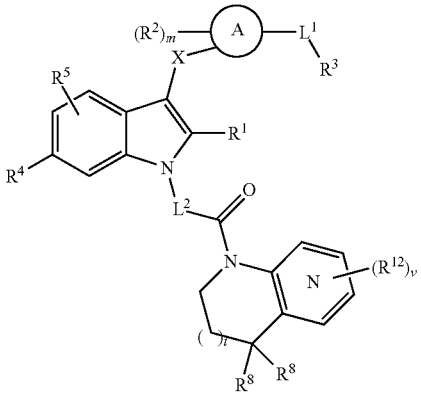

In some embodiments, the compound has the following structure of Formula (VI):

Formula (VI)

wherein, ring N is phenyl or a 6-membered heteroaryl containing 1 or 2 nitrogen atoms;

each $R^8$ substituent is independently H, halogen, OH, —CN, —NO$_2$, C$_1$-C$_6$alkyl, C$_1$-C$_6$fluoroalkyl, C$_1$-C$_6$deuteroalkyl, C$_1$-C$_6$heteroalkyl, C$_3$-C$_8$cycloalkyl, C$_1$-C$_6$alkoxy, C$_2$-C$_{10}$heterocycloalkyl, —C(=O)R$^9$, —S(=O)$_2$R$^9$, S(=O)R$^9$, SR$^9$, —S(=O)$_2$N(R$^{10}$)$_2$, —NR$^{10}$S(=O)$_2$R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, substituted or unsubstituted aryl, C$_1$-C$_6$alkylene-substituted or unsubstituted aryl, —Y—C$_1$-C$_6$alkylene-substituted or unsubstituted aryl, substituted or unsubstituted heteroaryl, C$_1$-C$_6$alkylene-substituted or unsubstituted heteroaryl, or —Y—C$_1$-C$_6$alkylene-substituted or unsubstituted heteroaryl;

Y is O or S;

or two $R^8$ substituents are taken together to form to form a substituted or unsubstituted ring containing 0, 1, 2, or 3 heteroatoms in the ring selected from —NR$^{11}$—, —S(=O)$_n$—, and —O—;

n is 0, 1, or 2;

t is 0 or 1;

each $R^{12}$ is independently selected from H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, C$_1$-C$_6$alkyl, C$_1$-C$_6$fluoroalkyl, C$_1$-C$_6$deuteroalkyl, C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted phenyl, or substituted or unsubstituted monocyclic heteroaryl; and v is 0 or 1.

In some embodiments, t is 0. In some embodiments, t is 1.

In some embodiments, the compound of Formula (VI) has the following structure:

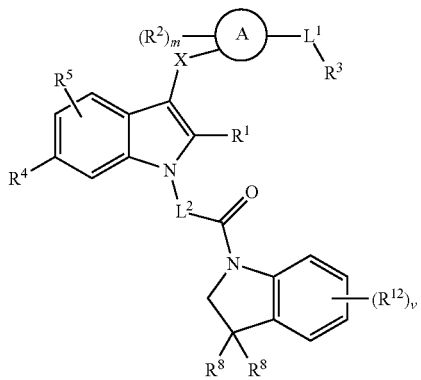

or a pharmaceutically acceptable salt, or solvate thereof.

In some embodiments, X is —S—.

In some embodiments, Ring A is phenyl, naphthyl, monocyclic heterocycloalkyl containing 1-2 N atoms and 0-1 O or S atoms, monocyclic heteroaryl containing 1-4 N atoms and 0 or 1 O or S atoms, monocyclic heteroaryl containing 0-4 N atoms and 1 O or S atoms, bicyclic heteroaryl containing 1-4 N atoms and 0 or 1 O or S atoms, or bicyclic heteroaryl containing 0-4 N atoms and 1 O or S atoms. In some embodiments, Ring A is phenyl, naphthyl, indanyl, indenyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl. In some embodiments, Ring A is phenyl, naphthyl, indanyl, or indenyl. In some embodiments, Ring A is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl. In some embodiments, Ring A is pyridinyl, pyrimidinyl, pyrazinyl, pyridazinyl, or triazinyl.

In some embodiments, Ring A is 1,3-phenylene or 2,6-pyridinylene. In some embodiments, Ring A is 1,3-phenylene. In some embodiments, Ring A is 2,6-pyridinylene.

In some embodiments, the compound has the following structure of Formula (VII):

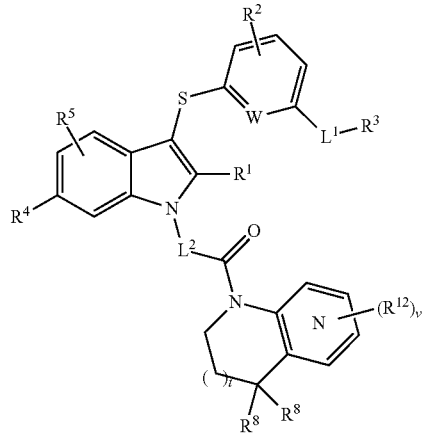

Formula (VII)

wherein,
W is CH, CF or N;
or a pharmaceutically acceptable salt, or solvate thereof.

In some embodiments, the compound of Formula (VII) has the following structure:

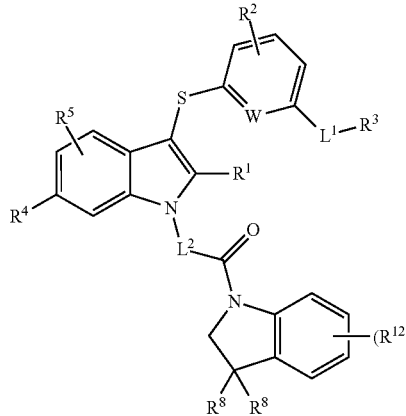

wherein,
W is CH, CF or N;
or a pharmaceutically acceptable salt, or solvate thereof.

In some embodiments, the compound of Formula (VII) has the following structure:

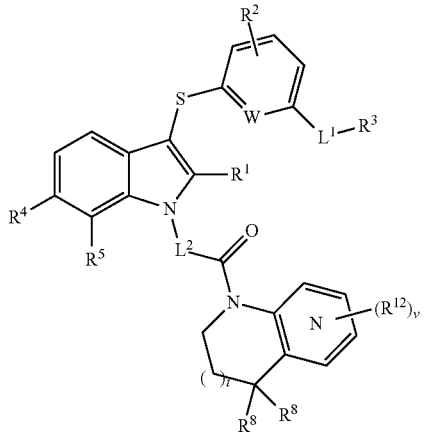

wherein,
W is CH, CF or N;
or a pharmaceutically acceptable salt, or solvate thereof.

In some embodiments, the compound of Formula (VII) has the following structure:

[Chemical structure of Formula with R², S, W, L¹—R³, R¹, R⁴, R⁵, L², N, O, (R¹²)ᵥ, R⁸, R⁸]

wherein,
W is CH, CF or N;
or a pharmaceutically acceptable salt, or solvate thereof In some embodiments, Ring A is furanyl, pyrrolyl, oxazolyl, thiazolyl, imidazolyl, pyrazolyl, triazolyl, tetrazolyl, isoxazolyl, isothiazolyl, oxadiazolyl, or thiadiazolyl.

In some embodiments, Ring A is quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, $L_2$ is absent or $C_1$-$C_4$ alkylene.

In some embodiments, $L_2$ is absent, —CH₂—, —CH(CH₃)—, —C(CH₃)₂—, or —(CH₂)₂—.

In some embodiments, $R^1$ is H, halogen, —CN, —C(=O)H, $C_1$-$C_4$alkyl, $C_3$-$C_6$cycloalkyl, or $C_1$-$C_4$fluoroalkyl. In some embodiments, $R^1$ is halogen, $C_1$-$C_4$alkyl, $C_3$-$C_6$cycloalkyl, or $C_1$-$C_4$fluoroalkyl. In some embodiments, $R^1$ is Cl, —CH₃, —CH₂CH₃, cyclopropyl, or —CF₃.

In some embodiments, the compound has the following structure of Formula (VIII):

Formula (VIII)

[Chemical structure]

or a pharmaceutically acceptable salt, or solvate thereof.

In some embodiments, the compound has the following structure of Formula (VIII):

Formula (VIII)

[Chemical structure]

or a pharmaceutically acceptable salt, or solvate thereof.

In some embodiments, the compound of Formula (VIII) has the following structure:

[Chemical structure]

or a pharmaceutically acceptable salt, or solvate thereof.

In some embodiments, the compound of Formula (VIII) has the following structure:

[Chemical structure]

or a pharmaceutically acceptable salt, or solvate thereof.

In some embodiments, the two $R^8$ substituents are joined together to form a substituted or unsubstituted cycloalkyl or substituted or unsubstituted heterocycloalkyl.

In some embodiments, the two $R^8$ substituents are joined together to form a substituted or unsubstituted $C_3$-$C_8$cycloalkyl. In some embodiments, the two $R^8$ substituents are joined together to form a substituted or unsubstituted cyclopropyl, substituted or unsubstituted cyclobutyl, substituted or unsubstituted cyclopentyl, or substituted or unsubstituted cyclohexyl. In some embodiments, the two $R^8$ substituents are joined together to form a cyclopropyl, cyclobutyl, cyclopentyl, or cyclohexyl. In some embodiments, the two $R^8$ substituents are joined together to form a cyclopropyl, cyclobutyl, or cyclopentyl. In some embodiments, the two $R^8$ substituents are joined together to form a cyclopropyl.

In some embodiments, the two $R^8$ substituents are joined together to form a cyclobutyl. In some embodiments, the two $R^8$ substituents are joined together to form a cyclopentyl.

In some embodiments, the two $R^8$ substituents are joined together to form a substituted or unsubstituted $C_2$-$C_8$heterocycloalkyl containing 1, 2, or 3 heteroatoms selected from $NR^{11}$ or O.

In some embodiments, each $R^8$ substituent is independently H, $C_1$-$C_6$alkyl, —CN, substituted or unsubstituted aryl, $C_1$-$C_6$alkylene-substituted or unsubstituted aryl, —O—$C_1$-$C_6$alkylene-substituted or unsubstituted aryl, substituted or unsubstituted heteroaryl, $C_1$-$C_6$alkylene-substituted or unsubstituted heteroaryl, or O—$C_1$-$C_6$alkylene-substituted or unsubstituted heteroaryl.

In some embodiments, each $R^8$ substituent is independently selected from the group consisting of H, —OH, —CN, $C_1$-$C_6$alkyl, $C_1$-$C_6$fluoroalkyl, or $C_1$-$C_6$deuteroalkyl. In some embodiments, each $R^8$ substituent is independently selected from the group consisting of H, —OH, —CN, $C_1$-$C_6$alkyl, or $C_1$-$C_6$fluoroalkyl. In some embodiments, each $R^8$ substituent is independently selected from the group consisting of H, —OH, —CN, —CH$_3$, —CH$_2$CH$_3$, —CH$_2$CH$_2$CH$_3$, —CH(CH$_3$)$_2$, —CH$_2$F, —CHF$_2$, —CF$_3$, or —CH$_2$CF$_3$. In some embodiments, each $R^8$ substituent is independently selected from the group consisting of H, —OH, —CN, —CH$_3$, —CH$_2$F, —CHF$_2$, or —CF$_3$. In some embodiments, each $R^8$ substituent is independently selected from the group consisting of H, —OH, —CN, —CH$_3$, or —CF$_3$.

In some embodiments, each $R^8$ substituent is H.

In some embodiments, each $R^{12}$ is independently selected from H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, $C_1$-$C_6$alkyl, $C_1$-$C_6$fluoroalkyl, $C_1$-$C_6$deuteroalkyl, $C_1$-$C_6$heteroalkyl. In some embodiments, each $R^{12}$ is independently selected from H, halogen, —CN, —OH, —OR$^9$, $C_1$-$C_6$alkyl, $C_1$-$C_6$fluoroalkyl, $C_1$-$C_6$deuteroalkyl, $C_1$-$C_6$heteroalkyl. In some embodiments, each $R^{12}$ is independently selected from H, halogen, —CN, —NO$_2$, —OH, —OR$^9$, —N(R$^{10}$)$_2$, $C_1$-$C_6$alkyl, $C_1$-$C_6$fluoroalkyl, $C_1$-$C_6$deuteroalkyl, $C_1$-$C_6$heteroalkyl. In some embodiments, each $R^{12}$ is independently selected from H, F, Cl, Br, —CN, —OH, —OC$_1$-$C_6$alkyl, —OC$_1$-$C_6$fluoroalkyl, $C_1$-$C_6$alkyl, or $C_1$-$C_6$fluoroalkyl. In some embodiments, each $R^{12}$ is independently selected from H, F, Cl, —OH, —CN, —OCH$_3$, —OCH$_2$CH$_3$, —OCH$_2$F, —OCHF$_2$, —OCF$_3$, —OCH$_2$CF$_3$, —CH$_3$, —CH$_2$CH$_3$, —CH$_2$F, —CHF$_2$, —CF$_3$, or —CH$_2$CF$_3$. In some embodiments, each $R^{12}$ is independently selected from H, F, Cl, —OH, —CN, —OCH$_3$, —CH$_2$F, —CHF$_2$, —CF$_3$, or —CH$_2$CF$_3$.

In some embodiments, $R^6$ is H, $C_1$-$C_6$alkyl, $C_1$-$C_6$fluoroalkyl, $C_1$-$C_6$deuteroalkyl, or $C_3$-$C_8$cycloalkyl; $R^7$ is $C_1$-$C_6$alkyl, $C_1$-$C_6$fluoroalkyl, $C_1$-$C_6$deuteroalkyl, substituted or unsubstituted cycloalkyl, substituted or unsubstituted heterocycloalkyl, substituted or unsubstituted aryl, substituted or unsubstituted heteroaryl, —C(O)R$^9$, N(R$^{10}$)$_2$, —S(O)$_2$R$^9$, or S(O)R$^9$; wherein if $R^7$ is substituted, then $R^7$ is substituted with 1 to 4 $R^8$ groups; and each $R^8$ substituent is independently H, halogen, OH, —CN, —NO$_2$, $C_1$-$C_6$alkyl, $C_1$-$C_6$fluoroalkyl, $C_1$-$C_6$deuteroalkyl, $C_1$-$C_6$heteroalkyl, $C_3$-$C_8$cycloalkyl, $C_1$-$C_6$alkoxy, $C_2$-$C_{10}$heterocycloalkyl, —C(O)R$^9$, —S(O)$_2$R$^9$, S(O)R$^9$, SR$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, substituted or unsubstituted aryl, $C_1$-$C_6$alkylene-substituted or unsubstituted aryl, —Y—$C_1$-$C_6$alkylene-substituted or unsubstituted aryl, substituted or unsubstituted heteroaryl, $C_1$-$C_6$alkylene-substituted or unsubstituted heteroaryl, or —Y—$C_1$-$C_6$alkylene-substituted or unsubstituted heteroaryl; Y is O or S; or two $R^8$ substituents on the same carbon atom are taken together to form =O, or two $R^8$ substituents on the same or different carbon atoms are taken together to form to form a substituted or unsubstituted ring containing 0, 1, 2, or 3 heteroatoms in the ring selected from —NR$^{11}$—, —S(=O)$_n$—, and —O—; n is 0, 1, or 2.

In some embodiments, X is —S—.

In some embodiments, Ring A is phenyl, naphthyl, indanyl, indenyl, monocyclic heterocycloalkyl containing 1-2 N atoms and 0-1 O or S atoms, monocyclic heteroaryl containing 1-4 N atoms and 0 or 1 O or S atoms, monocyclic heteroaryl containing 0-4 N atoms and 1 O or S atoms, bicyclic heteroaryl containing 1-4 N atoms and 0 or 1 O or S atoms, or bicyclic heteroaryl containing 0-4 N atoms and 1 O or S atoms. In some embodiments, Ring A is phenyl, naphthyl, indanyl, indenyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl. In some embodiments, Ring A is phenyl, naphthyl, indanyl, or indenyl. In some embodiments, Ring A is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl. In some embodiments, Ring A is pyridinyl, pyrimidinyl, pyrazinyl, pyridazinyl, or triazinyl.

In some embodiments, Ring A is 1,3-phenylene or 2,6-pyridinylene. In some embodiments, Ring A is 1,3-phenylene. In some embodiments, Ring A is 2,6-pyridinylene.

In some embodiments, the compound has the following structure of Formula (IX):

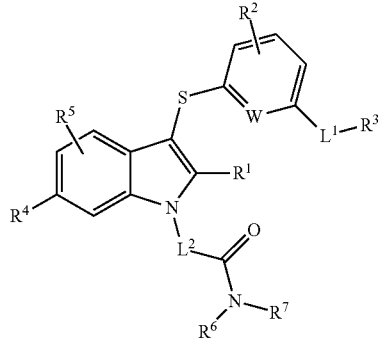

Formula (IX)

wherein,

W is CH, CF or N;

or a pharmaceutically acceptable salt, or solvate thereof.

In some embodiments, the compound of Formula (IX) has the following structure:

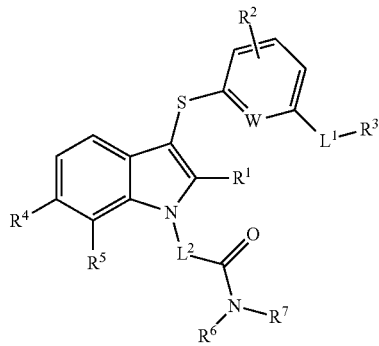

wherein,

W is CH, CF or N;

or a pharmaceutically acceptable salt, or solvate thereof.

In some embodiments, Ring A is furanyl, pyrrolyl, oxazolyl, thiazolyl, imidazolyl, pyrazolyl, triazolyl, tetrazolyl, isoxazolyl, isothiazolyl, oxadiazolyl, or thiadiazolyl.

In some embodiments, Ring A is quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, $L_2$ is absent or $C_1$-$C_4$ alkylene. In some embodiments, $L_2$ is absent, —$CH_2$—, —$CH(CH_3)$—, —$C(CH_3)_2$—, or —$(CH_2)_2$—.

In some embodiments, $R^1$ is H, halogen, —CN, —C(=O)H, $C_1$-$C_4$alkyl, $C_3$-$C_6$cycloalkyl, or $C_1$-$C_4$fluoroalkyl. In some embodiments, $R^1$ is halogen, $C_1$-$C_4$alkyl, $C_3$-$C_6$cycloalkyl, or $C_1$-$C_4$fluoroalkyl. In some embodiments, $R^1$ is Cl, —$CH_3$, —$CH_2CH_3$, cyclopropyl, or —$CF_3$.

In some embodiments, the compound has the following structure of Formula (X):

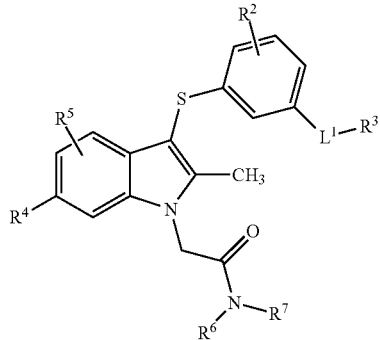

Formula (X)

or a pharmaceutically acceptable salt, or solvate thereof.

In some embodiments, the compound of Formula (X) has the following structure:

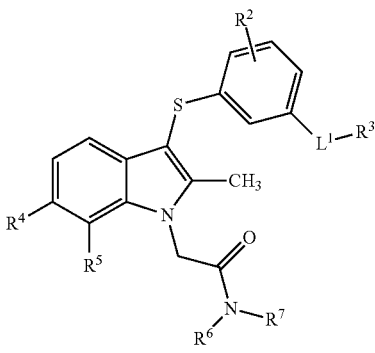

or a pharmaceutically acceptable salt, or solvate thereof.

In some embodiments, $R^6$ is H, $C_1$-$C_6$alkyl, or $C_1$-$C_6$fluoroalkyl. In some embodiments, $R^6$ is H or $C_1$-$C_4$alkyl. In some embodiments, $R^6$ is H or —$CH_3$.

In some embodiments, $R^7$ is $C_1$-$C_6$alkyl, $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, $C(O)R^9$, or —$S(O)_2R^9$.

In some embodiments, $R^7$ is substituted or unsubstituted phenyl, substituted or unsubstituted naphthyl, substituted or unsubstituted furanyl, substituted or unsubstituted substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted triazolyl, substituted or unsubstituted tetrazolyl, substituted or unsubstituted isoxazolyl, substituted or unsubstituted isothiazolyl, substituted or unsubstituted oxadiazolyl, substituted or unsubstituted thiadiazolyl, substituted or unsubstituted pyridinyl, substituted or unsubstituted pyrimidinyl, substituted or unsubstituted pyrazinyl, substituted or unsubstituted pyridazinyl, substituted or unsubstituted triazinyl, substituted or unsubstituted quinolinyl, substituted or unsubstituted isoquinolinyl, substituted or unsubstituted quinazolinyl, substituted or unsubstituted quinoxalinyl, substituted or unsubstituted naphthyridinyl, substituted or unsubstituted indolyl, substituted or unsubstituted indolinyl, substituted or unsubstituted indazolyl, substituted or unsubstituted benzoxazolyl, substituted or unsubstituted benzisoxazolyl, substituted or unsubstituted benzofuranyl, substituted or unsubstituted benzothienyl, substituted or unsubstituted benzothiazolyl, substituted or unsubstituted benzimidazolyl, substituted or unsubstituted purinyl, substituted or unsubstituted cinnolinyl, substituted or unsubstituted phthalazinyl, substituted or unsubstituted pteridinyl, substituted or unsubstituted pyridopyrimidinyl, substituted or unsubstituted pyrazolopyrimidinyl, or substituted or unsubstituted azaindolyl.

In some embodiments, $R^7$ is substituted or unsubstituted phenyl, substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted triazolyl, substituted or unsubstituted isoxazolyl, substituted or unsubstituted isothiazolyl, substituted or unsubstituted oxadiazolyl, substituted or unsubstituted thiadiazolyl, substituted or unsubstituted pyridinyl, substituted or unsubstituted pyrimidinyl, substituted or unsubstituted indolyl, substituted or unsubstituted indolinyl, or substituted or unsubstituted indazolyl.

In some embodiments, $R^7$ is $C_1$-$C_4$alkyl, $C_1$-$C_4$fluoroalkyl, substituted or unsubstituted cyclohexyl, substituted or unsubstituted cyclopentyl, substituted or unsubstituted cyclobutyl, substituted or unsubstituted cyclopropyl, —C(O)Me, or S(O)$_2$Me.

In some embodiments, $R^7$ is substituted with two $R^8$ groups on the same carbon, wherein the two $R^8$ groups are joined together to form a substituted or unsubstituted $C_3$-$C_8$cycloalkyl.

In some embodiments, $R^7$ is substituted with two $R^8$ groups on the same carbon, wherein the two $R^8$ groups are joined together to form a substituted or unsubstituted $C_2$-$C_8$heterocycloalkyl containing 1 or 2 heteroatoms selected from $NR^{11}$ or O.

In some embodiments, $R^2$ and $R^5$ are each independently H, halogen, —CN, —OH, $C_1$-$C_4$alkyl, $C_1$-$C_4$alkoxy, $C_1$-$C_4$fluoroalkoxy, or $C_1$-$C_4$fluoroalkyl.

In some embodiments, $R^2$ is H, F, Cl, —CN, —CH$_3$, —OCH$_3$, —CF$_3$, or —OCF$_3$.

In some embodiments, $R^5$ is H, F, Cl, —CN, —OH, —CH$_3$, —OCH$_3$, —CF$_3$, or —OCF$_3$. In some embodiments, $R^5$ is H, F, or Cl.

In some embodiments, $L^1$ is absent, $C_1$-$C_6$alkylene, or $C_3$-$C_6$cycloalkylene. In some embodiments, $L^1$ is absent, —CH$_2$—, —CH(CH$_3$)—, —C(CH$_3$)$_2$—, or —CH$_2$CH$_2$—. In some embodiments, $L^1$ is absent or —CH$_2$—. In some embodiments, $L^1$ is —CH$_2$—. In some embodiments, $L^1$ is absent.

In some embodiments, $R^3$ is —CO$_2$H, —CO$_2$(C$_1$-C$_6$alkyl), —B(OH)$_2$, —C(=O)NHSO$_2$R$^9$, —SO$_2$NHC(=O)R$^9$, tetrazolyl, —OP(=O)(OH)$_2$, —P(=O)(OH)$_2$, or carboxylic acid bioisostere. In some embodiments, $R^3$ is —CO$_2$H, —CO$_2$(C$_1$-C$_6$alkyl), or C(=O)NHSO$_2$R$^9$. In some embodiments, $R^3$ is —CO$_2$H or —CO$_2$(C$_1$-C$_6$alkyl). In some embodiments, $R^3$ is —CO$_2$H.

In some embodiments, $R^4$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, or $C_1$-$C_4$hydroxyalkyl.

In some embodiments, $R^4$ is halogen, —CN, —OH, $C_1$-$C_4$alkyl, $C_1$-$C_4$alkoxy, —S—$C_1$-$C_4$alkyl, $C_1$-$C_4$fluoroalkyl, or $C_1$-$C_4$fluoroalkoxy. In some embodiments, $R^4$ is F, Cl, Br, I, —CN, —OH, —CH$_3$, —CH$_2$CH$_3$, —CH(CH$_3$)$_2$, —OCH$_3$, —OCH$_2$CH$_3$, —CF$_3$, —OCF$_3$, or —S—CH$_3$. In some embodiments, $R^4$ is F, Cl, Br, or I. In some embodiments, $R^4$ is F or Cl.

In some embodiments, $R^2$ is H, F, Cl, —CN, —OH, —CH$_3$, —OCH$_3$, —CF$_3$, or —OCF$_3$; $L^1$ is absent, $C_1$-$C_6$alkylene, or $C_3$-$C_6$cycloalkylene; $R^3$ is —CO$_2$H, —CO$_2$(C$_1$-C$_6$alkyl), —B(OH)$_2$, or C(=O)NHSO$_2$R$^9$; $R^4$ is F, Cl, Br, I, —CN, —OH, —CH$_3$, —CH$_2$CH$_3$, —CH(CH$_3$)$_2$, —OCH$_3$, —OCH$_2$CH$_3$, —CF$_3$, —OCF$_3$, —S—CH$_3$, or —S(O)$_2$—CH$_3$; and $R^5$ is H, F, Cl, —CN, —OH, —CH$_3$, —OCH$_3$, —CF$_3$, or —OCF$_3$.

In some embodiments, $R^2$ is H, F, Cl, —CN, —OH, —CH$_3$, —OCH$_3$, —CF$_3$, or —OCF$_3$; $L^1$ is absent, —CH$_2$—, —CH(CH$_3$)—, or —CH$_2$CH$_2$—; $R^3$ is —CO$_2$H or —CO$_2$(C$_1$-C$_6$alkyl); $R^4$ is F, Cl, Br, —CN, —OCH$_3$, or —CF$_3$; and $R^5$ is H, F, Cl, —CN, —CH$_3$, —OCH$_3$, —CF$_3$, or —OCF$_3$.

In some embodiments, $R^2$ is H, F, Cl, —CH$_3$, —OCH$_3$, —CF$_3$, or —OCF$_3$; $L^1$ is absent or —CH$_2$—; $R^3$ is —CO$_2$H; $R^4$ is F or Cl; and $R^5$ is H, F, or Cl.

In some embodiments,

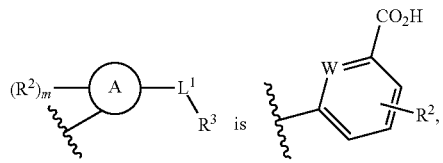

wherein W and $R^2$ are as defined in Tables 2 and 4. In some embodiments,

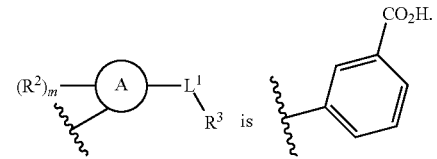

In some embodiments,

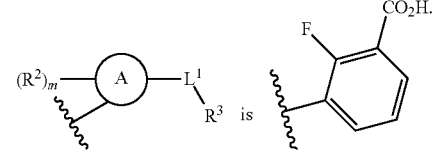

In some embodiments,

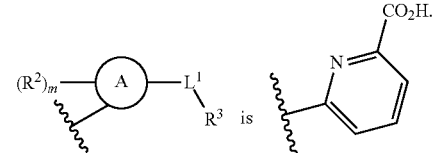

In some embodiments,

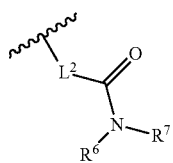

is R as defined in Tables 1 and 2.

In some embodiments,

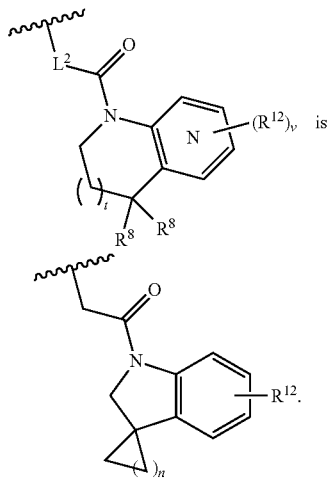

In some embodiments, $R^{12}$ and n are as defined in Table 3. In some embodiments, n is 1, 2, or 3. In some embodiments, n is 1. In some embodiments, n is 2. In some embodiments, n is 3.

In some embodiments, the compound of Formula (I) has the following structure:

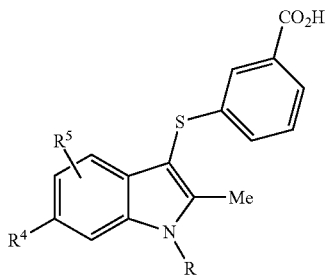

or a pharmaceutically acceptable salt, or solvate thereof.

In some embodiments, R, $R^4$ and $R^5$ are as defined in Table 1.

In some embodiments, the compound of Formula (I) has the following structure:

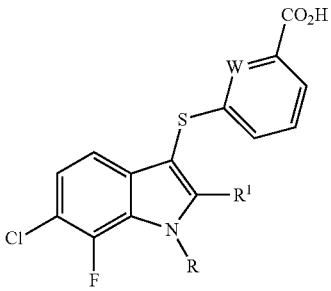

or a pharmaceutically acceptable salt, or solvate thereof.

In some embodiments, wherein R, $R^1$ and W are as defined in Table 2.

In some embodiments, wherein R, $R^1$ and W are as defined in Table 5.

In some embodiments, the compound of Formula (I) has one of the following structures:

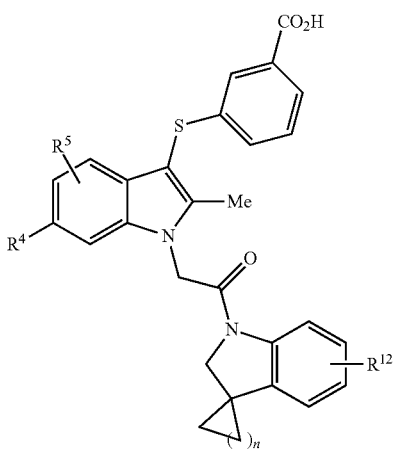

core A

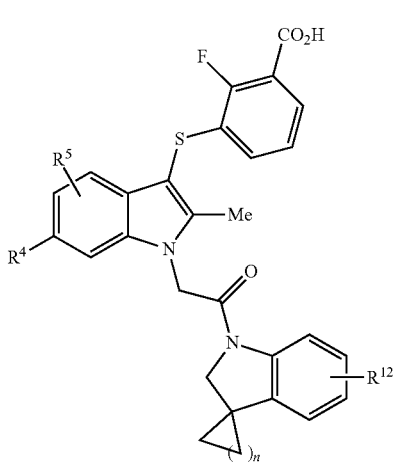

core B

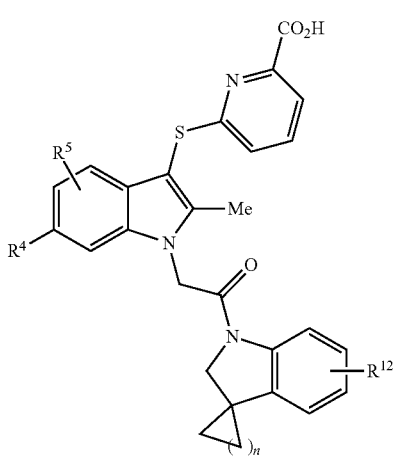

core C or a pharmaceutically acceptable salt, or solvate thereof.

In some embodiments, n, $R^{12}$, $R^4$ and $R^5$ are as defined in Table 3.

In some embodiments, the compound of Formula (I) has one of the following structures:

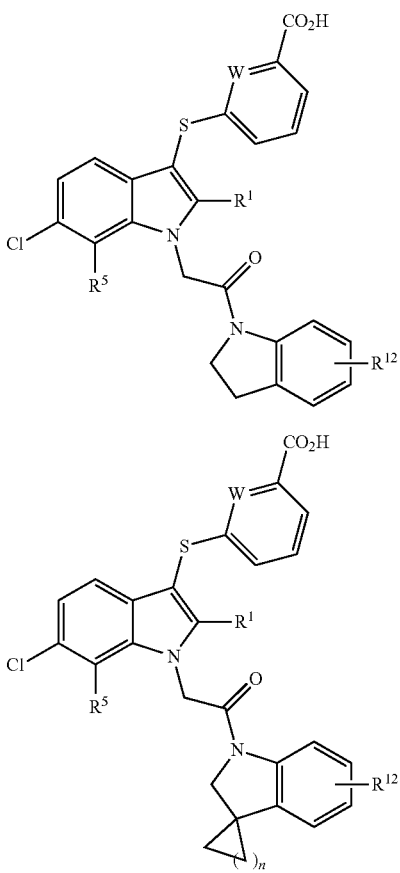

or a pharmaceutically acceptable salt, or solvate thereof.

In some embodiments, $R^1$, $R^5$, W, $R^{12}$, and n are as defined in Table 4.

Any combination of the groups described above for the various variables is contemplated herein. Throughout the specification, groups and substituents thereof are chosen by one skilled in the field to provide stable moieties and compounds.

Exemplary compounds include the following compounds:

TABLE 1

| Compound number | R | $R^4$ | $R^5$ |
|---|---|---|---|
| 1-1 | 2-(isopropylamino)-2-oxoethyl | Cl | 7-F |
| 1-2 | 2-(cyclohexylamino)-2-oxoethyl | Cl | 7-F |
| 1-3 | 2-(phenylamino)-2-oxoethyl | Cl | 7-F |
| 1-4 | 2-(3,5-dichlorophenylamino)-2-oxoethyl | Cl | 7-F |
| 1-5 | 2-(trifluoroethylamino)-2-oxoethyl | Cl | 7-F |
| 1-6 | 2-((1-methyl-1H-pyrazol-4-yl)amino | Cl | 7-F |
| 1-7 | 2-(dimethylamino)-2-oxoethyl | Cl | 7-F |
| 1-8 | 2-(methyl(phenyl)amino)-2-oxoethyl | Cl | 7-F |
| 1-9 | 2-oxo-2-(pyrrolidin-1-yl)ethyl | Cl | 7-F |
| 1-10 | 2-oxo-2-(piperidin-1-yl)ethyl | Cl | 7-F |
| 1-11 | 2-(isoxazol-4-ylamino)-2-oxoethyl | Cl | 7-F |
| 1-12 | 2-oxo-2-(2-oxo-1-oxa-3,8-diazaspiro[4.5]decan-8-yl)ethyl | Cl | 7-F |
| 1-13 | 2-(4-((3,4-difluorobenzyl)oxy)piperidin-1-yl)-2-oxoethyl | Cl | 7-F |
| 1-14 | 2-(indolin-1-yl)-2-oxoethyl | Cl | 7-F |
| 1-15 | 2-(3-(4-fluorobenzyl)piperidin-1-yl)-2-oxoethyl | Cl | 7-F |
| 1-16 | 3-oxo-3-(phenylamino)propyl | Cl | 7-F |
| 1-17 | benzylcarbamoyl | Cl | H |
| 1-18 | 2-oxo-2-(2-oxo-7-azaspiro[3.5]nonan-7-yl)ethyl | Cl | 7-F |
| 1-19 | 2-(2-cyano-7-azaspiro[3.5]nonan-7-yl)-2-oxoethyl | Cl | 7-F |
| 1-20 | 2-(3-(4-fluorophenyl)pyrrolidin-1-yl)-2-oxoethyl | Cl | 7-F |
| 1-21 | 2-(3-(4-fluorobenzyl)pyrrolidin-1-yl)-2-oxoethyl | Cl | 7-F |
| 1-22 | 2-(3-((4-fluorobenzyl)oxy)pyrrolidin-1-yl)-2-oxoethyl | Cl | 7-F |
| 1-23 | 2-(3-(4-trifluoromethyl benzyl)pyrrolidin-1-yl)-2-oxoethyl | Cl | 7-F |
| 1-24 | 2-(3-cyanopyrrolidin-1-yl)-2-oxoethyl | Cl | 7-F |
| 1-25 | 3-oxo-3-(pyrrolidin-1-yl)propyl | Cl | 7-F |
| 1-26 | 3-(indolin-1-yl)-3-oxopropyl | Cl | 7-F |
| 1-27 | 3-oxo-3-(spiro[cyclopropane-1,3'-indolin]-1'-yl)propyl | Cl | 7-F |
| 1-28 | 3-(5'-fluorospiro[cyclopropane-1,3'-indolin]-1'-yl)-3-oxopropyl | Cl | 7-F |
| 1-29 | 13-(5-fluoro-3,3-dimethylindolin-1-yl)-3-oxopropyl | Cl | 7-F |
| 1-30 | 3-(4'-fluorospiro[cyclobutane-1,3'-indolin]-1'-yl)-3-oxopropyl | Cl | 7-F |
| 1-31 | 2-oxo-2-(spiro[cyclopropane-1,3'-indolin]-1'-yl)ethyl | Cl | 7-F |
| 1-32 | 2-(5'-fluorospiro[cyclopropane-1,3'-indolin]-1'-yl)-2-oxoethyl | Cl | 7-F |
| 1-33 | 2-(4'-fluorospiro[cyclobutane-1,3'-indolin]-1'-yl)-2-oxoethyl | Cl | 7-F |
| 1-34 | 2-(5-fluoro-3,3-dimethylindolin-1-yl)-2-oxoethyl | Cl | 7-F |
| 1-35 | 2-oxo-2-(3-oxo-2,7-diazaspiro[4.5]decan-7-yl)ethyl | Cl | 7-F |
| 1-36 | 2-(3,4-dihydroquinolin-1(2H)-yl)-2-oxoethyl | Cl | 7-F |
| 1-37 | 2-(3-hydroxy-3-(trifluoromethyl)pyrrolidin-1-yl)-2-oxoethyl | Cl | 7-F |
| 1-38 | 2-(1'-methylspiro[indoline-3,4'-piperidin]-1-yl)-2-oxoethyl | Cl | 7-F |
| 1-39 | 2-oxo-2-(spiro[cyclopentane-1,3'-indolin]-1'-yl)ethyl | Cl | 7-F |
| 1-40 | 2-oxo-2-(1-(pyrrolidine-1-carbonyl)-6-azaspiro[2.5]octan-6-yl)ethyl | Cl | 7-F |
| 1-41 | 2-oxo-2-(2-oxo-1,7-diazaspiro[3.5]nonan-7-yl)ethyl | Cl | 7-F |
| 1-42 | 2-(3-(3,3-difluoropyrrolidin-1-yl)azetidin-1-yl)-2-oxoethyl | Cl | 7-F |
| 1-43 | 2-(2,4-dioxo-1,3,7-triazaspiro[4.4]nonan-7-yl)-2-oxoethyl | Cl | 7-F |
| 1-44 | 2-(4,4-dimethylpiperidin-1-yl)-2-oxoethyl | Cl | 7-F |
| 1-45 | 2-oxo-2-(3-oxo-2,8-diazaspiro[4.5]decan-8-yl)ethyl | Cl | 7-F |
| 1-46 | 2-oxo-2-(8-oxa-2-azaspiro[4.5]decan-2-yl)ethyl | Cl | 7-F |
| 1-47 | 2-oxo-2-(2-oxa-6-azaspiro[3.3]heptan-6-yl)ethyl | Cl | 7-F |
| 1-48 | 2-(3-(1,1-dioxidothiomorpholino)azetidin-1-yl)-2-oxoethyl | Cl | 7-F |
| 1-49 | 2-oxo-2-(7-oxo-2,6-diazaspiro[3.4]octan-2-yl)ethyl | Cl | 7-F |
| 1-50 | 2-oxo-2-(2-oxa-6-azaspiro[3.4]octan-6-yl)ethyl | Cl | 7-F |
| 1-51 | 2-((1R,5S,6r)-6-carbamoyl-3-azabicyclo[3.1.0]hexan-3-yl)-2-oxoethyl | Cl | 7-F |

TABLE 1-continued

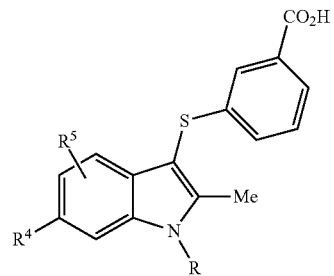

| Compound number | R | R⁴ | R⁵ |
|---|---|---|---|
| 1-52 | 2-(3-hydroxy-3-methylazetidin-1-yl)-2-oxoethyl | Cl | 7-F |
| 1-53 | 2-oxo-2-(10-oxo-3,9-diazaspiro[5.6]dodecan-3-yl)ethyl | Cl | 7-F |
| 1-54 | 2-(indolin-1-yl)-2-oxoethyl | F | 7-F |
| 1-55 | 2-(indolin-1-yl)-2-oxoethyl | F₅S— | 7-F |
| 1-56 | 2-oxo-2-(spiro[cyclopropane-1,3'-indolin]-1'-yl)ethyl | F | 7-F |
| 1-57 | 2-oxo-2-(spiro[cyclopropane-1,3'-indolin]-1'-yl)ethyl | F₅S— | 7-F |
| 1-58 | 2-(5-methoxy-indolin-1-yl)-2-oxoethyl | Cl | F |
| 1-59 | 2-oxo-2-(2-oxopyrrolidin-1-yl)ethyl | Cl | 7-F |
| 1-60 | 2-(4-(4-fluorobenzyl)piperidin-1-yl)-2-oxoethyl | Cl | 7-F |
| 1-61 | 2-(4-(2-(1H-pyrazol-1-yl)ethyl)piperidin-1-yl)-2-oxoethyl | Cl | 7-F |
| 1-62 | 2-oxo-2-(4-phenethylpiperidin-1-yl)ethyl | Cl | 7-F |
| 1-63 | 2-oxo-2-(4-(pyridin-4-ylmethyl)piperidin-1-yl)ethyl | Cl | 7-F |
| 1-64 | 2-(4-(1-methyl-1H-pyrazol-4-yl)piperidin-1-yl)-2-oxoethyl | Cl | 7-F |
| 1-65 | 2-(3-(4-fluorobenzyl)pyrrolidin-1-yl)-2-oxoethyl (enantiomer A) | Cl | 7-F |
| 1-66 | 2-(3-(4-fluorobenzyl)pyrrolidin-1-yl)-2-oxoethyl (enantiomer B) | Cl | 7-F |
| 1-67 | 2-(8-benzyl-2,8-diazaspiro[4.5]decan-2-yl)-2-oxoethyl | Cl | 7-F |
| 1-68 | 2-(7-methyl-2,7-diazaspiro[3.5]nonan-2-yl)-2-oxoethyl | Cl | 7-F |
| 1-69 | 2-(4-oxo-1-oxa-3,7-diazaspiro[4.5]decan-7-yl)ethyl | Cl | 7-F |
| 1-70 | 2-(4,6-difluoroindolin-1-yl)-2-oxoethyl | Cl | 7-F |
| 1-71 | 2-(5-chloroindolin-1-yl)-2-oxoethyl | Cl | 7-F |
| 1-72 | 2-(2,3-dihydro-1H-pyrrolo[2,3-b]pyridin-1-yl)-2-oxoethyl | Cl | 7-F |
| 1-73 | 2-(6-chloroindolin-1-yl)-2-oxoethyl | Cl | 7-F |
| 1-74 | 2-(3-(4-fluorophenyl)pyrrolidin-1-yl)-2-oxoethyl Enantiomer A | Cl | 7-F |
| 1-75 | 2-(3-(4-fluorophenyl)pyrrolidin-1-yl)-2-oxoethyl Enantiomer B | Cl | 7-F |
| 1-76 | 2-oxo-2-(3-phenethylpyrrolidin-1-yl)ethyl | Cl | 7-F |
| 1-77 | 2-oxo-2-(3-propylpyrrolidin-1-yl)ethyl | Cl | 7-F |
| 1-78 | 2-oxo-2-(3-(4-(trifluoromethyl)benzyl)pyrrolidin-1-yl)ethyl | Cl | 7-F |
| 1-79 | 2-(3,4-dihydroisoquinolin-2(1H)-yl)-2-oxoethyl | Cl | 7-F |
| 1-80 | 2-oxo-2-(6-(trifluoromethyl)indolin-1-yl)ethyl | Cl | 7-F |
| 1-81 | 2-(4-fluoroindolin-1-yl)-2-oxoethyl | Cl | 7-F |
| 1-82 | 2-(3-cyclopropyl-3-hydroxyazetidin-1-yl)-2-oxoethyl | Cl | 7-F |
| 1-83 | 2-(3-hydroxy-3-(trifluoromethyl)piperidin-1-yl)-2-oxoethyl | Cl | 7-F |
| 1-84 | 2-(3-hydroxy-3-(trifluoromethyl)azetidin-1-yl)-2-oxoethyl | Cl | 7-F |
| 1-85 | 2-(2-(1-methyl-1H-pyrazol-4-yl)pyrrolidin-1-yl)-2-oxoethyl | Cl | 7-F |
| 1-86 | 2-(3-(1H-pyrazol-1-yl)azetidin-1-yl)-2-oxoethyl | Cl | 7-F |
| 1-87 | 2-(7-methyl-1,7-diazaspiro[3.5]nonan-1-yl)-2-oxoethyl | Cl | 7-F |
| 1-88 | 2-oxo-2-(3-(pyridin-4-ylmethyl)pyrrolidin-1-yl)ethyl | Cl | 7-F |
| 1-89 | 2-oxo-2-(3-(pyridin-4-yl)pyrrolidin-1-yl)ethyl | Cl | 7-F |
| 1-90 | 2-(3-hydroxypyrrolidin-1-yl)-2-oxoethyl | Cl | 7-F |
| 1-91 | 2-(isoindolin-2-yl)-2-oxoethyl | Cl | 7-F |
| 1-92 | 2-(5-methylindolin-1-yl)-2-oxoethyl | Cl | 7-F |
| 1-93 | 2-(3-((1-methyl-1H-pyrazol-4-yl)methyl)pyrrolidin-1-yl)-2-oxoethyl | Cl | 7-F |

TABLE 1-continued

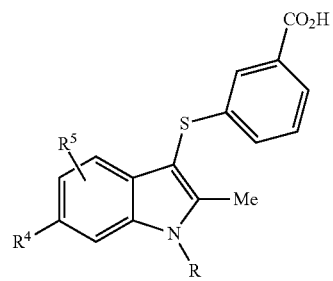

| Compound number | R | R⁴ | R⁵ |
|---|---|---|---|
| 1-94 | 2-(2-(2-(1H-pyrazol-1-yl)ethyl)piperidin-1-yl)-2-oxoethyl | Cl | 7-F |
| 1-95 | 2-oxo-2-(5-azaspiro[2.4]heptan-5-yl)ethyl | Cl | 7-F |
| 1-96 | 2-(3-(1-methyl-1H-pyrazol-4-yl)pyrrolidin-1-yl)-2-oxoethyl | Cl | 7-F |
| 1-97 | 2-(2,3-dihydro-1H-pyrrolo[2,3-c]pyridin-1-yl)-2-oxoethyl | Cl | 7-F |
| 1-98 | 2-(hexahydro-1H-isoindol-2(3H)-yl)-2-oxoethyl | Cl | 7-F |

TABLE 2

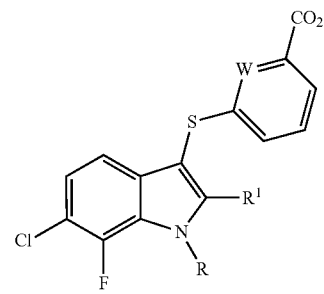

| Compound number | R | R¹ | W |
|---|---|---|---|
| 2-1 | 2-oxo-2-(2-oxo-1-oxa-3,8-diazaspiro[4.5]decan-8-yl)ethyl | —CH₃ | N |
| 2-2 | 2-oxo-2-(2-oxo-1-oxa-3,8-diazaspiro[4.5]decan-8-yl)ethyl | —CH₃ | CF |
| 2-3 | 2-(indolin-1-yl)-2-oxoethyl | —CH₃ | N |
| 2-4 | 2-(indolin-1-yl)-2-oxoethyl | —F | CH |
| 2-5 | 2-(indolin-1-yl)-2-oxoethyl | —Cl | CH |
| 2-6 | 2-(indolin-1-yl)-2-oxoethyl | —CN | CH |
| 2-7 | 2-(indolin-1-yl)-2-oxoethyl | —Br | CH |
| 2-8 | 2-(indolin-1-yl)-2-oxoethyl | —NH₂ | CH |
| 2-9 | 2-(indolin-1-yl)-2-oxoethyl | —CF₃ | CH |
| 2-10 | 2-(indolin-1-yl)-2-oxoethyl | —CD₃ | CH |
| 2-11 | 2-(indolin-1-yl)-2-oxoethyl | —CH₂OMe | CH |
| 2-12 | 2-(indolin-1-yl)-2-oxoethyl | —CH₂OH | CH |
| 2-13 | 2-(indolin-1-yl)-2-oxoethyl | -c-C₃H₅ | CH |
| 2-14 | 2-oxo-2-(spiro[cyclopropane-1,3'-indolin]-1'-yl)ethyl | F | CH |
| 2-15 | 2-oxo-2-(spiro[cyclopropane-1,3'-indolin]-1'-yl)ethyl | Cl | CH |
| 2-16 | 2-oxo-2-(spiro[cyclopropane-1,3'-indolin]-1'-yl)ethyl | CN | CH |
| 2-17 | 2-oxo-2-(spiro[cyclopropane-1,3'-indolin]-1'-yl)ethyl | Br | CH |
| 2-18 | 2-oxo-2-(spiro[cyclopropane-1,3'-indolin]-1'-yl)ethyl | —NH₂ | CH |
| 2-19 | 2-oxo-2-(spiro[cyclopropane-1,3'-indolin]-1'-yl)ethyl | —CF₃ | CH |
| 2-20 | 2-oxo-2-(spiro[cyclopropane-1,3'-indolin]-1'-yl)ethyl | —CD₃ | CH |

TABLE 2-continued

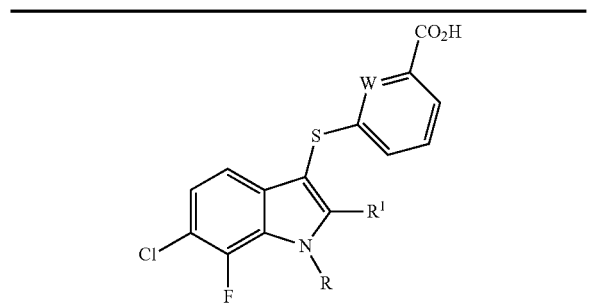
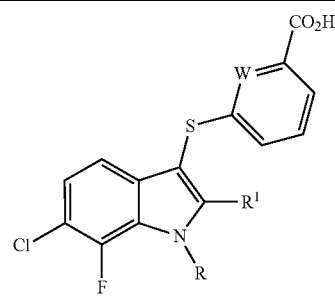

| Compound number | R | R¹ | W |
|---|---|---|---|
| 2-21 | 2-oxo-2-(spiro[cyclopropane-1,3'-indolin]-1'-yl)ethyl | —CH$_2$OMe | CH |
| 2-22 | 2-oxo-2-(spiro[cyclopropane-1,3'-indolin]-1'-yl)ethyl | —CH$_2$OH | CH |
| 2-23 | 2-oxo-2-(spiro[cyclopropane-1,3'-indolin]-1'-yl)ethyl | -c-C$_3$H$_5$ | CH |
| 2-24 | 2-oxo-2-(spiro[cyclopropane-1,3'-indolin]-1'-yl)ethyl | —F | N |
| 2-25 | 2-oxo-2-(spiro[cyclopropane-1,3'-indolin]-1'-yl)ethyl | —Cl | N |
| 2-26 | 2-oxo-2-(spiro[cyclopropane-1,3'-indolin]-1'-yl)ethyl | —CN | N |
| 2-27 | 2-oxo-2-(spiro[cyclopropane-1,3'-indolin]-1'-yl)ethyl | —Br | N |
| 2-28 | 2-oxo-2-(spiro[cyclopropane-1,3'-indolin]-1'-yl)ethyl | —NH$_2$ | N |
| 2-29 | 2-oxo-2-(spiro[cyclopropane-1,3'-indolin]-1'-yl)ethyl | —CF$_3$ | N |
| 2-30 | 2-oxo-2-(spiro[cyclopropane-1,3'-indolin]-1'-yl)ethyl | —CD$_3$ | N |
| 2-31 | 2-oxo-2-(spiro[cyclopropane-1,3'-indolin]-1'-yl)ethyl | —CH$_2$OMe | N |
| 2-32 | 2-oxo-2-(spiro[cyclopropane-1,3'-indolin]-1'-yl)ethyl | —CH$_2$OH | N |
| 2-33 | 2-oxo-2-(spiro[cyclopropane-1,3'-indolin]-1'-yl)ethyl | -c-C$_3$H$_5$ | N |
| 2-34 | 2-(indolin-1-yl)-2-oxoethyl | —F | CF |
| 2-35 | 2-(indolin-1-yl)-2-oxoethyl | —Cl | CF |
| 2-36 | 2-(indolin-1-yl)-2-oxoethyl | —CN | CF |
| 2-37 | 2-(indolin-1-yl)-2-oxoethyl | —Br | CF |
| 2-38 | 2-(indolin-1-yl)-2-oxoethyl | -c-C$_3$H$_5$ | CF |
| 2-39 | 2-(indolin-1-yl)-2-oxoethyl | —F | N |
| 2-40 | 2-(indolin-1-yl)-2-oxoethyl | —Cl | N |
| 2-41 | 2-(indolin-1-yl)-2-oxoethyl | —CN | N |
| 2-42 | 2-(indolin-1-yl)-2-oxoethyl | —Br | N |
| 2-43 | 2-(indolin-1-yl)-2-oxoethyl | -c-C$_3$H$_5$ | N |
| 2-44 | 2-oxo-2-(spiro[cyclopropane-1,3'-indolin]-1'-yl)ethyl | F | CF |
| 2-45 | 2-oxo-2-(spiro[cyclopropane-1,3'-indolin]-1'-yl)ethyl | Cl | CF |
| 2-46 | 2-oxo-2-(spiro[cyclopropane-1,3'-indolin]-1'-yl)ethyl | CN | CF |
| 2-47 | 2-oxo-2-(spiro[cyclopropane-1,3'-indolin]-1'-yl)ethyl | Br | CF |
| 2-48 | 2-oxo-2-(spiro[cyclopropane-1,3'-indolin]-1'-yl)ethyl | —NH$_2$ | CF |
| 2-49 | 2-oxo-2-(spiro[cyclopropane-1,3'-indolin]-1'-yl)ethyl | —CF$_3$ | CF |
| 2-50 | 2-oxo-2-(spiro[cyclopropane-1,3'-indolin]-1'-yl)ethyl | —CD$_3$ | CF |
| 2-51 | 2-oxo-2-(spiro[cyclopropane-1,3'-indolin]-1'-yl)ethyl | —CH$_2$OMe | CF |
| 2-52 | 2-oxo-2-(spiro[cyclopropane-1,3'-indolin]-1'-yl)ethyl | —CH$_2$OH | CF |
| 2-53 | 2-oxo-2-(spiro[cyclopropane-1,3'-indolin]-1'-yl)ethyl | -c-C$_3$H$_5$ | CF |
| 2-54 | 2-oxo-2-(spiro[cyclopropane-1,3'-indolin]-1'-yl)ethyl | CH$_3$ | N |
| 2-55 | 2-oxo-2-(spiro[cyclopropane-1,3'-indolin]-1'-yl)ethyl | CH$_3$ | CF |
| 2-56 | 2-(3-hydroxy-3-(trifluoromethyl)pyrrolidin-1-yl)-2-oxoethyl | CH$_3$ | N |
| 2-57 | 2-(3-hydroxy-3-(trifluoromethyl)pyrrolidin-1-yl)-2-oxoethyl | CH$_3$ | CF |
| 2-58 | (S)-2-(3-hydroxy-3-(trifluoromethyl)pyrrolidin-1-yl)-2-oxoethyl | CH$_3$ | CF |
| 2-59 | (R)-2-(3-hydroxy-3-(trifluoromethyl)pyrrolidin-1-yl)-2-oxoethyl | CH$_3$ | CF |
| 2-60 | 2-(2,3-dihydro-1H-pyrrolo[2,3-c]pyridin-1-yl)-2-oxoethyl | CH$_3$ | CF |
| 2-61 | 2-(3-hydroxy-3-methylpyrrolidin-1-yl)-2-oxoethyl | CH$_3$ | CF |
| 2-62 | 2-(3-(2-hydroxypropan-2-yl)pyrrolidin-1-yl)-2-oxoethyl | CH$_3$ | CF |
| 2-63 | 2-(3-cyclopropyl-3-hydroxyazetidin-1-yl)-2-oxoethyl | CH$_3$ | CF |
| 2-64 | 2-(3-(hydroxymethyl)pyrrolidin-1-yl)-2-oxoethyl | CH$_3$ | CF |
| 2-65 | 2-((3S,4S)-3-hydroxy-4-morpholinopyrrolidin-1-yl)-2-oxoethyl | CH$_3$ | CF |
| 2-66 | 2-((3R,4R)-3-fluoro-4-hydroxypyrrolidin-1-yl)-2-oxoethyl | CH$_3$ | CF |
| 2-67 | 2-(3-cyanoazetidin-1-yl)-2-oxoethyl | CH$_3$ | CF |
| 2-68 | 2-(3-hydroxy-3-phenylpyrrolidin-1-yl)-2-oxoethyl | CH$_3$ | CF |
| 2-69 | 2-((3S,4S)-3-(dimethylamino)-4-hydroxypyrrolidin-1-yl)-2-oxoethyl | CH$_3$ | CF |
| 2-70 | 2-((3S,4S)-3-hydroxy-4-(4-methylpiperazin-1-yl)pyrrolidin-1-yl)-2-oxoethyl | CH$_3$ | CF |
| 2-71 | 2-(3-((dimethylamino)methyl)azetidin-1-yl)-2-oxoethyl | CH$_3$ | CF |
| 2-72 | 2-oxo-2-(1,4-dioxa-7-azaspiro[4.4]nonan-7-yl)ethyl | CH$_3$ | CF |
| 2-73 | 2-(indolin-1-yl)ethyl | CH$_3$ | CF |
| 2-74 | 2-(spiro[cyclopropane-1,3'-indolin]-1'-yl)ethyl | CH$_3$ | CF |
| 2-75 | 2-(spiro[cyclobutane-1,3'-indolin]-1'-yl)ethyl | CH$_3$ | CF |

TABLE 3

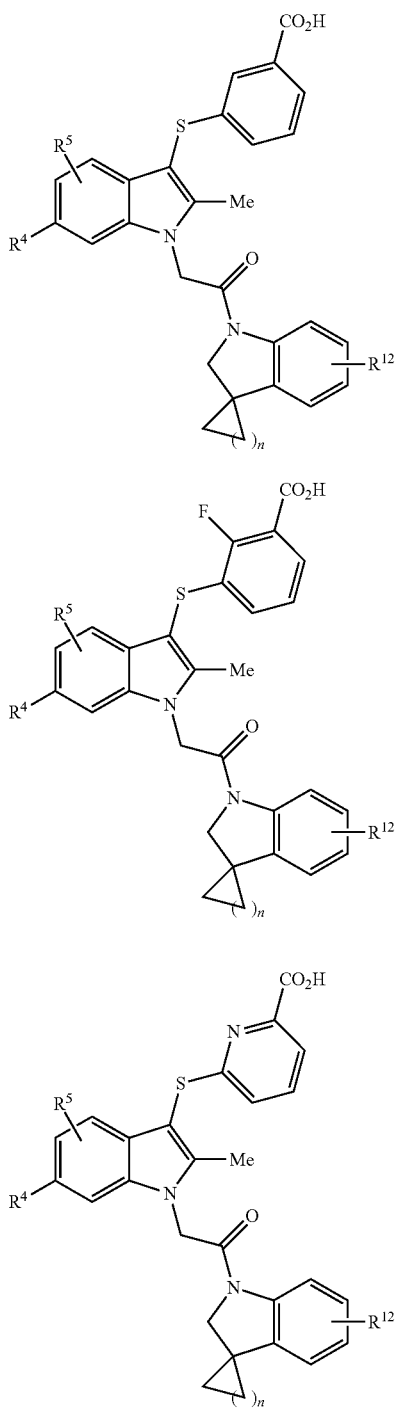

core A core B core C

| Compound number | core | n | R12 | R4 | R5 |
|---|---|---|---|---|---|
| 3-1 | A | 1 | 7-F | Cl | 7-F |
| 3-2 | A | 1 | 6-F | Cl | 7-F |
| 3-3 | A | 1 | 5-F | Cl | 7-F |
| 3-4 | A | 1 | 4-F | Cl | 7-F |
| 3-5 | A | 1 | 7-Cl | Cl | 7-F |
| 3-6 | A | 1 | 6-Cl | Cl | 7-F |
| 3-7 | A | 1 | 5-Cl | Cl | 7-F |
| 3-8 | A | 1 | 4-Cl | Cl | 7-F |
| 3-9 | A | 1 | 7-CN | Cl | 7-F |
| 3-10 | A | 1 | 6-CN | Cl | 7-F |
| 3-11 | A | 1 | 5-CN | Cl | 7-F |
| 3-12 | A | 1 | 4-CN | Cl | 7-F |
| 3-13 | A | 1 | 7-F | Cl | 7-H |
| 3-14 | A | 1 | 6-F | Cl | 7-H |
| 3-15 | A | 1 | 5-F | Cl | 7-H |
| 3-16 | A | 1 | 4-F | Cl | 7-H |
| 3-17 | A | 1 | 7-CF3 | Cl | 7-F |
| 3-18 | A | 1 | 6-CF3 | Cl | 7-F |
| 3-19 | A | 1 | 5-CF3 | Cl | 7-F |
| 3-20 | A | 1 | 4-CF3 | Cl | 7-F |
| 3-21 | B | 1 | 7-F | Cl | 7-F |
| 3-22 | B | 1 | 6-F | Cl | 7-F |
| 3-23 | B | 1 | 5-F | Cl | 7-F |
| 3-24 | B | 1 | 4-F | Cl | 7-F |
| 3-25 | B | 1 | 7-Cl | Cl | 7-F |
| 3-26 | B | 1 | 6-Cl | Cl | 7-F |
| 3-27 | B | 1 | 5-Cl | Cl | 7-F |
| 3-28 | B | 1 | 4-Cl | Cl | 7-F |
| 3-29 | B | 1 | 7-CN | Cl | 7-F |
| 3-30 | B | 1 | 6-CN | Cl | 7-F |
| 3-31 | B | 1 | 5-CN | Cl | 7-F |
| 3-32 | B | 1 | 4-CN | Cl | 7-F |
| 3-33 | B | 1 | 7-F | Cl | 7-H |
| 3-34 | B | 1 | 6-F | Cl | 7-H |
| 3-35 | B | 1 | 5-F | Cl | 7-H |
| 3-36 | B | 1 | 4-F | Cl | 7-H |
| 3-37 | B | 1 | 7-CF3 | Cl | 7-F |
| 3-38 | B | 1 | 6-CF3 | Cl | 7-F |
| 3-39 | B | 1 | 5-CF3 | Cl | 7-F |
| 3-40 | B | 1 | 4-CF3 | Cl | 7-F |
| 3-41 | C | 1 | 7-F | Cl | 7-F |
| 3-42 | C | 1 | 6-F | Cl | 7-F |
| 3-43 | C | 1 | 5-F | Cl | 7-F |
| 3-44 | C | 1 | 4-F | Cl | 7-F |
| 3-45 | C | 1 | 7-Cl | Cl | 7-F |
| 3-46 | C | 1 | 6-Cl | Cl | 7-F |
| 3-47 | C | 1 | 5-Cl | Cl | 7-F |
| 3-48 | C | 1 | 4-Cl | Cl | 7-F |
| 3-49 | C | 1 | 7-CN | Cl | 7-F |
| 3-50 | C | 1 | 6-CN | Cl | 7-F |
| 3-51 | C | 1 | 5-CN | Cl | 7-F |
| 3-52 | C | 1 | 4-CN | Cl | 7-F |
| 3-53 | C | 1 | 7-F | Cl | 7-H |
| 3-54 | C | 1 | 6-F | Cl | 7-H |
| 3-55 | C | 1 | 5-F | Cl | 7-H |
| 3-56 | C | 1 | 4-F | Cl | 7-H |
| 3-57 | C | 1 | 7-CF3 | Cl | 7-F |
| 3-58 | C | 1 | 6-CF3 | Cl | 7-F |
| 3-59 | C | 1 | 5-CF3 | Cl | 7-F |
| 3-60 | C | 1 | 4-CF3 | Cl | 7-F |
| 3-61 | A | 2 | 7-F | Cl | 7-F |
| 3-62 | A | 2 | 6-F | Cl | 7-F |
| 3-63 | A | 2 | 5-F | Cl | 7-F |
| 3-64 | A | 2 | 4-F | Cl | 7-F |
| 3-65 | A | 2 | 7-Cl | Cl | 7-F |
| 3-66 | A | 2 | 6-Cl | Cl | 7-F |
| 3-67 | A | 2 | 5-Cl | Cl | 7-F |
| 3-68 | A | 2 | 4-Cl | Cl | 7-F |
| 3-69 | A | 2 | 7-CN | Cl | 7-F |
| 3-70 | A | 2 | 6-CN | Cl | 7-F |
| 3-71 | A | 2 | 5-CN | Cl | 7-F |
| 3-72 | A | 2 | 4-CN | Cl | 7-F |
| 3-73 | A | 2 | 7-F | Cl | 7-H |
| 3-74 | A | 2 | 6-F | Cl | 7-H |
| 3-75 | A | 2 | 5-F | Cl | 7-H |
| 3-76 | A | 2 | 4-F | Cl | 7-H |
| 3-77 | A | 2 | 7-CF3 | Cl | 7-F |
| 3-78 | A | 2 | 6-CF3 | Cl | 7-F |
| 3-79 | A | 2 | 5-CF3 | Cl | 7-F |
| 3-80 | A | 2 | 4-CF3 | Cl | 7-F |
| 3-81 | B | 2 | 7-F | Cl | 7-F |
| 3-82 | B | 2 | 6-F | Cl | 7-F |
| 3-83 | B | 2 | 5-F | Cl | 7-F |
| 3-84 | B | 2 | 4-F | Cl | 7-F |
| 3-85 | B | 2 | 7-Cl | Cl | 7-F |
| 3-86 | B | 2 | 6-Cl | Cl | 7-F |
| 3-87 | B | 2 | 5-Cl | Cl | 7-F |
| 3-88 | B | 2 | 4-Cl | Cl | 7-F |
| 3-89 | B | 2 | 7-CN | Cl | 7-F |

TABLE 3-continued

| | | | | | |
|---|---|---|---|---|---|
| 3-90 | B | 2 | 6-CN | Cl | 7-F |
| 3-91 | B | 2 | 5-CN | Cl | 7-F |
| 3-92 | B | 2 | 4-CN | Cl | 7-F |
| 3-93 | B | 2 | 7-F | Cl | 7-H |
| 3-94 | B | 2 | 6-F | Cl | 7-H |
| 3-95 | B | 2 | 5-F | Cl | 7-H |
| 3-96 | B | 2 | 4-F | Cl | 7-H |
| 3-97 | B | 2 | 7-CF$_3$ | Cl | 7-F |
| 3-98 | B | 2 | 6-CF$_3$ | Cl | 7-F |
| 3-99 | B | 2 | 5-CF$_3$ | Cl | 7-F |
| 3-100 | B | 2 | 4-CF$_3$ | Cl | 7-F |
| 3-101 | C | 2 | 7-F | Cl | 7-F |
| 3-102 | C | 2 | 6-F | Cl | 7-F |
| 3-103 | C | 2 | 5-F | Cl | 7-F |
| 3-104 | C | 2 | 4-F | Cl | 7-F |
| 3-105 | C | 2 | 7-Cl | Cl | 7-F |
| 3-106 | C | 2 | 6-Cl | Cl | 7-F |
| 3-107 | C | 2 | 5-Cl | Cl | 7-F |
| 3-108 | C | 2 | 4-Cl | Cl | 7-F |
| 3-109 | C | 2 | 7-CN | Cl | 7-F |
| 3-110 | C | 2 | 6-CN | Cl | 7-F |
| 3-111 | C | 2 | 5-CN | Cl | 7-F |
| 3-112 | C | 2 | 4-CN | Cl | 7-F |
| 3-113 | C | 2 | 7-F | Cl | 7-H |
| 3-114 | C | 2 | 6-F | Cl | 7-H |
| 3-115 | C | 2 | 5-F | Cl | 7-H |
| 3-116 | C | 2 | 4-F | Cl | 7-H |
| 3-117 | C | 2 | 7-CF$_3$ | Cl | 7-F |
| 3-118 | C | 2 | 6-CF$_3$ | Cl | 7-F |
| 3-119 | C | 2 | 5-CF$_3$ | Cl | 7-F |
| 3-120 | C | 2 | 4-CF$_3$ | Cl | 7-F |
| 3-121 | A | 3 | 7-F | Cl | 7-F |
| 3-122 | A | 3 | 6-F | Cl | 7-F |
| 3-123 | A | 3 | 5-F | Cl | 7-F |
| 3-124 | A | 3 | 4-F | Cl | 7-F |
| 3-125 | A | 3 | 7-Cl | Cl | 7-F |
| 3-126 | A | 3 | 6-Cl | Cl | 7-F |
| 3-127 | A | 3 | 5-Cl | Cl | 7-F |
| 3-128 | A | 3 | 4-Cl | Cl | 7-F |
| 3-129 | A | 3 | 7-CN | Cl | 7-F |
| 3-130 | A | 3 | 6-CN | Cl | 7-F |
| 3-131 | A | 3 | 5-CN | Cl | 7-F |
| 3-132 | A | 3 | 4-CN | Cl | 7-F |
| 3-133 | A | 3 | 7-F | Cl | 7-H |
| 3-134 | A | 3 | 6-F | Cl | 7-H |
| 3-135 | A | 3 | 5-F | Cl | 7-H |
| 3-136 | A | 3 | 4-F | Cl | 7-H |
| 3-137 | A | 3 | 7-CF$_3$ | Cl | 7-F |
| 3-138 | A | 3 | 6-CF$_3$ | Cl | 7-F |
| 3-139 | A | 3 | 5-CF$_3$ | Cl | 7-F |
| 3-140 | A | 3 | 4-CF$_3$ | Cl | 7-F |
| 3-141 | B | 3 | 7-F | Cl | 7-F |
| 3-142 | B | 3 | 6-F | Cl | 7-F |
| 3-143 | B | 3 | 5-F | Cl | 7-F |
| 3-144 | B | 3 | 4-F | Cl | 7-F |
| 3-145 | B | 3 | 7-Cl | Cl | 7-F |
| 3-146 | B | 3 | 6-Cl | Cl | 7-F |
| 3-147 | B | 3 | 5-Cl | Cl | 7-F |
| 3-148 | B | 3 | 4-Cl | Cl | 7-F |
| 3-149 | B | 3 | 7-CN | Cl | 7-F |
| 3-150 | B | 3 | 6-CN | Cl | 7-F |
| 3-151 | B | 3 | 5-CN | Cl | 7-F |
| 3-152 | B | 3 | 4-CN | Cl | 7-F |
| 3-153 | B | 3 | 7-F | Cl | 7-H |
| 3-154 | B | 3 | 6-F | Cl | 7-H |
| 3-155 | B | 3 | 5-F | Cl | 7-H |
| 3-156 | B | 3 | 4-F | Cl | 7-H |
| 3-157 | B | 3 | 7-CF$_3$ | Cl | 7-F |
| 3-158 | B | 3 | 6-CF$_3$ | Cl | 7-F |
| 3-159 | B | 3 | 5-CF$_3$ | Cl | 7-F |
| 3-160 | B | 3 | 4-CF$_3$ | Cl | 7-F |
| 3-161 | C | 3 | 7-F | Cl | 7-F |
| 3-162 | C | 3 | 6-F | Cl | 7-F |
| 3-163 | C | 3 | 5-F | Cl | 7-F |
| 3-164 | C | 3 | 4-F | Cl | 7-F |
| 3-165 | C | 3 | 7-Cl | Cl | 7-F |
| 3-166 | C | 3 | 6-Cl | Cl | 7-F |
| 3-167 | C | 3 | 5-Cl | Cl | 7-F |
| 3-168 | C | 3 | 4-Cl | Cl | 7-F |
| 3-169 | C | 3 | 7-CN | Cl | 7-F |
| 3-170 | C | 3 | 6-CN | Cl | 7-F |
| 3-171 | C | 3 | 5-CN | Cl | 7-F |
| 3-172 | C | 3 | 4-CN | Cl | 7-F |
| 3-173 | C | 3 | 7-F | Cl | 7-H |
| 3-174 | C | 3 | 6-F | Cl | 7-H |
| 3-175 | C | 3 | 5-F | Cl | 7-H |
| 3-176 | C | 3 | 4-F | Cl | 7-H |
| 3-177 | C | 3 | 7-CF$_3$ | Cl | 7-F |
| 3-178 | C | 3 | 6-CF$_3$ | Cl | 7-F |
| 3-179 | C | 3 | 5-CF$_3$ | Cl | 7-F |
| 3-180 | C | 3 | 4-CF$_3$ | Cl | 7-F |
| 3-181 | A | 1 | 7-OMe | Cl | 7-F |
| 3-182 | A | 1 | 6-OMe | Cl | 7-F |
| 3-183 | A | 1 | 5-OMe | Cl | 7-F |
| 3-184 | A | 1 | 4-OMe | Cl | 7-F |
| 3-185 | A | 2 | 7-OMe | Cl | 7-F |
| 3-186 | A | 2 | 6-OMe | Cl | 7-F |
| 3-187 | A | 2 | 5-OMe | Cl | 7-F |
| 3-188 | A | 2 | 4-OMe | Cl | 7-F |
| 3-189 | A | 3 | 7-OMe | Cl | 7-F |
| 3-190 | A | 3 | 6-OMe | Cl | 7-F |
| 3-191 | A | 3 | 5-OMe | Cl | 7-F |
| 3-192 | A | 3 | 4-OMe | Cl | 7-F |
| 3-193 | B | 1 | 7-OMe | Cl | 7-F |
| 3-194 | B | 1 | 6-OMe | Cl | 7-F |
| 3-195 | B | 1 | 5-OMe | Cl | 7-F |
| 3-196 | B | 1 | 4-OMe | Cl | 7-F |
| 3-197 | B | 2 | 7-OMe | Cl | 7-F |
| 3-198 | B | 2 | 6-OMe | Cl | 7-F |
| 3-199 | B | 2 | 5-OMe | Cl | 7-F |
| 3-200 | B | 2 | 4-OMe | Cl | 7-F |
| 3-201 | B | 3 | 7-OMe | Cl | 7-F |
| 3-202 | B | 3 | 6-OMe | Cl | 7-F |
| 3-203 | B | 3 | 5-OMe | Cl | 7-F |
| 3-204 | B | 3 | 4-OMe | Cl | 7-F |
| 3-205 | C | 1 | 7-OMe | Cl | 7-F |
| 3-206 | C | 1 | 6-OMe | Cl | 7-F |
| 3-207 | C | 1 | 5-OMe | Cl | 7-F |
| 3-208 | C | 1 | 4-OMe | Cl | 7-F |
| 3-209 | C | 2 | 7-OMe | Cl | 7-F |
| 3-210 | C | 2 | 6-OMe | Cl | 7-F |
| 3-211 | C | 2 | 5-OMe | Cl | 7-F |
| 3-212 | C | 2 | 4-OMe | Cl | 7-F |
| 3-213 | C | 3 | 7-OMe | Cl | 7-F |
| 3-214 | C | 3 | 6-OMe | Cl | 7-F |
| 3-215 | C | 3 | 5-OMe | Cl | 7-F |
| 3-216 | A | 1 | H | Cl | 7-F |
| 3-217 | A | 2 | H | Cl | 7-F |
| 3-218 | A | 3 | H | Cl | 7-F |
| 3-219 | B | 1 | H | Cl | 7-F |
| 3-220 | B | 2 | H | Cl | 7-F |
| 3-221 | B | 3 | H | Cl | 7-F |
| 3-222 | C | 1 | H | Cl | 7-F |
| 3-223 | C | 2 | H | Cl | 7-F |
| 3-224 | C | 3 | H | Cl | 7-F |

TABLE 4

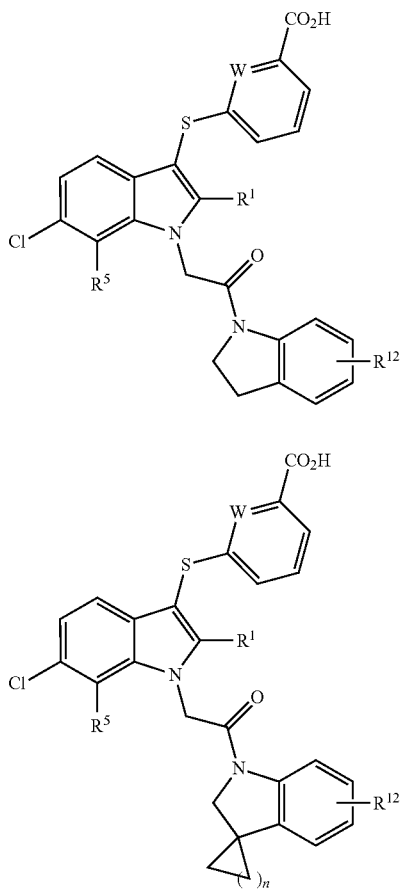

| Compound Number | core | R¹ | R⁵ | W | R¹² | n |
|---|---|---|---|---|---|---|
| 4-1 | A | Cl | H | CH | H | — |
| 4-2 | A | Br | H | CH | H | — |
| 4-3 | A | F | H | CH | H | — |
| 4-4 | A | CN | H | CH | H | — |
| 4-5 | A | c-C₃H₅ | H | CH | H | — |
| 4-6 | A | —NH₂ | H | CH | H | — |
| 4-7 | A | —OMe | H | CH | H | — |
| 4-8 | A | —CHO | H | CH | H | — |
| 4-9 | A | Cl | F | CH | H | — |
| 4-10 | A | Br | F | CH | H | — |
| 4-11 | A | F | F | CH | H | — |
| 4-12 | A | CN | F | CH | H | — |
| 4-13 | A | c-C₃H₅ | F | CH | H | — |
| 4-14 | A | NH2 | F | CH | H | — |
| 4-15 | A | —OMe | F | CH | H | — |
| 4-16 | A | —CHO | F | CH | H | — |
| 4-17 | A | Cl | H | CF | H | — |
| 4-18 | A | Br | H | CF | H | — |
| 4-19 | A | F | H | CF | H | — |
| 4-20 | A | CN | H | CF | H | — |
| 4-21 | A | c-C₃H₅ | H | CF | H | — |
| 4-22 | A | —NH₂ | H | CF | H | — |
| 4-23 | A | —OMe | H | CF | H | — |
| 4-24 | A | —CHO | H | CF | H | — |
| 4-25 | A | Cl | F | CF | H | — |
| 4-26 | A | Br | F | CF | H | — |
| 4-27 | A | F | F | CF | H | — |
| 4-28 | A | CN | F | CF | H | — |
| 4-29 | A | c-C₃H₅ | F | CF | H | — |
| 4-30 | A | NH₂ | F | CF | H | — |
| 4-31 | A | —OMe | F | CF | H | — |
| 4-32 | A | —CHO | F | CF | H | — |
| 4-33 | A | Cl | H | N | H | — |
| 4-34 | A | Br | H | N | H | — |
| 4-35 | A | F | H | N | H | — |
| 4-36 | A | CN | H | N | H | — |
| 4-37 | A | c-C₃H₅ | H | N | H | — |
| 4-38 | A | —NH₂ | H | N | H | — |
| 4-39 | A | —OMe | H | N | H | — |
| 4-40 | A | —CHO | H | N | H | — |
| 4-41 | A | Cl | F | N | H | — |
| 4-42 | A | Br | F | N | H | — |
| 4-43 | A | F | F | N | H | — |
| 4-44 | A | CN | F | N | H | — |
| 4-45 | A | c-C₃H₅ | F | N | H | — |
| 4-46 | A | —NH₂ | F | N | H | — |
| 4-47 | A | —OMe | F | N | H | — |
| 4-48 | A | —CHO | F | N | H | — |
| 4-49 | A | Cl | F | CF | 5-F | — |
| 4-50 | A | Br | F | CF | 5-F | — |
| 4-51 | A | CN | F | CF | 5-F | — |
| 4-52 | A | c-C₃H₅ | F | CF | 5-F | — |
| 4-53 | A | Cl | F | N | 5-F | — |
| 4-54 | A | Br | F | N | 5-F | — |
| 4-55 | A | CN | F | N | 5-F | — |
| 4-56 | A | c-C₃H₅ | F | N | 5-F | — |
| 4-57 | B | Cl | H | CH | H | 1 |
| 4-58 | B | Br | H | CH | H | 1 |
| 4-59 | B | F | H | CH | H | 1 |
| 4-60 | B | CN | H | CH | H | 1 |
| 4-61 | B | c-C₃H₅ | H | CH | H | 1 |
| 4-62 | B | —NH₂ | H | CH | H | 1 |
| 4-63 | B | —OMe | H | CH | H | 1 |
| 4-64 | B | —CHO | H | CH | H | 1 |
| 4-65 | B | Cl | F | CH | H | 1 |
| 4-66 | B | Br | F | CH | H | 1 |
| 4-67 | B | F | F | CH | H | 1 |
| 4-68 | B | CN | F | CH | H | 1 |
| 4-69 | B | c-C₃H₅ | F | CH | H | 1 |
| 4-70 | B | —NH₂ | F | CH | H | 1 |
| 4-71 | B | —OMe | F | CH | H | 1 |
| 4-72 | B | —CHO | F | CH | H | 1 |
| 4-73 | B | Cl | H | CF | H | 1 |
| 4-74 | B | Br | H | CF | H | 1 |
| 4-75 | B | F | H | CF | H | 1 |
| 4-76 | B | CN | H | CF | H | 1 |
| 4-77 | B | c-C₃H₅ | H | CF | H | 1 |
| 4-78 | B | —NH₂ | H | CF | H | 1 |
| 4-79 | B | —OMe | H | CF | H | 1 |
| 4-80 | B | —CHO | H | CF | H | 1 |
| 4-81 | B | Cl | F | CF | H | 1 |
| 4-82 | B | Br | F | CF | H | 1 |
| 4-83 | B | F | F | CF | H | 1 |
| 4-84 | B | CN | F | CF | H | 1 |
| 4-85 | B | c-C₃H₅ | F | CF | H | 1 |
| 4-86 | B | —NH₂ | F | CF | H | 1 |
| 4-87 | B | —OMe | F | CF | H | 1 |
| 4-88 | B | —CHO | F | CF | H | 1 |
| 4-89 | B | Cl | H | N | H | 1 |
| 4-90 | B | Br | H | N | H | 1 |
| 4-91 | B | F | H | N | H | 1 |
| 4-92 | B | CN | H | N | H | 1 |
| 4-93 | B | c-C₃H₅ | H | N | H | 1 |
| 4-94 | B | —NH₂ | H | N | H | 1 |
| 4-95 | B | —OMe | H | N | H | 1 |
| 4-96 | B | —CHO | H | N | H | 1 |
| 4-97 | B | Cl | F | N | H | 1 |
| 4-98 | B | Br | F | N | H | 1 |
| 4-99 | B | F | F | N | H | 1 |
| 4-100 | B | CN | F | N | H | 1 |
| 4-101 | B | c-C₃H₅ | F | N | H | 1 |
| 4-102 | B | —NH₂ | F | N | H | 1 |
| 4-103 | B | —OMe | F | N | H | 1 |
| 4-104 | B | —CHO | F | N | H | 1 |
| 4-105 | B | Cl | F | CF | 5-F | 1 |
| 4-106 | B | Br | F | CF | 5-F | 1 |
| 4-107 | B | CN | F | CF | 5-F | 1 |
| 4-108 | B | c-C₃H₅ | F | CF | 5-F | 1 |
| 4-109 | B | Cl | F | N | 5-F | 1 |
| 4-110 | B | Br | F | N | 5-F | 1 |
| 4-111 | B | CN | F | N | 5-F | 1 |
| 4-112 | B | c-C₃H₅ | F | N | 5-F | 1 |

TABLE 4-continued

| | | | | | | |
|---|---|---|---|---|---|---|
| 4-113 | B | Cl | F | CF | 5-OMe | 1 |
| 4-114 | B | Br | F | CF | 5-OMe | 1 |
| 4-115 | B | CN | F | CF | 5-OMe | 1 |
| 4-116 | B | c-C$_3$H$_5$ | F | CF | 5-OMe | 1 |
| 4-117 | B | Cl | F | N | 5-OMe | 1 |
| 4-118 | B | Br | F | N | 5-OMe | 1 |
| 4-119 | B | CN | F | N | 5-OMe | 1 |
| 4-120 | B | c-C$_3$H$_5$ | F | N | 5-OMe | 1 |
| 4-121 | B | Cl | F | CF | H | 2 |
| 4-122 | B | Br | F | CF | H | 2 |
| 4-123 | B | CN | F | CF | H | 2 |
| 4-124 | B | c-C$_3$H$_5$ | F | CF | H | 2 |
| 4-125 | B | Cl | F | N | H | 2 |
| 4-126 | B | Br | F | N | H | 2 |
| 4-127 | B | CN | F | N | H | 2 |
| 4-128 | B | c-C$_3$H$_5$ | F | N | H | 2 |
| 4-129 | B | Cl | F | CF | H | 3 |
| 4-130 | B | Br | F | CF | H | 3 |
| 4-131 | B | CN | F | CF | H | 3 |
| 4-132 | B | c-C$_3$H$_5$ | F | CF | H | 3 |
| 4-133 | B | Cl | F | N | H | 3 |
| 4-134 | B | Br | F | N | H | 3 |
| 4-135 | B | CN | F | N | H | 3 |
| 4-136 | B | c-C$_3$H$_5$ | F | N | H | 3 |
| 4-137 | B | Cl | F | CF | 4-F | 2 |
| 4-138 | B | Br | F | CF | 4-F | 2 |
| 4-139 | B | CN | F | CF | 4-F | 2 |
| 4-140 | B | c-C$_3$H$_5$ | F | CF | 4-F | 2 |
| 4-141 | B | Cl | F | N | 4-F | 2 |
| 4-142 | B | Br | F | N | 4-F | 2 |
| 4-143 | B | CN | F | N | 4-F | 2 |
| 4-144 | B | c-C$_3$H$_5$ | F | N | 4-F | 2 |
| 4-145 | B | Cl | F | CF | 5-OMe | 2 |
| 4-146 | B | Br | F | CF | 5-OMe | 2 |
| 4-147 | B | CN | F | CF | 5-OMe | 2 |
| 4-148 | B | c-C$_3$H$_5$ | F | CF | 5-OMe | 2 |
| 4-149 | B | Cl | F | N | 5-OMe | 2 |
| 4-150 | B | Br | F | N | 5-OMe | 2 |
| 4-151 | B | CN | F | N | 5-OMe | 2 |
| 4-152 | B | c-C$_3$H$_5$ | F | N | 5-OMe | 2 |
| 4-153 | B | Cl | F | CF | 5-Cl | 3 |
| 4-154 | B | Br | F | CF | 5-Cl | 3 |
| 4-155 | B | CN | F | CF | 5-Cl | 3 |
| 4-156 | B | c-C$_3$H$_5$ | F | CF | 5-Cl | 3 |
| 4-157 | B | Cl | F | N | 5-Cl | 3 |
| 4-158 | B | Br | F | N | 5-Cl | 3 |
| 4-159 | B | CN | F | N | 5-Cl | 3 |
| 4-160 | B | c-C$_3$H$_5$ | F | N | 5-Cl | 3 |
| 4-161 | B | Cl | F | CF | 5-OMe | 3 |
| 4-162 | B | Br | F | CF | 5-OMe | 3 |
| 4-163 | B | CN | F | CF | 5-OMe | 3 |
| 4-164 | B | c-C$_3$H$_5$ | F | CF | 5-OMe | 3 |
| 4-165 | B | Cl | F | N | 5-OMe | 3 |
| 4-166 | B | Br | F | N | 5-OMe | 3 |
| 4-167 | B | CN | F | N | 5-OMe | 3 |
| 4-168 | B | c-C$_3$H$_5$ | F | N | 5-OMe | 3 |

TABLE 5

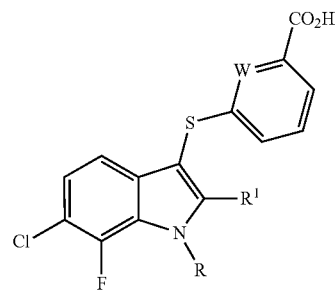

| Compound Number | R$^1$ | R | W |
|---|---|---|---|
| 5-1 | Cl | (2-(spiro[cyclobutane-1,3'-indolin]-1'-yl)ethyl) | CF |
| 5-2 | Cl | (2-(spiro[cyclopropane-1,3'-indolin]-1'-yl)ethyl) | CF |
| 5-3 | cC$_3$H$_5$ | (2-(spiro[cyclobutane-1,3'-indolin]-1'-yl)ethyl) | CF |
| 5-4 | cC$_3$H$_5$ | (2-(indolin-1-yl)ethyl) | CF |
| 5-5 | Cl | (2-(3-hydroxy-3-(trifluoromethyl)pyrrolidin-1-yl)-2-oxoethyl) | CF |
| 5-6 | cC$_3$H$_5$ | (2-(3-hydroxy-3-(trifluoromethyl)pyrrolidin-1-yl)-2-oxoethyl) | CF |
| 5-7 | cC$_3$H$_5$ | (2-(methoxy(methyl)amino)-2-oxoethyl) | CF |

Additional exemplary compounds include the following structures A1, A2, A3, A4 and A5 where R represents a radical linked through an amide bond.

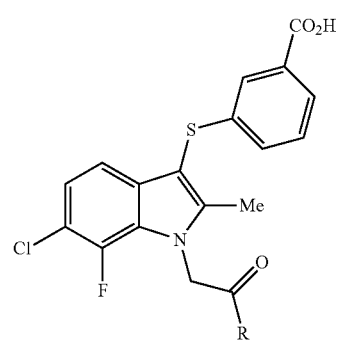

A1

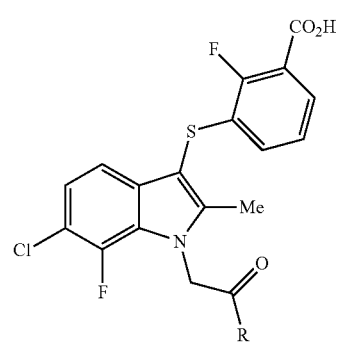

A2

-continued

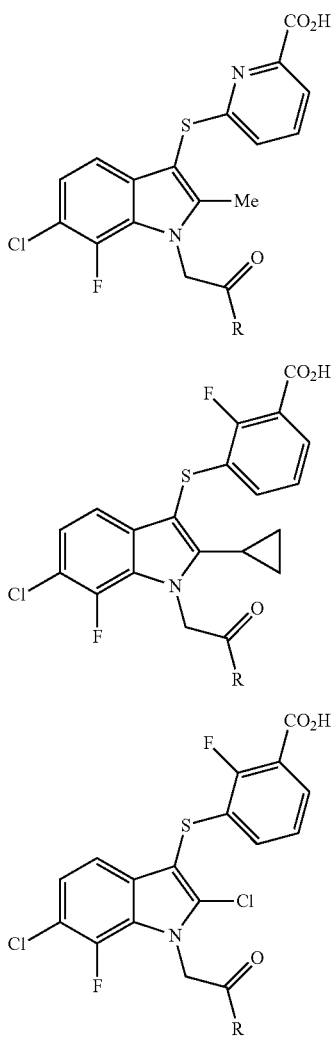

The R-group is selected from the following amines: Isoindoline; 5-methyl-2,3-dihydro-1H-indole; 1-ethyl-5-pyrrolidin-2-yl-1H-pyrazole; 3-(cyclopropylmethyl)sulfonylazetidine; 2-aza-bicyclo[2.1.1]hexane; 5-azaspiro[2.4]heptane hydrochloride; pyrrolidin-3-ol hydrochloride hydrate; 4-pyrrolidin-3-ylpyridine; octahydro-1H-isoindole; 1-(2-piperidinylmethyl)indoline dihydrochloride; 2-[2-(1H-pyrazol-1-yl)ethyl]piperidine; 1H,2H,3H-pyrrolo[2,3-c]pyridine dihydrochloride; 2,3-dihydro-1H-pyrrolo[3,2-c]pyridine hydrochloride; 4-(pyrrolidin-3-ylmethyl)pyridine; 1-methyl-4-(pyrrolidin-3-yl)-1H-pyrazole; 7-methyl-1,7-diazaspiro[3.5]nonane dihydrochloride; 1-(azetidin-3-yl)-1H-pyrazole; 3-cyclopropylazetidin-3-ol hydrochloride; 3-(trifluoromethyl)azetidin-3-ol hydrochloride; 1-methyl-4-(pyrrolidin-2-yl)-1H-pyrazole; 1-methyl-4-(pyrrolidin-3-ylmethyl)-1H-pyrazole; and 3-(trifluoromethyl)piperidin-3-ol Representative compounds include:
3-((6-Chloro-1-(2-((3,5-dichlorophenyl)amino)-2-oxoethyl)-7-fluoro-2-methyl-1H-indol-3-yl)thio)benzoic acid;
3-((6-Chloro-7-fluoro-2-methyl-1-(2-oxo-2-(phenylamino)ethyl)-1H-indol-3-yl)thio)benzoic acid;
3-((6-Chloro-7-fluoro-2-methyl-1H-(2-(((1-methyl-1H-pyrazol-4-yl)amino)-2-oxoethyl)-1H-indol-3-yl)thio)benzoic acid;
3-((6-Chloro-7-fluoro-1-(2-(isoxazol-4-ylamino)-2-oxoethyl)-2-methyl-1H-indol-3-yl)thio)benzoic acid;
2-(6-Chloro-7-fluoro-2-methyl-3-((3-propionylphenyl)thio)-1H-indol-1-yl)-N-(2,2,2-trifluoroethyl)acetamide;
3-((6-Chloro-7-fluoro-2-methyl-1-(2-oxo-2-(pyrrolidin-1-yl)ethyl)-1H-indol-3-yl)thio)benzoic acid;
3-((6-Chloro-7-fluoro-2-methyl-1-(2-(methyl(phenyl)amino)-2-oxoethyl)-1H-indol-3-yl)thio)benzoic acid;
3-((6-Chloro-1-(2-(cyclohexylamino)-2-oxoethyl)-7-fluoro-2-methyl-1H-indol-3-yl)thio)benzoic acid;
3-((6-Chloro-7-fluoro-1-(2-(isopropylamino)-2-oxoethyl)-2-methyl-1H-indol-3-yl)thio)benzoic acid;
3-((6-Chloro-1-(2-(dimethylamino)-2-oxoethyl)-7-fluoro-2-methyl-1H-indol-3-yl)thio)benzoic acid;
3-((1-(Benzylcarbamoyl)-6-chloro-2-methyl-1H-indol-3-yl)thio)benzoic acid;
3-((6-Chloro-7-fluoro-2-methyl-1-(2-oxo-2-(piperidin-1-yl)ethyl)-1H-indol-3-yl)thio)benzoic acid;
3-((6-Chloro-1-(2-(4-((3,4-difluorobenzyl)oxy)piperidin-1-yl)-2-oxoethyl)-7-fluoro-2-methyl-1H-indol-3-yl)thio)benzoic acid;
3-((6-Chloro-7-fluoro-1-(2-(3-(4-fluorobenzyl)piperidin-1-yl)-2-oxoethyl)-2-methyl-1H-indol-3-yl)thio)benzoic acid;
3-((6-Chloro-7-fluoro-2-methyl-1-(2-(2-oxo-1-oxa-3,8-diazaspiro[4.5]decan-8-yl)acetyl)-1H-indol-3-yl)thio)benzoic acid;
3-((6-Chloro-7-fluoro-2-methyl-1-(3-oxo-3-(phenylamino)propyl)-1H-indol-3-yl)thio)benzoic acid;
3-((6-Chloro-7-fluoro-1-(2-(indolin-1-yl)-2-oxoethyl)-2-methyl-1H-indol-3-yl)thio)benzoic acid;
3-((6-Chloro-7-fluoro-2-methyl-1-(2-oxo-2-(2-oxo-7-azaspiro[3.5]nonan-7-yl)ethyl)-1H-indol-3-yl)thio)benzoic acid;
3-((6-Chloro-1-(2-(2-cyano-7-azaspiro[3.5]nonan-7-yl)-2-oxoethyl)-7-fluoro-2-methyl-1H-indol-3-yl)thio)benzoic acid;
3-((6-Chloro-7-fluoro-1-(2-(3-(4-fluorophenyl)pyrrolidin-1-yl)-2-oxoethyl)-2-methyl-1H-indol-3-yl)thio)benzoic acid;
3-((6-Chloro-7-fluoro-1-(2-(3-(4-fluorobenzyl)pyrrolidin-1-yl)-2-oxoethyl)-2-methyl-1H-indol-3-yl)thio)benzoic acid;
3-((6-Chloro-7-fluoro-1-(2-(3-((4-fluorobenzyl)oxy)pyrrolidin-1-yl)-2-oxoethyl)-2-methyl-1H-indol-3-yl)thio)benzoic acid;
3-((6-Chloro-7-fluoro-1-(2-(3-((4-trifluoromethylbenzyl)pyrrolidin-1-yl)-2-oxoethyl)-2-methyl-1H-indol-3-yl)thio)benzoic acid;
3-((6-Chloro-7-fluoro-1-(2-(3-cyanopyrrolidin-1-yl)-2-oxoethyl)-2-methyl-1H-indol-3-yl)thio)benzoic acid;
3-((6-Chloro-7-fluoro-2-methyl-1-(3-oxo-3-(pyrrolidin-1-yl)propyl)-1H-indol-3-yl)thio)benzoic acid;
3-((6-Chloro-7-fluoro-1-(3-(indolin-1-yl)-3-oxopropyl)-2-methyl-1H-indol-3-yl)thio)benzoic acid;
3-((6-Chloro-7-fluoro-2-methyl-1-(3-oxo-3-(spiro[cyclopropane-1,3'-indolin]-1'-yl)propyl)-1H-indol-3-yl)thio)benzoic acid;
3-((6-Chloro-7-fluoro-2-methyl-1-(2-oxo-2-(spiro[cyclopropane-1,3'-indolin]-1'-yl)ethyl)-1H-indol-3-yl)thio)benzoic acid;
3-((6-Chloro-7-fluoro-1-(2-(5'-fluorospiro[cyclopropane-1,3'-indolin]-1'-yl)-2-oxoethyl)-2-methyl-1H-indol-3-yl)thio)benzoic acid;
3-((6-Chloro-7-fluoro-1-(2-(4'-fluorospiro[cyclobutane-1,3'-indolin]-1'-yl)-2-oxoethyl)-2-methyl-1H-indol-3-yl)thio)benzoic acid;

3-((6-Chloro-7-fluoro-1-(2-(6-fluoro-3,3-dimethylindolin-1-yl)-2-oxoethyl)-2-methyl-1H-indol-3-yl)thio)benzoic acid;

3-((6-Chloro-7-fluoro-2-methyl-1-(2-oxo-2-(3-oxo-2,7-diazaspiro[4.5]decan-7-yl)ethyl)-1H-indol-3-yl)thio)benzoic acid;

3-((6-Chloro-1-(2-(3,4-dihydroquinolin-1(2H)-yl)-2-oxoethyl)-7-fluoro-2-methyl-1H-indol-3-yl)thio)benzoic acid;

3-((6-Chloro-7-fluoro-1-(2-(3-hydroxy-3-(trifluoromethyl)pyrrolidin-1-yl)-2-oxoethyl)-2-methyl-1H-indol-3-yl)thio)benzoic acid;

3-((6-Chloro-7-fluoro-2-methyl-1-(2-(1'-methylspiro[indoline-3,4'-piperidin]-1-yl)-2-oxoethyl)-1H-indol-3-yl)thio)benzoic acid;

3-((6-Chloro-7-fluoro-2-methyl-1-(2-oxo-2-(spiro[cyclopentane-1,3'-indolin]-1'-yl)ethyl)-1H-indol-3-yl)thio)benzoic acid;

3-((6-Chloro-7-fluoro-2-methyl-1-(2-oxo-2-(1-(pyrrolidine-1-carbonyl)-6-azaspiro[2.5]octan-6-yl)ethyl)-1H-indol-3-yl)thio)benzoic acid;

3-((6-Chloro-7-fluoro-2-methyl-1-(2-oxo-2-(2-oxo-1,7-diazaspiro[3.5]nonan-7-yl)ethyl)-1H-indol-3-yl)thio)benzoic acid;

3-((6-Chloro-1-(2-(3-(3,3-difluoropyrrolidin-1-yl)azetidin-1-yl)-2-oxoethyl)-7-fluoro-2-methyl-1H-indol-3-yl)thio)benzoic acid;

3-((6-Chloro-1-(2-(2,4-dioxo-1,3,7-triazaspiro[4.4]nonan-7-yl)-2-oxoethyl)-7-fluoro-2-methyl-1H-indol-3-yl)thio)benzoic acid;

3-((6-Chloro-1-(2-(4,4-dimethylpiperidin-1-yl)-2-oxoethyl)-7-fluoro-2-methyl-1H-indol-3-yl)thio)benzoic acid;

3-((6-Chloro-7-fluoro-2-methyl-1-(2-oxo-2-(3-oxo-2,8-diazaspiro[4.5]decan-8-yl)ethyl)-1H-indol-3-yl)thiobenzoic acid;

3-((6-Chloro-7-fluoro-2-methyl-1-(2-oxo-2-(8-oxa-2-azaspiro[4.5]decan-2-yl)ethyl)-1H-indol-3-yl)thio)benzoic acid;

3-((6-Chloro-7-fluoro-2-methyl-1-(2-oxo-2-(2-oxa-6-azaspiro[3.3]heptan-6-yl)ethyl)-1H-indol-3-yl)thio)benzoic acid;

3-((6-Chloro-1-(2-(3-(1,1-dioxidothiomorpholino)azetidin-1-yl)-2-oxoethyl)-7-fluoro-2-methyl-1H-indol-3-yl)thio)benzoic acid;

3-((6-Chloro-7-fluoro-2-methyl-1-(2-oxo-2-(7-oxo-2,6-diazaspiro[3.4]octan-2-yl)ethyl)-1H-indol-3-yl)thio)benzoic acid;

3-((6-Chloro-7-fluoro-2-methyl-1-(2-oxo-2-(2-oxa-6-azaspiro[3.4]octan-6-yl)ethyl)-1H-indol-3-yl)thio)benzoic acid;

3-((1-(2-((1R,5S,6R)-6-Carbamoyl-3-azabicyclo[3.1.0]hexan-3-yl)-2-oxoethyl)-6-chloro-7-fluoro-2-methyl-1H-indol-3-yl)thio)benzoic acid;

3-((6-Chloro-7-fluoro-1-(2-(3-hydroxy-3-methylazetidin-1-yl)-2-oxoethyl)-2-methyl-1H-indol-3-yl)thio)benzoic acid;

3-((6-Chloro-7-fluoro-2-methyl-1-(2-oxo-2-(10-oxo-3,9-diazaspiro[5.6]dodecan-3-yl)ethyl)-1H-indol-3-yl)thio)benzoic acid;

3-((6-Chloro-7-fluoro-2-methyl-1-(2-oxo-2-(2-oxopyrrolidin-1-yl)ethyl)-1H-indol-3-yl)thio)benzoic acid;

3-((6-Chloro-7-fluoro-1-(2-(4-(4-fluorobenzyl)piperidin-1-yl)-2-oxoethyl)-2-methyl-1H-indol-3-yl)thio)benzoic acid;

3-((1-(2-(4-(2-(1H-Pyrazol-1-yl)ethyl)piperidin-1-yl)-2-oxoethyl)-6-chloro-7-fluoro-2-methyl-1H-indol-3-yl)thio)benzoic acid;

3-((6-Chloro-7-fluoro-2-methyl-1-(2-oxo-2-(4-phenethylpiperidin-1-yl)ethyl)-1H-indol-3-yl)thio)benzoic acid;

3-((6-Chloro-7-fluoro-2-methyl-1-(2-oxo-2-(4-(pyridin-4-ylmethyl)piperidin-1-yl)ethyl)-1H-indol-3-yl)thio)benzoic acid;

3-((6-Chloro-7-fluoro-2-methyl-1-(2-(4-(1-methyl-1H-pyrazol-4-yl)piperidin-1-yl)-2-oxoethyl)-1H-indol-3-yl)thio)benzoic acid;

3-((6-Chloro-7-fluoro-1-(2-(3-(4-fluorobenzyl)pyrrolidin-1-yl)-2-oxoethyl)-2-methyl-1H-indol-3-yl)thio)benzoic acid Enantiomer A;

3-((6-Chloro-7-fluoro-1-(2-(3-(4-fluorobenzyl)pyrrolidin-1-yl)-2-oxoethyl)-2-methyl-1H-indol-3-yl)thio)benzoic acid Enantiomer B;

3-((1-(2-(8-Benzyl-2,8-diazaspiro[4.5]decan-2-yl)-2-oxoethyl)-6-chloro-7-fluoro-2-methyl-1H-indol-3-yl)thio)benzoic acid;

3-((6-Chloro-7-fluoro-2-methyl-1-(2-(7-methyl-2,7-diazaspiro[3.5]nonan-2-yl)-2-oxoethyl)-1H-indol-3-yl)thio)benzoic acid;

3-((6-Chloro-7-fluoro-2-methyl-1-(2-oxo-2-(2-oxo-1-oxa-3,7-diazaspiro[4.5]decan-7-yl)ethyl)-1H-indol-3-yl)thio)benzoic acid;

3-((6-Chloro-1-(2-(4,6-difluoroindolin-1-yl)-2-oxoethyl)-7-fluoro-2-methyl-1H-indol-3-yl)thio)benzoic acid;

3-((6-Chloro-1-(2-(5-chloroindolin-1-yl)-2-oxoethyl)-7-fluoro-2-methyl-1H-indol-3-yl)thio)benzoic acid;

3-((6-Chloro-1-(2-(6-chloroindolin-1-yl)-2-oxoethyl)-7-fluoro-2-methyl-1H-indol-3-yl)thio)benzoic acid;

3-((6-Chloro-1-(2-(2,3-dihydro-1H-pyrrolo[2,3-b]pyridin-1-yl)-2-oxoethyl)-7-fluoro-2-methyl-1H-indol-3-yl)thio)benzoic acid;

3-((6-Chloro-7-fluoro-1-(2-(3-(4-fluorophenyl)pyrrolidin-1-yl)-2-oxoethyl)-2-methyl-1H-indol-3-yl)thio)benzoic acid Enantiomer A;

3-((6-Chloro-7-fluoro-1-(2-(3-(4-fluorophenyl)pyrrolidin-1-yl)-2-oxoethyl)-2-methyl-1H-indol-3-yl)thio)benzoic acid Enantiomer B;

6-((6-Chloro-7-fluoro-2-methyl-1-(2-oxo-2-(2-oxo-1-oxa-3,8-diazaspiro[4.5]decan-8-yl)ethyl)-1H-indol-3-yl)thio)picolinic acid;

Methyl 6-((6-chloro-7-fluoro-1-(2-(indolin-1-yl)-2-oxoethyl)-2-methyl-1H-indol-3-yl)thio)picolinate;

6-((6-Chloro-7-fluoro-2-methyl-1-(2-oxo-2-(spiro[cyclopropane-1,3'-indolin]-1'-yl)ethyl)-1H-indol-3-yl)thio)picolinic acid;

3-((6-Chloro-7-fluoro-2-methyl-1-(2-oxo-2-(spiro[cyclopropane-1,3'-indolin]-1'-yl)ethyl)-1H-indol-3-yl)thio)-2-fluorobenzoic acid;

3-((6-Chloro-1-(2-(5-methoxyindolin-1-yl)-2-oxoethyl)-7-fluoro-2-methyl-1H-indol-3-yl)thio)benzoic acid;

3-[6-Chloro-7-fluoro-1-[2-(5'-fluorospiro[cyclopropane-1,3'-indoline]-1'-yl)-2-oxo-ethyl]-2-methyl-indol-3-yl]sulfanyl-2-fluoro-benzoic acid;

6-((6-Chloro-7-fluoro-1-(2-(4'-fluorospiro[cyclobutane-1,3'-indolin]-1'-yl)-2-oxoethyl)-2-methyl-1H-indol-3-yl)thio)picolinic acid;

3-((6-Chloro-7-fluoro-1-(2-(4'-fluorospiro[cyclobutane-1,3'-indolin]-1'-yl)-2-oxoethyl)-2-methyl-1H-indol-3-yl)thio)-2-fluorobenzoic acid;

3-((6-Chloro-7-fluoro-2-methyl-1-(2-oxo-2-(spiro[cyclopentane-1,3'-indolin]-1'-yl)ethyl)-1H-indol-3-yl)thio)-2-fluorobenzoic acid;

3-((6-Chloro-7-fluoro-2-methyl-1-(2-oxo-2-(3-phenethyl-pyrrolidin-1-yl)ethyl)-1H-indol-3-yl)thio)benzoic acid;
3-((6-Chloro-7-fluoro-2-methyl-1-(2-oxo-2-(3-propylpyrrolidin-1-yl)ethyl)-1H-indol-3-yl)thio)benzoic acid;
3-((6-Chloro-7-fluoro-2-methyl-1-(2-oxo-2-(3-(4-(trifluoromethyl)benzyl)pyrrolidin-1-yl)ethyl)-1H-indol-3-yl)thio)benzoic acid;
3-((6-Chloro-1-(2-(3,4-dihydroisoquinolin-2(1H)-yl)-2-oxoethyl)-7-fluoro-2-methyl-1H-indol-3-yl)thio)benzoic acid;
3-((6-Chloro-7-fluoro-2-methyl-1-(2-oxo-2-(6-(trifluoromethyl)indolin-1-yl)ethyl)-1H-indol-3-yl)thio)benzoic acid;
3-((6-Chloro-7-fluoro-1-(2-(4-fluoroindolin-1-yl)-2-oxoethyl)-2-methyl-1H-indol-3-yl)thio)benzoic acid;
3-((6-Chloro-1-(2-(3-cyclopropyl-3-hydroxyazetidin-1-yl)-2-oxoethyl)-7-fluoro-2-methyl-1H-indol-3-yl)thio)benzoic acid;
3-((6-Chloro-7-fluoro-1-(2-(3-hydroxy-3-(trifluoromethyl)piperidin-1-yl)-2-oxoethyl)-2-methyl-1H-indol-3-yl)thio)benzoic acid;
3-((6-Chloro-7-fluoro-1-(2-(3-hydroxy-3-(trifluoromethyl)azetidin-1-yl)-2-oxoethyl)-2-methyl-1H-indol-3-yl)thio)benzoic acid;
3-((6-Chloro-7-fluoro-2-methyl-1-(2-(2-(1-methyl-1H-pyrazol-4-yl)pyrrolidin-1-yl)-2-oxoethyl)-1H-indol-3-yl)thio)benzoic acid;
3-((1-(2-(3-(1H-Pyrazol-1-yl)azetidin-1-yl)-2-oxoethyl)-6-chloro-7-fluoro-2-methyl-1H-indol-3-yl)thio)benzoic acid;
6-((6-Chloro-7-fluoro-1-(2-(3-hydroxy-3-(trifluoromethyl)pyrrolidin-1-yl)-2-oxoethyl)-2-methyl-1H-indol-3-yl)thio)picolinic acid;
3-((6-chloro-7-fluoro-1-(2-(3-hydroxy-3-(trifluoromethyl)pyrrolidin-1-yl)-2-oxoethyl)-2-methyl-1H-indol-3-yl)thio)-2-fluorobenzoic acid;
3-((6-Chloro-7-fluoro-2-methyl-1-(2-(7-methyl-1,7-diazaspiro[3.5]nonan-1-yl)-2-oxoethyl)-1H-indol-3-yl)thio)benzoic acid;
3-((6-Chloro-7-fluoro-2-methyl-1-(2-oxo-2-(3-(pyridin-4-ylmethyl)pyrrolidin-1-yl)ethyl)-1H-indol-3-yl)thio)benzoic acid;
3-((6-Chloro-7-fluoro-2-methyl-1-(2-oxo-2-(3-(pyridin-4-yl)pyrrolidin-1-yl)ethyl)-1H-indol-3-yl)thio)benzoic acid;
3-((6-Chloro-7-fluoro-1-(2-(3-hydroxypyrrolidin-1-yl)-2-oxoethyl)-2-methyl-1H-indol-3-yl)thio)benzoic acid;
3-((6-Chloro-7-fluoro-1-(2-(isoindolin-2-yl)-2-oxoethyl)-2-methyl-1H-indol-3-yl)thio)benzoic acid;
3-((6-Chloro-7-fluoro-2-methyl-1-(2-(5-methylindolin-1-yl)-2-oxoethyl)-1H-indol-3-yl)thio)benzoic acid;
3-((6-Chloro-7-fluoro-2-methyl-1-(2-(3-((1-methyl-1H-pyrazol-4-yl)methyl)pyrrolidin-1-yl)-2-oxoethyl)-1H-indol-3-yl)thio)benzoic acid;
3-((1-(2-(2-(2-(1H-Pyrazol-1-yl)ethyl)piperidin-1-yl)-2-oxoethyl)-6-chloro-7-fluoro-2-methyl-1H-indol-3-yl)thio)benzoic acid;
3-((6-Chloro-7-fluoro-2-methyl-1-(2-oxo-2-(5-azaspiro[2.4]heptan-5-yl)ethyl)-1H-indol-3-yl)thio)benzoic acid;
3-((6-Chloro-7-fluoro-2-methyl-1-(2-(3-(1-methyl-1H-pyrazol-4-yl)pyrrolidin-1-yl)-2-oxoethyl)-1H-indol-3-yl)thio)benzoic acid;
3-((6-Chloro-1-(2-(2,3-dihydro-1H-pyrrolo[2,3-c]pyridin-1-yl)-2-oxoethyl)-7-fluoro-2-methyl-1H-indol-3-yl)thio)benzoic acid;
3-((6-Chloro-7-fluoro-1-(2-(hexahydro-1H-isoindol-2(3H)-yl)-2-oxoethyl)-2-methyl-1H-indol-3-yl)thio)benzoic acid;
3-((6-chloro-7-fluoro-1-(2-(indolin-1-yl)ethyl)-2-methyl-1H-indol-3-yl)thio)-2-fluorobenzoic acid;
3-((6-Chloro-1-(2-(2,3-dihydro-1H-pyrrolo[2,3-c]pyridin-1-yl)-2-oxoethyl)-7-fluoro-2-methyl-1H-indol-3-yl)thio)-2-fluorobenzoic acid;
3-((6-Chloro-7-fluoro-1-(2-(3-hydroxy-3-methylpyrrolidin-1-yl)-2-oxoethyl)-2-methyl-1H-indol-3-yl)thio)-2-fluorobenzoic acid;
3-((6-Chloro-7-fluoro-2-methyl-1-(2-oxo-2-(spiro[cyclobutane-1,3'-indolin]-1'-yl)ethyl)-1H-indol-3-yl)thio)-2-fluorobenzoic acid;
3-((6-chloro-7-fluoro-2-methyl-1-(2-(spiro[cyclopropane-1,3'-indolin]-1'-yl)ethyl)-1H-indol-3-yl)thio)-2-fluorobenzoic acid;
3-((6-Chloro-7-fluoro-2-methyl-1-(2-(spiro[cyclobutane-1,3'-indolin]-1'-yl)ethyl)-1H-indol-3-yl)thio)-2-fluorobenzoic acid;
3-((6-Chloro-7-fluoro-2-methyl-1-(2-oxo-2-(spiro[cyclopentane-1,3'-indolin]-1'-yl)ethyl)-1H-indol-3-yl)thio)-2-fluoro-N-(phenylsulfonyl)benzamide;
3-((6-Chloro-7-fluoro-1-(2-(3-(2-hydroxypropan-2-yl)pyrrolidin-1-yl)-2-oxoethyl)-2-methyl-1H-indol-3-yl)thio)-2-fluorobenzoic acid;
3-((6-Chloro-1-(2-(3-cyclopropyl-3-hydroxyazetidin-1-yl)-2-oxoethyl)-7-fluoro-2-methyl-1H-indol-3-yl)thio)-2-fluorobenzoic acid;
(R)-3-((6-Chloro-7-fluoro-1-(2-(3-(hydroxymethyl)pyrrolidin-1-yl)-2-oxoethyl)-2-methyl-1H-indol-3-yl)thio)-2-fluorobenzoic acid;
3-((6-Chloro-7-fluoro-1-(2-((3S,4S)-3-hydroxy-4-morpholinopyrrolidin-1-yl)-2-oxoethyl)-2-methyl-1H-indol-3-yl)thio)-2-fluorobenzoic acid;
3-((6-Chloro-7-fluoro-1-(2-((3R,4R)-3-fluoro-4-hydroxypyrrolidin-1-yl)-2-oxoethyl)-2-methyl-1H-indol-3-yl)thio)-2-fluorobenzoic acid;
(S)-3-((6-chloro-7-fluoro-1-(2-(3-hydroxy-3-(trifluoromethyl)pyrrolidin-1-yl)-2-oxoethyl)-2-methyl-1H-indol-3-yl)thio)-2-fluorobenzoic acid;
(R)-3-((6-chloro-7-fluoro-1-(2-(3-hydroxy-3-(trifluoromethyl)pyrrolidin-1-yl)-2-oxoethyl)-2-methyl-1H-indol-3-yl)thio)-2-fluorobenzoic acid;
3-((6-Chloro-1-(2-(3-cyanoazetidin-1-yl)-2-oxoethyl)-7-fluoro-2-methyl-1H-indol-3-yl)thio)-2-fluorobenzoic acid;
3-((6-Chloro-7-fluoro-1-(2-(3-hydroxy-3-phenylpyrrolidin-1-yl)-2-oxoethyl)-2-methyl-1H-indol-3-yl)thio)-2-fluorobenzoic acid;
3-((6-Chloro-1-(2-((3S,4S)-3-(dimethylamino)-4-hydroxypyrrolidin-1-yl)-2-oxoethyl)-7-fluoro-2-methyl-1H-indol-3-yl)thio)-2-fluorobenzoic acid;
3-((6-Chloro-7-fluoro-1-(2-((3S,4S)-3-hydroxy-4-(4-methylpiperazin-1-yl)pyrrolidin-1-yl)-2-oxoethyl)-2-methyl-1H-indol-3-yl)thio)-2-fluorobenzoic acid;
3-((6-Chloro-1-(2-(3-((dimethylamino)methyl)azetidin-1-yl)-2-oxoethyl)-7-fluoro-2-methyl-1H-indol-3-yl)thio)-2-fluorobenzoic acid;
3-((6-Chloro-7-fluoro-2-methyl-1-(2-oxo-2-(1,4-dioxa-7-azaspiro[4.4]nonan-7-yl)ethyl)-1H-indol-3-yl)thio)-2-fluorobenzoic acid;
3-((2,6-dichloro-7-fluoro-1-(2-oxo-2-(spiro[cyclobutane-1,3'-indolin]-1'-yl)ethyl)-1H-indol-3-yl)thio)-2-fluorobenzoic acid;

3-((2,6-dichloro-7-fluoro-1-(2-oxo-2-(spiro[cyclopropane-1,3'-indolin]-1'-yl)ethyl)-1H-indol-3-yl)thio)-2-fluorobenzoic acid;

3-((6-chloro-2-cyclopropyl-7-fluoro-1-(2-(indolin-1-yl)-2-oxoethyl)-1H-indol-3-yl)thio)-2-fluorobenzoic acid;

3-((6-chloro-2-cyclopropyl-7-fluoro-1-(2-oxo-2-(spiro[cyclobutane-1,3'-indolin]-1'-yl)ethyl)-1H-indol-3-yl)thio)-2-fluorobenzoic acid;

3-((6-chloro-2-cyclopropyl-7-fluoro-1-(2-oxo-2-(spiro[cyclopropane-1,3'-indolin]-1'-yl)ethyl)-1H-indol-3-yl)thio)-2-fluorobenzoic acid;

3-((2,6-dichloro-7-fluoro-1-(2-(3-hydroxy-3-(trifluoromethyl)pyrrolidin-1-yl)-2-oxoethyl)-1H-indol-3-yl)thio)-2-fluorobenzoic acid;

3-((6-chloro-2-cyclopropyl-7-fluoro-1-(2-(3-hydroxy-3-(trifluoromethyl)pyrrolidin-1-yl)-2-oxoethyl)-1H-indol-3-yl)thio)-2-fluorobenzoic acid;

3-((6-chloro-2-cyclopropyl-7-fluoro-1-(2-(methoxy(methyl)amino)-2-oxoethyl)-1H-indol-3-yl)thio)-2-fluorobenzoic acid;

or a pharmaceutically acceptable salt, or solvate thereof.

In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviours. Also, because the salt-forming molecule can be in equilibrium with a neutral form, passage through biological membranes can be adjusted.

In some embodiments, pharmaceutically acceptable salts are obtained by reacting a compound described herein with an acid. In some embodiments, the compound described herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (− L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (− L); salicylic acid; sebacic acid; stearic acid; succinic acid; sulfuric acid; tartaric acid (+ L); thiocyanic acid; toluenesulfonic acid (p); and undecylenic acid.

In some embodiments, a compound described herein is prepared as a chloride salt, sulfate salt, bromide salt, mesylate salt, maleate salt, citrate salt or phosphate salt. In some embodiments, a compound described herein is prepared as a hydrochloride salt.

In some embodiments, pharmaceutically acceptable salts are obtained by reacting a compound described herein with a base. In some embodiments, the compound described herein is acidic and is reacted with a base. In such situations, an acidic proton of the compound described herein is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt. In some embodiments, the compounds provided herein are prepared as a sodium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), crystalline forms (also known as polymorphs), or pharmaceutically acceptable salts of compounds described herein, as well as active metabolites of these compounds having the same type of activity.

In some embodiments, sites on the organic radicals (e.g. alkyl groups, aromatic rings) of compounds described herein are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In some embodiments, the compounds described herein possess one or more stereocenters and each stereocenter exists independently in either the R or S configuration. The compounds presented herein include all diastereomeric, enantiomeric, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound described herein as set forth herein are included within the scope of the claims. In some cases, some of the herein-described compounds is a prodrug for another derivative or active compound.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

Synthesis of Compounds

Compounds described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Indoles are readily prepared by chemical synthesis using standard methodologies as described in the review "Practical methodologies for the synthesis of indoles" Humphrey and Kuethe, *Chem. Rev.*, 2006, 106, 2875-2911. Compounds are prepared using standard organic chemistry techniques such as those described in, for example, March's Advanced Organic Chemistry, 6th Edition, John Wiley and Sons, Inc. Alternative reaction conditions for the synthetic transformations described herein may be employed such as variation of solvent, reaction temperature, reaction time, as well as different chemical reagents and other reaction conditions. The starting materials are available from commercial sources or are readily prepared.

Indole containing compounds of general structure I-5 and I-7 may be prepared in a variety of ways. For example, as shown in Scheme I, a hydrazine of general structure I-1 can be N-alkylated using standard conditions to afford the hydrazine I-2. Upon reaction with acetone, a Fisher-indole condensation then affords the indole I-4. Reversing the order of reactions (Fisher-indolization to yield I-3 then N-alkylation) provides an alternate way to synthesize I-4. Functionalization at C-3 of the indole I-4 can be carried out to generate the thioether I-5 (using a thiol and NCS in an inert solvent such as $CH_2Cl_2$). Similarly, reaction of I-3 with a thiol to generate the 3-substituted indole I-5 in which R=H can be followed by alkylation on the nitrogen. In the case where the thiol contains a benzoate ester the product is 1-6. The ester can then be hydrolyzed to the corresponding acid I-7. Using alternative thiols, compounds of general structure I-5 can be prepared in which ring A is a heterocycloalkyl or heteroaryl substituted with a carboxylic acid, ester or carboxylic acid equivalent. For example, picolinic acid derivatives can be prepared in this manner.

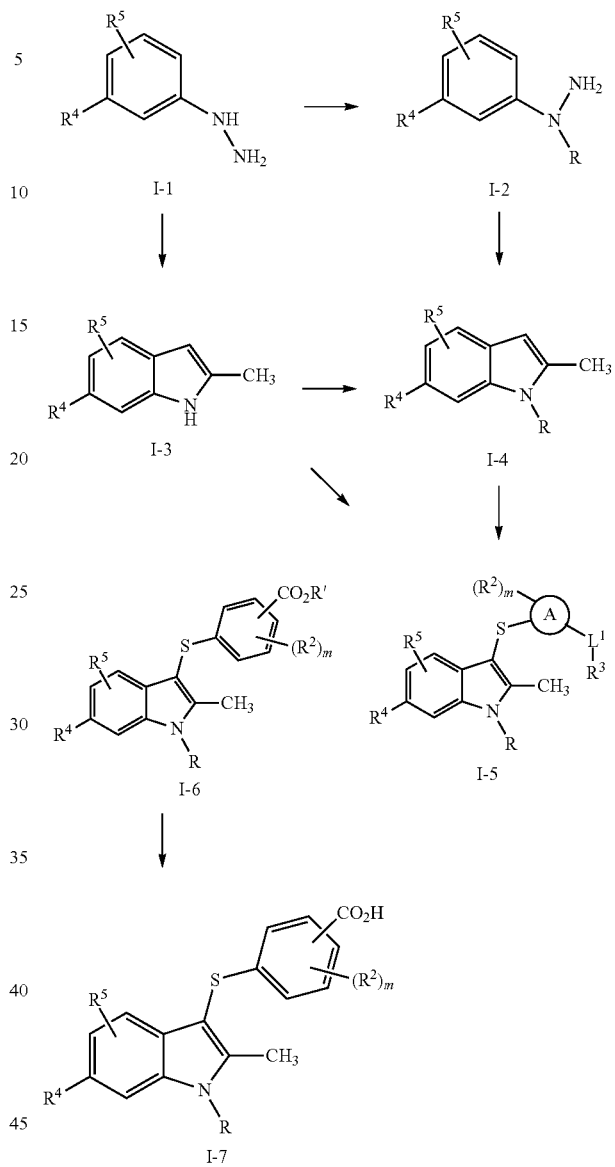

As shown in Scheme II, indoles containing 3-sulfides are prepared from hydrazines I-1 or I-2 using the Fisher-indole reaction with the appropriate α-thioether ketone. The sulfides II-2 may then be oxidized to the corresponding sulfoxide or sulfone (II-3).

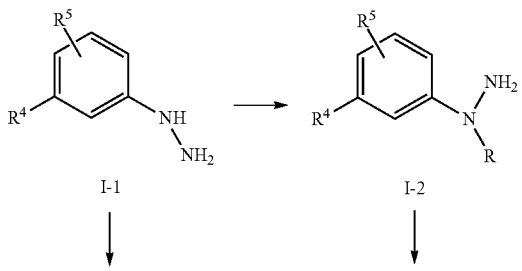

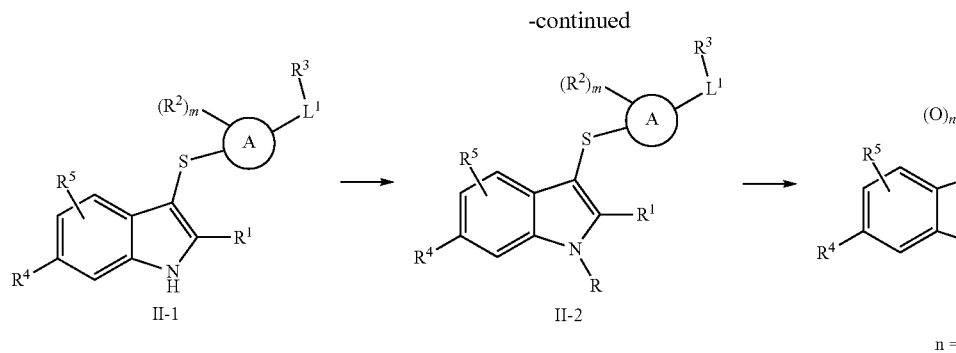

As shown in Scheme III, 3-H indoles (III-1) may be functionalized directly to introduce a 3-sulfide group using a variety of reaction conditions including, for example, a disulfide in the presence of NaH in a suitable organic solvent such as DMF or alternatively, a thiol in the presence of NCS in an inert solvent such as $CH_2Cl_2$.

Scheme III

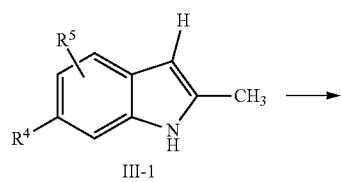

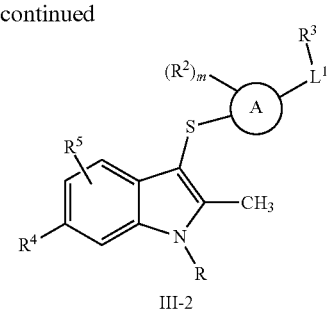

N—H Indoles of general structure IV-1 may be further modified as shown in Scheme IV.

Scheme IV

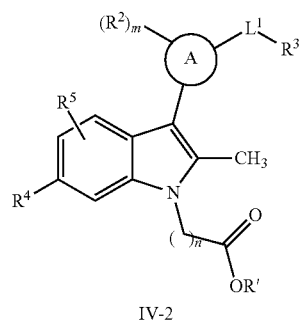

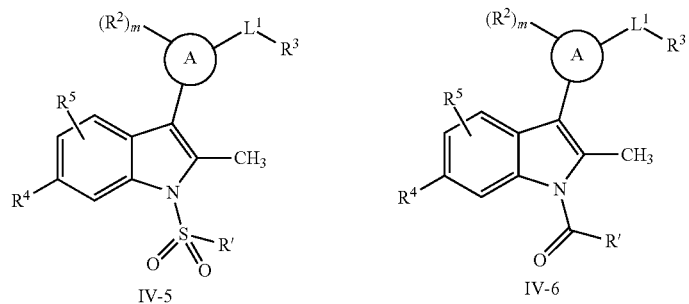

IV-5     IV-6     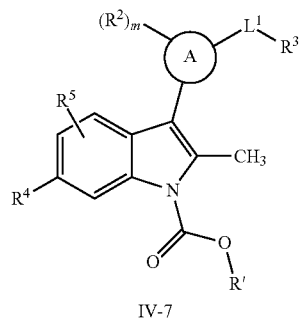

IV-7

Treatment with a base such as NaH followed by alkylation with an electrophile such as BrCH$_2$CO$_2$R' can then form compounds of general structure IV-2. Deprotection of the ester can then generate the corresponding acid which can be further reacted to generate, as examples, amides (e.g. IV-3), acylhydrazines, and the like. Alkylation with, for example BrCH$_2$C(=O)NR'R", will generate amides (and amide derivatives) of general structure IV-3. Deprotonation of IV-1 followed (e.g. by using NaH) by treatment with a variety of electrophiles (e.g. R'SO$_2$Cl; R'COCl, R'OCOCl) can then afford a series of N-functionalized compounds of general structures IV-4 to IV-7.

The Bartoli indole synthesis is shown in Scheme V and requires an ortho-substituted nitrobenzene (V-1).

Scheme V

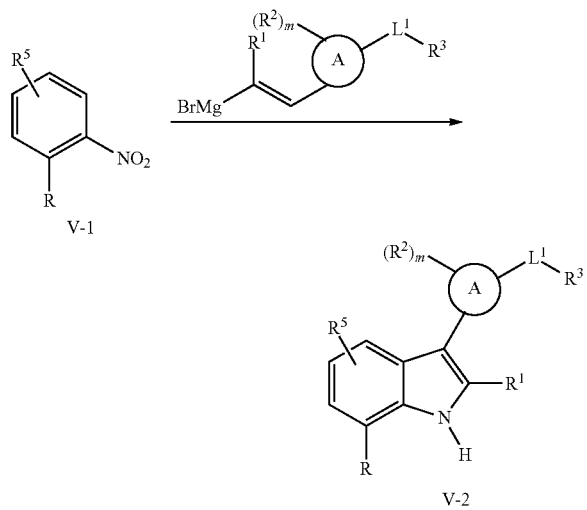

Treatment of V-1 with a vinyl magnesium Grignard reagent results in an indole of general structure V-2.

The Leimgruber-Batcho indole synthesis is described in Scheme VI.

Scheme VI

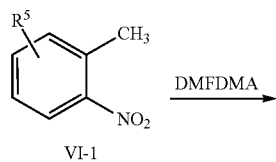

Substituted O-nitrotoluene VI-1 can be reacted with dimethylformamide dimethyl acetal (DMFDMA) to provide the vinyl intermediate VI-2. Reductive cyclization using, for example, Scheme VII describes the synthesis of indoles functionalized in the 2-position.

Scheme VII

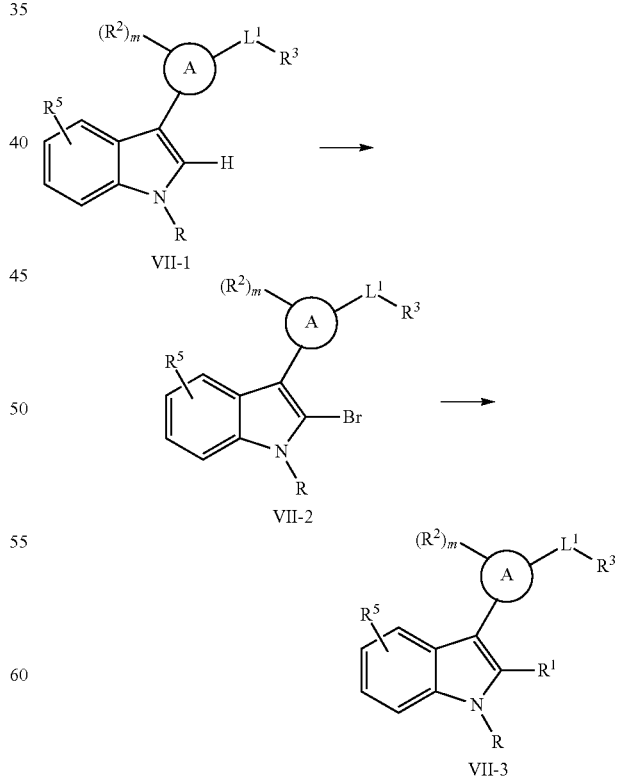

Treatment of 2-H indoles of general structure VII-1 with NBS/CCl$_4$ results in the 2-bromo indole VII-2. The bromine of VII-2 can then be further reacted to introduce other functionality. For example, cyclopropyl boronic acid under palladium catalysis will introduce a cyclopropyl group and similar reaction conditions may be used to introduce other alkyl groups (e.g. $CD_3$); $Zn(CN)_2$ under palladium catalysis will introduce a nitrile group.

An alternative procedure used to introduce 2-substituents onto the indole core is shown in Scheme VIII.

Scheme VIII

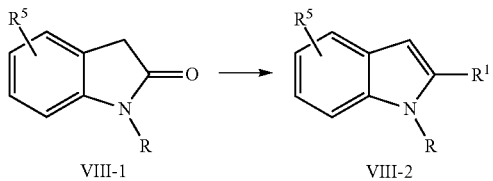

As shown in Scheme VIII, the procedure used to introduce 2-substituents onto the indole core commences with the 2-oxoindole VIII-1 which, upon treatment with $POCl_3$ yields the 2-chloro derivative VIII-2 (X=Cl) and $POBr_3$ yields VIII-2 (X=Br). The intermediate VIII-2 can then be further manipulated to introduce other substituents using standard chemistry and afford the desired indoles. In some embodiments, compounds described herein are synthesized as outlined in the Examples.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl.

Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers refers to a divalent alkyl radical. Any of the above mentioned monovalent alkyl groups may be an alkylene by abstraction of a second hydrogen atom from the alkyl. In some embodiments, an alkelene is a $C_1$-$C_6$alkylene. In other embodiments, an alkylene is a $C_1$-$C_4$alkylene. Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

"Deuteroalkyl" refers to an alkyl group where 1 or more hydrogen atoms of an alkyl are replaced with deuterium.

The term "alkenyl" refers to a type of alkyl group in which at least one carbon-carbon double bond is present. In one embodiment, an alkenyl group has the formula —C(R)=$CR_2$, wherein R refers to the remaining portions of the alkenyl group, which may be the same or different. In some embodiments, R is H or an alkyl. Non-limiting examples of an alkenyl group include —CH=$CH_2$, —C($CH_3$)=$CH_2$, —CH=$CHCH_3$, —C($CH_3$)=$CHCH_3$, and —$CH_2$CH=$CH_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. Non-limiting examples of an alkynyl group include —C≡CH, —C≡$CCH_3$—C≡$CCH_2CH_3$, —$CH_2$C≡CH.

An "alkoxy" group refers to a (alkyl)O— group, where alkyl is as defined herein.

The term "alkylamine" refers to the —N(alkyl)$_x$H$_y$ group, where x is 0 and y is 2, or where x is 1 and y is 1, or where x is 2 and y is 0.

The term "aromatic" refers to a planar ring having a delocalized π-electron system containing 4n+2 π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic.

The term "carboxylic acid bioisostere" refers to a functional group or moiety that exhibits similar physical, biological and/or chemical properties as a carboxylic acid moiety. Examples of carboxylic acid bioisosteres include, but are not limited to,

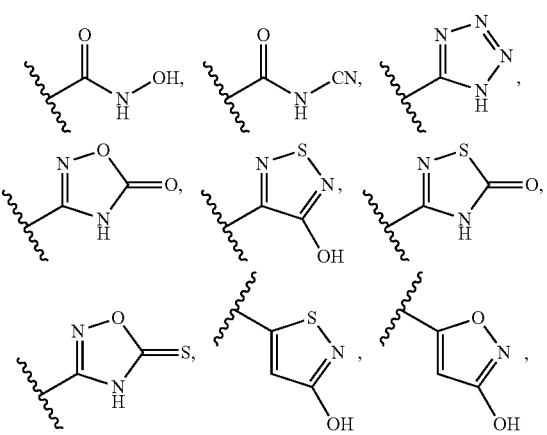

-continued

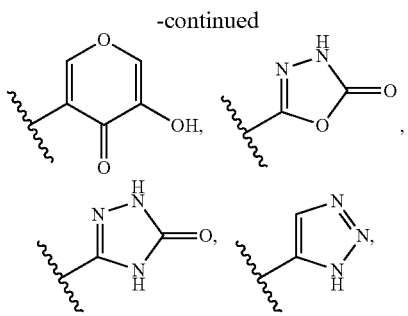

and the like.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a $C_6$-$C_{10}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[1.1.1]pentyl. In some embodiments, a cycloalkyl is a $C_3$-$C_6$cycloalkyl.

The term "halo" or, alternatively, "halogen" or "halide" means fluoro, chloro, bromo or iodo. In some embodiments, halo is fluoro, chloro, or bromo.

The term "fluoroalkyl" refers to an alkyl in which one or more hydrogen atoms are replaced by a fluorine atom. In one aspect, a fluoroalkyl is a $C_1$-$C_6$fluoroalkyl.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Monocyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" or "heteroalicyclic" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from halogen, —CN, —$NH_2$, —NH(alkyl), —N(alkyl)$_2$, —OH, —$CO_2H$, —$CO_2$alkyl, —C(=O)$NH_2$, —C(=O)NH(alkyl), —C(=O)N(alkyl)$_2$, —S(=O)$_2NH_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, —$NH_2$, —NH($CH_3$), —N($CH_3$)$_2$, —OH, —$CO_2H$, —$CO_2$($C_1$-$C_4$alkyl), —C(=O)$NH_2$, —C(=O)NH($C_1$-$C_4$alkyl), —C(=O)N($C_1$-$C_4$alkyl)$_2$, —S(=O)$_2NH_2$, —S(=O)$_2$NH($C_1$-$C_4$alkyl), —S(=O)$_2$N($C_1$-$C_4$alkyl)$_2$, $C_1$-$C_4$alkyl, $C_3$-$C_6$cycloalkyl, $C_1$-$C_4$fluoroalkyl, $C_1$-$C_4$heteroalkyl, $C_1$-$C_4$alkoxy, $C_1$-$C_4$fluoroalkoxy, —S$C_1$-$C_4$alkyl, —S(=O)$C_1$-$C_4$alkyl, and —S(=O)$_2C_1$-$C_4$alkyl. In some embodiments, optional substituents are independently selected from halogen, —CN, —$NH_2$, —OH, —NH($CH_3$), —N($CH_3$)$_2$, —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic) includes oxo (=O).

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist. In some embodiments, a modulator is a degrader.

The terms "administer," "administering", "administration," and the like, as used herein, refer to the methods that may be used to enable delivery of compounds or compositions to the desired site of biological action. These methods include, but are not limited to, oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein, or a pharmaceutically acceptable salt thereof, and a co-agent, are both administered to a patient simultaneously in the form of a single entity or dosage. The term "non-fixed combination" means that the active ingredients, e.g. a compound described herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may also be formulated in rectal compositions such as suppositories or retention enemas, e.g., containing conventional suppository bases such as cocoa butter, polyethylene glycol, or other glycerides.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds described herein, or a pharmaceutically acceptable salt thereof, are used in the preparation of medicaments for the treatment of diseases or conditions in a mammal that would benefit from inhibition or reduction of autotaxin activity. Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Combination Treatments

In certain instances, it is appropriate to administer at least one compound described herein, or a pharmaceutically acceptable salt thereof, in combination with one or more other therapeutic agents. In certain embodiments, the pharmaceutical composition further comprises one or more anticancer agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound described herein, or a pharmaceutically acceptable salt thereof, is co-administered with a second therapeutic agent, wherein the compound described herein, or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply be additive of the two therapeutic agents or the patient experiences a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens is optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound described herein, or a pharmaceutically acceptable salt thereof, is initiated prior to, during, or after treatment with a second agent described herein, and continues until any time during treatment with the second agent or after termination of treatment with the second agent. It also includes treatments in which a compound described herein, or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

Exemplary Agent for Use in Combination Therapy

In some embodiments, a compound described herein, or a pharmaceutically acceptable salt thereof, is administered in combination with chemotherapy, hormone blocking therapy, radiation therapy, monoclonal antibodies, or combinations thereof.

Hormone blocking therapy includes the use of agents that block the production of estrogens or block the estrogen receptors. In some embodiments, hormone blocking therapy includes the use of estrogen receptor modulators and/or aromatase inhibitors. Estrogen receptor modulators include triphenylethylene derivatives (e.g. tamoxifen, toremifene, droloxifene, 3-hydroxytamoxifen, idoxifene, TAT-59 (a phosphorylated derivative of 4-hydroxytamoxifen) and GW5638 (a carboxylic acid derivative of tamoxifen)); non-steroidal estrogen receptor modulators (e.g. raloxifene, LY353381 (SERM3) and LY357489); steroidal estrogen receptor modulators (e.g. ICI-182,780). Aromatase inhibitors include steroidal aromatase inhibitors and non-steroidal aromatase inhibitors. Steroidal aromatase inhibitors include, but are not limited to, such exemestane. Non-steroidal aromatase inhibitors include, but are not limited to, as anastrozole, and letrozole.

Chemotherapy includes the use of anti-cancer agents.

In some embodiments, anti-cancer agents for use in combination with a compound described herein, or a pharmaceutically acceptable salt thereof, include one or more of the following: abiraterone; abarelix; abraxane, adriamycin; actinomycin; acivicin; aclarubicin; acodazole hydrochloride; acronine; adozelesin; aldesleukin; alemtuzumab; allopurinol; alitretinoin; altretamine; ametantrone acetate; aminoglutethimide; aminolevulinic acid; amifostine; amsacrine; anastrozole; anthramycin; aprepitant; arsenic trioxide; asparaginase; asperlin; azacitidine; azetepa; azotomycin; batimastat; bendamustine hydrochloride; benzodcpa; bevacizumab; bexarotenc; bicalutamide; bisantrene hydrochloride; bisnafide dimesylate; bizelesin; bleomycin; bleomycin sulfate; bortezomib; brequinar sodium; bropirimine; busulfan; cactinomycin; calusterone; caracemide; carbetimer; carboplatin; carmustine; carubicin hydrochloride; carzelesin; capecitabine; cedefingol; cetuximab; chlorambucil; cirolemycin; cisplatin; cladribine; clofarabine; crisnatol mesylate; cyclophosphamide; cytarabine; dacarbazine; dasatinib; daunorubicin hydrochloride; dactinomycin; darbepoetin alfa; decitabine; degarelix; denileukin diftitox; dexormaplatin; dexrazoxane hydrochloride; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; eltrombopag olamine; enloplatin; enpromate; epipropidine; epirubicin hydrochloride; epoetin alfa; erbulozole; erlotinib hydrochloride; esorubicin hydrochloride; estramustine; estramustine phosphate sodium; etanidazole; etoposide; etoposide phosphate; etoprine; everolimus; exemestane; fadrozole hydrochloride; fazarabine; fenretinide; filgrastim; floxuridine; fludarabine phosphate; fluorouracil; flurocitabine; fosquidone; fostriecin sodium; fulvestrant; gefitinib; gemcitabine; gemcitabine hydrochloride; gemcitabine-cisplatin; gemtuzumab ozogamicin; goserelin acetate; histrelin acetate; hydroxyurea; idarubicin hydrochloride; ifosfamide; iimofosine; ibritumomab tiuxetan; idarubicin; ifosfamide; imatinib mesylate; imiquimod; interleukin Il (including recombinant interleukin II, or r1L2), interferon alfa-2a; interferon alfa-2b; interferon alfa-n1; interferon alfa-n3; interferon beta-1 a; interferon gamma-1 b; iproplatin; irinotecan hydrochloride; ixabepilone; lanreotide acetate; lapatinib; lenalidomide; letrozole; leuprolide acetate; leucovorin calcium; leuprolide acetate; levamisole; liposomal cytarabine; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; methoxsalen; metoprine; meturedepa; mitindomide; mitocarcin; mitocromin; mitogillin; mitomalcin; mitomycin C; mitosper; mitotane; mitoxantrone hydrochloride; mycophenolic acid; nandrolone phenpropionate; nelarabine; nilotinib; nocodazoie; nofetumomab; nogalamycin; ofatumumab; oprelvekin; ormaplatin; oxaliplatin; oxisuran; paclitaxel; palifermin; palonosetron hydrochloride; pamidronate; pegfilgrastim; pemetrexed disodium; pentostatin; panitumumab; pazopanib hydrochloride; pemetrexed disodium; plerixafor; pralatrexate; pegaspargase; peliomycin; pentamustine; peplomycin sulfate; perfosfamide; pipobroman; piposulfan; piroxantrone hydrochloride; plicamycin; plomestane; pomalidomide, porfimer sodium; porfiromycin; prednimustine; procarbazine hydrochloride; puromycin; puromycin hydrochloride; pyrazofurin; quinacrine; raloxifene hydrochloride; rasburicase; recombinant HPV bivalent vaccine; recombinant HPV quadrivalent vaccine; riboprine; rogletimide; rituximab; romidepsin; romiplostim; safingol; safingol hydrochloride; sargramostim; semustine; simtrazene; sipuleucel-T; sorafenib; sparfosate sodium; sparsomycin; spirogermanium hydrochloride; spiromustine; spiroplatin; streptonigrin; streptozocin; sulofenur; sunitinib malate; talisomycin; tamoxifen citrate; tecogalan sodium; tegafur; teloxantrone hydrochloride; temozolomide; temoporfin; temsirolimus; teniposide; teroxirone; testolactone; thalidomide; thiamiprine; thioguanine; thiotepa; tiazofurin; tirapazamine; topotecan hydrochloride; toremifene; tositumomab and I$^{131}$ Iodine tositumomab; trastuzumab; trestolone acetate; tretinoin; triciribine phosphate; trimetrexate; trimetrexate glucuronate; triptorelin; tubulozole hydrochloride; uracil mustard; uredepa; valrubicin;

vapreotide; verteporfin; vinblastine; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorinostat; vorozole; zeniplatin; zinostatin; zoledronic acid; and zorubicin hydrochloride.

Monoclonal antibodies include, but are not limited to, trastuzumab (Herceptin) and rituximab (Rituxan).

In some embodiments, the at least one additional chemotherapeutic agent is selected from, by way of example only, alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

In one aspect, the compound described herein, or a pharmaceutically acceptable salt thereof, is administered or formulated in combination with one or more anti-cancer agents. In some embodiments, one or more of the anti-cancer agents are proapoptotic agents. Examples of anti-cancer agents include, but are not limited to, any of the following: gossypol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib, geldanamycin, 17-N-Allylamino-17-Demethoxygeldanamycin (17-AAG), flavopiridol, LY294002, bortezomib, carfilzomib, trastuzumab, BAY 11-7082, PKC412, or PD184352, paclitaxel, and analogs of paclitaxel. Compounds that have the basic taxane skeleton as a common structure feature, have also been shown to have the ability to arrest cells in the G2-M phases due to stabilized microtubules and are optionally useful for treating cancer in combination with the compounds described herein.

Further examples of anti-cancer agents for use in combination with a compound described herein, or a pharmaceutically acceptable salt thereof, include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; activin inhibitors, PKM2 inhibitors, c-fms inhibitors and histone deacetylase inhibitors. Further examples of anti-cancer agents for use in combination with a compound described herein, or a pharmaceutically acceptable salt thereof, include aromatase inhibitors. Aromatase inhibitors include steroidal aromatase inhibitors and non-steroidal aromatase inhibitors. Steroidal aromatase inhibitors include, but are not limited to, exemestane. Non-steroidal aromatase inhibitors include, but are not limited to, anastrozole, and letrozole.

Yet other anticancer agents for use in combination with a compound described herein, or a pharmaceutically acceptable salt thereof, include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.).

Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products for use in combination with a compound described herein, or a pharmaceutically acceptable salt thereof, include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents for use in combination with a compound described herein, or a pharmaceutically acceptable salt thereof, include, but are not limited to, nitrogen mustards (e.g., mechloroethamine, cyclophosphamide, chlorambucil, meiphalan, etc.), ethylenimine and methylmelamines (e.g., hexamethylymelamine, thiotepa), alkyl sulfonates (e.g., busulfan), nitrosoureas (e.g., carmustine, lomusitne, semustine, streptozocin, etc.), or triazenes (decarbazine, etc.).

In some embodiments, a compound described herein, or a pharmaceutically acceptable salt thereof, is used to treat cancer in combination with: an antiestrogen (e.g., tamoxifen), an antiandrogen (e.g., bicalutamide, flutamide), a gonadotropin releasing hormone analog (e.g., leuprolide).

Other agents that are optionally used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules include without limitation the following marketed drugs and drugs in development: Erbulozole, Dolastatin 10, Mivobulin isethionate, Vincristine, NSC-639829, Discodermolide, ABT-751, Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride, Epothilones (such as Epothilone A, Epothilone B, Epothilone C, Epothilone D, Epothilone E, Epothilone F, Epothilone B N-oxide, Epothilone A N-oxide, 16-aza-epothilone B, 21-aminoepothilone B, 21-hydroxyepothilone D, 26-fluoroepothilone, Auristatin PE, Soblidotin, Vincristine sulfate, Cryptophycin 52, Vitilevuamide, Tubulysin A, Canadensol, Centaureidin, Oncocidin A1 Fijianolide B, Laulimalide, Narcosine, Nascapine, Hemiasterlin, Vanadocene acetylacetonate, Indanocine Eleutherobins (such as Desmethyleleutherobin, Desaetyleleutherobin, isoeleutherobin A, and Z-Eleutherobin), Caribaeoside, Caribaeolin, Halichondrin B, Diazonamide A, Taccalonolide A, Diozostatin, (−)-Phenylahistin, Myoseverin B, Resverastatin phosphate sodium.

In one aspect, a compound described herein, or a pharmaceutically acceptable salt thereof, is co-administered with thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

In some embodiments, a compound described herein, or a pharmaceutically acceptable salt thereof, is used in combination with anti-emetic agents to treat nausea or emesis, which result from the use of a compound described herein, or a pharmaceutically acceptable salt thereof, anti-cancer agent(s) and/or radiation therapy.

Anti-emetic agents include, but are not limited to: neurokinin-1 receptor antagonists, 5HT3 receptor antagonists (such as ondansetron, granisetron, tropisetron, palonosetron, and zatisetron), $GABA_B$ receptor agonists (such as baclofen), corticosteroids (such as dexamethasone, prednisone, prednisolone, or others), dopamine antagonists (such as, but not limited to, domperidone, droperidol, haloperidol, chlorpromazine, promethazine, prochlorperazine, metoclopramide), antihistamines (H1 histamine receptor antagonists, such as but not limited to, cyclizine, diphenhydramine, dimenhydrinate, meclizine, promethazine, hydroxyzine), cannabinoids (such as but not limited to, cannabis, marinol, dronabinol), and others (such as, but not limited to, trimethobenzamide; ginger, emetrol, propofol).

In some embodiments, a compound described herein, or a pharmaceutically acceptable salt thereof, is used in combination with an agent useful in the treatment of anemia. Such an anemia treatment agent is, for example, a continuous eythropoiesis receptor activator (such as epoetin-c).

In some embodiments, a compound described herein, or a pharmaceutically acceptable salt thereof, is used in combination with an agent useful in the treatment of neutropenia. Examples of agents useful in the treatment of neutropenia include, but are not limited to, a hematopoietic growth factor which regulates the production and function of neutrophils such as a human granulocyte colony stimulating factor, (G-CSF). Examples of a G-CSF include filgrastim.

In one aspect, a compound described herein, or a pharmaceutically acceptable salt thereof, is administered in combination with one or more immunosuppressants. Immunosuppressive therapy is clinically used to treat or prevent the rejection of transplanted organs and tissues (e.g. bone marrow, heart, kidney, liver); treatment of autoimmune diseases or diseases that are most likely of autoimmune origin (e.g. rheumatoid arthritis, myasthenia gravis, systemic lupus erythematosus, Crohn's disease, and ulcerative colitis); and treatment of some other non-autoimmune inflammatory diseases (e.g. long term allergic asthma control), and in the treatment of fibrotic conditions.

In some embodiments, a compound described herein, or a pharmaceutically acceptable salt thereof, is administered with a corticosteroid. In some embodiments, a compound described herein, or a pharmaceutically acceptable salt thereof, is administered with an a therapeutic agent selected from among: Calcineurin inhibitors (such as, but not limited to, cyclosporin, tacrolimus); mTOR inhibitors (such as, but not limited to, sirolimus, everolimus); anti-proliferatives (such as, but not limited to, azathioprine, mycophenolic acid); corticosteroids (such as, but not limited to, prednisone, cortisone acetate, prednisolone, methylprednisolone, dexamethasone, betamethasone, triamcinolone, beclometasone, fludrocortisone acetate, deoxycorticosterone acetate, aldosterone, hydrocortisone); antibodies (such as, but not limited to, monoclonal anti-IL-2Rα receptor antibodies (basiliximab, daclizumab), polyclonal anti-T-cell antibodies (anti-thymocyte globulin (ATG), anti-lymphocyte globulin (ALG)), B-cell antagonists, rituximab, natalizumab.

Other therapeutic agents include, but are not limited to: cyclophosphamide, penicillamine, cyclosporinc, nitrosourcas, cisplatin, carboplatin, oxaliplatin, methotrcxate, azathioprinc, mercaptopurine, pyrimidine analogues, protein synthesis inhibitors, dactinomycin, anthracyclines, mitomycin C, bleomycin, mithramycin, Atgam$^{(R)}$, Thymoglobuline®, OKT3®, basiliximab, daclizumab, cyclosporin, tacrolimus, sirolimus, Interferons (IFN-β, IFN-γ), opioids, TNF binding proteins (infliximab, etanercept, adalimumab, golimumab), leflunomide, gold thioglucose, gold thiomalate, aurofin, sulfasalazine, hydroxychloroquinine, minocycline, rapamicin, mycophenolic acid, mycophenolate mofetil, FTY720, as well as those listed in U.S. Pat. No. 7,060,697.

In one embodiment, a compound described herein, or a pharmaceutically acceptable salt thereof, is administered in combination with Cyclosporin A (CsA) or tacrolimus (FK506). In one embodiment, a compound described herein, or a pharmaceutically acceptable salt thereof, is administered to a mammal in combination with an anti-inflammatory agent including, but not limited to, non-steroidal anti-inflammatory drugs (NSAIDs), phosphodiesterase-4 inhibitors. JNK kinase inhibitors and corticosteroids (glucocorticoids).

In some embodiments, a compound described herein, or a pharmaceutically acceptable salt thereof, is administered with corticosteroids. Corticosteroids, include, but are not limited to: betamethasone, prednisone, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

In one embodiment, a compound described herein, or a pharmaceutically acceptable salt thereof, is administered to a mammal in combination with a non-steroidal anti-inflammatory drug (NSAID). NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, flurobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, lumiracoxib, CS-502, JTE-522, L-745,337 and NS398).

In some embodiments, a compound described herein, or a pharmaceutically acceptable salt thereof, is co-administered with an analgesic.

In some embodiments, a compound described herein, or a pharmaceutically acceptable salt thereof, is used in combination with radiation therapy (or radiotherapy). Radiation therapy is the treatment of cancer and other diseases with ionizing radiation. Radiation therapy is optionally used to treat localized solid tumors, such as cancers of the skin, tongue, larynx, brain, breast, prostate, colon, liver, uterus and/or cervix. It is also optionally used to treat leukemia and lymphoma (cancers of the blood-forming cells and lymphatic system, respectively).

A technique for delivering radiation to cancer cells is to place radioactive implants directly in a tumor or body cavity.

This is called internal radiotherapy (brachytherapy, interstitial irradiation, and intracavitary irradiation are types of internal radiotherapy.) Using internal radiotherapy, the radiation dose is concentrated in a small area, and the patient stays in the hospital for a few days. Internal radiotherapy is frequently used for cancers of the tongue, uterus, prostate, colon, and cervix.

The term "radiotherapy" or "ionizing radiation" include all forms of radiation, including but not limited to α, β, and γ radiation and ultraviolet light.

EXAMPLES

The following examples are provided for illustrative purposes only and not to limit the scope of the claims provided herein.

Synthesis of Int-A

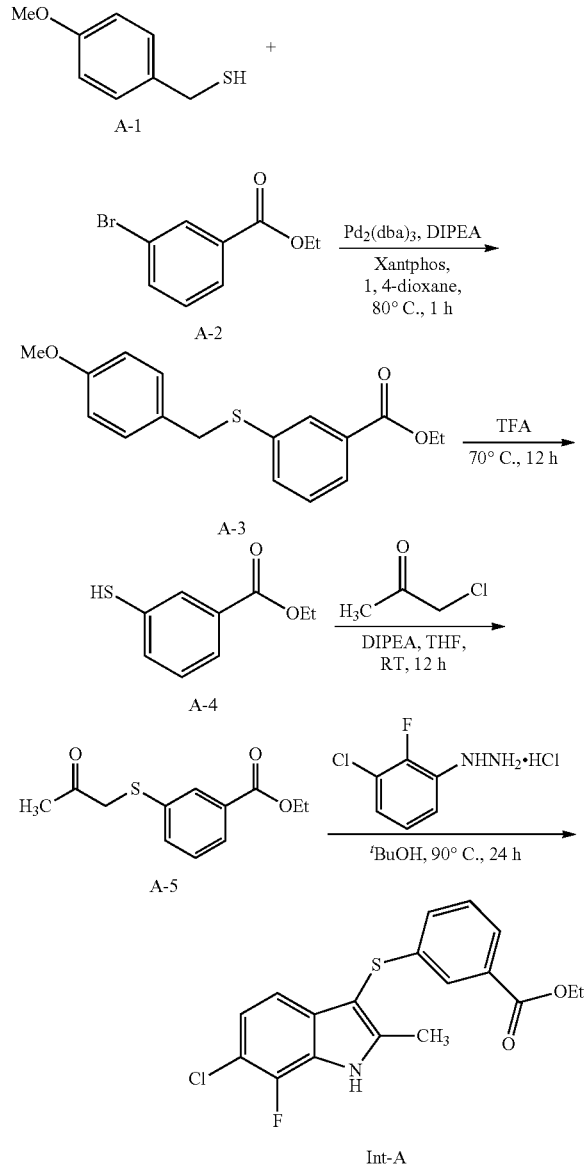

Step 1: Ethyl 3-((4-methoxybenzyl)thio)benzoate (A-3)

A solution of 1, 4-dioxane (250 mL) was degassed for 30 min and to this were added ethyl 3-bromobenzoate A-2 (6.7 g, 43.6 mmol) in 1, 4-dioxane (30 mL), (4-methoxyphenyl)methanethiol A-1 (10 g, 43.6 mmol), xantphos (1.2 g, 2.18 mmol), Pd$_2$(dba)$_3$ (990 mg, 1.09 mmol), DIPEA (16 mL, 87.3 mmol) at RT. The reaction was heated to 80° C. and stirred for 1 h. The reaction progress was monitored by TLC. After reaction completion, the reaction mixture was diluted with water (40 mL) and extracted with EtOAc (2×40 mL). The combined organic extracts were dried over Na$_2$SO$_4$, filtered and concentrated under reduced pressure to obtain crude material. The crude material was purified through silica gel flash column chromatography using 3% EtOAc/Hexanes to afford compound A-3 (10 g, 77%) as pale green semi-solid. $^1$H NMR (500 MHz, CDCl$_3$): δ 7.98 (s, 1H), 7.83 (d, J=8.0 Hz, 1H), 7.44-7.41 (m, 1H), 7.32-7.28 (m, 1H), 7.25-7.10 (m, 2H), 6.81 (d, J=9.0 Hz, 2H), 4.38-4.34 (m, 2H), 4.11 (s, 2H), 3.80 (s, 3H), 1.38 (t, J=7.0 Hz, 3H).

Step 2: Ethyl 3-mercaptobenzoate (A-4)

A stirred solution of compound A-3 (10 g, 33.3 mmol) in TFA (16.6 mL) was heated to 70° C. and stirred for 12 h. The reaction progress was monitored by TLC; after reaction completion, the volatile reagents and solvent were removed under reduced pressure. The residue was dissolved in ice water (20 mL), basified with solid NaHCO$_3$ and extracted with EtOAc (2×30 mL). The combined organic extracts were dried over Na$_2$SO$_4$, filtered and concentrated under reduced pressure to obtain crude material. The crude material was purified through silica gel flash column chromatography using 3% EtOAc/Hexanes to afford compound A-4 (4.66 g, 77%) as pale brown syrup. $^1$H NMR (400 MHz, CDCl$_3$): δ 7.95 (s, 1H), 7.94-7.80 (m, 1H), 7.45-7.42 (m, 1H), 7.28 (t, J=8.0 Hz, 1H), 4.37 (q, 2H), 3.54 (s, 1H), 1.39 (t, J=7.2 Hz, 3H).

Step 3: Ethyl 3-((2-oxopropyl)thio)benzoate (A-5)

To a stirred solution of compound A-4 (4.6 g, 25.27 mmol) in THF (164 mL) under inert atmosphere was added chloroacetone (4.67 g, 50.54 mmol) dropwise at 0° C. The reaction mixture was warmed to RT. DIPEA (13.9 mL, 75.82 mmol) was added, and the reaction mixture was stirred for 12 h. The reaction progress was monitored by TLC; after reaction completion, the reaction mixture was diluted with water (30 mL) and extracted with EtOAc (2×30 mL). The combined organic extracts were dried over Na$_2$SO$_4$, filtered and concentrated under reduced pressure to obtain crude material. The crude material was purified through silica gel flash column chromatography using 8% EtOAc/Hexanes to afford compound A-5 (5.25 g, 88%) as pale brown syrup. $^1$H NMR (400 MHz, CDCl$_3$): δ 8.00 (s, 1H), 7.89-7.87 (m, 1H), 7.52-7.49 (m, 1H), 7.36 (t, J=8.0 Hz, 1H), 4.37 (q, 2H), 3.72 (s, 2H), 2.29 (s, 3H), 1.39 (t, J=6.8 Hz, 3H). LC-MS: 98%; (M+H$_2$O)$^+$ Found=256.2; (column: X Select C-18, 50×3.0 mm, 3.5 μm); RT 3.67 min. 5 mM NH$_4$OAc: ACN; 0.8 mL/min).

Step 4: Ethyl 3-((6-chloro-7-fluoro-2-methyl-1H-indol-3-yl)thio)benzoate (Int-A)

To a stirred solution of compound A-5 (5.25 g, 22.05 mmol) in t-BuOH (200 mL) under inert atmosphere was added (3-chloro-2-fluorophenyl) hydrazine hydrochloride (6.5 g, 33.08 mmol) at RT. The reaction mixture was heated to 90° C. and stirred for 24 h. The reaction progress was monitored by TLC; after reaction completion, the reaction mixture was diluted with ice cold water (30 mL) and extracted with EtOAc (2×30 mL). The combined organic extracts were dried over Na2SO4, filtered and concentrated under reduced pressure to obtain crude material. The crude material was purified through silica gel flash column chromatography using 3% EtOAc/hexanes to afford Int-A (3.5 g, 44%) as an off-white solid. $^1$H NMR (400 MHz, CDCl$_3$): 8.52 (br s, 1H), 7.77 (s, 1H), 7.73 (d, J=8.0 Hz, 1H), 7.25-7.17 (m, 2H), 7.12-7.05 (m, 2H), 4.32 (q, 2H), 2.53 (s, 3H), 1.34 (t, J=6.8 Hz, 3H).

Synthesis of Ethyl 2-fluoro-3-mercaptobenzoate (Int-B)

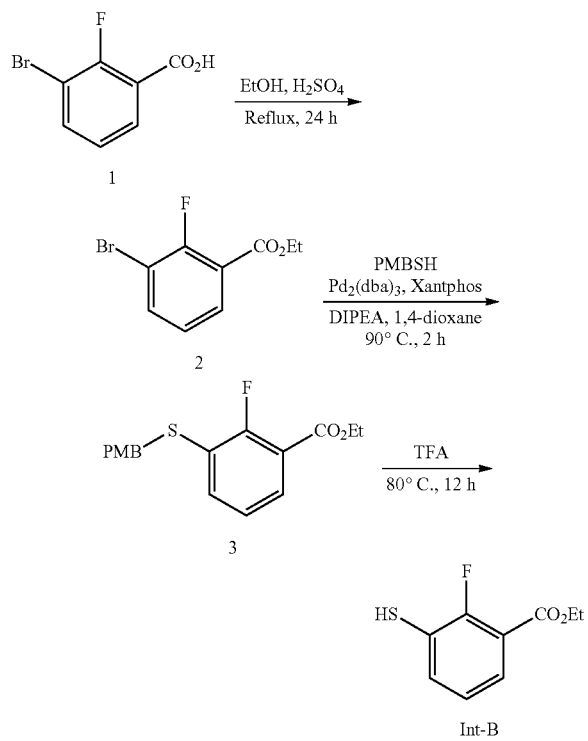

Step 1: Ethyl 3-bromo-2-fluorobenzoate (2)

To a stirred solution of 3-bromo-2-fluorobenzoic acid 1 (25.0 g, 114.15 mmol) in ethanol (400 mL) was added conc. H$_2$SO$_4$ (3 mL) at RT and stirred at reflux temperature for 24 h. The reaction was monitored by LC-MS; after completion of the reaction, the reaction mixture was concentrated to obtain the residue. The residue was diluted with EtOAc (500 mL), washed with water (300 mL), brine (300 mL), dried over Na$_2$SO$_4$, filtered and concentrated under reduced pressure to afford compound 2 (26.0 g, 92%) as a light yellow liquid. $^1$H NMR (400 MHz, CDCl$_3$): δ7.88-7.84 (m, 1H), 7.72-7.69 (m, 1H), 7.08-7.04 (m, 1H), 4.39 (q, J=7.2 Hz, 2H), 1.39 (t, J=7.2 Hz, 3H).

Step 2: Ethyl 2-fluoro-3-((4-methoxybenzyl)thio)benzoate (3)

1,4-dioxane (250 mL) was degassed by purging with N$_2$ gas for 30 min and to this, were added a solution of compound 2 (13.2 g, 53.4 mmol) in 1,4-dioxane (50 mL; degassed), (4-methoxyphenyl)methanethiol (PMBSH) (8.2 g, 53.4 mmol), xantphos (1.54 g, 2.66 mmol), diisopropyl ethyl amine (19.6 mL, 106.8 mmol) and Pd$_2$(dba)$_3$ (1.22 g, 1.33 mmol) at RT. The reaction mixture was heated to 90° C. and stirred for 2 h. The reaction was monitored by TLC; after completion of the reaction, the reaction mixture was diluted with hexane (450 mL) and stirred at RT for 15 min. The resultant solution was filtered through celite and washed with hexane (100 mL). The filtrate was washed water (250 mL) dried over Na$_2$SO$_4$, filtered and concentrated under reduced pressure to obtain the crude. This was purified by silica gel column chromatography using 3-4% EtOAc/Hexanes to afford compound 3 (15 g, 88%) as pale yellow solid. $^1$H NMR (500 MHz, CDCl$_3$): δ 7.78-7.74 (m, 1H), 7.43-7.39 (m, 1H), 7.19 (d, J=8.0 Hz, 2H), 7.07-7.04 (m, 1H), 6.80 (d, J=8.0 Hz, 2H), 4.41 (q, J=7.2 Hz, 2H), 4.08 (s, 2H), 3.78 (s, 3H), 1.41 (t, J=7.2 Hz, 3H). LC-MS: m/z (M−H)$^+$ Found=318.9.

Step 3: Ethyl 2-fluoro-3-mercaptobenzoate (Int-B)

A stirred solution of compound 3 (30.0 g, 93.75 mmol) in TFA (54.5 mL) was heated to 80° C. and stirred for 12 h under inert atmosphere. The reaction was monitored by TLC; after completion of the reaction, the volatiles were removed under reduced pressure. The residue was dissolved in ice-cold water (100 mL), basified with solid sodium bicarbonate and extracted with EtOAc (2×200 mL). The combined organic extracts were dried over Na$_2$SO$_4$, filtered and concentrated under reduced pressure to obtain the crude. This was purified by silica gel column chromatography using 3% EtOAc/Hexanes to afford compound Int-B (11.7 g, 62%) as a pale brown syrup. $^1$H NMR (500 MHz, CDCl$_3$): δ 7.70-7.66 (m, 1H), 7.48-7.44 (m, 1H), 7.08-7.04 (m, 1H), 4.20 (q, J=7.5 Hz, 2H), 3.67 (s, 1H), 1.40 (t, J=7.5 Hz, 3H); LC-MS: m/z (M−H)$^+$ Found=199.0.

Example 1

3-((6-Chloro-1-(2-((3,5-dichlorophenyl)amino)-2-oxoethyl)-7-fluoro-2-methyl-1H-indol-3-yl)thio)benzoic acid (Compound 1-4)

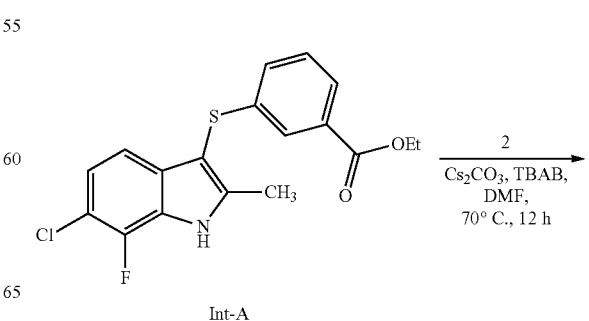

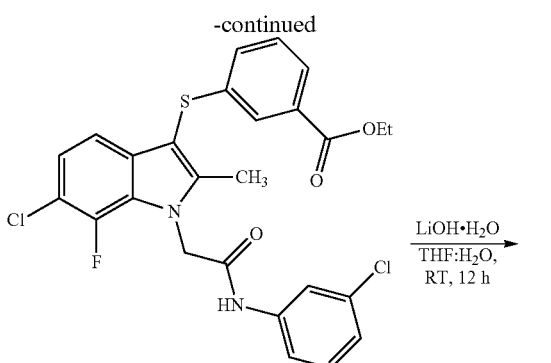

3

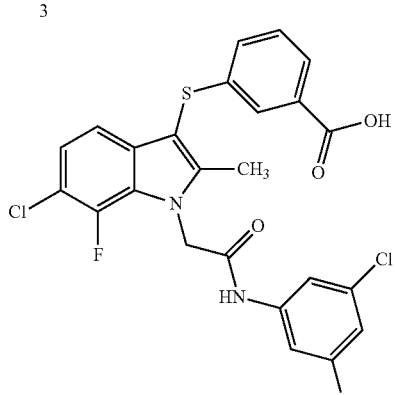

Compound 1-4

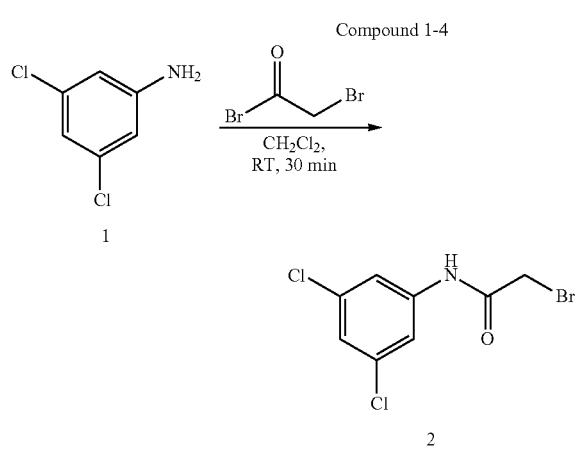

Step 1: 2-Bromo-N-(3,5-dichlorophenyl)acetamide (2)

To a stirred solution of bromo acetyl bromide (3.3 g, 16.41 mmol) in CH$_2$Cl$_2$ (15 mL) was added 3, 5-dichloroaniline 1 (2.65 g, 16.41 mmol) in CH$_2$Cl$_2$ (10 mL) for 10 min at RT and stirred for 30 min. The reaction progress was monitored by TLC; after reaction completion, the volatile reagents and solvent were removed under reduced pressure. The residue was diluted with water (40 mL) and extracted with CH$_2$Cl$_2$ (2×40 mL). The combined organic extracts were dried over Na$_2$SO$_4$, filtered and concentrated under reduced pressure to obtain compound 2 (3.8 g, 65%) as an off-white solid. $^1$H NMR (500 MHz, CDCl$_3$): δ 8.13 (br s, 1H), 7.51 (s, 2H), 7.16 (s, 1H), 4.01 (s, 2H).

Step 2: 2-(6-Chloro-7-fluoro-2-methyl-3-((3-propionylphenyl)thio)-1H-indol-1-yl)-N-(3,5-dichlorophenyl)acetamide (3)

To a stirred solution of Int-A (100 mg, 0.27 mmol) in DMF (5 mL) under inert atmosphere were added compound 2 (156 mg, 0.55 mmol), Bu$_4$NBr (4.4 mg, 0.013 mmol), and Cs$_2$CO$_3$ (179 mg, 0.55 mmol) at RT. The reaction mixture was heated to 70° C. and stirred for 12 h. The reaction progress was monitored by TLC; after reaction completion, the reaction mixture was diluted with water (15 mL) and extracted with EtOAc (2×25 mL). The combined organic extracts were dried over Na$_2$SO$_4$, filtered and concentrated under reduced pressure to obtain crude material. The crude material was purified through silica gel flash column chromatography using 3% EtOAc/hexanes to afford compound 100 mg of 3 with impurity as colorless semi-solid. $^1$H NMR (500 MHz, DMSO-d$_6$): δ 10.85 (s, 1H), 7.67-7.61 (m, 4H), 7.36 (t, J=8.0 Hz, 1H), 7.31 (s, 1H), 7.20-7.16 (m, 3H), 5.2 (s, 2H), 4.27-4.24 (m, 2H), 2.08 (s, 3H), 1.27-1.23 (m, 3H).

Step 3: 3-((6-Chloro-1-(2-((3, 5-dichlorophenyl)amino)-2-oxoethyl)-7-fluoro-2-methyl-1H-indol-3-yl)thio)benzoic acid (Compound 1-4)

To a stirred solution of compound 3 (100 mg) in THF:H$_2$O (1:1, 4 mL) was added LiOH monohydrate (35.6 mg, 0.84 mmol) at RT. The reaction mixture was stirred for 12 h. The reaction progress was monitored by TLC; after reaction completion, the volatile reagents and solvent were removed under reduced pressure. The residue was dissolved in water (20 mL), acidified with 2 M HCl solution to adjust pH~4 and the aqueous layer was extracted with EtOAc (2×20 mL). The combined organic extracts were dried over Na$_2$SO$_4$, filtered and concentrated under reduced pressure to obtain crude material. The crude material was purified through silica gel flash column chromatography using 30% EtOAc/hexanes to afford 20 mg of compound 1-4 as an off-white solid. $^1$H NMR (500 MHz, DMSO-d$_6$): δ 13.00 (br s, 1H), 10.84 (s, 1H), 7.67-7.61 (m, 4H), 7.36 (t, J=8.0 Hz, 1H), 7.31 (s, 1H), 7.20-7.16 (m, 3H), 5.27 (s, 2H), 2.48 (s, 3H). MS (ESI): m/z (M−H)$^+$ Found=535.2. HPLC: 98.9%; (column: Acquity UPLC BEH C-18 (2.1×50 mm, 1.7 µ); RT 3.18 min. ACN: 0.025% TFA (aq); 0.5 mL/min.

Example 2

3-((6-Chloro-7-fluoro-2-methyl-1-(2-oxo-2-(phenylamino)ethyl)-1H-indol-3-yl)thio)benzoic acid (Compound 1-3)

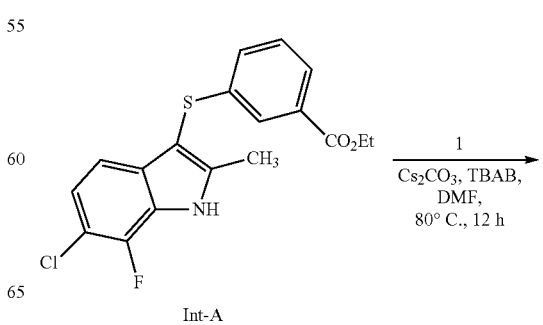

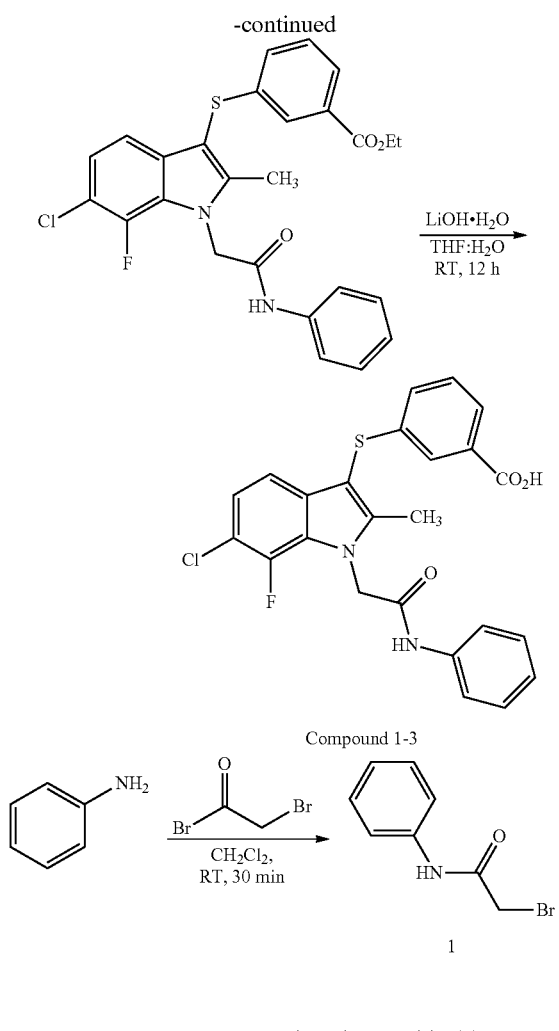

Compound 1-3

Step 1: 2-Bromo-N-phenylacetamide (1)

To a stirred solution of aniline (1.5 g, 16.12 mmol) in CH$_2$Cl$_2$ (15 mL) under inert atmosphere was added bromo acetyl bromide (3.2 g, 16.12 mmol) in CH$_2$Cl$_2$ (5 mL) dropwise for 5 min at RT. The reaction mixture was stirred for 30 min. The reaction progress was monitored by TLC; after reaction completion, the volatile reagents and solvent were removed under reduced pressure. The residue was triturated with CH$_2$Cl$_2$ (2×15 mL) to afford compound 1 (1.4 g, 41%) as pale brown solid. $^1$H NMR (500 MHz, CDCl$_3$): δ 8.11 (br s, 1H), 7.53 (d, J=8.0 Hz, 2H), 7.37-7.34 (m, 2H), 7.17 (t, J=7.5 Hz, 1H), 4.02 (s, 2H). LC-MS: 99. %; (M+2)$^+$ Found=214.2; (column: X-Bridge C-18, 50×3.0 mm, 3.5 μm); RT 3.88 min. 5 mM NH$_4$OAc: ACN; 0.8 mL/min).

Step 2: Ethyl 3-((6-chloro-7-fluoro-2-methyl-1-(2-oxo-2-(phenylamino)ethyl)-1H-indol-3-yl)thio)benzoate (2)

To a stirred solution of Int-A (100 mg, 0.27 mmol) in DMF (5 mL) under inert atmosphere were added compound 1 (65 mg, 0.30 mmol), Bu$_4$NBr (4.4 mg, 0.013 mmol), Cs$_2$CO$_3$ (179 mg, 0.55 mmol) at RT. The reaction mixture was heated to 80° C. and stirred for 12 h. The reaction progress was monitored by TLC; after reaction completion, the reaction mixture was diluted with water (15 mL) and extracted with EtOAc (2×20 mL). The combined organic extracts were dried over Na$_2$SO$_4$, filtered and concentrated under reduced pressure to obtain crude material. The crude material was purified through silica gel flash column chromatography using 5% EtOAc/hexanes to afford compound 2 (90 mg, 66%) as an off-white solid. $^1$H NMR (500 MHz, DMSO-d$_6$): δ 10.48 (s, 1H), 7.69-7.59 (m, 4H), 7.39 (t, J=8.0 Hz, 2H), 7.33 (t, J=8.0 Hz, 2H), 7.23-7.20 (m, 3H), 7.18-7.06 (m, 1H), 5.26 (s, 2H), 4.25 (q, 2H), 1.28-1.23 (m, 3H). LC-MS: 93.7%; (M–H)$^+$ Found=495.2; (column: X-Bridge C-18, 50×3.0 mm, 3.5 μm); RT 5.51 min. 5 mM NH$_4$OAc: ACN; 0.8 mL/min).

Step 3: 3-((6-Chloro-7-fluoro-2-methyl-1-(2-oxo-2-(phenylamino)ethyl)-1H-indol-3-yl)thio)benzoic acid (Compound 1-3)

To a stirred solution of compound 2 (90 mg, 0.18 mmol) in THF:H$_2$O (1:1, 4 mL) was added LiOH monohydrate (30.4 mg, 0.72 mmol) at 0° C. The reaction mixture was warmed to RT and stirred for 12 h. The reaction progress was monitored by TLC; after reaction completion, the solvents were removed under reduced pressure. The residue was dissolved in water (10 mL) and acidified with 2N HCl to pH~2. The aqueous layer was extracted with EtOAc (2×15 mL). The combined organic extracts were dried over Na$_2$SO$_4$, filtered and concentrated under reduced pressure to obtain the crude material. The crude material was triturated with n-pentane (2×3 mL) to afford compound 1-3 (35 mg, 42%) as pale yellow solid. $^1$H NMR (400 MHz, DMSO-d$_6$): δ 13.4 (bs, 1H), 10.49 (s, 1H), 7.67 (d, J=7.6 Hz, 1H), 7.63-7.59 (m, 3H), 7.38-7.30 (m, 3H), 7.22-7.16 (m, 3H), 7.08 (t, J=7.6 Hz, 1H), 5.26 (s, 2H), 2.50 (s, 3H). Mass: (M+H)$^+$ Found=469.4. HPLC (purity): 95.5%; (column: Acquity UPLC BEH C-18 (2.1×50 mm, 1.7 μ); RT 2.78 min. ACN: 0.025% TFA (aq); 0.5 mL/min.

Example 3

3-((6-Chloro-7-fluoro-2-methyl-1-(2-((1-methyl-1H-pyrazol-4-yl)amino)-2-oxoethyl)-1H-indol-3-yl)thio)benzoic acid (Compound 1-6)

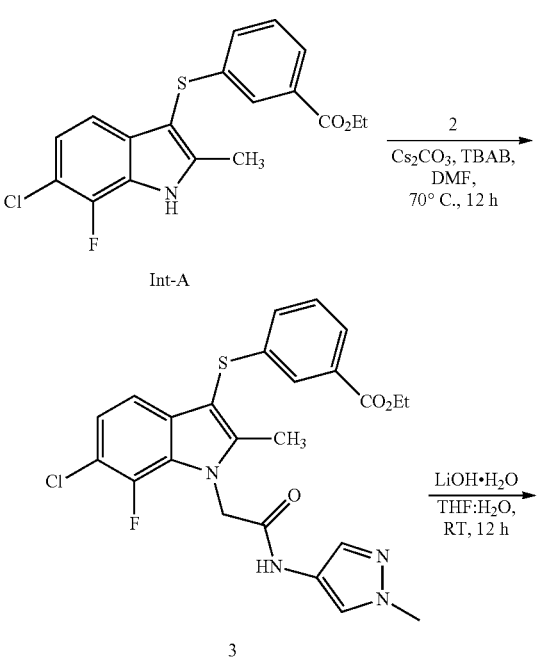

Step 3: 3-((6-Chloro-7-fluoro-2-methyl-1-(2-((1-methyl-1H-pyrazol-4-yl)amino)-2-oxoethyl)-1H-indol-3-yl)thio)benzoic acid (Compound 1-6)

To a stirred solution of compound 3 (55 mg, 0.11 mmol) in THF:H₂O (1:1, 6 mL) was added LiOH monohydrate (18.4 mg, 0.44 mmol) at 0° C. The reaction mixture was warmed to RT and stirred for 8 h. The reaction progress was monitored by TLC; after reaction completion, the solvents were removed under reduced pressure. The residue was dissolved in water (10 mL) and acidified with 2N HCl to pH~4. The aqueous layer was extracted with EtOAc (2×25 mL). The combined organic extracts were dried over Na₂SO₄, filtered and concentrated under reduced pressure to obtain the crude material. The crude material was triturated with n-pentane (2×5 mL), CH₂Cl₂ (2×5 mL) to afford compound 1-6 (29 mg, 57%) as an off-white solid. ¹H NMR (400 MHz, CDCl₃): δ 13.00 (br s, 1H), 10.46 (s, 1H), 7.84 (s, 1H), 7.67 (d, J=7.6 Hz, 1H), 7.62 (s, 1H), 7.43 (s, 1H), 7.36 (t, J=7.6 Hz, 1H), 7.21-7.15 (m, 3H), 5.19 (s, 2H), 3.77 (s, 3H), 2.50 (s, 3H). Mass: (M+H)⁺ Found=474.2. HPLC: 97.3%; (column: Acquity UPLC BEH C-18 (2.1×50 mm, 1.7 μ); RT 2.40 min. ACN: 0.025% TFA (aq); 0.5 mL/min.

Example 4

3-((6-Chloro-7-fluoro-1-(2-(isoxazol-4-ylamino)-2-oxoethyl)-2-methyl-1H-indol-3-yl)thio)benzoic acid (Compound 1-11)

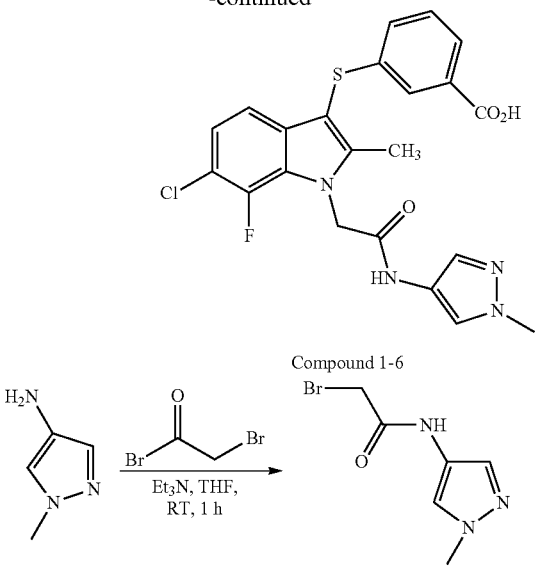

Compound 1-6

Step 1: 2-Bromo-N-(1-methyl-1H-pyrazol-4-yl)acetamide (2)

To a stirred solution of 1-methyl-1H-pyrazol-4-amine 1 (50 mg, 0.51 mmol) in THF (1 mL) were added bromo acetyl bromide (0.05 mL, 0.61 mmol), TEA (0.1 mL, 0.77 mmol) at 0° C. The reaction mixture was warmed to RT and stirred for 1 h. The reaction progress was monitored by TLC; after reaction completion, the reaction mixture was diluted with water (15 mL) and extracted with EtOAc (2×20 mL). The combined organic extracts were dried over Na₂SO₄, filtered and concentrated under reduced pressure to obtain compound 2 (90 mg, 80%) as pale brown semi-solid. ¹H NMR (400 MHz, CDCl₃): δ 8.12 (br s, 1H), 7.93 (s, 1H), 7.50 (s, 1H), 4.02 (s, 2H), 3.90 (s, 3H). LC-MS: 90.0%; (M+2)⁺ Found=218.0; (column: X-Select C-18, 50×3.0 mm, 3.5 μm); RT 4.24 min. 5 mM NH₄OAc: ACN; 0.8 mL/min).

Step 2: Ethyl 3-((6-chloro-7-fluoro-2-methyl-1-(2-((1-methyl-1H-pyrazol-4-yl)amino)-2-oxoethyl)-1H-indol-3-yl)thio)benzoate (3)

To a stirred solution of Int-A (100 mg, 0.27 mmol) in DMF (5 mL) under inert atmosphere were added compound 2 (72.80 mg, 0.33 mmol), Bu₄NBr (4.4 mg, 0.013 mmol) and Cs₂CO₃ (179 mg, 0.55 mmol) at RT. The reaction mixture was heated to 70° C. and stirred for 12 h. The reaction progress was monitored by TLC; after reaction completion, the reaction mixture was diluted with water (15 mL) and extracted with EtOAc (2×25 mL). The combined organic extracts were dried over Na₂SO₄, filtered and concentrated under reduced pressure to obtain the crude material. The crude material was purified through silica gel flash column chromatography using 1% EtOAc/hexanes to afford compound 3 (55 mg, 40%) as pale blue solid. ¹H NMR (500 MHz, CDCl₃): δ 8.17 (br s, 1H), 8.07 (br s, 1H), 7.73-7.72 (m, 2H), 7.67 (br s, 1H), 7.24-7.21 (m, 2H), 7.15-7.14 (m, 1H), 7.10-7.07 (m, 1H), 5.14 (s, 2H), 4.31 (q, 2H), 3.95 (s, 3H), 2.46 (s, 3H), 1.36-1.33 (m, 3H). LC-MS: 97.9%; (M+H)⁺ Found=180.5; (column: Eclipse XDB C-18, 150× 4.6 mm, 5 μm); RT 6.31 min. 5 mM NH₄OAc: ACN; 1.0 mL/min).

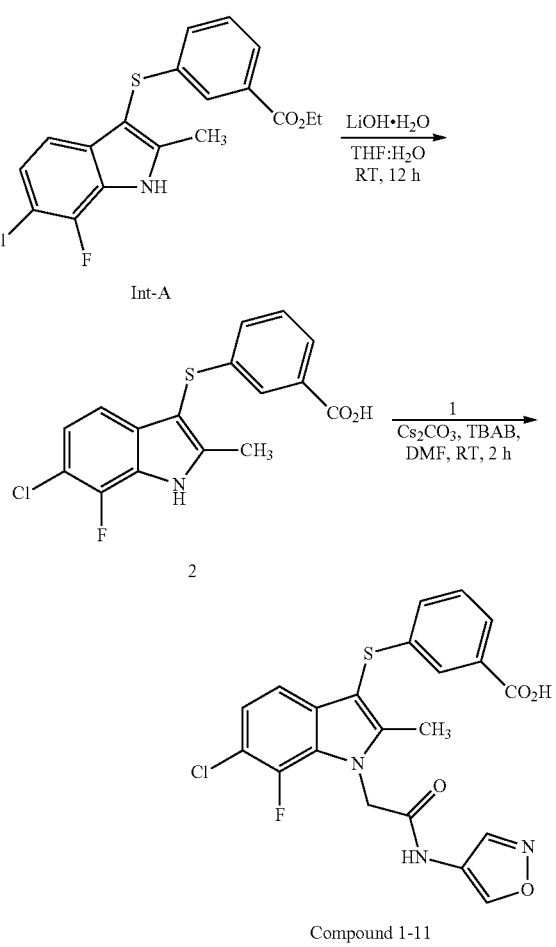

Compound 1-11

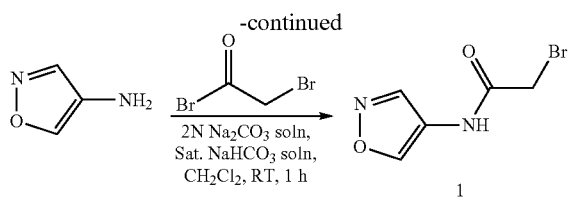

Step 1: 2-Bromo-N-(isoxazol-4-yl)acetamide (1)

To a stirred solution of isoxazol-4-amine (200 mg, 1.66 mmol) in $CH_2Cl_2$ (5 mL) under inert atmosphere were added 2 N $Na_2CO_3$ solution (2.6 mL), saturated $NaHCO_3$ solution (5.6 mL), and bromo acetyl bromide (669 mg, 3.33 mmol) at 0° C. The reaction mixture was warmed to RT and stirred for 1 h. The reaction progress was monitored by TLC; after reaction completion, the reaction mixture was diluted with water (15 mL) and extracted with $CH_2Cl_2$ (2×25 mL). The combined organic extracts were dried over $Na_2SO_4$, filtered and concentrated under reduced pressure to obtain the crude material. The crude material was purified through silica gel flash column chromatography using 25% EtOAc/hexanes to afford compound 1 (300 mg, 88%) as an off-white solid. $^1$H NMR (400 MHz, $CDCl_3$): δ 8.99 (s, 1H), 8.43 (s, 1H), 8.10 (br s, 1H), 4.04 (s, 2H). LC-MS: 98.0%; $(M+2)^+$ Found=203.5; (column: X Select C-18, 50×3.0 mm, 3.5 μm); RT 1.80 min. 5 mM $NH_4OAc$: ACN; 0.8 mL/min).

Step 2: 3-((6-Chloro-7-fluoro-2-methyl-1H-indol-3-yl)thio)benzoic acid (2)

To a stirred solution of Int-A (200 mg, 0.55 mmol) in THF:$H_2O$ (1:1, 6 mL) was added LiOH monohydrate (92.8 mg, 2.20 mmol) at 0° C. The reaction mixture was warmed to RT and stirred for 12 h. The reaction progress was monitored by TLC; after reaction completion, the solvents were removed under reduced pressure. The residue was dissolved in water (15 mL) and acidified with 2 N HCl to pH~5. The aqueous layer was extracted with EtOAc (2×20 mL). The combined organic extracts were dried over $Na_2SO_4$, filtered and concentrated under reduced pressure to obtain the crude material. The crude material was triturated with n-pentane (2×5 mL) to afford compound 2 (150 mg, 83%) as yellow solid. $^1$H NMR (400 MHz, DMSO-$d_6$): δ 12.98 (br s, 1H), 12.42 (s, 1H), 7.64 (d, J=7.6 Hz, 1H), 7.48 (s, 1H), 7.36-7.32 (m, 1H), 7.24-7.21 (m, 1H), 7.15-7.10 (m, 2H), 2.50 (s, 3H).

Step 3: 3-((6-Chloro-7-fluoro-1-(2-(isoxazol-4-ylamino)-2-oxoethyl)-2-methyl-1H-indol-3-yl) thio) benzoic acid (Compound 1-11)

To a stirred solution of compound 2 (100 mg, 0.29 mmol) in DMF (5 mL) under inert atmosphere were added compound 1 (122 mg, 0.59 mmol), $Bu_4NBr$ (4.8 mg, 0.014 mmol), $Cs_2CO_3$ (389 mg, 1.09 mmol) at 0° C. The reaction mixture was warmed to RT and stirred for 2 h. The reaction progress was monitored by TLC; after reaction completion, the reaction mixture was diluted with water (15 mL) and acidified with 2N HCl to pH~4. The aqueous layer was extracted with EtOAc (2×25 mL). The combined organic extracts were dried over $Na_2SO_4$, filtered and concentrated under reduced pressure to obtain the crude material. The crude material was purified through preparative HPLC to afford compound 1-11 (10 mg, 7%) as an off-white solid. $^1$H NMR (400 MHz, $CD_3OD$): δ 9.02 (s, 1H), 8.54 (s, 1H), 7.73 (d, J=8.4 Hz, 2H), 7.30 (t, J=7.6 Hz, 1H), 7.22-7.20 (m, 2H), 7.11 (t, J=8.4 Hz, 1H), 5.27 (s, 2H), 2.52 (s, 3H). Mass: $(M+H)^+$ Found=460.3. HPLC: 95.8%; (column: Eclipse-XDB-C18 (150×4.6 mm, 5 μm); RT 7.87 min. ACN: 5 mM $NH_4OAc$; 1.0 mL/min.

Example 5

2-(6-Chloro-7-fluoro-2-methyl-3-((3-propionylphenyl)thio)-1H-indol-1-yl)-N-(2,2,2-trifluoroethyl) acetamide (Compound 1-5)

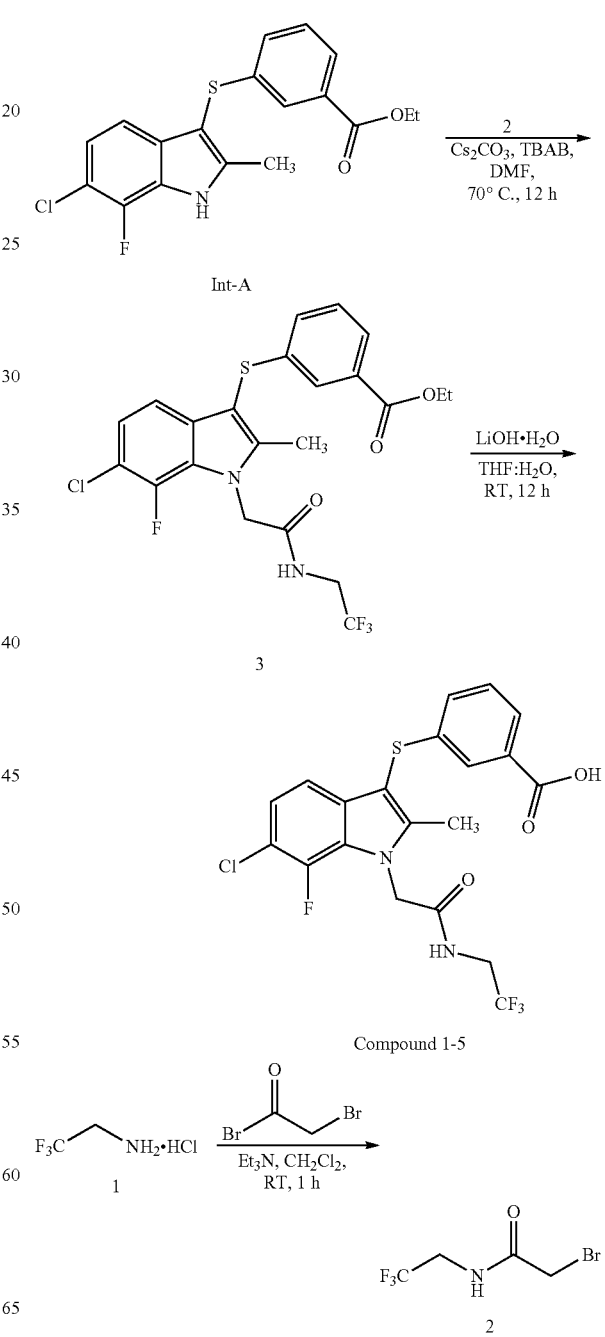

Step 1: 2-Bromo-N-(2,2,2-trifluoroethyl)acetamide (2)

To a stirred solution of 2,2,2-trifluoroethan-1-amine hydrochloride 1 (471 mg, 3.48 mmol) in CH$_2$Cl$_2$ (10 mL) under inert atmosphere were added bromo acetyl bromide (700 mg, 3.48 mmol) in CH$_2$Cl$_2$ (5 mL) for 10 min and TEA (1 mL, 6.96 mmol) at 0° C. The reaction mixture was warmed to RT and stirred for 1 h. The reaction progress was monitored by TLC; after reaction completion, the reaction mixture was diluted with aqueous NaHCO$_3$ solution (15 mL) and extracted with CH$_2$Cl$_2$ (2×30 mL). The combined organic extracts were dried over Na$_2$SO$_4$, filtered and concentrated under reduced pressure to obtain the crude material. The crude material was purified through silica gel flash column chromatography using 10% EtOAc/hexanes to afford compound 2 (600 mg, 78%) as pale yellow solid. $^1$H NMR (500 MHz, CDCl$_3$): δ 6.73 (br s, 1H), 4.11 (s, 2H), 3.99-3.92 (m, 2H). LC-MS: 86.1%; (M)$^+$ Found=219.8; (column: X-Bridge C-18, 50×3.0 mm, 3.5 µm); RT 1.71 min. 5 mM NH$_4$OAc: ACN; 0.8 mL/min).

Step 2: 2-(6-Chloro-7-fluoro-2-methyl-3-((3-propionylphenyl)thio)-1H-indol-1-yl)-N-(2,2,2-trifluoroethyl)acetamide (3)

To a stirred solution of Int-A (70 mg, 0.19 mmol) in DMF (5 mL) under inert atmosphere were added compound 2 (42.5 mg, 0.19 mmol), Bu$_4$NBr (3.1 mg, 0.009 mmol), Cs$_2$CO$_3$ (125 mg, 0.38 mmol) at RT. The reaction mixture was heated to 80° C. and stirred for 12 h. The reaction progress was monitored by TLC; after reaction completion, the reaction mixture was diluted with water (15 mL) and extracted with EtOAc (2×25 mL). The combined organic extracts were dried over Na$_2$SO$_4$, filtered and concentrated under reduced pressure to obtain the crude material. The crude material was purified through silica gel flash column chromatography using 10% EtOAc/hexanes to afford compound 3 (50 mg, 52%) as an off-white solid. $^1$H NMR (400 MHz, DMSO-d$_6$): δ 9.05 (t, J=6.4 Hz, 1H), 7.68-7.62 (m, 2H), 7.36 (t, J=7.6 Hz, 1H), 7.17 (d, J=4.0 Hz, 3H), 5.13 (s, 2H), 4.27-4.22 (m, 2H), 4.04-3.95 (m, 2H), 2.42 (s, 3H), 1.26 (t, J=7.2 Hz, 3H). LC-MS: 99.7%; (M+H)$^+$ Found=503.4; (column: X-Bridge C-18, 50×3.0 mm, 3.5 µm); RT 4.40 min. 5 mM NH$_4$OAc: ACN; 0.8 mL/min).

Step 3: 3-((6-Chloro-7-fluoro-2-methyl-1-(2-oxo-2-((2,2,2-trifluoroethyl)amino)ethyl)-1H-indol-3-yl)thio)benzoic acid (Compound 1-5)

To a stirred solution of compound 3 (50 mg, 0.09 mmol) in THF:H$_2$O (1:1, 2 mL) was added LiOH monohydrate (16.7 mg, 0.39 mmol) at 0° C. The reaction mixture was warmed to RT and stirred for 12 h. The reaction progress was monitored by TLC; after reaction completion, the solvents were removed under reduced pressure. The residue was dissolved in water (3 mL), acidified with 2 N HCl to pH~4 and extracted with EtOAc (2×15 mL). The combined organic extracts were dried over Na$_2$SO$_4$, filtered and concentrated under reduced pressure to obtain the crude material. The crude material was triturated with n-pentane (2×3 mL), CH$_2$C$_2$(2×3 mL) to afford compound 1-5 (20 mg, 43%) as an off-white solid. $^1$H NMR (500 MHz, DMSO-d$_6$): δ 13.00 (br s, 1H), 9.04 (t, J=6.0 Hz, 1H), 7.64 (d, J=8.0 Hz, 1H), 7.59 (s, 1H), 7.33 (t, J=7.5 Hz, 1H), 7.17 (t, J=7.5 Hz, 3H), 5.11 (s, 2H), 3.99-3.96 (m, 2H), 2.41 (s, 3H). Mass: (M+H)$^+$ Found=475.6. HPLC: 98.8%; (column: Acquity UPLC BEH C-18 (2.1×50 mm, 1.7 µ); RT 2.64 min. ACN: 0.025% TFA (aq); 0.5 mL/min.

Example 6

3-((6-Chloro-7-fluoro-2-methyl-1-(2-oxo-2-(pyrrolidin-1-yl)ethyl)-1H-indol-3-yl)thio)benzoic acid (Compound 1-9)

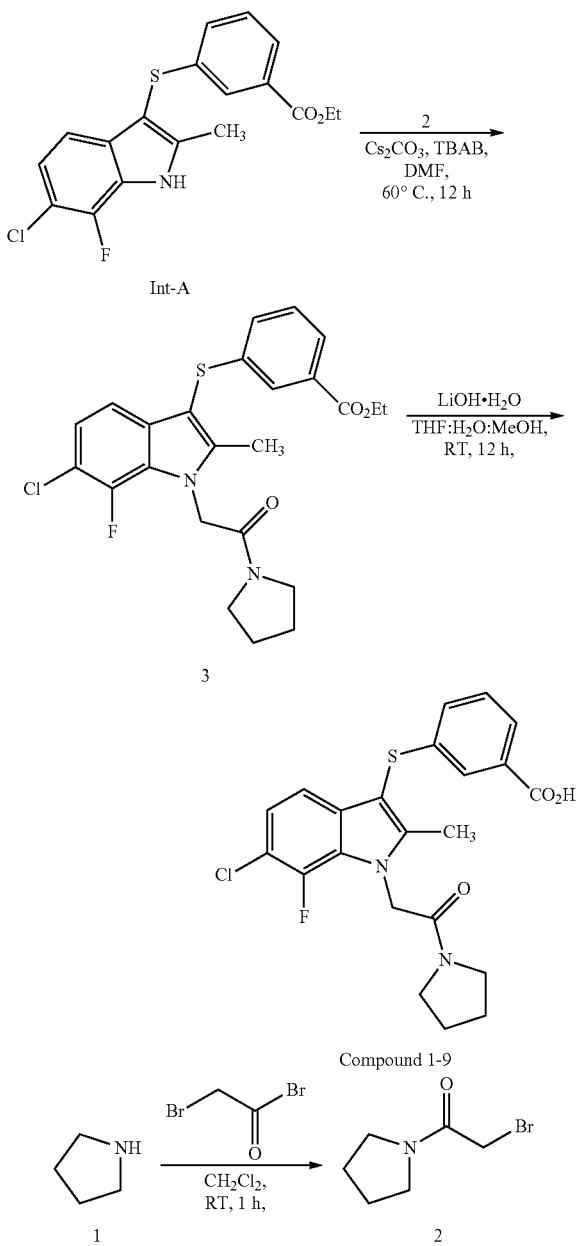

Step 1: 2-Bromo-1-(pyrrolidin-1-yl)ethan-1-one (2)

To a stirred solution of bromoacetyl bromide (1 g, 4.97 mmol) in CH$_2$Cl$_2$ (20 mL) under inert atmosphere was added pyrrolidine (706 mg, 9.95 mmol) at 0° C. and stirred for 10 min. The reaction mixture was warmed to RT and stirred for 1 h. The reaction progress was monitored by TLC;

after reaction completion, the reaction mixture was diluted with 20% NaHCO$_3$ solution (10 mL) and extracted with CH$_2$Cl$_2$ (2×10 mL). The combined organic extracts were dried over Na$_2$SO$_4$, filtered and concentrated under reduced pressure to obtain the crude material. The crude material was purified through silica gel flash column chromatography using 5% MeOH/CH$_2$Cl$_2$ to afford compound 2 (700 mg, 74%) as colorless oil. $^1$H NMR (500 MHz, CDCl$_3$): δ 3.80 (s, 2H), 3.54-3.48 (m, 4H), 2.04-1.98 (m, 2H), 1.92-1.87 (m, 2H); LC-MS: 95.5%; (M+H)$^+$ Found=193.9; (column: X Bridge C-18, 50×3.0 mm, 3.5 μm); RT 1.93 min. 5 mM NH$_4$OAc: ACN; 0.8 mL/min).

Step 2: Ethyl 3-((6-chloro-7-fluoro-2-methyl-1-(2-oxo-2-(pyrrolidin-1-yl)ethyl)-1H-indol-3-yl)thio) benzoate (3)

To a stirred solution of Int-A (70 mg, 0.19 mmol) in DMF (0.5 mL) under inert atmosphere were added compound 2 (37 mg, 0.19 mmol), Cs$_2$CO$_3$ (125 mg, 0.38 mmol) and Bu$_4$NBr (3.1 mg, 0.009 mmol) at RT. The reaction mixture was heated to 60° C. and stirred for 12 h. The reaction progress was monitored by TLC; after reaction completion, the reaction mixture was diluted with water (10 mL) and extracted with EtOAc (2×10 mL). The combined organic extracts were dried over Na$_2$SO$_4$, filtered and concentrated under reduced pressure to obtain the crude material. The crude material was purified through silica gel flash column chromatography using 30% EtOAc/hexanes to afford compound 3 (60 mg, 65%) as an off-white solid. $^1$H NMR (400 MHz, CDCl$_3$): 7.84 (s, 1H), 7.70 (d, J=8.0 Hz, 1H), 7.21-7.17 (m, 2H), 7.05-7.01 (m, 2H), 5.04 (s, 2H), 4.35-4.30 (q, 2H), 3.60-3.52 (m, 4H), 2.46 (s, 3H), 2.13-2.06 (m, 2H), 1.96-1.89 (m, 2H), 1.37-1.34 (m, 3H); LC-MS: 92.2%; (M+H)$^+$ Found=475.7; (column: X Bridge C-18, 50×3.0 mm, 3.5 μm); RT 5.38 min. 5 mM aq NH$_4$OAc: ACN; 0.8 mL/min).

Step 3: 3-((6-Chloro-7-fluoro-2-methyl-1-(2-oxo-2-(pyrrolidin-1-yl)ethyl)-1H-indol-3-yl)thio)benzoic acid (Compound 1-9)

To a stirred solution of compound 3 (60 mg, 0.12 mmol) in THF:MeOH:H$_2$O (3:1:1, 5 mL) under inert atmosphere was added LiOH monohydrate (25 mg, 0.63 mmol) at 0° C. The reaction mixture was warmed to RT and stirred for 12 h. The reaction progress was monitored by TLC; after reaction completion, the reaction mixture was diluted with water (10 mL), acidified with citric acid solution (10 mL) to obtain a solid which was filtered and dried under reduced pressure to afford compound 1-9 (30 mg, 53%) as an off-white solid. $^1$H NMR (400 MHz, DMSO-d$_6$): δ 13.05 (s, 1H), 7.65 (d, J=7.6 Hz, 1H), 7.59 (s, 1H), 7.34 (t, J=7.6 Hz, 1H), 7.19-7.13 (m, 3H), 5.23 (s, 2H), 3.61-3.58 (m, 2H), 3.37-3.31 (m, 2H), 2.41 (s, 3H), 2.01-1.94 (m, 2H), 1.86-1.79 (m, 2H); MS (ESI): m/z (M+H)$^+$ Found=447.5; HPLC: 97.3%; (column: Acquity UPLC BEH-C-18 (2.1×50 mm, 1.7 μ); RT 2.65 min. ACN: 0.025% aq TFA; 0.5 mL/min.

Example 7

3-((6-Chloro-7-fluoro-2-methyl-1-(2-(methyl(phenyl)amino)-2-oxoethyl)-1H-indol-3-yl)thio)benzoic acid (Compound 1-8)

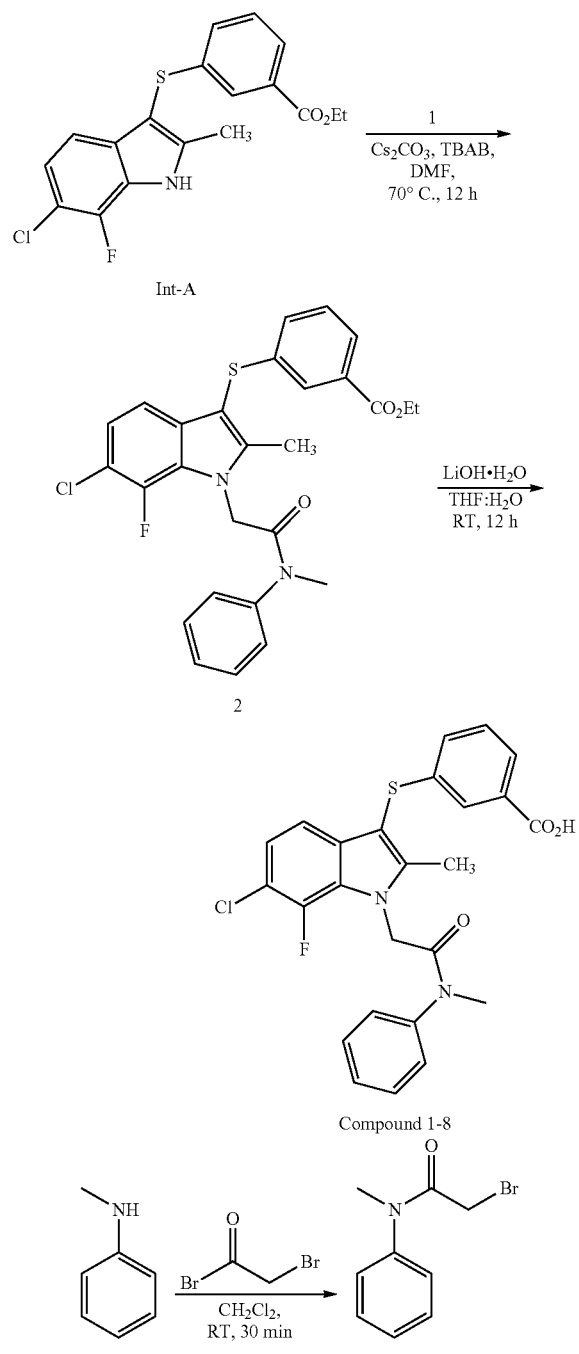

Step 1: 2-Bromo-N-methyl-N-phenylacetamide (1)

To a stirred solution of N-methylaniline (1 g, 9.34 mmol) in CH$_2$Cl$_2$ (10 mL) under inert atmosphere was added bromo acetyl bromide (2 g, 9.34 mmol) in CH$_2$Cl$_2$ (5 mL) dropwise for 5 min at RT. The reaction mixture was stirred for 30 min. The reaction progress was monitored by TLC; after reaction completion, the reaction mixture was diluted with water (20 mL) and extracted with CH$_2$Cl$_2$ (2×25 mL). The combined organic extracts were dried over Na$_2$SO$_4$, filtered and concentrated under reduced pressure to obtain compound 1 (1.5 g, 71%) as an off-white solid. $^1$H NMR (400 MHz, CDCl$_3$): δ 7.47-7.37 (m, 3H), 7.30-7.27 (m, 2H), 3.67 (s, 2H), 3.31 (s, 3H). LC-MS: 99.1%; (M+2)$^+$ Found=230; (column: X-Bridge C-18, 50×3.0 mm, 3.5 μm); RT 2.93 min. 5 mM NH$_4$OAc: ACN; 0.8 mL/min).

Step 2: Ethyl 3-((6-chloro-7-fluoro-2-methyl-1-(2-(methyl(phenyl)amino)-2-oxoethyl)-1H-indol-3-yl)thio)benzoate (2)

To a stirred solution of Int-A (100 mg, 0.27 mmol) in DMF (5 mL) under inert atmosphere were added compound 1 (63 mg, 0.27 mmol), Bu$_4$NBr (4.4 mg, 0.013 mmol), Cs$_2$CO$_3$ (179 mg, 0.55 mmol) at RT. The reaction mixture was heated to 70° C. and stirred for 12 h. The reaction progress was monitored by TLC; after reaction completion, the reaction mixture was diluted with water (15 mL) and extracted with EtOAc (2×20 mL). The combined organic extracts were dried over Na$_2$SO$_4$, filtered and concentrated under reduced pressure to obtain the crude material. The crude material was purified through silica gel flash column chromatography using 10% EtOAc/hexanes to afford compound 2 (85 mg, 61%) as an off-white solid. $^1$H NMR (400 MHz, CDCl$_3$): δ 7.81 (s, 1H), 7.69 (d, J=7.2 Hz, 1H), 7.56-7.52 (m, 3H), 7.47-7.43 (m, 2H), 7.19-7.15 (m, 2H), 7.03-7.00 (m, 2H), 4.79 (s, 2H), 4.32 (q, 2H), 3.33 (s, 3H), 2.40 (s, 3H), 1.34 (t, J=7.2 Hz, 3H).

Step 3: 3-((6-Chloro-7-fluoro-2-methyl-1-(2-(methyl(phenyl)amino)-2-oxoethyl)-1H-indol-3-yl)thio)benzoic acid (Compound 1-8)

To a stirred solution of compound 2 (80 mg, 0.15 mmol) in THF:H$_2$O (1:1, 6 mL) was added LiOH monohydrate (26 mg, 0.62 mmol) at 0° C. The reaction mixture was warmed to RT and stirred for 12 h. The reaction progress was monitored by TLC; after reaction completion, the solvents were removed under reduced pressure. The residue was dissolved in water (15 mL) and acidified with 2 N HCl to pH~4. The aqueous layer was extracted with EtOAc (2×15 mL). The combined organic extracts were dried over Na$_2$SO$_4$, filtered and concentrated under reduced pressure to obtain the crude material. The crude material was triturated with n-pentane (2×3 mL), CH$_2$Cl$_2$ (2×4 mL) to afford compound 1-8 (30 mg, 40%) as pale brown solid. $^1$H NMR (500 MHz, DMSO-d$_6$): δ 12.98 (br s, 1H), 7.63 (d, J=7.5 Hz, 2H), 7.58-7.55 (m, 4H), 7.46 (br s, 1H), 7.32 (t, J=7.5 Hz, 2H), 7.13 (d, J=5.0 Hz, 2H), 4.87 (br s, 2H), 3.22 (s, 2H), 2.47-2.40 (s, 3H). Mass: (M+H)$^+$ Found=483.8. HPLC: 97.12%; (column: Acquity UPLC BEH C-18 (2.1×50 mm, 1.7 μ); RT 2.99 min. ACN: 0.025% TFA (Aq); 0.5 mL/min.

Example 8

3-((6-Chloro-1-(2-(cyclohexylamino)-2-oxoethyl)-7-fluoro-2-methyl-1H-indol-3-yl)thio)benzoic acid (Compound 1-2)

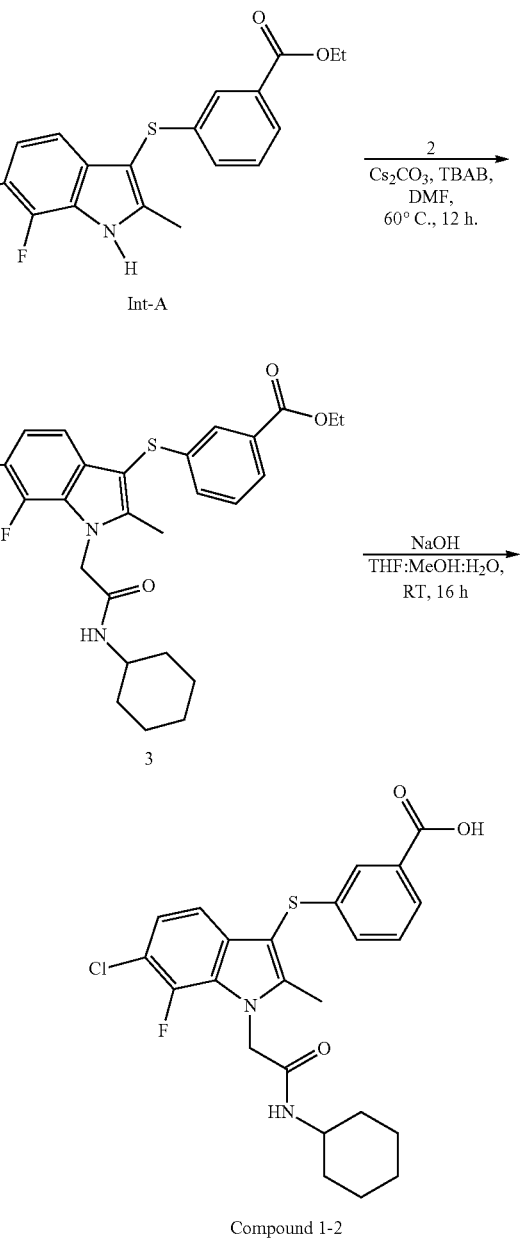

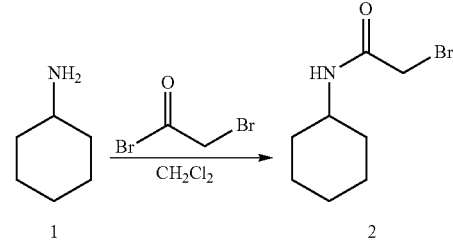

Step 1: 2-Bromo-N-cyclohexylacetamide (2)

To a stirred solution of bromoacetyl bromide (1 g, 4.95 mmol) in $CH_2Cl_2$ (10 mL) under inert atmosphere was added cyclohexyl amine 1 (0.98 g, 9.9 mmol) dropwise for 10 min at 0° C. This reaction mixture was stirred at RT for 1 h. The reaction progress was monitored by TLC; after reaction completion, the reaction mixture was diluted with water (20 mL) and extracted with $CH_2Cl_2$ (2×25 mL). The combined organic extracts were dried over $Na_2SO_4$, filtered and concentrated under reduced pressure to obtain the crude material. The crude material was purified by silica gel flash column chromatography to afford 2 (0.815 g, 75.4%) as off-white solid. $^1H$ NMR (500 MHz, $CDCl_3$): δ 8.12 (d, J=6.5 Hz, 1H), 3.79 (s, 2H), 3.50-3.48 (m, 1H), 1.71-1.65 (m, 4H), 1.55-1.52 (m, 1H), 1.29-1.18 (m, 2H), 1.17-1.11 (m, 3H); LC-MS: 99.8%; $(M+H)^+$ Found=219.9; (column: X Bridge C-18, 50×3.0 mm, 3.5 μm); RT 2.88 min. 5 mM $NH_4OAc$: ACN; 0.8 mL/min).

Step 2: Ethyl-3-((6-chloro-1-(2-(cyclohexamino)-2-oxoethyl)-7-fluoro-2-methyl-1H-indol-3-yl)thio)benzoate (3)

To a stirred solution of Int-A (0.1 g, 0.27 mmol), in DMF (10 mL) under inert atmosphere were added 2 (0.061 g, 0.27 mmol), and $Cs_2CO_3$ (0.18 g, 0.55 mmol) followed by TBAB (0.004 g, 0.013 mmol) at RT. This reaction mixture was stirred at 60° C. for 12 h. After reaction completion by TLC, the reaction mixture was diluted with cold water (15 mL) and extracted with EtOAc (3×10 mL). The combined organic layers were washed with brine (15 mL), dried over $Na_2SO_4$ and concentrated under reduced pressure to obtain the crude material. The crude material was purified by silica gel flash column chromatography to afford 3 (0.101 g, 74.8%) as off-white solid. $^1H$ NMR (500 MHz, $CDCl_3$): δ 8.23 (d, J=8 Hz, 1H), 7.66 (d, J=8 Hz, 1H), 7.62 (s, 1H), 7.38-7.35 (m, 1H), 7.18-7.16 (m, 2H), 4.98 (s, 2H), 4.24 (q, J=7 Hz, 2H), 3.57-3.54 (m, 1H), 2.42 (s, 3H), 1.77-1.53 (m, 5H), 1.35-1.12 (m, 8H); LC-MS: 88.4%; $(M+2)^+$ Found=505; (column: X Bridge C-18, 50×3.0 mm, 3.5 μm); RT 5.70 min. 5 Mm aq $NH_4OAc$: ACN; 0.8 mL/min).

Step 3: 3-((6-Chloro-1-(2-(cyclohexylamino)-2-oxoethyl)-7-fluoro-2-methyl-1H-indol-3-yl)thio)benzoic acid (Compound 1-2)

To a stirred solution of compound 3 (0.09 g, 0.18 mmol) in THF:MeOH:$H_2O$ (3:1:1, 15 mL) was added NaOH (0.014 g, 0.36 mmol) at 0° C. The reaction mixture was stirred at RT for 16 h. After reaction completion by TLC, the reaction mixture was concentrated under reduced pressure. The residue was diluted with water (10 mL) and extracted with diethyl ether (2×10 mL). The aqueous layer was cooled to 0° C., pH was adjusted to 3 by 1N HCl (aq) and extracted with $CH_2Cl_2$ (2×15 mL). The combined organic layers were dried over $Na_2SO_4$ and concentrated under reduced pressure to obtain the crude material. The crude material was triturated with n-pentane to afford compound 1-2 (0.049 g, 56.3%) as an off white solid. $^1H$ NMR (500 MHz, DMSO-$d_6$): δ 13.0 (br s, 1H), 8.23 (d, J=8.0 Hz, 1H), 7.66 (d, J=7.5 Hz, 1H), 7.60 (s, 1H), 7.35-7.32 (m, 1H), 7.17 (dd, J=8.5, 14.5 Hz, 2H), 4.98 (s, 2H), 3.56-3.55 (m, 1H), 2.42 (s, 3H), 1.77-1.67 (m, 4H), 1.56-1.53 (m, 1H), 1.27-1.14 (m, 5H); LC-MS: 97.7%; $(M+H)^+$ Found=475; (column: X Bridge C-18, 50×3.0 mm, 3.5 μm); RT 5.70 min. 5 mM Aq $NH_4OAc$: ACN; 0.8 mL/min). HPLC: 98.3%; (column: Acquity UPLC BEH-C-18 (2.1×50 mm, 1.7 μ); RT 2.87 min. ACN: 0.025% aq TFA; 0.5 mL/min.

Example 9

3-((6-Chloro-7-fluoro-1-(2-(isopropylamino)-2-oxo-ethyl)-2-methyl-1H-indol-3-yl)thio)benzoic acid (Compound 1-1)

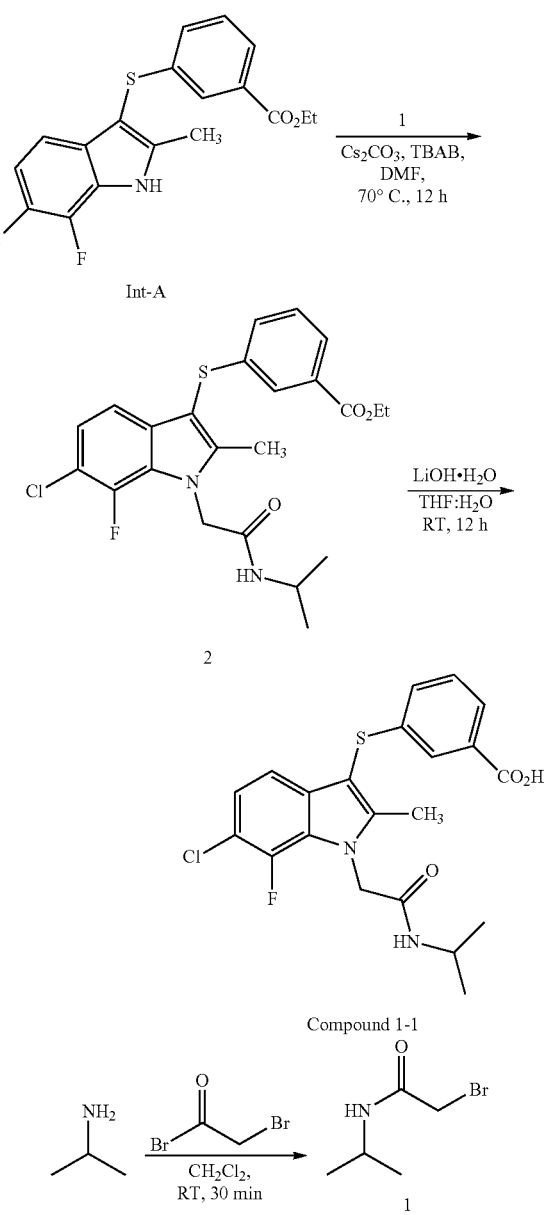

Step 1: 2-Bromo-N-isopropylacetamide (1)

To a stirred solution of propan-2-amine (587 mg, 9.94 mmol) in $CH_2Cl_2$ (10 mL) under inert atmosphere was added bromo acetyl bromide (2 g, 9.94 mmol) in $CH_2Cl_2$ (5 mL) dropwise for 5 min at RT. The reaction mixture was stirred for 30 min. The reaction progress was monitored by TLC; after reaction completion, the reaction mixture was diluted with water (20 mL) and extracted with CH$_2$Cl$_2$ (2×25 mL). The combined organic extracts were dried over Na$_2$SO$_4$, filtered and concentrated under reduced pressure to obtain the crude material. The crude material was purified through silica gel flash column chromatography using 5% EtOAc/hexanes to afford compound 1 (530 mg, 31%) as an off-white solid. $^1$H NMR (500 MHz, CDCl$_3$): δ 6.28 (bs, 1H), 4.09-4.03 (m, 1H), 3.85 (s, 2H), 1.19 (d, J=6.5 Hz, 6H). LC-MS: 97.0%; (M+H)$^+$ Found=180.5; (column: Eclipse XDB C-18, 150×4.6 mm, 5 µm); RT 6.31 min. 5 mM NH$_4$OAc: ACN; 1.0 mL/min).

Step 2: Ethyl 3-((6-Chloro-7-fluoro-1-(2-(isopropylamino)-2-oxoethyl)-2-methyl-1H-indol-3-yl)thio)benzoate (2)

To a stirred solution of Int-A (100 mg, 0.27 mmol) in DMF (5 mL) under inert atmosphere were added compound 1 (50 mg, 0.27 mmol), Bu$_4$NBr (4.4 mg, 0.013 mmol), Cs$_2$CO$_3$ (179 mg, 0.55 mmol) at RT. The reaction mixture was heated to 70° C. and stirred for 12 h. The reaction progress was monitored by TLC; after reaction completion, the reaction mixture was diluted with water (15 mL) and extracted with EtOAc (2×20 mL). The combined organic extracts were dried over Na$_2$SO$_4$, filtered and concentrated under reduced pressure to obtain the crude material. The crude material was purified through silica gel flash column chromatography using 15% EtOAc/hexanes to afford compound 2 (105 mg, 83%) as pale brown solid. $^1$H NMR (500 MHz, CDCl$_3$): δ 7.78 (s, 1H), 7.73 (d, J=8.5 Hz, 1H), 7.24-7.19 (m, 2H), 7.12-7.07 (m, 2H), 5.18 (d, J=7.0 Hz, 1H), 4.92 (s, 2H), 4.34-4.30 (m, 2H), 4.14-4.10 (m, 1H), 2.48 (s, 3H), 1.36-1.25 (m, 2H), 1.19 (s, 6H). LC-MS: 98.6%; (M+H)$^+$ Found=463.4; (column: X-Bridge C-18, 50×3.0 mm, 3.5 µm); RT 4.61 min. 5 mM NH$_4$OAc: ACN; 0.8 mL/min).

Step 3: 3-((6-Chloro-7-fluoro-1-(2-(isopropylamino)-2-oxoethyl)-2-methyl-1H-indol-3-yl)thio)benzoic acid (Compound 1-1)

To a stirred solution of compound 2 (90 mg, 0.19 mmol) in THF:H$_2$O (1:1, 4 mL) was added LiOH monohydrate (32.7 mg, 0.77 mmol) at 0° C. The reaction mixture was warmed to RT and stirred for 12 h. The reaction progress was monitored by TLC; after reaction completion, the solvents were removed under reduced pressure. The residue was dissolved in water (15 mL) and acidified with 1 N HCl to pH~4. The aqueous layer was extracted with EtOAc (2×15 mL). The combined organic extracts were dried over Na$_2$SO$_4$, filtered and concentrated under reduced pressure to obtain the crude material. The crude material was triturated with n-pentane (2×5 mL) to afford compound 1-1 (20 mg, 24%) as an off-white solid. $^1$H NMR (400 MHz, DMSO-d$_6$): δ 12.98 (br s, 1H), 8.22 (d, J=7.6 Hz, 1H), 7.65 (d, J=7.6 Hz, 1H), 7.60 (s, 1H), 7.34 (t, J=7.6 Hz, 1H), 7.19-7.14 (m, 2H), 4.96 (s, 2H), 3.90-3.82 (m, 1H), 2.42 (s, 3H), 1.10 (d, J=6.8 Hz, 6H). Mass: (M+H)$^+$ Found=435.5. HPLC: 96.8%; (column: Acquity UPLC BEH C-18 (2.1×50 mm, 1.7 µ); RT 2.59 min. ACN: 0.025% TFA (aq); 0.5 mL/min.

Example 10

3-((6-Chloro-1-(2-(dimethylamino)-2-oxoethyl)-7-fluoro-2-methyl-1H-indol-3-yl)thio)benzoic acid (Compound 1-7)

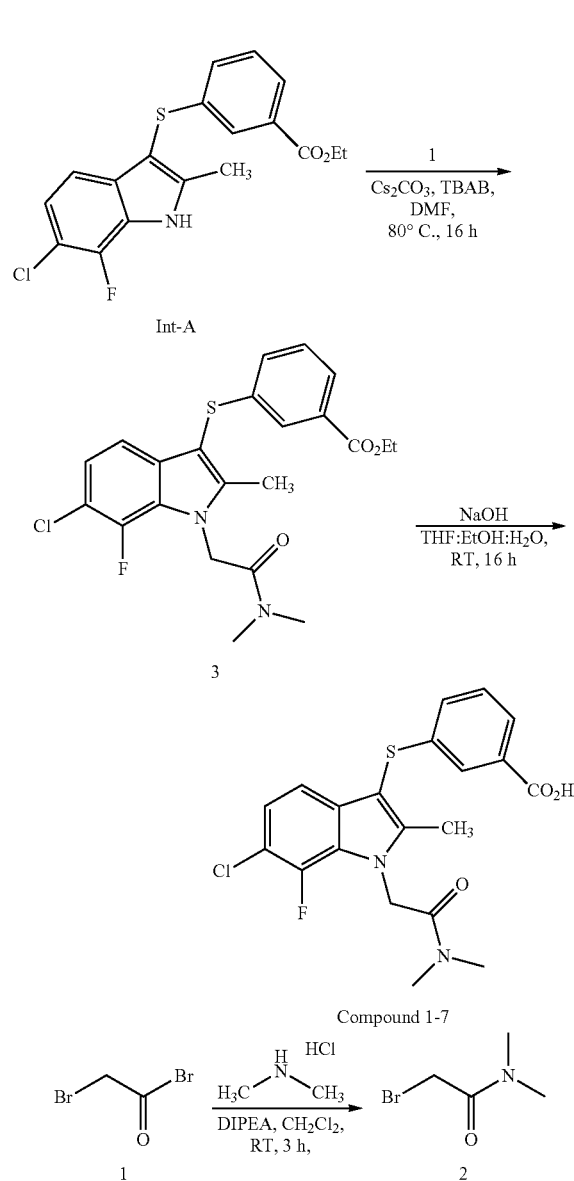

Step 1: 2-Bromo-N, N-dimethylacetamide (2)

To a stirred solution of N, N-dimethylamine.HCl (2 g, 24.52 mmol) in CH$_2$Cl$_2$ (20 mL) under inert atmosphere were added DIPEA (12.6 mL, 73.55 mmol) and bromoacetyl bromide 1 (9.89 g, 19.04 mmol) at 0° C. The reaction mixture was warmed to RT and stirred for 3 h. The reaction progress was monitored by TLC; after reaction completion, the reaction mixture was diluted with water (50 mL) and extracted with CH$_2$Cl$_2$ (2×50 mL). The combined organic extracts were dried over Na$_2$SO$_4$, filtered and concentrated under reduced pressure to obtain the crude material. The crude material was purified through silica gel flash column chromatography using 30% EtOAc/hexanes to afford compound 2 (1.7 μ, 42%) as brown liquid. ¹H NMR (400 MHz, CDCl₃): δ 3.86 (s, 2H), 3.10 (s, 3H), 2.99 (s, 3H); LC-MS: 71.2%; (M+2)⁺ Found=168; (column: X Bridge C-18, 50×3.0 mm, 3.5 μm); RT 1.19 min. 5 mM NH₄OAc: ACN; 0.8 mL/min).

Step 2: Ethyl 3-((6-chloro-1-(2-(dimethylamino)-2-oxoethyl)-7-fluoro-2-methyl-1H-indol-3-yl)thio)benzoate (3)

To a stirred solution of Int-A (50 g, 0.13 mmol) in DMF (3 mL) under inert atmosphere were added compound 5 (25 mg, 0.15 mmol), Cs₂CO₃ (89 mg, 0.27 mmol) and Bu₄NBr (2.2 mg, 0.006 mmol) at RT. The reaction mixture was heated to 80° C. and stirred for 16 h. The reaction progress was monitored by TLC; after reaction completion, the reaction mixture was diluted with water (20 mL) and extracted with EtOAc (2×20 mL). The combined organic extracts were dried over Na₂SO₄, filtered and concentrated under reduced pressure to obtain the crude material. The crude material was purified through silica gel flash column chromatography using 30% EtOAc/hexanes to afford compound 3 (50 mg, 81%) as brown syrup. ¹H NMR (400 MHz, CDCl₃): δ 7.84-7.83 (m, 1H), 7.70 (d, J=7.6 Hz, 1H), 7.21-7.17 (m, 2H), 7.05-7.01 (m, 2H), 5.12 (s, 2H), 4.34 (q, 2H), 3.18 (s, 3H), 3.03 (s, 3H), 2.44 (s, 3H), 1.37 (t, J=7.2 Hz, 3H); LC-MS: 93.2%; (M+H)⁺ Found=449.4; (column: X Bridge C-18, 50×3.0 mm, 3.5 μm); RT 5.24 min. 5 mM aq NH₄OAc: ACN; 0.8 mL/min).

Step 3: 3-((6-Chloro-1-(2-(dimethylamino)-2-oxoethyl)-7-fluoro-2-methyl-1H-indol-3-yl)thio)benzoic acid (Compound 1-7)

To a stirred solution of compound 3 (50 mg, 0.11 mmol) in THF:EtOH:H₂O (3:1:1, 4 mL) under inert atmosphere was added NaOH (13 mg, 0.33 mmol) at RT. The reaction mixture was stirred for 16 h. The reaction progress was monitored by TLC; after reaction completion, the reaction mixture was diluted with water (10 mL), acidified with citric acid solution (10 mL) and extracted with EtOAc (2×20 mL). The combined organic extracts were dried over Na₂SO₄, filtered and concentrated under reduced pressure to obtain the crude material. The crude material was triturated with diethyl ether (2×10 mL) to afford compound 1-7 (20 mg, 43%) as white solid. ¹H NMR (400 MHz, DMSO-d₆): δ 12.98 (br s, 1H), 7.64 (d, J=7.6 Hz, 1H), 7.59 (s, 1H), 7.36-7.33 (m, 1H), 7.19-7.13 (m, 3H), 5.32 (s, 2H), 3.13 (s, 3H), 2.89 (s, 3H), 2.40 (s, 3H); MS (ESI): m/z (M+H)⁺ Found=421.5; HPLC: 97.6%; (column: Acquity UPLC BEH-C-18 (2.1×50 mm, 1.7 μ); RT 2.54 min. ACN: 0.025% aq TFA; 0.5 mL/min.

Example 11

3-((1-(Benzylcarbamoyl)-6-chloro-2-methyl-1H-indol-3-yl)thio)benzoic acid (Compound 1-17)

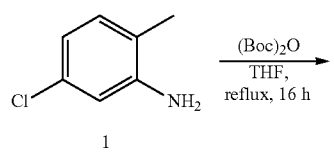

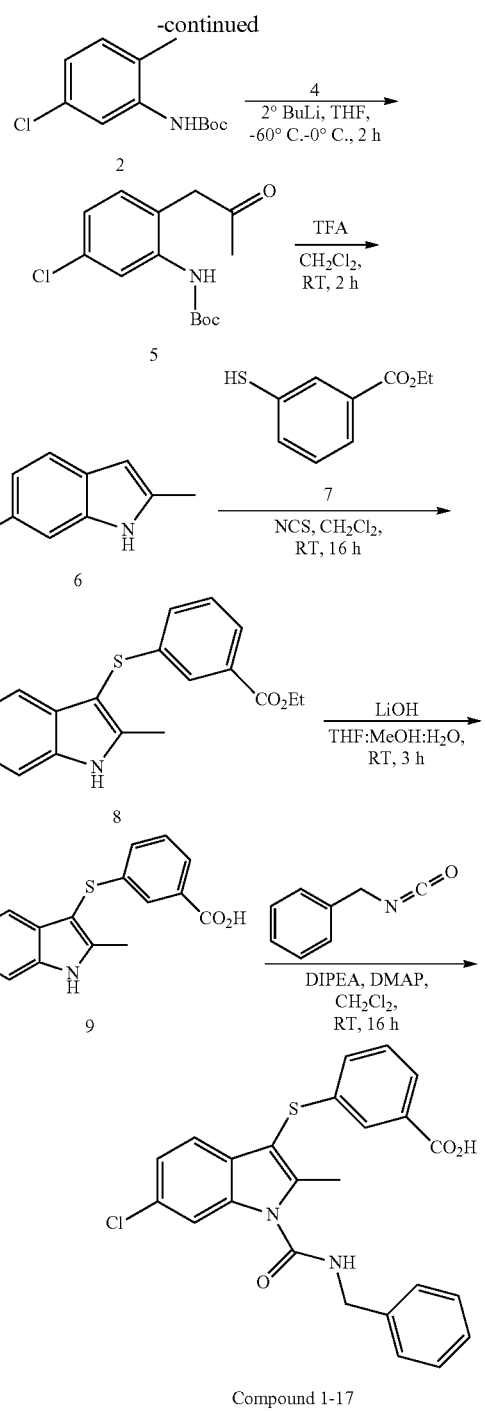

Compound 1-17

Step 1:
tert-Butyl(5-chloro-2-methylphenyl)carbamate (2)

To a stirred solution of 5-chloro-2-methylaniline 1 (5 g, 35.31 mmol) in THF (100 mL) under inert atmosphere was added Boc-anhydride (9.2 g, 42.37 mmol) at RT. The reaction mixture was stirred at reflux temperature for 16 h. The reaction progress was monitored by TLC; after reaction completion, the volatile reagents and solvent were concentrated under reduced pressure. The residue was diluted with water (40 mL) and extracted with EtOAc (2×60 mL). The combined organic extracts were washed with water (50 mL), dried over $Na_2SO_4$, filtered and concentrated under reduced pressure to obtain the compound 2 (8 g, 94%) as an off-white solid. This compound was carried on to the next step without further purification. $^1$H NMR (500 MHz, DMSO-$d_6$): δ 8.63 (br s, 1H), 7.46 (s, 1H), 7.16 (d, J=8.0 Hz, 1H), 7.06-7.04 (m, 1H), 2.17 (s, 3H), 1.46 (s, 9H); LC-MS: 99.8%; (M−H)$^+$ Found=240.2; (column: X-Bridge C-18, 150×3.0 mm, 3.5 μm); RT 4.86 min. 5 mM $NH_4OAc$: ACN; 0.8 mL/min).

Step 2: N-Methoxy-N-methylacetamide (4)

To a stirred solution of N, O-dimethylhydroxylamine hydrochloride 3 (25 g, 256.4 mmol) in $CH_2Cl_2$ (400 mL) under inert atmosphere was added TEA (51.8 g, 512.8 mmol), and the reaction mixture was stirred for 20 min. Acetyl chloride (22.5 g, 282.0 mmol) was added to the reaction mixture at RT, and the reaction mixture stirred for 1 h. The reaction progress was monitored by TLC; after reaction completion, the reaction mixture quenched with saturated $NaHCO_3$ solution (250 mL) and extracted with $CH_2Cl_2$ (2×250 mL). The combined organic extracts were washed with 1 N HCl solution (100 mL), water (100 mL), brine solution (100 mL), dried over $Na_2SO_4$, filtered and concentrated under reduced pressure to obtain the crude material. The crude material was distilled at 50° C. to get 4 (11.5 g, 56%) as colorless liquid. $^1$H NMR (500 MHz, $CDCl_3$): δ 3.68 (s, 3H), 3.17 (s, 3H), 2.11 (s, 3H); LC-MS: 97.3%; (M+H)$^+$ Found=104.4; (column: X bridge C-18, 50×3.0 mm, 3.5 μm); RT 0.63 min. 5 mM $NH_4OAc$: ACN; 0.8 mL/min).

Step 3: tert-Butyl(5-chloro-2-(2-oxopropyl)phenyl) carbamate (5)

To a stirred solution of compound 2 (5 g, 20.69 mmol) in THF (40 mL) under inert atmosphere was added sec-BuLi (31.8 mL, 41.4 mmol) at −40° C. The reaction mixture was stirred at −20° C. for 15 min. Then compound 4 (2.3 g, 22.76 mmol) in THF (30 mL) was added to the reaction mixture at −60° C., and the reaction mixture was stirred for 1 h. The reaction mixture was warmed to RT and stirred for 1 h. The reaction progress was monitored by TLC; after reaction completion, the reaction mixture was quenched with saturated $NH_4Cl$ solution (100 mL) and extracted with EtOAc (2×100 mL). The combined organic extracts were washed with brine solution (100 mL), dried over $Na_2SO_4$, filtered and concentrated under reduced pressure to obtain the crude material. The crude material was recrystallized with n-hexane to afford compound 5 (2.3 g, 39%) as an off-white solid. $^1$H NMR (500 MHz, DMSO-$d_6$): δ 8.70 (s, 1H), 7.48 (s, 1H), 7.15-7.09 (m, 2H), 3.77 (s, 2H), 2.07 (s, 3H), 1.43 (s, 9H); LC-MS: 71.3%; (M+H) Found=282.2; (column: X Bridge C-18, 50×3.0 mm, 3.5 μm); RT 3.92 min. 5 mM $NH_4OAc$: ACN; 0.8 mL/min).

Step 4: 6-Chloro-2-methyl-1H-indole (6)

To a stirred solution of compound 5 (2.3 g, 8.12 mmol) in $CH_2Cl_2$ (40 mL) under inert atmosphere was added TFA (7.5 mL) at RT. The reaction mixture was stirred for 2 h. The reaction progress was monitored by TLC; after reaction completion, the reaction mixture was quenched with water (40 mL) and extracted with $CH_2Cl_2$ (2×50 mL). The combined organic extracts were washed with saturated $NaHCO_3$ solution (40 mL), brine solution (40 mL), dried over $Na_2SO_4$, filtered and concentrated under reduced pressure to obtain the crude material. The crude material was recrystallized with 5% EtOAc/hexanes to afford compound 6 (1 g, 77%) as an off-white solid. $^1$H NMR (500 MHz, DMSO-$d_6$): δ 11.02 (br s, 1H), 7.36 (d, J=8.0 Hz, 1H), 7.25 (s, 1H), 6.90 (d, J=8.5 Hz, 1H), 6.11 (s, 1H), 2.34 (s, 3H); LC-MS: 93.5%; (M−H)$^+$ Found=164; (column: X Bridge C-18, 50×3.0 mm, 3.5 μm); RT 3.99 min. 5 mM $NH_4OAc$: ACN; 0.8 mL/min).

Step 5: Ethyl 3-((6-chloro-2-methyl-1H-indol-3-yl) thio)benzoate (8)

To a stirred solution of compound 6 (900 mg, 5.45 mmol) in $CH_2Cl_2$ (60 mL) under inert atmosphere was added NCS (750 mg, 5.45 mmol) at 0° C. The reaction mixture was warmed to RT and stirred for 1 h. Then compound 7 (1 g, 5.45 mmol) was added to the reaction mixture at RT, and the reaction mixture was stirred for 16 h. The reaction progress was monitored by TLC; after reaction completion, the reaction mixture was diluted with water (50 mL) and extracted with $CH_2Cl_2$ (2×50 mL). The combined organic extracts were washed with water (50 mL), brine solution (50 mL), dried over $Na_2SO_4$, filtered and concentrated under reduced pressure to obtain the crude material. The crude material was purified through silica gel flash column chromatography using 15% EtOAc/hexanes to afford compound 8 (700 mg, 37%) as colorless oil. $^1$H NMR (500 MHz, $CDCl_3$): δ 8.30-8.28 (m, 1H), 7.78 (s, 1H), 7.72 (d, J=8.0 Hz, 1H), 7.40 (d, J=8.0 Hz, 1H), 7.34-7.33 (m, 1H), 7.20 (t, J=8.0 Hz, 1H), 7.12-6.98 (m, 2H), 4.33-4.28 (m, 2H), 2.53 (s, 3H), 1.37 (t, J=6.00 Hz, 3H); LC-MS: 88.9%; (M−H)$^+$ Found=344.2; (column: X Bridge C-18, 50×3.0 mm, 3.5 μm); RT 4.51 min. 5 mM $NH_4OAc$: ACN; 0.8 mL/min).

Step 6: 3-((6-Chloro-2-methyl-1H-indol-3-yl)thio) benzoic acid (9)

To a stirred solution of compound 8 (400 mg, 1.15 mmol) in THF:MeOH:$H_2O$ (2:2:1, 40 mL) was added LiOH monohydrate (244 mg, 5.79 mmol) at RT, and the reaction mixture was stirred for 3 h. The reaction progress was monitored by TLC; after reaction completion, the reaction mixture was diluted with water (10 mL), acidified with 1N HCl to pH~2 and extracted with EtOAc (2×20 mL). The combined organic extracts were washed with brine solution (20 mL), dried over $Na_2SO_4$, filtered and concentrated under reduced pressure to obtain the crude material. The crude material was triturated with n-pentane to afford compound 9 (300 mg, 82%) as brown solid. $^1$H NMR (500 MHz, DMSO-$d_6$): δ 12.95 (brs, 1H), 11.85 (s, 1H), 7.61 (d, J=7.5 Hz, 1H), 7.44 (d, J=12.0 Hz, 2H), 7.33-7.27 (m, 1H), 7.20 (d, J=8.5 Hz, 2H), 7.03 (d, J=8.5 Hz, 1H), 2.43 (s, 3H); LC-MS: 97.7%; (M)$^+$ Found=317.2; (column: X Bridge C-18, 50×3.0 mm, 3.5 μm); RT 3.43 min. 5 mM $NH_4OAc$ in water: ACN; 0.8 mL/min).

Step 7: 3-((1-(Benzylcarbamoyl)-6-chloro-2-methyl-1H-indol-3-yl)thio)benzoic acid (Compound 1-17)

To a stirred solution of compound 9 (50 mg, 0.15 mmol) in $CH_2Cl_2$ (5 mL) under inert atmosphere were added DIPEA (41 mg, 0.31 mmol), benzyl isocyanate (32 mg, 0.23 mmol) and DMAP (catalytic amount) min at RT, and the reaction mixture was stirred for 16 h. The reaction progress was monitored by TLC; after reaction completion, the reaction mixture was diluted with water (20 mL) and extracted with CH$_2$Cl$_2$ (2×20 mL). The combined organic extracts were washed with brine solution (15 mL), dried over Na$_2$SO$_4$, filtered and concentrated under reduced pressure to obtain the crude material. The crude material was purified through preparative HPLC to afford compound 1-17 (7.5 mg, 10%) as an off-white solid. $^1$H NMR (400 MHz, DMSO-d$_6$): δ 12.99 (br s, 1H), 9.24-9.21 (m, 1H), 7.69-7.65 (m, 2H), 7.60 (s, 1H), 7.45-7.19 (m, 9H), 4.56-4.55 (m, 2H), 2.59 (s, 3H); MS (ESI): m/z (M+H)$^+$ Found=468.3; HPLC: 94.1%; (column: Acquity UPLC BEH-C-18 (2.1 mm×50, 1.7µ); RT 2.94 min. ACN: 0.025% aq TFA; 0.50 mL/min.

Example 12

3-((6-Chloro-7-fluoro-2-methyl-1-(2-oxo-2-(piperidin-1-yl)ethyl)-1H-indol-3-yl)thio)benzoic acid (Compound 1-10)

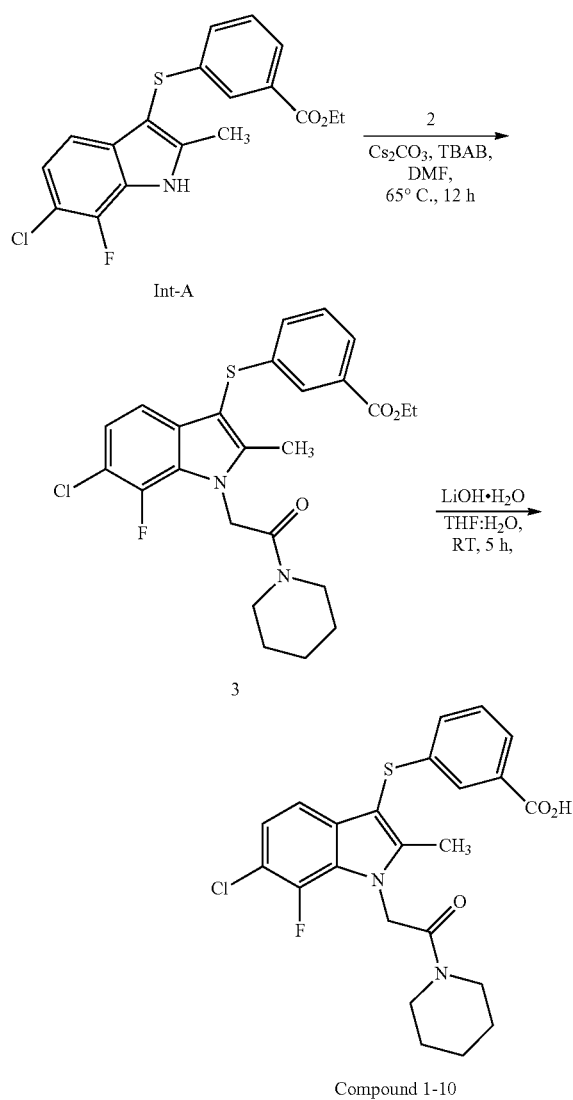

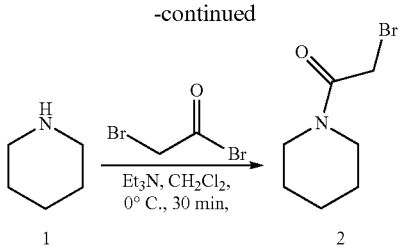

Step 1: 2-Bromo-1-(piperidin-1-yl)ethan-1-one (2)

To a stirred solution of piperidine 1 (1 g, 11.76 mmol) in CH$_2$Cl$_2$ (20 mL) under inert atmosphere were added bromoacetyl bromide (2.83 g, 14.11 mmol) and TEA (1.42 g, 14.11 mmol) at 0° C. The reaction mixture was stirred for 30 min. The reaction progress was monitored by TLC; after reaction completion, the reaction mixture was diluted with saturated NaHCO$_3$ solution (10 mL) and extracted with CH$_2$Cl$_2$ (2×10 mL). The combined organic extracts were dried over Na$_2$SO$_4$, filtered and concentrated under reduced pressure to obtain the crude material. The crude material was purified through silica gel flash column chromatography using 2% MeOH/CH$_2$Cl$_2$ to afford compound 2 (800 mg, 33%) as yellow oil. $^1$H NMR (500 MHz, CDCl$_3$): δ 3.88 (s, 2H), 3.54-3.44 (m, 4H), 1.66-1.62 (m, 6H); LC-MS: 97.0%; (M+H)$^+$ Found=206; (column: X select C-18, 50×3.0 mm, 3.5 µm); RT 2.69 min. 5 mM NH$_4$OAc: ACN; 0.8 mL/min).

Step 2: Ethyl 3-((6-chloro-7-fluoro-2-methyl-1-(2-oxo-2-(piperidin-1-yl)ethyl)-1H-indol-3-yl)thio)benzoate (3)

To a stirred solution of Int-A (75 mg, 0.20 mmol) in DMF (5 mL) under inert atmosphere were added compound 2 (51 mg, 0.24 mmol), Cs$_2$CO$_3$ (134 mg, 0.41 mmol) and Bu$_4$NBr (3.3 mg, 0.01 mmol) at RT. The reaction mixture was heated to 60° C. and stirred for 12 h. The reaction progress was monitored by TLC; after reaction completion, the reaction mixture was diluted with water (10 mL) and extracted with EtOAc (2×15 mL). The combined organic extracts were dried over Na$_2$SO$_4$, filtered and concentrated under reduced pressure to obtain the crude material. The crude material was purified through silica gel flash column chromatography using 20% EtOAc/hexanes to afford compound 3 (65 mg, 64%) as colorless oil. $^1$H NMR (400 MHz, CDCl$_3$): δ 7.85 (s, 1H), 7.70 (d, J=8.0 Hz, 1H), 7.21-7.17 (m, 2H), 7.05-7.01 (m, 2H), 5.12 (s, 2H), 4.35-4.30 (m, 2H), 3.59-3.52 (m, 4H), 2.43 (s, 3H), 1.77-1.75 (m, 3H), 1.72-1.62 (m, 3H), 1.37-1.34 (m, 3H); LC-MS: 96.4%; (M+H)$^+$ Found=489.4; (column: X select C-18, 50×3.0 mm, 3.5 µm); RT 4.78 min. 5 mM NH$_4$OAc: ACN; 0.8 mL/min).

Step 3: 3-((6-Chloro-7-fluoro-2-methyl-1-(2-oxo-2-(piperidin-1-yl)ethyl)-1H-indol-3-yl)thio)benzoic acid (Compound 1-10)

To a stirred solution of compound 3 (65 mg, 0.13 mmol) in THF:H$_2$O (4:1, 5 mL) was added LiOH.H$_2$O (21 mg, 0.53 mmol) at 0° C. The reaction mixture was warmed to RT and stirred for 5 h. The reaction progress was monitored by TLC; after reaction completion, the solvents were removed under reduced pressure. The residue was diluted with water (10 mL), acidified with citric acid solution (20 mL) to pH~2 to obtain a solid which was filtered and dried under reduced pressure to afford compound 1-10 (60 mg, 98%) as an off-white solid. $^1$H NMR (500 MHz, DMSO-$d_6$): δ 12.98 (br s, 1H), 7.65 (d, J=7.0 Hz, 1H), 7.59 (s, 1H), 7.36-7.33 (m, 1H), 7.18-7.13 (m, 3H), 5.33 (s, 2H), 3.54-3.45 (m, 4H), 2.39 (s, 3H), 1.64-1.62 (m, 4H), 1.48-1.46 (m, 2H); LC-MS: 97.4%; (M+H)$^+$ Found=461; (column: X select C-18, 50×3.0 mm, 3.5 μm); RT 3.14 min. 5 mM NH$_4$OAc: ACN; 0.8 mL/min); HPLC: 97.61%; (column: Acquity UPLC BEH-C-18 (2.1×50 mm, 1.7 μ); RT 2.82 min. ACN: 0.025% Aq TFA; 0.5 mL/min.

Example 13

3-((6-Chloro-1-(2-(4-((3,4-difluorobenzyl)oxy)piperidin-1-yl)-2-oxoethyl)-7-fluoro-2-methyl-1H-indol-3-yl)thio)benzoic acid(Compound 1-13)

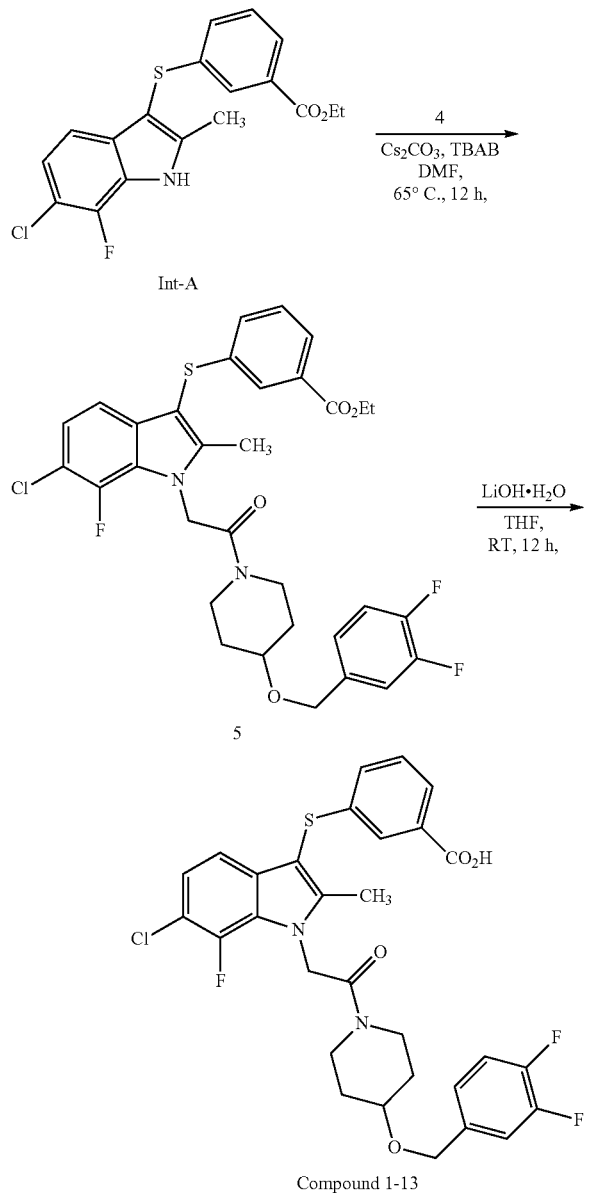

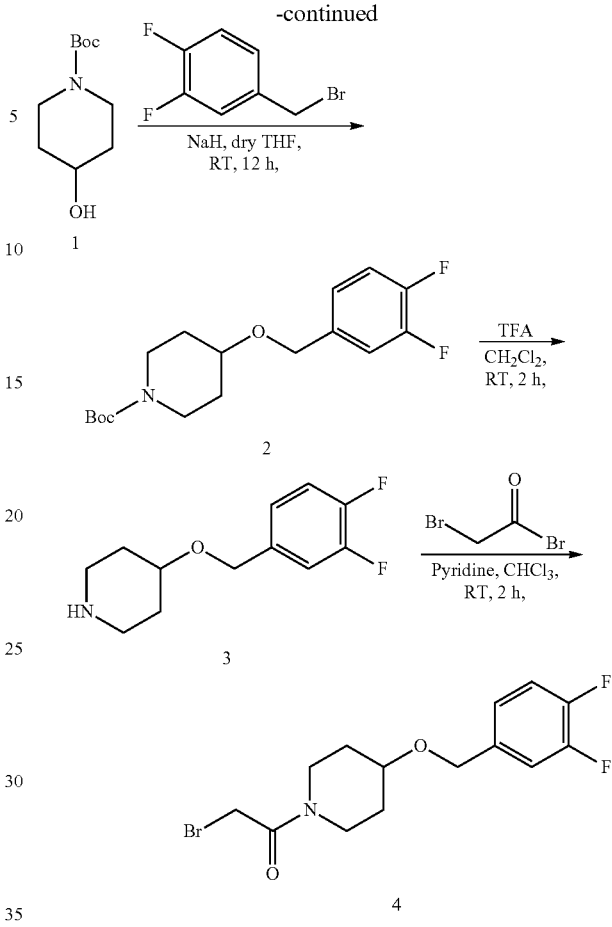

Step 1: tert-Butyl 4-((3,4-difluorobenzyl)oxy)piperidine-1-carboxylate(2)

To a stirred solution of tert-butyl 4-hydroxypiperidine-1-carboxylate 1 (500 mg, 2.48 mmol) in dry THF (50 mL) under inert atmosphere were added NaH (89 mg, 3.73 mmol) at 0° C. The reaction mixture was stirred for 5 min. Then 4-(bromomethyl)-1, 2-difluorobenzene (566 mg, 2.73 mmol) was added to the reaction mixture. The reaction mixture was warmed to RT and stirred for 12 h. The reaction progress was monitored by TLC; after reaction completion, the reaction mixture was diluted with water (20 mL) and extracted with EtOAc (2×20 mL). The combined organic extracts were dried over Na$_2$SO$_4$, filtered and concentrated under reduced pressure to obtain the crude material. The crude material was purified through silica gel flash column chromatography using 5% EtOAc/hexanes to afford compound 2 (517 mg, 63%) as yellow oil. $^1$H NMR (500 MHz, CDCl$_3$): δ 7.19-7.09 (m, 2H), 7.04-7.03 (m, 1H), 4.49 (s, 2H), 3.79-3.74 (m, 2H), 3.57-3.52 (m, 1H), 3.13-3.08 (m, 2H), 1.87-1.84 (m, 2H), 1.62-1.54 (m, 2H), 1.45 (s, 9H); LC-MS: 83.9%; (M-Boc)$^+$ Found=228.2; (column: X select C-18, 50×3.0 mm, 3.5 μm); RT 4.52 min. 5 mM NH$_4$OAc: ACN; 0.8 mL/min).

Step 2: 4-((3,4-Difluorobenzyl)oxy)piperidine (3)

To a stirred solution of compound 2 (517 mg, 1.58 mmol) in CH$_2$Cl$_2$ (20 mL) under inert atmosphere was added TFA (0.5 mL) at 0° C. The reaction mixture was warmed to RT and stirred for 2 h. The reaction progress was monitored by TLC; after reaction completion, the reaction mixture was diluted with saturated NaHCO₃ solution (20 mL) and extracted with CH₂Cl₂ (2×20 mL). The combined organic extracts were dried over Na₂SO₄, filtered and concentrated under reduced pressure to obtain the crude compound 3 as brown oil.

Step 3: 2-Bromo-1-(4-((3,4-difluorobenzyl)oxy) piperidin-1-yl)ethan-1-one (4)

To a stirred solution of compound 3 (300 mg) in CHCl₃ (25 mL) under inert atmosphere were added pyridine (156 mg, 1.98 mmol) and bromoacetyl bromide (398 mg, 1.98 mmol) at 0° C. The reaction mixture was warmed to RT and stirred for 2 h. The reaction progress was monitored by TLC; after reaction completion, the reaction mixture was diluted with water (20 mL) and extracted with CH₂Cl₂ (2×20 mL). The combined organic extracts were dried over Na₂SO₄, filtered and concentrated under reduced pressure to obtain the crude material. The crude material was purified through silica gel flash column chromatography using 70% EtOAc/hexanes to afford compound 4 (200 mg, 44%) as colorless oil. $^1$H NMR (500 MHz, CDCl₃): δ 7.19-7.04 (m, 3H), 4.51-4.47 (m, 2H), 3.87 (s, 2H), 3.70-3.66 (m, 3H), 3.51-3.47 (m, 1H), 3.38-3.36 (m, 1H), 1.94-1.85 (m, 2H), 1.79-1.54 (m, 2H); LC-MS: 95.4%; (M+2)⁺ Found=350.2; (column: X select CSH C-18, 50×3.0 mm, 3.5 μm); RT 3.58 min. 5 mM aq NH₄OAc: ACN; 0.8 mL/min).

Step 4: Ethyl 3-((6-chloro-1-(2-(4-((3, 4-difluorobenzyl)oxy)piperidin-1-yl)-2-oxoethyl)-7-fluoro-2-methyl-1H-indol-3-yl)thio)benzoate (5)

To a stirred solution of Int-A (75 mg, 0.20 mmol) in DMF (5 mL) under inert atmosphere were added compound 4 (79 mg, 0.22 mmol), Cs₂CO₃ (135 mg, 0.41 mmol) and Bu₄NBr (3.3 mg, 0.01 mmol) at RT. The reaction mixture was heated to 65° C. and stirred for 12 h. The reaction progress was monitored by TLC; after reaction completion, the reaction mixture was diluted with water (10 mL) and extracted with EtOAc (2×20 mL). The combined organic extracts were dried over Na₂SO₄, filtered and concentrated under reduced pressure to obtain the crude material. The crude material was purified through silica gel flash column chromatography using 20% EtOAc/hexanes to afford compound 5 (65 mg, 50%) as colorless oil. $^1$H NMR (500 MHz, CDCl₃): δ 7.83 (s, 1H), 7.71-7.69 (m, 1H), 7.25-7.18 (m, 4H), 7.07-7.02 (m, 3H), 5.55-5.07 (m, 2H), 4.57-4.50 (m, 2H), 4.35-4.30 (m, 2H), 3.92-3.81 (m, 2H), 3.80-3.78 (m, 1H), 3.56-3.51 (m, 1H), 3.49-3.42 (m, 1H), 2.44 (s, 3H), 2.09-2.01 (m, 1H), 1.98-1.91 (m, 1H), 1.84-1.65 (m, 1H), 1.33 (m, 3H); LC-MS: 94.9%; (M+H)⁺ Found=631.5; (column: X select C-18, 50×3.0 mm, 3.5 μm); RT 4.82 min. 5 mM aq NH₄OAc: ACN; 0.8 mL/min).

Step 5: 3-((6-Chloro-1-(2-(4-((3, 4-difluorobenzyl) oxy)piperidin-1-yl)-7-fluoro-2-methyl-1H-indol-3-yl)thio)benzoic acid (Compound 1-13)

To a stirred solution of compound 5 (65 mg, 0.10 mmol) in THF (5 mL) under inert atmosphere was added LiOH monohydrate (12 mg, 0.30 mmol) at 0° C. The reaction mixture was warmed to RT and stirred for 12 h. The reaction progress was monitored by TLC; after reaction completion, the solvents were removed under reduced pressure. The residue was acidified with citric acid solution (10 mL) to obtain a solid which was filtered and dried under reduced pressure to afford compound 1-13 (15 mg, 19%) as an off-white solid. $^1$H NMR (400 MHz, CD₃OD): δ 7.73-7.68 (m, 2H), 7.31-7.19 (m, 4H), 7.15-7.13 (m, 3H), 7.12-7.05 (m, 1H), 5.36 (s, 2H), 4.59 (s, 2H), 3.92-3.81 (m, 2H), 3.80-3.78 (m, 1H), 3.56-3.51 (m, 1H), 3.49-3.42 (m, 1H), 2.44 (s, 3H), 2.09-2.01 (m, 1H), 1.98-1.91 (m, 1H), 1.84-1.65 (m, 1H); LC-MS: 93.4%; (M+H)⁺ Found=603.5; (column: X select C-18, 50×3.0 mm, 3.5 μm); RT 3.55 min. 5 mM NH₄OAc: ACN; 0.8 mL/min); HPLC: 95.7%; (column: Eclipse XDB C-18, 150×4.6 mm, 5 μm); RT 9.64 min. 5 mM aq NH₄OAc: ACN; 1.0 mL/min).

Example 14

3-((6-Chloro-7-fluoro-1-(2-(3-(4-fluorobenzyl)piperidin-1-yl)-2-oxoethyl)-2-methyl-1H-indol-3-yl) thio)benzoic acid (Compound 1-15)

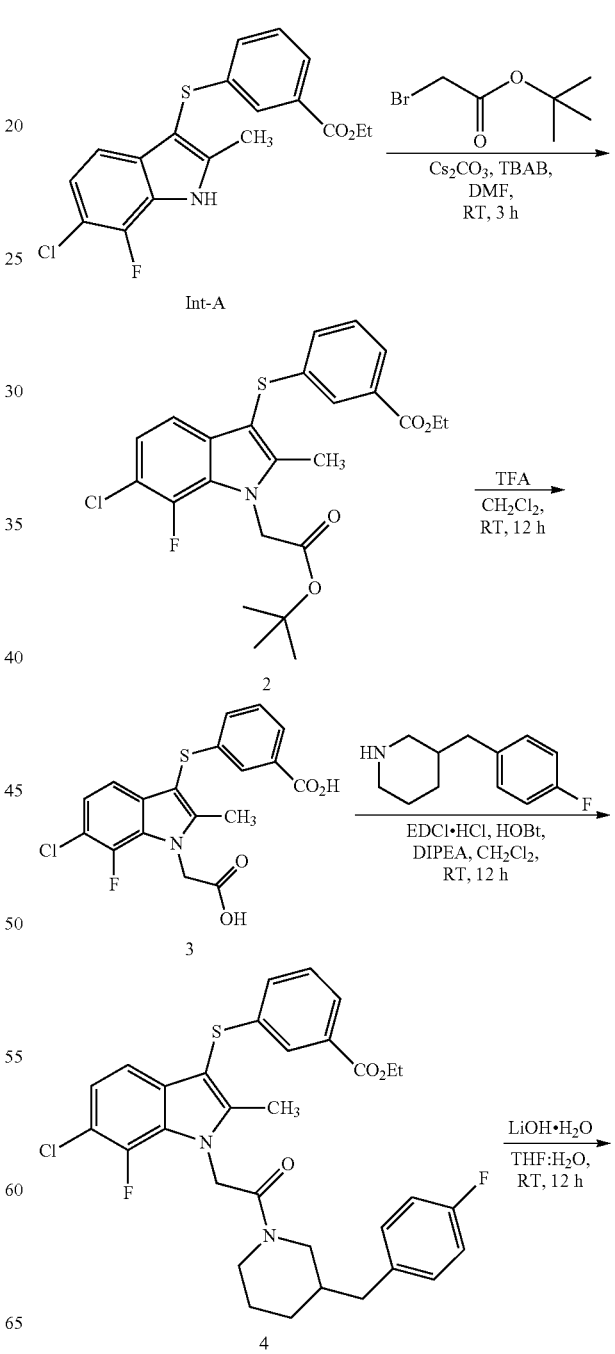

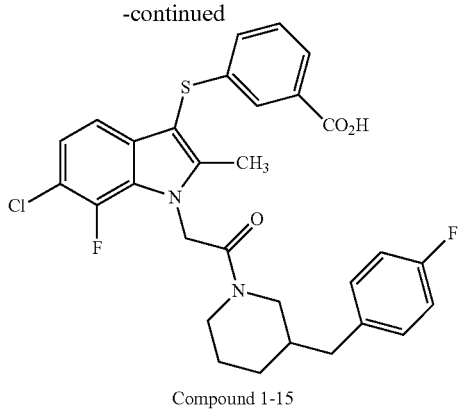

Compound 1-15

Step 1: Ethyl 3-((1-(2-(tert-butoxy)-2-oxoethyl)-6-chloro-7-fluoro-2-methyl-1H-indol-3-yl)thio)benzoate (2)

To a stirred solution of Int-A (500 mg, 1.38 mmol) in DMF (12 mL) under inert atmosphere were added tert-butyl bromo acetate (0.33 mL, 2.07 mmol), Bu$_4$NBr (22.2 mg, 0.06 mmol), Cs$_2$CO$_3$ (897 mg, 2.76 mmol) at RT. The reaction mixture was stirred for 3 h. The reaction progress was monitored by TLC; after reaction completion, the reaction mixture was diluted with ice water (25 mL) and extracted with EtOAc (2×25 mL). The combined organic extracts were dried over Na$_2$SO$_4$, filtered and concentrated under reduced pressure to obtain compound 2 (55 mg, 83%) as pale green semi-solid. $^1$H NMR (500 MHz, CDCl$_3$): δ 7.84 (s, 1H), 7.74 (d, J=7.5 Hz, 1H), 7.24-7.19 (m, 2H), 7.10-7.04 (m, 2H), 4.97 (s, 2H), 4.34 (q, 2H), 2.47 (s, 3H), 1.49 (s, 9H), 1.39-1.36 (m, 3H).

Step 2: 2-(6-Chloro-3-((3-(ethoxycarbonyl)phenyl)thio)-7-fluoro-2-methyl-1H-indol-1-yl)acetic acid (3)

To a stirred solution of compound 2 (547 mg, 1.14 mmol) in CH$_2$Cl$_2$ (15 mL) under inert atmosphere was added TFA (2 mL) at RT. The reaction mixture was stirred for 12 h. The reaction progress was monitored by TLC; after reaction completion, the volatile reagent and solvent were removed under reduced pressure. The residue was diluted with water (25 mL) and extracted with CH$_2$Cl$_2$ (2×25 mL). The combined organic extracts were dried over Na$_2$SO$_4$, filtered and concentrated under reduced pressure to obtain compound 3 (450 mg, 94%) as pale brown solid. $^1$H NMR (400 MHz, DMSO-d$_6$): δ 13.51 (br s, 1H), 7.67-7.65 (m, 1H), 7.61-7.60 (m, 1H), 7.36 (t, J=8.0 Hz, 1H), 7.20-7.17 (m, 3H), 5.11 (s, 2H), 4.24 (q, 2H), 2.50 (s, 3H), 1.25 (t, J=7.2 Hz, 3H).

Step 3: Ethyl 3-((6-chloro-7-fluoro-1-(2-(3-(4-fluorobenzyl)piperidin-1-yl)-2-oxoethyl)-2-methyl-1H-indol-3-yl)thio)benzoate (4)

To a stirred solution of compound 3 (80 mg, 0.19 mmol) in CH$_2$Cl$_2$ (4 mL) under inert atmosphere were added EDCI.HCl (54 mg, 0.28 mmol), HOBt (38 mg, 0.28 mmol), 3-(4-fluorobenzyl)piperidine (52.5 mg, 0.22 mmol), and DIPEA (0.1 mL, 0.57 mmol) at RT. The reaction mixture was stirred for 12 h. The reaction progress was monitored by TLC; after reaction completion, the reaction mixture was quenched with water (20 mL) and extracted with CH$_2$Cl$_2$ (2×25 mL). The combined organic extracts were dried over Na$_2$SO$_4$, filtered and concentrated under reduced pressure to obtain the crude material. The crude material was purified through silica gel flash column chromatography using 10% EtOAc/hexanes to afford compound 4 (70 mg, 62%) as an off-white solid. $^1$H NMR (500 MHz, CDCl$_3$): 7.87-7.72 (m, 2H), 7.23-7.19 (m, 2H), 7.10-7.04 (m, 5H), 6.98-6.95 (m, 1H), 5.17-5.10 (m, 2H), 5.03-4.94 (m, 2H), 4.41-4.36 (m, 2H), 2.53-2.31 (m, 4H), 2.16-1.88 (m, 2H), 1.44-1.24 (m, 4H), 0.97-0.87 (m, 4H). LC-MS: 97.4%; (M)$^+$ Found=597.6; (column: X Select C-18, 50×3.0 mm, 3.5 μm); RT 5.14 min. 5 mM NH$_4$OAc: ACN; 0.8 mL/min).

Step 4: 3-((6-Chloro-7-fluoro-1-(2-(3-(4-fluorobenzyl)piperidin-1-yl)-2-oxoethyl)-2-methyl-1H-indol-3-yl)thio)benzoic acid (Compound 1-15)

To a stirred solution of compound 4 (70 mg, 0.11 mmol) in THF:H$_2$O (1:1, 6 mL) was added LiOH monohydrate (19.6 mg, 0.46 mmol) at 0° C. The reaction mixture was warmed to RT and stirred for 12 h. The reaction progress was monitored by TLC; after reaction completion, the solvents were removed under reduced pressure. The residue was dissolved in water (10 mL) and acidified with 2 N HCl to pH~4. The aqueous layer was extracted with EtOAc (2×20 mL). The combined organic extracts were dried over Na$_2$SO$_4$, filtered and concentrated under reduced pressure to obtain the crude material. The crude material was triturated with n-pentane (2×5 mL), CH$_2$Cl$_2$ (2×5 mL) to afford compound 1-15 (30 mg, 45%) as white solid. $^1$H NMR (400 MHz, DMSO-d$_6$): δ 13.00 (br s, 1H), 7.65 (d, J=7.6 Hz, 1H), 7.58 (s, 1H), 7.35-7.27 (m, 2H), 7.22-7.05 (m, 6H), 5.38-5.27 (m, 2H), 4.06 (d, J=13.6 Hz, 1H), 3.86 (d, J=13.6 Hz, 1H), 3.16 (t, J=12.0 Hz, 1H), 2.96 (t, J=12.0 Hz, 1H), 2.76-2.71 (m, 1H), 2.50-2.49 (m, 1H), 2.38 (s, 3H), 1.84-1.50 (m, 3H), 1.27-1.19 (m, 2H). Mass: (M+H)$^+$ Found=571.6. HPLC: 96.9%; (column: Acquity BEH C-18 (50×2.1 mm, 1.7 μ); RT 3.15 min. ACN: 0.025% TFA (aq); 0.5 mL/min.

Example 15

3-((6-Chloro-7-fluoro-2-methyl-1-(2-(2-oxo-1-oxa-3,8-diazaspiro[4.5]decan-8-yl)acetyl)-1H-indol-3-yl)thio)benzoic acid (Compound 1-12)

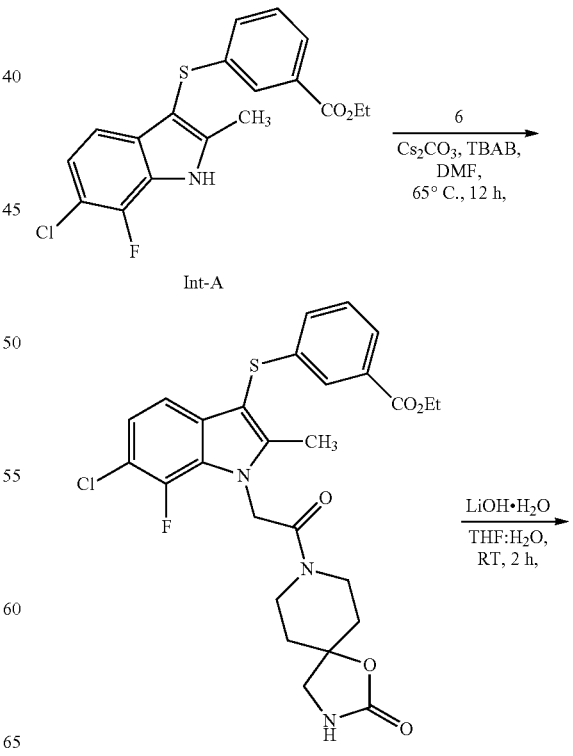

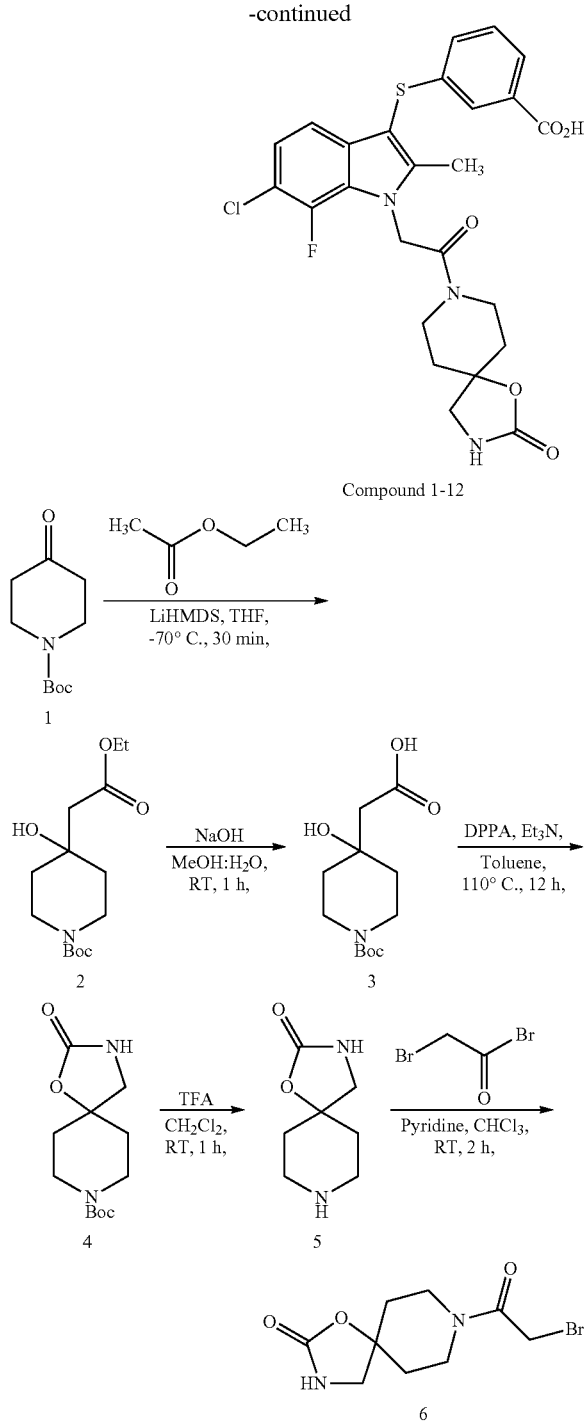

Compound 1-12

Step 1: tert-Butyl 4-(2-ethoxy-2-oxoethyl)-4-hydroxypiperidine-1-carboxylate (2)

To a stirred solution of LiHMDS (1.81 g, 10.85 mmol) in THF (10 mL) under inert atmosphere was added EtOAc (955 mg, 10.85 mmol) dropwise for 10 min at −70° C. The reaction mixture was stirred for 15 min. Then tert-butyl 4-oxopiperidine-1-carboxylate 1 (2 g, 10.85 mmol) in THF (10 mL) was added to the reaction mixture. The reaction mixture was stirred for 30 min. The reaction progress was monitored by TLC; after reaction completion, the reaction mixture was diluted with water (20 mL) and extracted with $CH_2Cl_2$ (2×20 mL). The combined organic extracts were dried over $Na_2SO_4$, filtered and concentrated under reduced pressure to obtain compound 2 (2.4 g, 83%) as colorless oil. $^1H$ NMR (500 MHz, $CDCl_3$): δ 4.20-4.16 (m, 2H), 3.83-3.80 (m, 2H), 3.23-3.18 (m, 2H), 2.46 (s, 2H), 1.67-1.65 (m, 2H), 1.57-1.48 (m, 2H), 1.47 (m, 9H), 1.29-1.26 (m, 3H); LC-MS: 96.5%; (M-Boc)$^+$ Found=188.2; (column: X select CSH C-18, 50×3.0 mm, 3.5 μm); RT 3.82 min. 5 mM Aq $NH_4OAc$: ACN; 0.8 mL/min).

Step 2: 2-(1-(tert-Butoxycarbonyl)-4-hydroxypiperidin-4-yl)acetic acid (3)

To a stirred solution of compound 2 (2.4 g, 8.36 mmol) in MeOH:$H_2O$ (4:1, 20 mL) under inert atmosphere was added NaOH (400 mg, 10.03 mmol) at 0° C. The reaction mixture was warmed to RT and stirred for 1 h. The reaction progress was monitored by TLC; after reaction completion, the solvents were removed under reduced pressure. The residue was diluted with water (50 mL) and extracted with $CH_2Cl_2$ (2×50 mL). The combined organic extracts were washed with citric acid solution (50 mL), dried over $Na_2SO_4$, filtered and concentrated under reduced pressure to obtain the compound 3 (2.1 g, 97%) as colorless oil. $^1H$ NMR (500 MHz, $CDCl_3$): δ 3.84-3.81 (m, 2H), 3.23-3.18 (m, 2H), 2.53 (s, 2H), 1.72-1.70 (m, 2H), 1.55-1.52 (m, 2H), 1.45 (s, 9H); LC-MS: 95.9%; (M+H)$^+$ Found=258.2; (column: X select C-18, 50×3.0 mm, 3.5 μm); RT 2.21 min. 5 mM $NH_4OAc$: ACN; 0.8 mL/min).

Step 3: tert-Butyl 2-oxo-1-oxa-3,8-diazaspiro[4.5]decane-8-carboxylate (4)

To a stirred solution of compound 3 (2.1 g, 8.10 mmol) in toluene (50 mL) under inert atmosphere were added TEA (884 mg, 8.75 mmol) and DPPA (3 g, 10.94 mmol) at RT. The reaction mixture was heated to 110° C. and stirred for 12 h. The reaction progress was monitored by TLC; after reaction completion, the reaction mixture was diluted with water (20 mL) and extracted with $CH_2Cl_2$ (2×20 mL). The combined organic extracts were dried over $Na_2SO_4$, filtered and concentrated under reduced pressure to obtain the crude material. The crude material was purified through silica gel flash column chromatography eluting with EtOAc to afford compound 4 (1.3 g, 63%) as an off-white solid. $^1H$ NMR (500 MHz, DMSO-$d_6$): δ 7.50 (s, 1H), 3.55-3.51 (m, 2H), 3.30-3.23 (m, 4H), 2.50-1.70 (m, 2H), 1.67-1.62 (m, 2H), 1.39 (s, 9H); LC-MS: 88.4%; (M-Boc)$^+$ Found=157.3; (column: X select CSH C-18, 50×3.0 mm, 3.5 μm); RT 3.28 min. 5 mM $NH_4OAc$ in water: ACN; 0.8 mL/min).

Step 4: 1-Oxa-3,8-diazaspiro[4.5]decan-2-one (5)

To a stirred solution of compound 4 (50 mg, 0.19 mmol) in $CH_2Cl_2$ (5 mL) under inert atmosphere was added TFA (2 mL) at 0° C. The reaction mixture was warmed to RT and stirred for 1 h. The reaction progress was monitored by TLC; after reaction completion, the volatile reagent and solvent were concentrated under reduced pressure to obtain compound 5 (60 mg, crude) as colorless oil. This compound was carried on to the next step without further purification.

Step 5: 8-(2-Bromoacetyl)-1-oxa-3,8-diazaspiro[4.5]decan-2-one (6)

To a stirred solution of compound 5 (200 mg, 1.27 mmol) in $CHCl_3$ (10 mL) under inert atmosphere were added bromoacetyl bromide (307 mg, 1.52 mmol) and pyridine (151 mg, 1.91 mmol) at 0° C. The reaction mixture was warmed to RT and stirred for 2 h. The reaction progress was monitored by TLC; after reaction completion, the reaction mixture was diluted with water (20 mL) and extracted with CH$_2$Cl$_2$ (2×20 mL). The combined organic extracts were dried over Na$_2$SO$_4$, filtered and concentrated under reduced pressure to obtain the crude material. The crude material was purified through silica gel flash column chromatography using 8% MeOH/CH$_2$Cl$_2$ to afford compound 6 (50 mg, 14%) as yellow oil. $^1$H NMR (500 MHz, CDCl$_3$): δ 4.99 (br s, 1H), 4.43-4.40 (m, 1H), 3.98-3.93 (m, 1H), 3.84-3.81 (m, 1H), 3.77-3.74 (m, 1H), 3.57 (t, J=12 Hz, 1H), 3.38 (s, 2H), 3.17 (t, J=12 Hz, 1H), 2.100-2.02 (m, 2H), 1.90-1.84 (m, 1H), 1.74-1.68 (m, 1H); LC-MS: 79.6%; (M+2)$^+$ Found=279.1; (column: X select C-18, 50×3.0 mm, 3.5 μm); RT 2.23 min. 5 mM NH$_4$OAc: ACN; 0.8 mL/min).

Step 6: Ethyl 3-((6-chloro-7-fluoro-2-methyl-1-(2-(2-oxo-1-oxa-3,8-diazaspiro[4.5]decan-8-yl)acetyl)-1H-indol-3-yl)thio)benzoate (7)

To a stirred solution of Int-A (60 mg, 0.16 mmol) in DMF (2 mL) under inert atmosphere were added compound 6 (55 mg, 0.19 mmol), Cs$_2$CO$_3$ (107 mg, 0.33 mmol) and Bu$_4$NBr (2.66 mg, 0.05 mmol) at RT. The reaction mixture was heated to 65° C. and stirred for 12 h. The reaction progress was monitored by TLC; after reaction completion, the reaction mixture was diluted with water (20 mL) and extracted with EtOAc (2×20 mL). The combined organic extracts were dried over Na$_2$SO$_4$, filtered and concentrated under reduced pressure to obtain the crude material. The crude material was purified through silica gel flash column chromatography using 80% EtOAc/hexanes to afford compound 7 (30 mg, 32%) as brown solid. $^1$H NMR (500 MHz, CD$_3$OD-d$_4$): δ 7.95 (s, 1H), 7.67-7.66 (m, 1H), 7.62 (s, 1H), 7.57 (s, 1H), 7.38-7.35 (m, 1H), 7.19-7.14 (m, 2H), 5.40-5.34 (m, 2H), 4.27-4.22 (m, 2H), 3.58-3.56 (m, 2H), 3.34-3.30 (m, 2H), 2.88 (s, 2H), 2.40 (s, 3H), 1.96-1.87 (m, 2H), 1.89-1.85 (m, 2H), 1.32-1.28 (m, 3H); LC-MS: 91.4%; (M+H$_2$O)$^+$ Found=577.7; (column: X select CSH C-18, 50×3.0 mm, 3.5 μm); RT 4.83 min. 5 mM aq NH$_4$OAc: ACN; 0.8 mL/min).

Step 7: 3-((6-Chloro-7-fluoro-2-methyl-1-(2-(2-oxo-1-oxa-3,8-diazaspiro[4.5]decan-8-yl)acetyl)-1H-indol-3-yl)thio)benzoic acid (Compound 1-12)

To a stirred solution of compound 7 (25 mg, 0.04 mmol) in THF:H$_2$O (1:1, 2 mL) was added LiOH monohydrate (5.3 mg, 0.13 mmol) at 0° C.; warmed to RT. The reaction mixture was stirred for 2 h. The reaction progress was monitored by TLC; after reaction completion, the solvents were removed under reduced pressure. The residue was acidified with citric acid solution (10 mL) and extracted with CH$_2$Cl$_2$ (2×10 mL). The combined organic extracts were dried over Na$_2$SO$_4$, filtered and concentrated under reduced pressure to obtain compound 1-12 (7 mg, 29%) as an off-white solid. $^1$H NMR (400 MHz, CD$_3$OD): δ 7.70 (s, 1H), 7.69-7.67 (m, 1H), 7.24-7.19 (m, 2H), 7.12-7.04 (m, 2H), 5.43-5.31 (m, 2H), 4.20-4.16 (m, 1H), 3.96-3.92 (m, 1H), 3.69-3.64 (m, 1H), 3.47-3.42 (m, 3H), 2.44 (s, 3H), 2.14-2.07 (m, 1H), 2.00-1.94 (m, 2H), 1.85-1.78 (m, 1H); LC-MS: 89.3%; (M+H)$^+$ Found=530.8; (column: X select C-18, 50×3.0 mm, 3.5 μm); RT 3.04 min. 5 mM Aq NH$_4$OAc: ACN; 0.8 mL/min); HPLC: 90.3%; (column: Eclipse-XDB-C-18 (150×4.6 mm, 5 μm); RT 7.67 min. ACN: 5 mM NH$_4$OAc; 1.0 mL/min.

Example 16

3-((6-Chloro-7-fluoro-2-methyl-1-(3-oxo-3-(phenylamino)propyl)-1H-indol-3-yl)thio)benzoic acid (Compound 1-16)

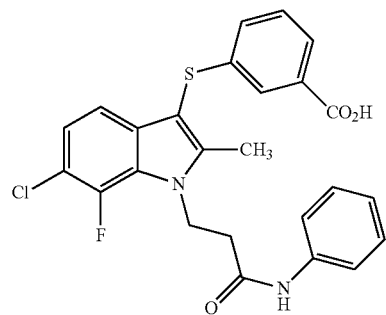 [SMILES: Cc1c(Sc2cccc(C(=O)O)c2)c2ccc(Cl)c(F)c2n1CCC(=O)Nc1ccccc1]

The title compound (1-16) was prepared using the procedure for Example 14, using tert-butyl 3-bromopropionate in Step 1 and aniline in Step 3. Mass: (M+H)$^+$ Found=481.5.

Example 17

3-((6-Chloro-7-fluoro-1-(2-(indolin-1-yl)-2-oxoethyl)-2-methyl-1H-indol-3-yl)thio)benzoic acid (Compound 1-14)

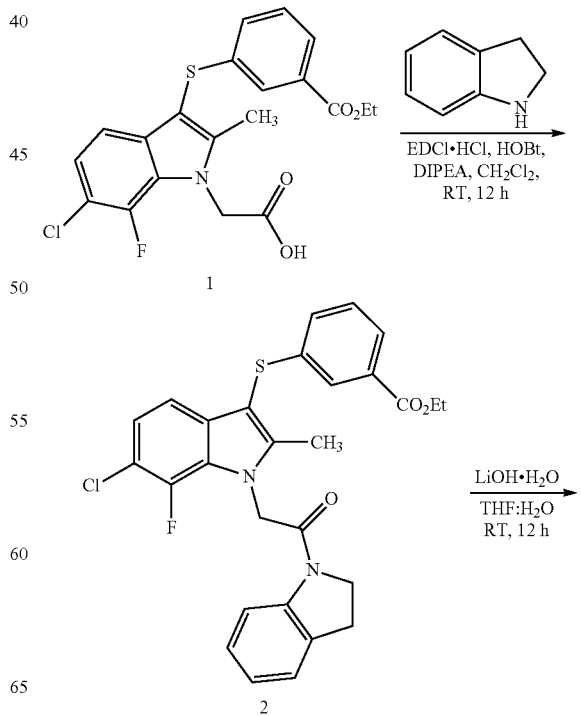

137
-continued

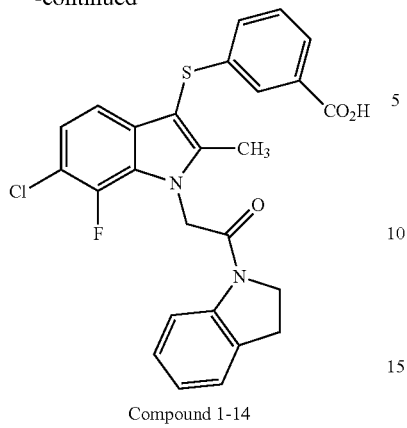

Compound 1-14

Step 1: Ethyl 3-((6-chloro-7-fluoro-1-(2-(indolin-1-yl)-2-oxoethyl)-2-methyl-1H-indol-3-yl)thio)benzoate (2)

To a stirred solution of 1 (Example 14, Step 2; 100 mg, 0.23 mmol) in CH$_2$Cl$_2$ (5 mL) under inert atmosphere were added EDCI.HCl (54.7 mg, 0.28 mmol), HOBt (38 mg, 0.28 mmol), indoline (0.32 mL, 0.28 mmol), and DIPEA (0.13 mL, 0.71 mmol) at RT. The reaction mixture was stirred for 5 h. The reaction progress was monitored by TLC; after reaction completion, the reaction mixture was diluted with water (20 mL) and extracted with CH$_2$Cl$_2$ (2×25 mL). The combined organic extracts were dried over Na$_2$SO$_4$, filtered and concentrated under reduced pressure to obtain the crude material. The crude material was purified through silica gel flash column chromatography using 10% EtOAc/hexanes to afford compound 2 (55 mg, 44%) as pale pink solid. $^1$H NMR (500 MHz, CDCl$_3$): δ 8.14 (d, J=7.5 Hz, 1H), 7.84 (s, 1H), 7.72 (d, J=7.5 Hz, 1H), 7.25-7.18 (m, 4H), 7.10-7.04 (m, 3H), 5.19 (s, 2H), 4.35-4.31 (m, 2H), 4.25 (t, J=8.0 Hz, 2H), 3.36 (t, J=8.0 Hz, 2H), 2.49 (s, 3H), 1.36 (t, J=7.0 Hz, 3H).

Step 2: 3-((6-Chloro-7-fluoro-1-(2-(indolin-1-yl)-2-oxoethyl)-2-methyl-1H-indol-3-yl)thio)benzoic acid (Compound 1-14)

To a stirred solution of compound 2 (55 mg, 0.10 mmol) in THF:H$_2$O (1:1, 4 mL) was added LiOH monohydrate (17.7 mg, 0.42 mmol) at 0° C. The reaction mixture was warmed to RT and stirred for 12 h. The reaction progress was monitored by TLC; after reaction completion, the solvents were removed under reduced pressure. The residue was dissolved in water (10 mL) and acidified with 2 N HCl to pH~5. The aqueous layer was extracted with EtOAc (2×20 mL). The combined organic extracts were dried over Na$_2$SO$_4$, filtered and concentrated under reduced pressure to obtain the crude material. The crude material was triturated with n-pentane (2×5 mL) to afford compound 1-14 (30 mg, 58%) as an off-white solid. $^1$H NMR (400 MHz, DMSO-d$_6$): δ 13.02 (br s, 1H), 7.96 (d, J=7.6 Hz, 1H), 7.67 (d, J=7.6 Hz, 1H), 7.61 (s, 1H), 7.37 (t, J=8.0 Hz, 1H), 7.30 (d, J=7.2 Hz, 1H), 7.23-7.13 (m, 4H), 7.04 (t, J=7.2 Hz, 1H), 5.44 (s, 2H), 4.32 (t, J=8.4 Hz, 2H), 3.28 (t, J=8.4 Hz, 2H), 2.49 (s, 3H). Mass: (M+H)$^+$ Found=495.4. HPLC: 94.4%; (column: Acquity BEH C-18 (50×2.1 mm, 1.7µ); RT 2.94 min. ACN: 0.025% TFA (aq); 0.5 mL/min.

138

Example 18

3-((6-Chloro-7-fluoro-2-methyl-1-(2-oxo-2-(2-oxo-7-azaspiro[3.5]nonan-7-yl)ethyl)-1H-indol-3-yl)thio)benzoic acid (Compound 1-18)

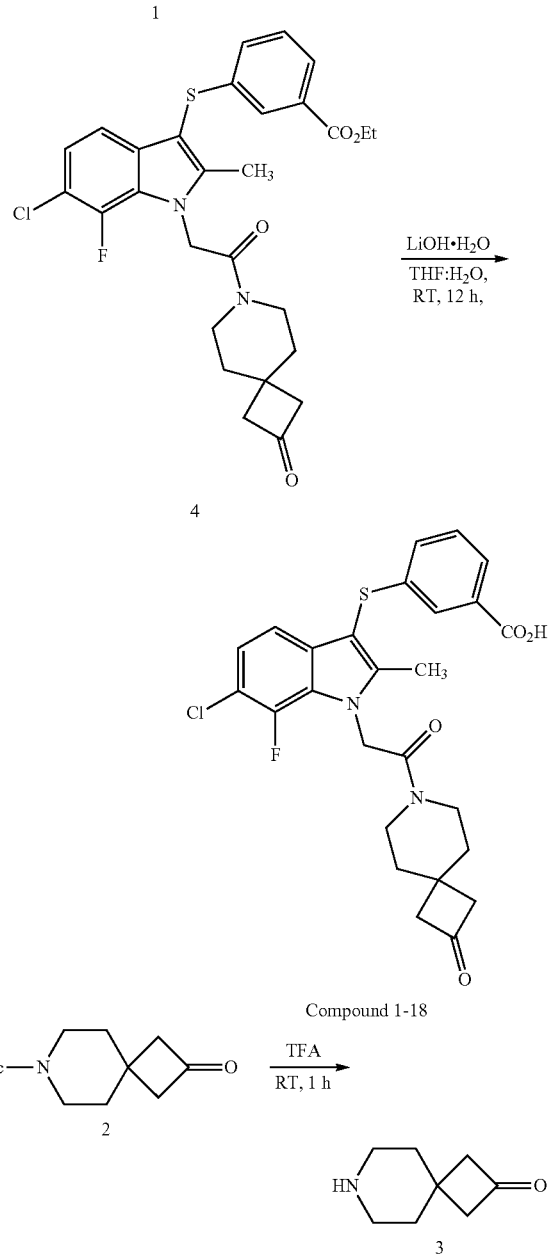

Step 1: 7-Azaspiro[3.5]nonan-2-one (3)

A solution of tert-butyl 2-oxo-7-azaspiro[3.5]nonane-7-carboxylate 2 (100 mg, 0.41 mmol) in TFA (0.5 mL) under inert atmosphere was stirred at RT for 1 h. The reaction progress was monitored by TLC; after reaction completion, the mixture was concentrated under reduced pressure to obtain the crude compound 3 (58 mg) as yellow oil. This compound was carried on to the next step without further purification.

Step 2: Ethyl 3-((6-chloro-7-fluoro-2-methyl-1-(2-oxo-2-(2-oxo-7-azaspiro[3.5]nonan-7-yl)ethyl)-1H-indol-3-yl)thio)benzoate (4)

To a stirred solution of compound 1 (Example 14, Step 2; 88 mg, 0.21 mmol) in CH$_2$Cl$_2$ (20 mL) under inert atmosphere were added compound 3 (58 mg, 0.41 mmol), EDCI.HCl (119 mg, 0.62 mmol), HOBt (84 mg, 0.62 mmol) and DIPEA (107 mg, 0.83 mmol) at 0° C. The reaction mixture was warmed to RT and stirred for 12 h. The reaction progress was monitored by TLC; after reaction completion, the reaction mixture was diluted with water (10 mL) and extracted with CH$_2$Cl$_2$ (2×10 mL). The combined organic extracts were dried over Na$_2$SO$_4$, filtered and concentrated under reduced pressure to obtain to obtain the crude material. The crude material was purified through silica gel flash column chromatography using 20% EtOAc/hexanes to afford compound 4 (70 mg, 31%) as an off-white solid. $^1$H NMR (500 MHz, CDCl$_3$): δ 7.83 (s, 1H), 7.71 (d, J=7.5 Hz, 1H), 7.22-7.18 (m, 2H), 7.06-7.03 (m, 2H), 5.15 (s, 2H), 4.35-4.31 (m, 2H), 3.65-3.58 (m, 4H), 2.92 (s, 4H), 2.44 (s, 3H), 1.92-1.81 (m, 4H), 1.37-1.31 (m, 3H); LC-MS: 81.6%; (M+H)$^+$ Found=543.6; (column: X select C-18, 50×3.0 mm, 3.5 μm); RT 4.51 min. 5 mM NH$_4$OAc: ACN; 0.8 mL/min).

Step 3: 3-((6-Chloro-7-fluoro-2-methyl-1-(2-oxo-2-(2-oxo-7-azaspiro[3.5]nonan-7-yl)ethyl)-1H-indol-3-yl)thio)benzoic acid (Compound 1-18)

To a stirred solution of compound 4 (70 mg, 0.12 mmol) in THF:H$_2$O (1:1, 10 mL) under inert atmosphere was added LiOH monohydrate (15.4 mg, 0.38 mmol) at 0° C. The reaction mixture was warmed to RT and stirred for 12 h. The reaction progress was monitored by TLC; after reaction completion, the reaction mixture was diluted with water (5 mL), acidified with citric acid solution (5 mL) to obtain the solid which was filtered and dried under reduced pressure to afford compound 1-18 (25 mg, 38%) as an off-white solid. $^1$H NMR (400 MHz, CD$_3$OD): δ 7.73-7.69 (m, 2H), 7.27-7.19 (m, 2H), 7.16-7.13 (m, 1H), 7.09-7.05 (m, 1H), 5.38 (s, 2H), 3.70-3.68 (m, 4H), 2.93 (s, 4H), 2.45 (s, 3H), 1.95-1.92 (m, 2H), 1.81-1.78 (m, 2H); MS (ESI): m/z (M+H)$^+$ Found=515.5; HPLC: 95.8%; (column: Acquity-BEH-C-18 (50×2.1 mm, 1.7μ); RT 2.58 min. ACN: 0.025% aq TFA; 0.50 mL/min.

Example 19

3-((6-Chloro-1-(2-(2-cyano-7-azaspiro[3.5]nonan-7-yl)-2-oxoethyl)-7-fluoro-2-methyl-1H-indol-3-yl)thio)benzoic acid (Compound 1-19)

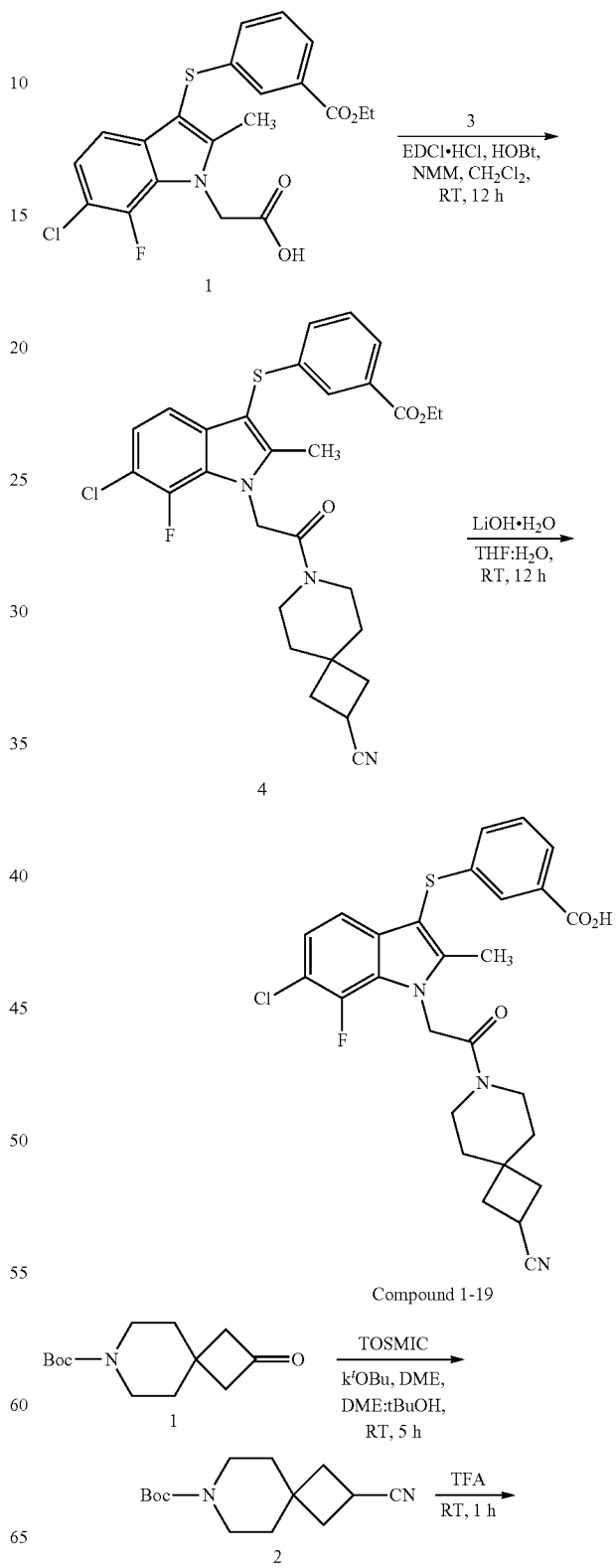

-continued

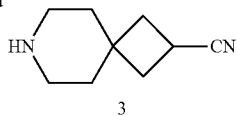

3

Step 1: tert-Butyl 2-cyano-7-azaspiro[3.5]nonane-7-carboxylate (2)

To a stirred solution of tert-butyl 2-oxo-7-azaspiro[3.5]nonane-7-carboxylate 1 (Example 14, Step 2; 400 mg, 1.67 mmol) in DME (4 mL) under inert atmosphere were added p-tosyl methyl isocyanide (366 mg, 1.87 mmol), KOt-Bu (376 mg, 3.34 mmol) in DME: t-BuOH (1:1.4 mL) at 10° C. The reaction mixture was warmed to RT and stirred for 5 h. The reaction progress was monitored by TLC; after reaction completion, the reaction mixture was diluted with water (20 mL) and extracted with EtOAc (2×25 mL). The combined organic extracts were dried over $Na_2SO_4$, filtered and concentrated under reduced pressure to obtain the crude material. The crude material was purified through silica gel flash column chromatography using 10% EtOAc/hexanes to afford compound 2 (60 mg, 14%) as colorless oil. $^1$H NMR (500 MHz, $CDCl_3$): δ 3.33-3.29 (m, 4H), 3.10-3.06 (m, 1H), 2.43-2.18 (m, 4H), 1.64-1.62 (m, 2H), 1.55-1.54 (m, 2H), 1.43 (s, 9H).

Step 2: 7-Azaspiro[3.5]nonane-2-carbonitrile (3)

A solution of compound 2 (60 mg, 0.24 mmol) in TFA (0.5 mL) under inert atmosphere was stirred at RT for 1 h. The reaction progress was monitored by TLC; after reaction completion, the volatile reagent and solvent were removed under reduced pressure to obtain the crude material. The crude material was carried on to the next step without further purification.

Step 3: Ethyl 3-((6-chloro-1-(2-(2-cyano-7-azaspiro[3.5]nonan-7-yl)-2-oxoethyl)-7-fluoro-2-methyl-1H-indol-3-yl)thio)benzoate (4)

To a stirred solution of compound 3 (36 mg, 0.24 mmol) in $CH_2Cl_2$ (10 mL) under inert atmosphere were added 1 (50 mg, 0.12 mmol), EDCI.HCl (69 mg, 0.36 mmol), HOBt (49 mg, 0.36 mmol), and NMM (73 mg, 0.72 mmol) at 0° C. The reaction mixture was warmed to RT and stirred for 12 h. The reaction progress was monitored by TLC; after reaction completion, the reaction mixture was diluted with water (10 mL) and extracted with $CH_2Cl_2$ (2×20 mL). The combined organic extracts were dried over $Na_2SO_4$, filtered and concentrated under reduced pressure to obtain the crude material. The crude material was purified through silica gel flash column chromatography using 25% EtOAc/hexanes to afford compound 4 (30 mg, 23%) as colorless oil. $^1$H NMR (400 MHz, $CDCl_3$): δ 7.82 (s, 1H), 7.70 (d, J=8.0 Hz, 1H), 7.22-7.17 (m, 2H), 7.05-6.99 (m, 2H), 5.11 (s, 2H), 4.32 (q, 2H), 3.56-3.49 (m, 4H), 3.11-3.10 (m, 1H), 2.44 (s, 3H), 2.38-2.25 (m, 4H), 1.91-1.87 (m, 2H), 1.81-1.75 (m, 2H), 1.41-1.29 (m, 2H). LC-MS: 78.2%; (M+H)$^+$ Found=554.5; (column: X-Select C-18, 50×3.0 mm, 3.5 μm); RT 4.58 min. 5 mM $NH_4OAc$: ACN; 0.8 mL/min).

Step 4: 3-((6-Chloro-1-(2-(2-cyano-7-azaspiro[3.5]nonan-7-yl)-2-oxoethyl)-7-fluoro-2-methyl-1H-indol-3-yl)thio)benzoic acid (Compound 1-19)

To a stirred solution of compound 4 (30 mg, 0.05 mmol) in THF:$H_2O$ (1:1, 5 mL) was added LiOH monohydrate (4.33 mg, 0.10 mmol) at 0° C. The reaction mixture was warmed to RT and stirred for 12 h. The reaction progress was monitored by TLC; after reaction completion, the volatile reagents and solvent were removed under reduced pressure. The residue was dissolved in water (10 mL) and acidified with citric acid. The aqueous layer was extracted with $CH_2Cl_2$ (2×10 mL). The combined organic extracts were dried over $Na_2SO_4$, filtered and concentrated under reduced pressure to obtain the crude material. The crude material was purified through preparative HPLC to afford compound 1-19 (30 mg, 35%) as an off-white solid. $^1$H NMR (400 MHz, DMSO-$d_6$): δ 13.00 (br s, 1H), 7.64 (d, J=7.6 Hz, 1H), 7.58 (s, 1H), 7.31 (t, J=8.0 Hz, 1H), 7.19-7.12 (m, 3H), 5.33 (s, 2H), 3.50-3.40 (m, 2H), 3.38-3.31 (m, 3H), 2.17 (s, 3H), 2.13-2.11 (m, 2H), 2.09-2.08 (m, 2H), 1.73-1.69 (m, 2H), 1.58-1.52 (m, 2H). Mass: (M+H)$^+$ Found=527.5. HPLC (purity): 93.5%; (column: Eclipse XDB C-18 (150×4.6 mm, 5μ); RT 8.46 min. 5 mM $NH_4OAc$: ACN; 1.0 mL/min.

Example 20

3-((6-Chloro-7-fluoro-1-(2-(3-(4-fluorophenyl)pyrrolidin-1-yl)-2-oxoethyl)-2-methyl-1H-indol-3-yl)thio)benzoic acid (Compound 1-20)

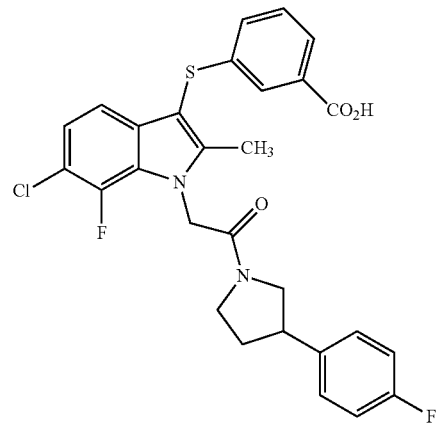 [SMILES: Cc1c(Sc2cccc(C(=O)O)c2)c2ccc(Cl)c(F)c2n1CC(=O)N1CCC(c2ccc(F)cc2)C1]

The title compound (1-20) was prepared using the procedure for Example 14, using 3-(4-fluorophenyl)pyrrolidine in Step 3. [M+H]$^+$ Found=542.2

Example 21

3-((6-Chloro-7-fluoro-1-(2-(3-(4-fluorobenzyl)pyrrolidin-1-yl)-2-oxoethyl)-2-methyl-1H-indol-3-yl)thio)benzoic acid (Compound 1-21)

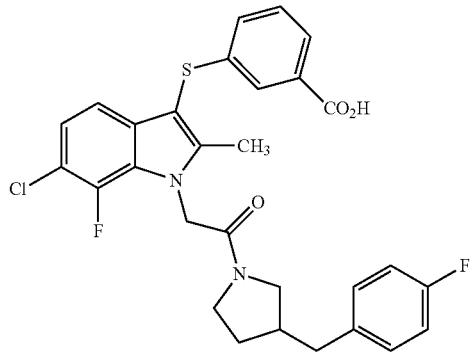 [SMILES: Cc1c(Sc2cccc(C(=O)O)c2)c2ccc(Cl)c(F)c2n1CC(=O)N1CCC(Cc2ccc(F)cc2)C1]

The title compound (1-21) was prepared using the procedure for Example 14, using 3-(4-fluorobenzyl)pyrrolidine in Step 3. [M+H]⁺ Found=555.7

Example 22

3-((6-Chloro-7-fluoro-1-(2-(3-((4-fluorobenzyl)oxy)pyrrolidin-1-yl)-2-oxoethyl)-2-methyl-1H-indol-3-yl)thio)benzoic acid (Compound 1-22)

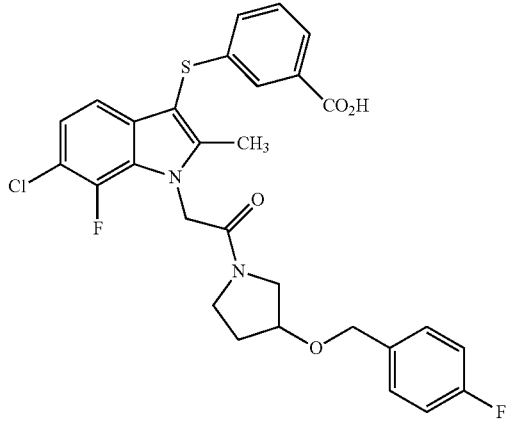 [SMILES: Cc1c(Sc2cccc(C(=O)O)c2)c2ccc(Cl)c(F)c2n1CC(=O)N1CCC(OCc2ccc(F)cc2)C1]

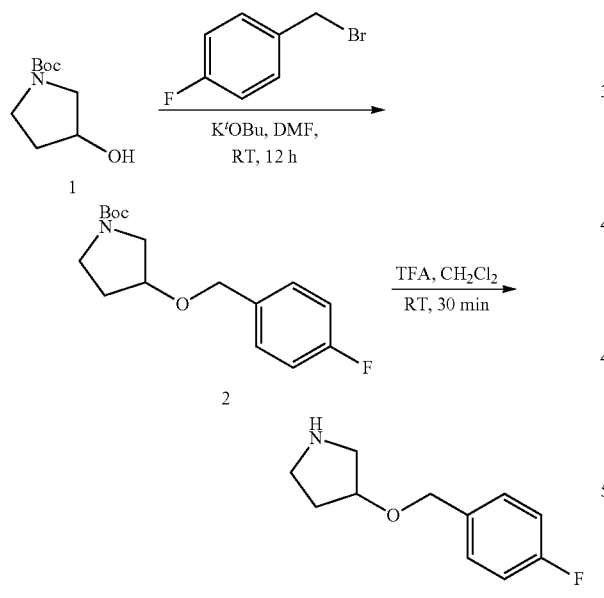

Step 1: tert-Butyl 3-((4-fluorobenzyl)oxy)pyrrolidine-1-carboxylate (2)

To a stirred solution of tert-butyl 3-hydroxypyrrolidine-1-carboxylate 1 (200 mg, 1.06 mmol) in DMF (5 mL) under inert atmosphere were added 1-(bromomethyl)-4-fluorobenzene (222 mg, 1.17 mmol), KOBuᵗ (131.7 mg, 1.17 mmol) at RT and stirred for 12 h. The reaction was monitored by TLC; after completion of the reaction, the reaction mixture was diluted with water (25 mL) and extracted with EtOAc (2×30 mL). The combined organic extracts were dried over $Na_2SO_4$, filtered and concentrated under reduced pressure to obtain the crude. The crude was purified through silica gel column chromatography using 10% EtOAc/Hexanes to afford compound 2 (270 mg, 85%) as a colorless oily liquid. ¹H NMR (500 MHz, CDCl₃): δ 7.36-7.27 (m, 2H), 7.07-7.02 (m, 2H), 4.48 (s, 2H), 4.12-4.11 (m, 1H), 3.46-3.43 (m, 2H), 2.05-1.93 (m, 2H), 1.63-1.61 (m, 1H), 1.46 (s, 9H), 0.89-0.84 (m, 1H).

Step 2: 3-((4-Fluorobenzyl)oxy)pyrrolidine (3)

To a stirred solution of compound 2 (270 mg, 0.91 mmol) in CH₂Cl₂ (5 mL) under inert atmosphere was added TFA (1 mL) at RT and stirred for 30 min. The reaction was monitored by TLC; after completion of the reaction, the volatiles were removed under reduced pressure to obtain the crude. The crude was co-distilled with toluene (2×5 mL) to afford compound 100 mg of crude 3 as a brown liquid. ¹H NMR (400 MHz, DMSO-d₆): δ 8.98 (bs, 1H), 7.41-7.38 (m, 2H), 7.20-7.15 (m, 2H), 4.47 (d, J=6.8 Hz, 2H), 4.29-4.27 (m, 1H), 3.34-3.16 (m, 4H), 2.14-2.08 (m, 1H), 2.02-1.92 (m, 1H); LC-MS: 83.19%; (M+H)⁺ Found=196.1; (column: X Select CSH C-18, 50×3.0 mm, 3.5 μm); RT 2.07 min. 5 mM NH₄OAc: ACN; 0.8 mL/min).

Step 3: 3-((6-Chloro-7-fluoro-1-(2-(3-((4-fluorobenzyl)oxy)pyrrolidin-1-yl)-2-oxoethyl)-2-methyl-1H-indol-3-yl)thio)benzoic acid (Compound 1-22)

The title compound (1-22) was prepared using the procedure for Example 14, using 3-((4-fluorobenzyl)oxy)pyrrolidine 3 in Step 3. ¹H NMR (400 MHz, CD₃OD-d₄): δ 7.73-7.69 (m, 2H), 7.43-7.36 (m, 2H), 7.27-7.15 (m, 2H), 7.13-7.00 (m, 4H), 5.27-5.22 (m, 2H), 4.61-4.59 (m, 2H), 4.40-4.27 (m, 1H), 3.85-3.75 (m, 2H), 3.68-3.47 (m, 2H), 2.49 (s, 3H), 2.33-2.17 (m, 2H), 2.09-2.04 (m, 1H); Mass: (M)⁺ Found=571.6.

Example 23

3-((6-Chloro-7-fluoro-1-(2-(3-((4-trifluoromethylbenzyl)pyrrolidin-1-yl)-2-oxoethyl)-2-methyl-1H-indol-3-yl)thio)benzoic acid (Compound 1-23)

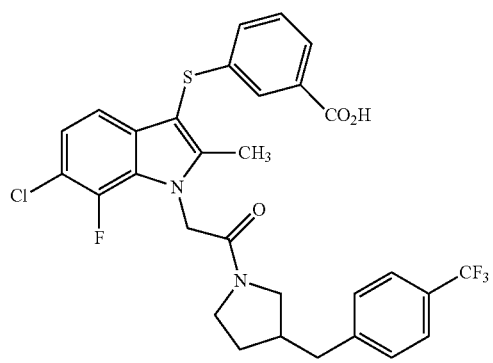 [SMILES: Cc1c(Sc2cccc(C(=O)O)c2)c2ccc(Cl)c(F)c2n1CC(=O)N1CCC(Cc2ccc(C(F)(F)F)cc2)C1]

The title compound (1-23) may be prepared using the procedure for Example 14, using 3-((4-trifluoromethylbenzyl)pyrrolidine in Step 3.

Example 24

3-((6-Chloro-7-fluoro-1-(2-(3-cyanopyrrolidin-1-yl)-2-oxoethyl)-2-methyl-1H-indol-3-yl)thio)benzoic acid (Compound 1-24)

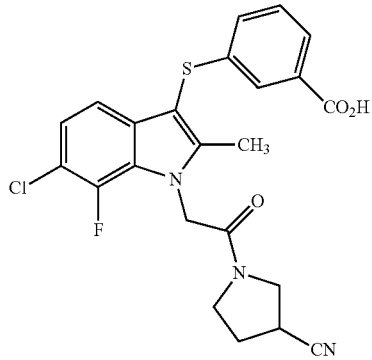 [SMILES: Cc1c(Sc2cccc(C(=O)O)c2)c2ccc(Cl)c(F)c2n1CC(=O)N1CCC(C#N)C1]

The title compound (1-24) was prepared using the procedure for Example 14, using 3-cyanopyrrolidine in Step 3. $^1$H NMR (500 MHz, DMSO-$d_6$): δ 13.01 (br s, 1H), 7.66 (d, J=8.0 Hz, 1H), 7.60 (s, 1H), 7.35-7.32 (m, 1H), 7.14-7.08 (m, 3H), 5.28-5.22 (m, 2H), 4.02-3.97 (m, 1H), 3.84- 3.44 (m, 4H), 2.38 (s, 3H), 2.20-2.16 (m, 1H), 2.08-2.02 (m, 1H); Mass: (M+H)$^+$ Found=470.2.

Example 25

3-((6-Chloro-7-fluoro-2-methyl-1-(3-oxo-3-(pyrrolidin-1-yl)propyl)-1H-indol-3-yl)thio)benzoic acid (Compound 1-25)

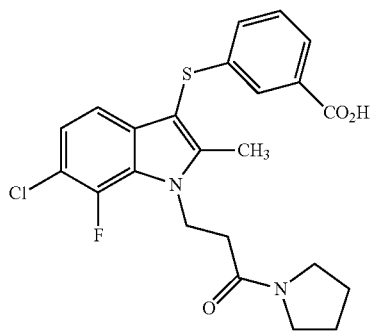 [SMILES: Cc1c(Sc2cccc(C(=O)O)c2)c2ccc(Cl)c(F)c2n1CCC(=O)N1CCCC1]

The title compound (1-25) was prepared using the procedure for Example 14, using tert-butyl 3-bromopropionate in Step 1 and pyrrolidine in Step 3. $^1$H NMR (400 MHz, DMSO-$d_6$): δ 13.04 (br s, 1H), 7.65 (d, J=8.0 Hz, 1H), 7.55 (s, 1H), 7.33 (t, J=8.0 Hz, 1H), 7.20-7.17 (m, 3H), 4.56 (t, J=7.2 Hz, 2H), 3.30-3.25 (m, 4H), 2.78 (t, J=7.2 Hz, 2H), 2.54 (s, 3H), 1.81-1.68 (m, 4H); Mass: (M+H)$^+$ Found=461.3.

Example 26

3-((6-Chloro-7-fluoro-1-(3-(indolin-1-yl)-3-oxopropyl)-2-methyl-1H-indol-3-yl)thio)benzoic acid (Compound 1-26)

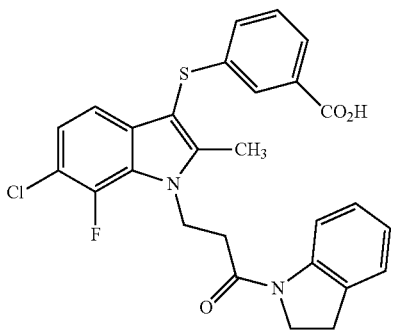 [SMILES: Cc1c(Sc2cccc(C(=O)O)c2)c2ccc(Cl)c(F)c2n1CCC(=O)N1CCc2ccccc21]

The title compound (1-26) was prepared using the procedure for Example 14, using tert-butyl 3-bromopropionate in Step 1 and indoline in Step 3. $^1$H NMR (400 MHz, DMSO-$d_6$): δ 13.04 (br s, 1H), 8.08 (d, J=8.0 Hz, 1H), 7.65 (d, J=8.0 Hz, 1H), 7.57 (s, 1H), 7.31 (t, J=7.6 Hz, 1H), 7.23-7.14 (m, 5H), 6.99 (t, J=7.2 Hz, 1H), 4.66 (t, J=7.2 Hz, 2H), 4.04 (t, J=8.4 Hz, 2H), 3.16-3.01 (m, 4H), 2.58 (s, 3H); Mass: (M+H)+Found=509.5.

Example 27

3-((6-Chloro-7-fluoro-2-methyl-1-(3-oxo-3-(spiro[cyclopropane-1,3'-indolin]-1'-yl)propyl)-1H-indol-3-yl)thio)benzoic acid (Compound 1-27)

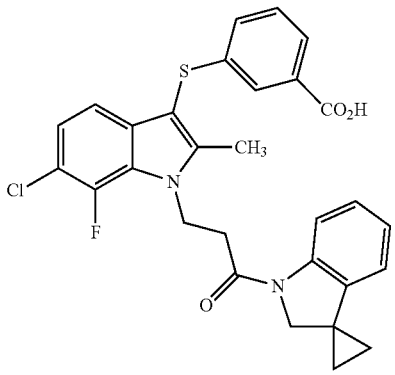 [SMILES: Cc1c(Sc2cccc(C(=O)O)c2)c2ccc(Cl)c(F)c2n1CCC(=O)N1CC2(CC2)c2ccccc21]

The title compound (1-27) may be prepared using the procedure for Example 14, using tert-butyl 3-bromopropionate in Step 1 and spiro[cyclopropane-1,3'-indoline] in Step 3.

Example 28

3-((6-Chloro-7-fluoro-2-methyl-1-(2-oxo-2-(spiro[cyclopropane-1,3'-indolin]-1'-yl)ethyl)-1H-indol-3-yl)thio)benzoic acid (Compound 1-31)

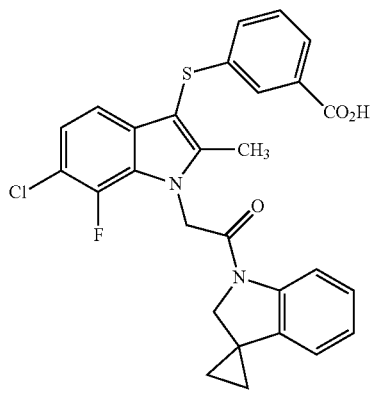 [SMILES: Cc1c(Sc2cccc(C(=O)O)c2)c2ccc(Cl)c(F)c2n1CC(=O)N1CC2(CC2)c2ccccc21]

The title compound (1-31) was prepared using the procedure for Example 14, using spiro[cyclopropane-1,3'-indoline] in Step 3. [M+Na]$^+$ Found=542.85

Example 29

3-((6-Chloro-7-fluoro-1-(2-(5'-fluorospiro[cyclopropane-1,3'-indolin]-1'-yl)-2-oxoethyl)-2-methyl-1H-indol-3-yl)thio)benzoic acid (Compound 1-32)

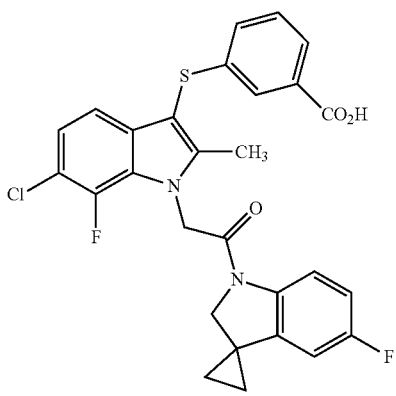 [SMILES: Cc1c(Sc2cccc(C(=O)O)c2)c2ccc(Cl)c(F)c2n1CC(=O)N1CC2(CC2)c2cc(F)ccc21]

The title compound (1-32) was prepared using the procedure for Example 14, using 5'-fluorospiro[cyclopropane-1,3'-indoline] in Step 3. [M+Na]$^+$ Found=560.80

Example 30

3-((6-Chloro-7-fluoro-1-(2-(4'-fluorospiro[cyclobutane-1,3'-indolin]-1'-yl)-2-oxoethyl)-2-methyl-1H-indol-3-yl)thio)benzoic acid (Compound 1-33)

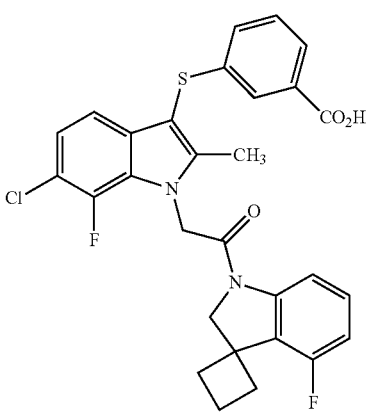

The title compound (1-33) was prepared using the procedure for Example 14, using 4'-fluorospiro[cyclobutane-1,3'-indoline] in Step 3. [M+Na]$^+$ Found=574.8

Example 31

3-((6-Chloro-7-fluoro-1-(2-(6-fluoro-3,3-dimethylindolin-1-yl)-2-oxoethyl)-2-methyl-1H-indol-3-yl)thio)benzoic acid (Compound 1-34)

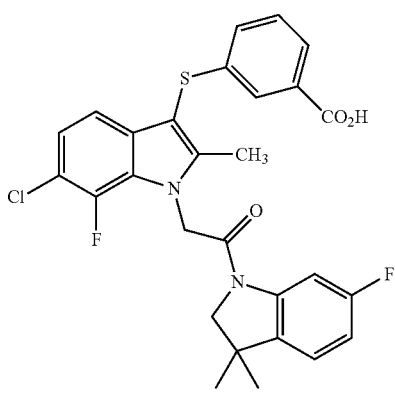 [SMILES: Cc1c(Sc2cccc(C(=O)O)c2)c2ccc(Cl)c(F)c2n1CC(=O)N1CC(C)(C)c2ccc(F)cc21]

The title compound (1-34) was prepared using the procedure for Example 14, using 6-fluoro-3,3-dimethylindoline in Step 3. [M+Na]$^+$ Found=562.85

Example 32

3-((6-Chloro-7-fluoro-2-methyl-1-(2-oxo-2-(3-oxo-2,7-diazaspiro[4.5]decan-7-yl)ethyl)-1H-indol-3-yl)thio)benzoic acid (Compound 1-35)

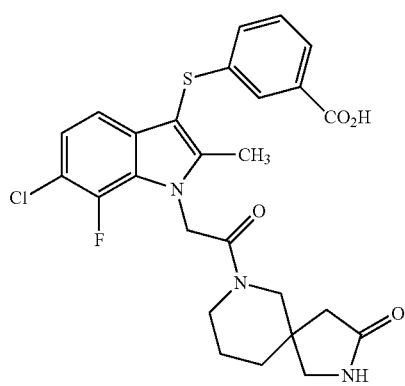 [SMILES: Cc1c(Sc2cccc(C(=O)O)c2)c2ccc(Cl)c(F)c2n1CC(=O)N1CCCC2(CNC(=O)C2)C1]

The title compound (1-35) was prepared using the procedure for Example 14, using 2,7-diazaspiro[4.5]decan-3-one in Step 3. [M+Na]$^+$ Found=551.80

Example 33

3-((6-Chloro-1-(2-(3,4-dihydroquinolin-1(2H)-yl)-2-oxoethyl)-7-fluoro-2-methyl-1H-indol-3-yl)thio)benzoic acid (Compound 1-36)

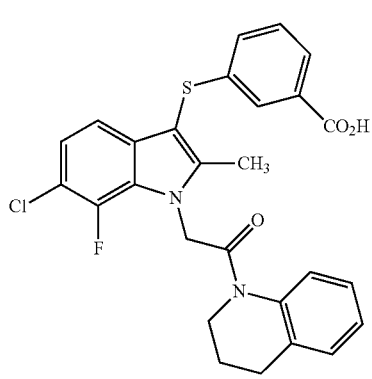 [SMILES: Cc1c(Sc2cccc(C(=O)O)c2)c2ccc(Cl)c(F)c2n1CC(=O)N1CCCc2ccccc21]

The title compound (1-36) was prepared using the procedure for Example 14, using 1,2,3,4-tetrahydroquinoline in Step 3. [M+Na]$^+$ Found=530.85

Example 34

3-((6-Chloro-7-fluoro-1-(2-(3-hydroxy-3-(trifluoromethyl)pyrrolidin-1-yl)-2-oxoethyl)-2-methyl-1H-indol-3-yl)thio)benzoic acid (Compound 1-37)

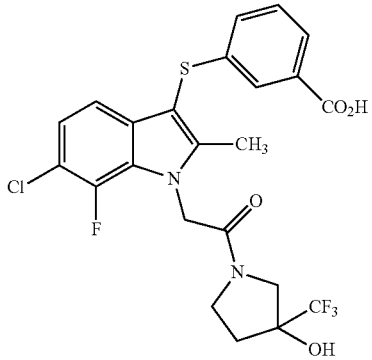 [SMILES: Cc1c(Sc2cccc(C(=O)O)c2)c2ccc(Cl)c(F)c2n1CC(=O)N1CCC(O)(C(F)(F)F)C1]

The title compound (1-37) was prepared using the procedure for Example 14, using 3-(trifluoromethyl)pyrrolidin-3-ol in Step 3. [M+H]$^+$ Found=530.8

Example 35

3-((6-Chloro-7-fluoro-2-methyl-1-(2-(1'-methylspiro[indoline-3,4'-piperidin]-1-yl)-2-oxoethyl)-1H-indol-3-yl)thio)benzoic acid (Compound 1-38)

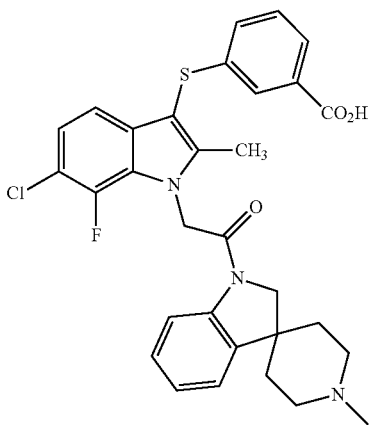 [SMILES: Cc1c(Sc2cccc(C(=O)O)c2)c2ccc(Cl)c(F)c2n1CC(=O)N1CC2(CCN(C)CC2)c2ccccc21]

The title compound (1-38) was prepared using the procedure for Example 14, using 1'-methylspiro[indoline-3,4'-piperidine] in Step 3. [M+Na]$^+$ Found=577.9

Example 36

3-((6-Chloro-7-fluoro-2-methyl-1-(2-oxo-2-(spiro[cyclopentane-1,3'-indolin]-1'-yl)ethyl)-1H-indol-3-yl)thio)benzoic acid (Compound 1-39)

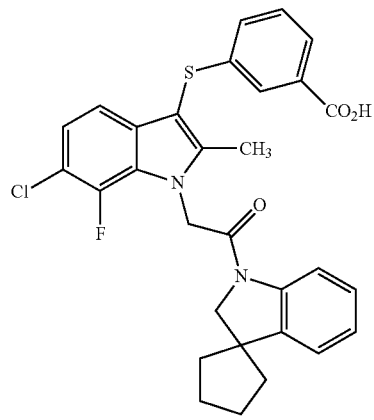 [SMILES: Cc1c(Sc2cccc(C(=O)O)c2)c2ccc(Cl)c(F)c2n1CC(=O)N1CC2(CCCC2)c2ccccc21]

The title compound (1-39) was prepared using the procedure for Example 14, using spiro[cyclopentane-1,3'-indoline] in Step 3. [M+Na]⁺ Found=570.95

Example 37

3-((6-Chloro-7-fluoro-2-methyl-1-(2-oxo-2-(1-(pyrrolidine-1-carbonyl)-6-azaspiro[2.5]octan-6-yl)ethyl)-1H-indol-3-yl)thio)benzoic acid (Compound 1-40)

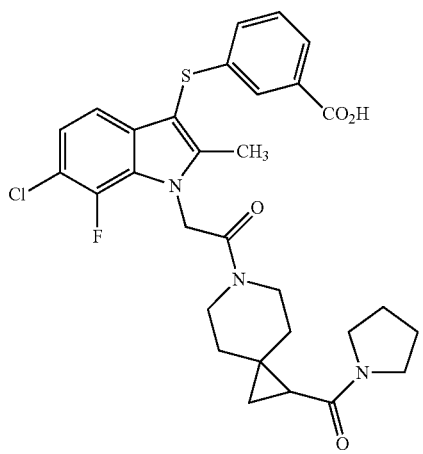 [SMILES: Cc1c(Sc2cccc(C(=O)O)c2)c2ccc(Cl)c(F)c2n1CC(=O)N1CCC2(CC1)CC2C(=O)N1CCCC1]

The title compound (1-40) was prepared using the procedure for Example 14, using pyrrolidin-1-yl(6-azaspiro[2.5]octan-1-yl)methanone in Step 3. [M+Na]⁺ Found=583.9

Example 38

3-((6-Chloro-7-fluoro-2-methyl-1-(2-oxo-2-(2-oxo-1,7-diazaspiro[3.5]nonan-7-yl)ethyl)-1H-indol-3-yl)thio)benzoic acid (Compound 1-41)

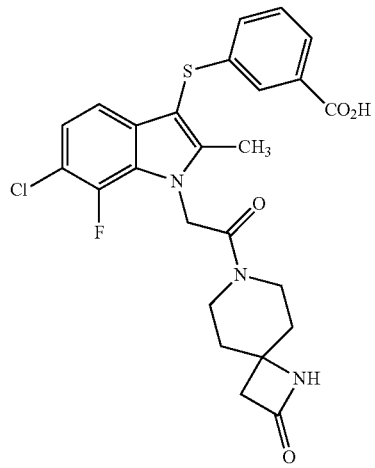 [SMILES: Cc1c(Sc2cccc(C(=O)O)c2)c2ccc(Cl)c(F)c2n1CC(=O)N1CCC2(CC1)CC(=O)N2]

The title compound (1-41) was prepared using the procedure for Example 14, using 1,7-diazaspiro[3.5]nonan-2-one in Step 3. [M+Na]⁺ Found=537.9

Example 39

3-((6-Chloro-1-(2-(3-(3,3-difluoropyrrolidin-1-yl)azetidin-1-yl)-2-oxoethyl)-7-fluoro-2-methyl-1H-indol-3-yl)thio)benzoic acid (Compound 1-42)

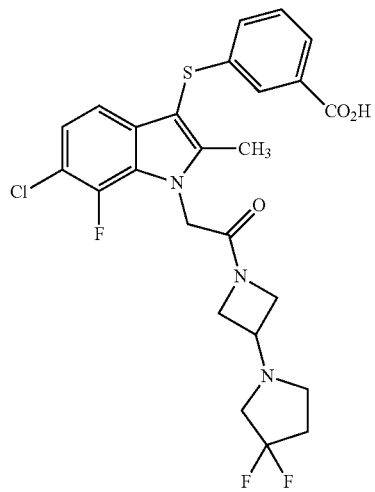 [SMILES: Cc1c(Sc2cccc(C(=O)O)c2)c2ccc(Cl)c(F)c2n1CC(=O)N1CC(N2CCC(F)(F)C2)C1]

The title compound (1-42) was prepared using the procedure for Example 14, using 1-(azetidin-3-yl)-3,3-difluoropyrrolidine in Step 3. [M+Na]⁺ Found=559.85

Example 40

3-((6-Chloro-1-(2-(2,4-dioxo-1,3,7-triazaspiro[4.4]nonan-7-yl)-2-oxoethyl)-7-fluoro-2-methyl-1H-indol-3-yl)thio)benzoic acid (Compound 1-43)

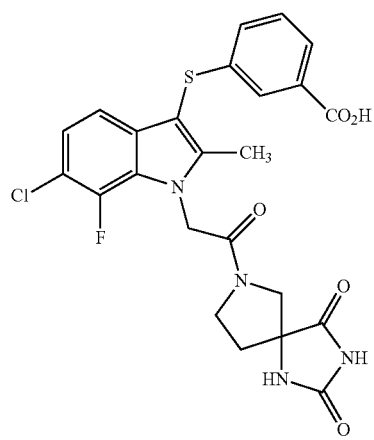 [SMILES: Cc1c(Sc2cccc(C(=O)O)c2)c2ccc(Cl)c(F)c2n1CC(=O)N1CCC2(C1)NC(=O)NC2=O]

The title compound (1-43) may be prepared using the procedure for Example 14, using 1,3,7-triazaspiro[4.4]nonane-2,4-dione in Step 3.

Example 41

3-((6-Chloro-1-(2-(4,4-dimethylpiperidin-1-yl)-2-oxoethyl)-7-fluoro-2-methyl-1H-indol-3-yl)thio)benzoic acid (Compound 1-44)

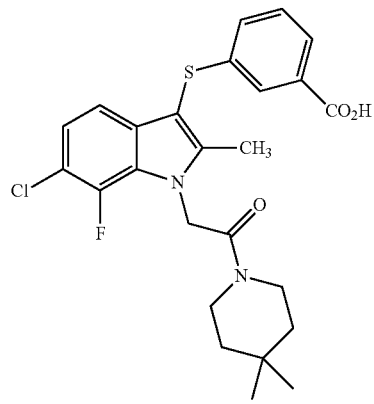 [SMILES: Cc1c(Sc2cccc(C(=O)O)c2)c2ccc(Cl)c(F)c2n1CC(=O)N1CCC(C)(C)CC1]

The title compound (1-44) was prepared using the procedure for Example 14, using 4,4-dimethylpiperidine in Step 3. [M+Na]$^+$ Found=510.95

Example 42

3-((6-Chloro-7-fluoro-2-methyl-1-(2-oxo-2-(3-oxo-2,8-diazaspiro[4.5]decan-8-yl)ethyl)-1H-indol-3-yl)thio)benzoic acid (Compound 1-45)

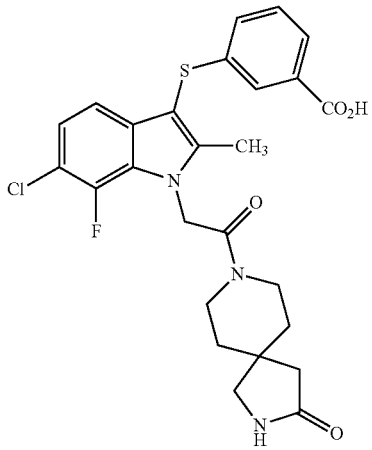 [SMILES: Cc1c(Sc2cccc(C(=O)O)c2)c2ccc(Cl)c(F)c2n1CC(=O)N1CCC2(CC1)CNC(=O)C2]

The title compound (1-45) was prepared using the procedure for Example 14, using 2,8-diazaspiro[4.5]decan-3-one in Step 3. [M+Na]$^+$ Found=551.9

Example 43

3-((6-Chloro-7-fluoro-2-methyl-1-(2-oxo-2-(8-oxa-2-azaspiro[4.5]decan-2-yl)ethyl)-1H-indol-3-yl)thio)benzoic acid (Compound 1-46)

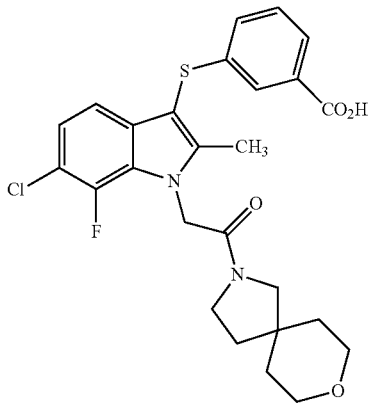 [SMILES: Cc1c(Sc2cccc(C(=O)O)c2)c2ccc(Cl)c(F)c2n1CC(=O)N1CCC2(CCOCC2)C1]

The title compound (1-46) was prepared using the procedure for Example 14, using 8-oxa-2-azaspiro[4.5]decane in Step 3. [M+Na]$^+$ Found=538.9

Example 44

3-((6-Chloro-7-fluoro-2-methyl-1-(2-oxo-2-(2-oxa-6-azaspiro[3.3]heptan-6-yl)ethyl)-1H-indol-3-yl)thio)benzoic acid (Compound 1-47)

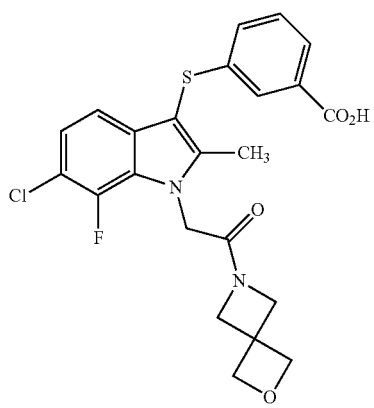 [SMILES: Cc1c(Sc2cccc(C(=O)O)c2)c2ccc(Cl)c(F)c2n1CC(=O)N1CC2(COC2)C1]

The title compound (1-47) may be prepared using the procedure for Example 14, using 2-oxa-6-azaspiro[3.3]heptane in Step 3.

Example 45

3-((6-Chloro-1-(2-(3-(1,1-dioxidothiomorpholino)azetidin-1-yl)-2-oxoethyl)-7-fluoro-2-methyl-1H-indol-3-yl)thio)benzoic acid (Compound 1-48)

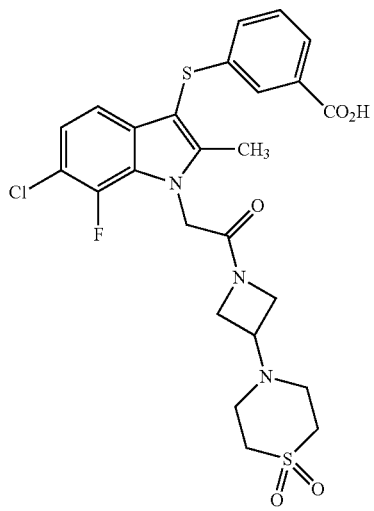 [SMILES: Cc1c(Sc2cccc(C(=O)O)c2)c2ccc(Cl)c(F)c2n1CC(=O)N1CC(N2CCS(=O)(=O)CC2)C1]

The title compound (1-48) was prepared using the procedure for Example 14, using 4-(azetidin-3-yl)thiomorpholine 1,1-dioxide in Step 3. [M+H]$^+$ Found=565.95

Example 46

3-((6-Chloro-7-fluoro-2-methyl-1-(2-oxo-2-(7-oxo-2,6-diazaspiro[3.4]octan-2-yl)ethyl)-1H-indol-3-yl)thio)benzoic acid (Compound 1-49)

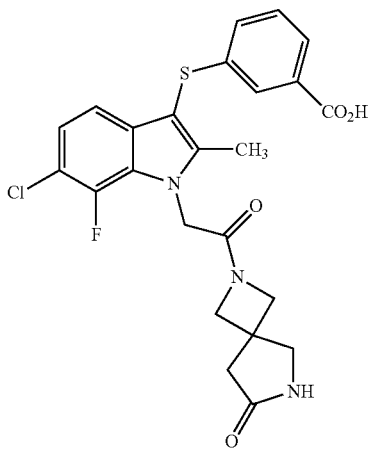 [SMILES: Cc1c(Sc2cccc(C(=O)O)c2)c2ccc(Cl)c(F)c2n1CC(=O)N1CC2(CNC(=O)C2)C1]

The title compound (1-49) was prepared using the procedure for Example 14, using 2,6-diazaspiro[3.4]octan-7-one in Step 3. [M+Na]$^+$ Found=523.9

Example 47

3-((6-Chloro-7-fluoro-2-methyl-1-(2-oxo-2-(2-oxa-6-azaspiro[3.4]octan-6-yl)ethyl)-1H-indol-3-yl)thio)benzoic acid (Compound 1-50)

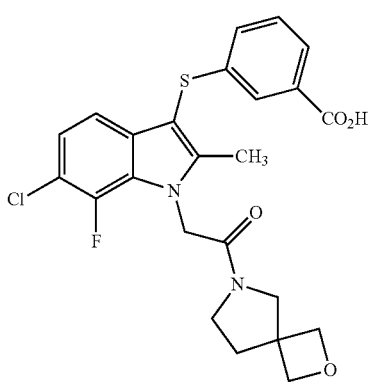 [SMILES: Cc1c(Sc2cccc(C(=O)O)c2)c2ccc(Cl)c(F)c2n1CC(=O)N1CCC2(COC2)C1]

The title compound (1-50) was prepared using the procedure for Example 14, using 2-oxa-6-azaspiro[3.4]octane in Step 3. [M+H]$^+$ Found=510.9

Example 48

3-((1-(2-(((1R,5S,6R)-6-Carbamoyl-3-azabicyclo[3.1.0]hexan-3-yl)-2-oxoethyl)-6-chloro-7-fluoro-2-methyl-1H-indol-3-yl)thio)benzoic acid (Compound 1-51)

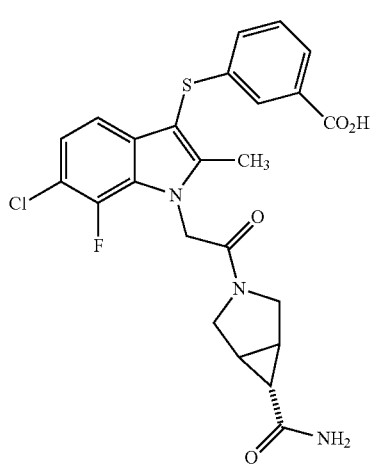

The title compound (1-51) was prepared using the procedure for Example 14, using (1R,5S,6R)-3-azabicyclo[3.1.0]hexane-6-carboxamide in Step 3. [M+Na]⁺ Found=523.9

Example 49

3-((6-Chloro-7-fluoro-1-(2-(3-hydroxy-3-methylazetidin-1-yl)-2-oxoethyl)-2-methyl-1H-indol-3-yl)thio)benzoic acid (Compound 1-52)

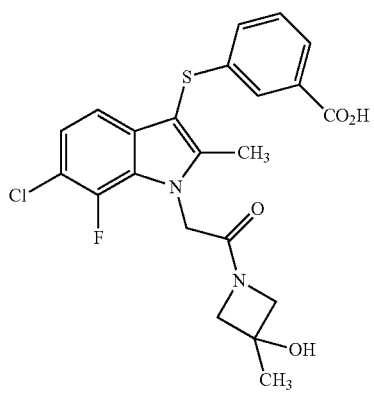 [SMILES: Cc1c(Sc2cccc(C(=O)O)c2)c2ccc(Cl)c(F)c2n1CC(=O)N1CC(C)(O)C1]

The title compound (1-52) was prepared using the procedure for Example 14, using 3-methylazetidin-3-ol in Step 3. [M+Na]⁺ Found=484.80

Example 50

3-((6-Chloro-7-fluoro-2-methyl-1-(2-oxo-2-(10-oxo-3,9-diazaspiro[5.6]dodecan-3-yl)ethyl)-1H-indol-3-yl)thio)benzoic acid (Compound 1-53)

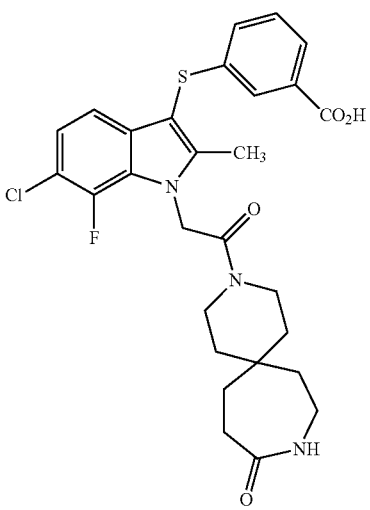 [SMILES: Cc1c(Sc2cccc(C(=O)O)c2)c2ccc(Cl)c(F)c2n1CC(=O)N1CCC2(CCNC(=O)CC2)CC1]

The title compound (1-53) was prepared using the procedure for Example 14, using 3,9-diazaspiro[5.6]dodecan-10-one in Step 3. [M+Na]⁺ Found=579.95

Example 51

3-((6-Chloro-7-fluoro-2-methyl-1-(2-oxo-2-(2-oxopyrrolidin-1-yl)ethyl)-1H-indol-3-yl)thio)benzoic acid (Compound 1-59)

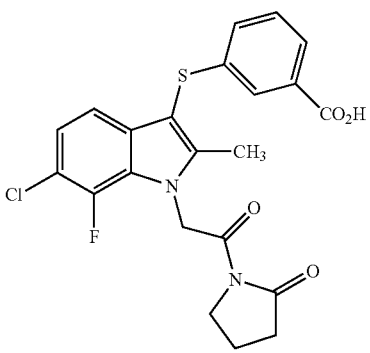 [SMILES: Cc1c(Sc2cccc(C(=O)O)c2)c2ccc(Cl)c(F)c2n1CC(=O)N1CCCC1=O]

The title compound (1-59) was prepared using the procedure for Example 1, using pyrrolin-2-one and pyridine in Step 1 [M+H]⁺ Found=461.4

Example 52

3-((6-Chloro-7-fluoro-1-(2-(4-(4-fluorobenzyl)piperidin-1-yl)-2-oxoethyl)-2-methyl-1H-indol-3-yl)thio)benzoic acid (Compound 1-60)

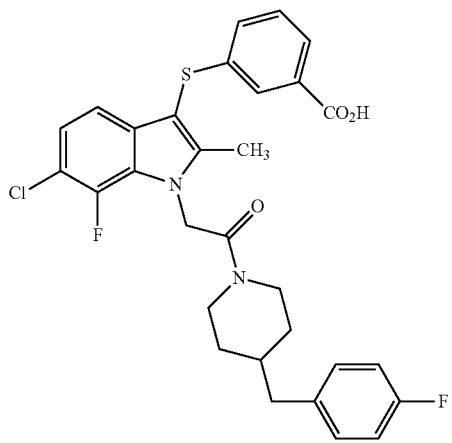 [SMILES: Cc1c(Sc2cccc(C(=O)O)c2)c2ccc(Cl)c(F)c2n1CC(=O)N1CCC(Cc2ccc(F)cc2)CC1]

The title compound (1-60) was prepared using the procedure for Example 14, using 4-[(4-fluorophenyl)methyl]piperidine in Step 3. $^1$H NMR (400 MHz, CD$_3$OD-d$_4$): δ 7.70 (s, 1H), 7.63 (d, J=8.0 Hz, 1H), 7.23-7.12 (m, 3H), 7.06-7.02 (m, 1H), 7.00-6.98 (m, 4H), 5.30 (q, 2H), 4.45 (d, J=13.2 Hz, 1H), 4.07 (d, J=13.2 Hz, 1H), 3.31-3.28 (m, 1H), 2.73-2.70 (m, 1H), 2.67-2.60 (m, 2H), 2.43 (s, 3H), 2.21-2.17 (m, 2H), 2.04 (d, J=8.4 Hz, 1H), 1.91-1.86 (m, 2H); LC-MS: 98.2%; (M+H)$^+$ Found=569.6.

Example 53

3-((1-(2-(4-(2-(1H-Pyrazol-1-yl)ethyl)piperidin-1-yl)-2-oxoethyl)-6-chloro-7-fluoro-2-methyl-1H-indol-3-yl)thio)benzoic acid (Compound 1-61)

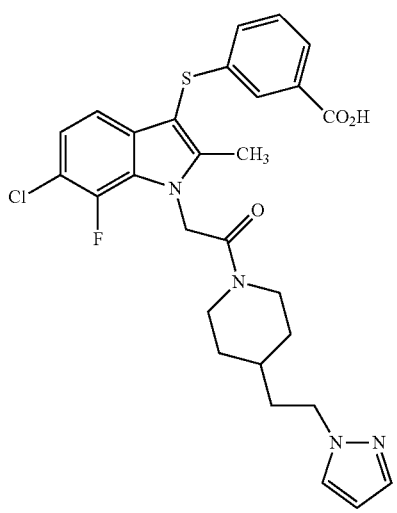 [SMILES: Cc1c(Sc2cccc(C(=O)O)c2)c2ccc(Cl)c(F)c2n1CC(=O)N1CCC(CCn2cccn2)CC1]

The title compound (1-61) was prepared using the procedure for Example 14, using 4-(2-pyrazolo-1-ylethyl)piperidine in Step 3. $^1$H NMR (400 MHz, DMSO-d$_6$): δ 12.99 (br s, 1H), 7.75 (s, 1H), 7.65 (d, J=7.6 Hz, 1H), 7.59 (s, 1H), 7.42 (s, 1H), 7.34 (t, J=7.6 Hz, 1H), 7.19-7.13 (m, 3H), 6.22 (s, 1H), 5.33 (q, 2H), 4.28-4.25 (m, 1H), 4.17 (t, J=7.2 Hz, 2H), 3.98-3.95 (m, 1H), 3.12-3.06 (m, 1H), 2.64-2.58 (m, 1H), 2.39 (s, 3H), 1.81-1.74 (m, 4H), 1.51-1.49 (m, 1H), 1.24-1.22 (m, 1H), 1.06-1.02 (m, 1H); Mass: (M+H)$^+$ Found=555.6.

Example 54

3-((6-Chloro-7-fluoro-2-methyl-1-(2-oxo-2-(4-phenethylpiperidin-1-yl)ethyl)-1H-indol-3-yl)thio)benzoic acid (Compound 1-62)

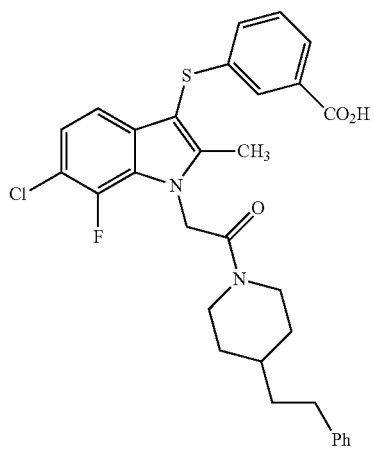 [SMILES: Cc1c(Sc2cccc(C(=O)O)c2)c2ccc(Cl)c(F)c2n1CC(=O)N1CCC(CCc2ccccc2)CC1]

The title compound (1-62) was prepared using the procedure for Example 14, using 4-phenethylpiperidine in Step 3. $^1$H NMR (400 MHz, DMSO-d$_6$): δ 12.99 (br s, 1H), 7.64 (d, J=7.6 Hz, 1H), 7.59 (s, 1H), 7.36-7.30 (m, 3H), 7.28-7.15 (m, 6H), 5.33 (q, 2H), 4.30 (d, J=12.8 Hz, 1H), 3.98 (d, J=12.8 Hz, 1H), 3.11 (t, J=12.4 Hz, 1H), 2.65-2.61 (m, 3H), 2.40-2.38 (m, 3H), 1.85 (dd, J=12.8 Hz, 2H), 1.57-1.54 (m, 3H), 1.27-1.22 (m, 1H), 1.07-1.02 (m, 1H); Mass: (M+H)$^+$ Found=565.6.

Example 55

3-((6-Chloro-7-fluoro-2-methyl-1-(2-oxo-2-(4-(pyridin-4-ylmethyl)piperidin-1-yl)ethyl)-1H-indol-3-yl)thio)benzoic acid (Compound 1-63)

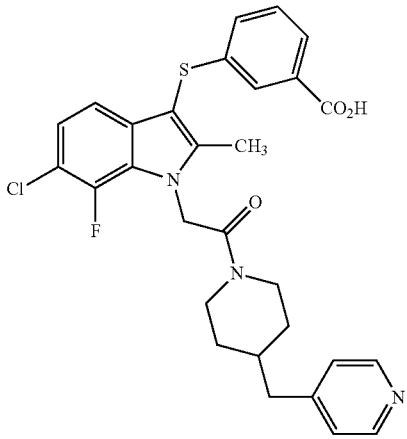 [SMILES: Cc1c(Sc2cccc(C(=O)O)c2)c2ccc(Cl)c(F)c2n1CC(=O)N1CCC(Cc2ccncc2)CC1]

The title compound (1-63) was prepared using the procedure for Example 14, using 4-(4-piperidylmethyl)pyridine in Step 3. $^1$H NMR (400 MHz, DMSO-d$_6$): δ 12.50 (br s, 1H), 8.47 (d, J=5.6 Hz, 2H), 7.60 (t, J=7.6 Hz, 2H), 7.27-7.24 (m, 3H), 7.19-7.12 (m, 2H), 7.06 (d, J=7.6 Hz, 1H), 5.32 (q, 2H), 4.30-4.26 (m, 1H), 4.03-3.96 (m, 1H), 3.16-3.07 (m, 1H), 2.66-2.62 (m, 3H), 2.58 (s, 3H), 1.98-1.90 (m, 2H), 1.70-1.67 (m, 1H), 1.61-1.58 (m, 1H), 1.29-1.26 (m, 2H); Mass: (M+H)$^+$ Found=552.6.

Example 56

3-((6-Chloro-7-fluoro-2-methyl-1-(2-(4-(1-methyl-1H-pyrazol-4-yl)piperidin-1-yl)-2-oxoethyl)-1H-indol-3-yl)thio)benzoic acid (Compound 1-64)

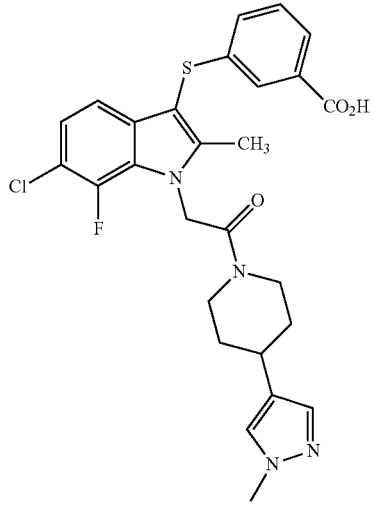 [SMILES: Cc1c(Sc2cccc(C(=O)O)c2)c2ccc(Cl)c(F)c2n1CC(=O)N1CCC(c2cnn(C)c2)CC1]

The title compound (1-64) was prepared using the procedure for Example 14, using 4-(1-methylpyrazol-4yl)piperidine in Step 3. $^1$H NMR (500 MHz, DMSO-d$_6$): δ 7.55 (t, J=6.0 Hz, 3H), 7.32 (s, 1H), 7.19-7.09 (m, 3H), 6.88 (d, J=7.5 Hz, 1H), 5.35 (q, 2H), 4.34-4.32 (m, 1H), 4.03-4.01 (m, 1H), 3.78 (s, 3H), 3.25-3.23 (m, 1H), 2.80-2.75 (m, 2H), 2.40 (s, 3H), 2.00-1.98 (m, 1H), 1.89-1.88 (m, 1H), 1.54-1.52 (m, 1H), 1.10-1.07 (m, 1H); Mass: (M+H)$^+$ Found=541.7.

Example 57

3-((6-Chloro-7-fluoro-1-(2-(3-(4-fluorobenzyl)pyrrolidin-1-yl)-2-oxoethyl)-2-methyl-1H-indol-3-yl)thio)benzoic acid Enantiomer A (Compound 1-65) and Example 58: 3-((6-Chloro-7-fluoro-1-(2-(3-(4-fluorobenzyl)pyrrolidin-1-yl)-2-oxoethyl)-2-methyl-1H-indol-3-yl)thio)benzoic acid Enantiomer B (Compound 1-66)

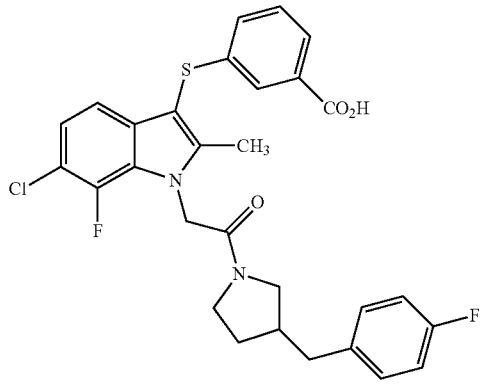 [SMILES: Cc1c(Sc2cccc(C(=O)O)c2)c2ccc(Cl)c(F)c2n1CC(=O)N1CCC(Cc2ccc(F)cc2)C1]

Racemic 3-((6-chloro-7-fluoro-1-(2-(3-(4-fluorobenzyl)pyrrolidin-1-yl)-2-oxoethyl)-2-methyl-1H-indol-3-yl)thio)benzoic acid (compound 1-21; Example 21) was separated using chiral phase HPLC (Chiralcel-OD-H; 250×4.6 mm, 5 μm; Mobile phase (A) 0.1% TFA in n-Hexane (B) IPA (A:B:87:13); flow Rate: 1.0 mL/min). The first compound eluted afforded 3-((6-chloro-7-fluoro-1-(2-(3-(4-fluorobenzyl)pyrrolidin-1-yl)-2-oxoethyl)-2-methyl-1H-indol-3-yl)thio)benzoic acid Enantiomer A (1-65). Chiral HPLC: 100% R$_t$=25.46 min MS (ESI): m/z 541.5 [M+1]$^+$. The second compound eluted afforded 3-((6-chloro-7-fluoro-1-(2-(3-(4-fluorobenzyl)pyrrolidin-1-yl)-2-oxoethyl)-2-methyl-1H-indol-3-yl)thio)benzoic acid Enantiomer B (1-66). Chiral HPLC: 99.4% R$_t$=30.58 min MS (ESI): m/z (M+H)$^+$ Found=541.5.

Example 59

3-((1-(2-(8-Benzyl-2,8-diazaspiro[4.5]decan-2-yl)-2-oxoethyl)-6-chloro-7-fluoro-2-methyl-1H-indol-3-yl)thio)benzoic acid (Compound 1-67)

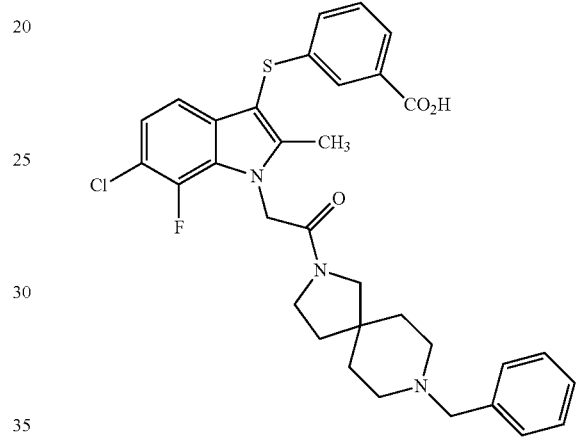

The title compound (1-67) was prepared using the procedure or Example 14, using 8-benzyl-3,8-diazaspiro[4.5]decane in Step 3. $^1$H NMR (400 MHz, CD$_3$OD-d$_4$): δ 7.69-7.64 (m, 2H), 7.46-7.39 (m, 5H), 7.23-7.14 (m, 4H), 5.23 (s, 2H), 4.00-3.99 (m, 2H), 3.78 (t, J=7.2 Hz, 1H), 3.64-3.58 (m, 2H), 3.50-3.49 (m, 1H), 3.41-3.39 (m, 1H), 3.04-2.84 (m, 3H), 2.50 (s, 3H), 2.49-2.46 (m, 1H), 2.05-2.01 (m, 1H), 1.96-1.77 (m, 4H); Mass: (M+H)$^+$ Found=607.1.

Example 60

3-((6-Chloro-7-fluoro-2-methyl-1-(2-(7-methyl-2,7-diazaspiro[3.5]nonan-2-yl)-2-oxoethyl)-1H-indol-3-yl)thio)benzoic acid (Compound 1-68)

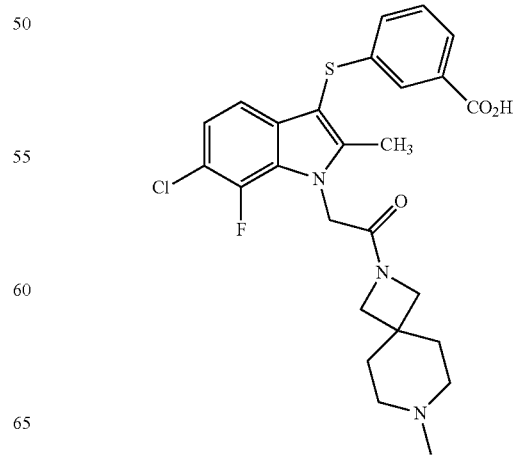

The title compound (1-68) was prepared using the procedure for Example 14, using 7-methyl-2,7-diazaspiro[3.5]nonane in Step 3. [M+Na]+ Found=515.5

The title compound (1-70) was prepared using the procedure for Example 14, 4,6-difluoroindoline in Step 3. [M+Na]+ Found=552.8

Example 61

3-((6-Chloro-7-fluoro-2-methyl-1-(2-oxo-2-(2-oxo-1-oxa-3,7-diazaspiro[4.5]decan-7-yl)ethyl)-1H-indol-3-yl)thio)benzoic acid (Compound 1-69)

Example 63

3-((6-Chloro-1-(2-(5-chloroindolin-1-yl)-2-oxo-ethyl)-7-fluoro-2-methyl-1H-indol-3-yl)thio)benzoic acid (Compound 1-71)

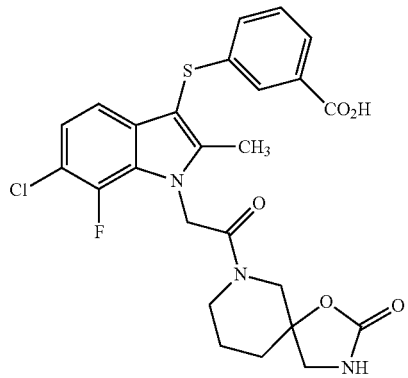 [SMILES: Cc1c(Sc2cccc(C(=O)O)c2)c2ccc(Cl)c(F)c2n1CC(=O)N1CCCC2(CNC(=O)O2)C1]

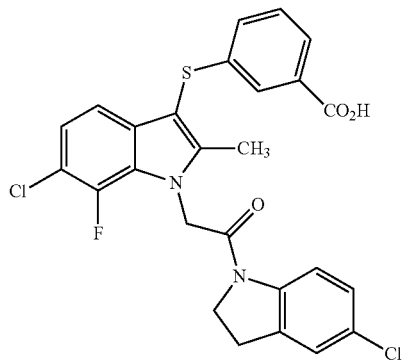

The title compound (1-69) was prepared using the procedure for Example 14, using 4-oxa-2,9-diazaspiro[4.5]decan-3-one in Step 3. [M+Na]+ Found=553.85

The title compound (1-71) was prepared using the procedure for Example 14, 5-chloroindoline in Step 3. [M+Na]+ Found=550.8

Example 62

3-((6-Chloro-1-(2-(4,6-difluoroindolin-1-yl)-2-oxo-ethyl)-7-fluoro-2-methyl-1H-indol-3-yl)thio)benzoic acid (Compound 1-70)

Example 64

3-((6-Chloro-1-(2-(6-chloroindolin-1-yl)-2-oxo-ethyl)-7-fluoro-2-methyl-1H-indol-3-yl)thio)benzoic acid (Compound 1-73)

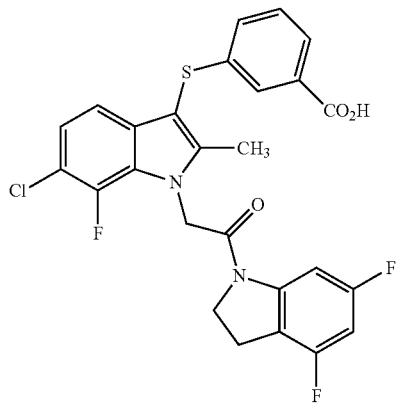 [SMILES: Cc1c(Sc2cccc(C(=O)O)c2)c2ccc(Cl)c(F)c2n1CC(=O)N1CCc2c(F)cc(F)cc21]

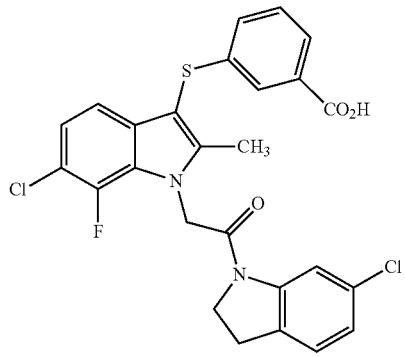 [SMILES: Cc1c(Sc2cccc(C(=O)O)c2)c2ccc(Cl)c(F)c2n1CC(=O)N1CCc2ccc(Cl)cc21]

The title compound (1-73) was prepared using the procedure for Example 14, 6-chloroindoline in Step 3. [M+Na]+ Found=550.8

Example 65

3-((6-Chloro-1-(2-(2,3-dihydro-1H-pyrrolo[2,3-b]pyridin-1-yl)-2-oxoethyl)-7-fluoro-2-methyl-1H-indol-3-yl)thio)benzoic acid (Compound 1-72)

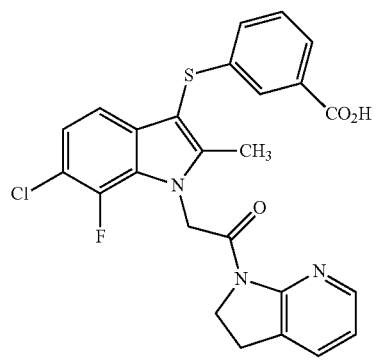 [SMILES: Cc1c(Sc2cccc(C(=O)O)c2)c2ccc(Cl)c(F)c2n1CC(=O)N1CCc2cccnc21]

The title compound (1-72) was prepared using the procedure for Example 14, 2,3-dihydro-1H-pyrrolo[2,3-b]pyridine in Step 3. [M+Na]+ Found=517.85

Example 66

3-((6-Chloro-7-fluoro-1-(2-(3-(4-fluorophenyl)pyrrolidin-1-yl)-2-oxoethyl)-2-methyl-1H-indol-3-yl)thio)benzoic acid Enantiomer A (Compound 1-74) and Example 67: 3-((6-Chloro-7-fluoro-1-(2-(3-(4-fluorophenyl)pyrrolidin-1-yl)-2-oxoethyl)-2-methyl-1H-indol-3-yl)thio)benzoic acid Enantiomer B (Compound 1-75)

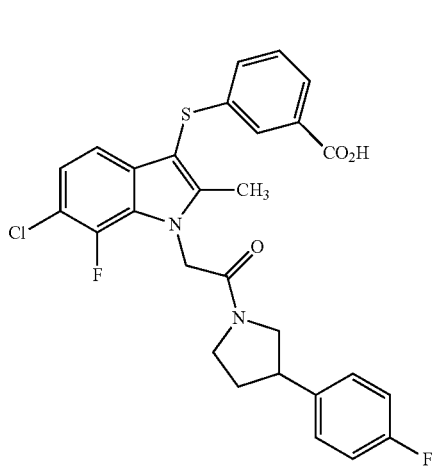 [SMILES: Cc1c(Sc2cccc(C(=O)O)c2)c2ccc(Cl)c(F)c2n1CC(=O)N1CCC(c2ccc(F)cc2)C1]

Racemic 3-((6-chloro-7-fluoro-1-(2-(3-(4-fluorophenyl)pyrrolidin-1-yl)-2-oxoethyl)-2-methyl-1H-indol-3-yl)thio)benzoic acid (Example 1-20) was separated using chiral phase HPLC (Chiralcel OD-H). The first compound eluted afforded 3-((6-Chloro-7-fluoro-1-(2-(3-(4-fluorophenyl)pyrrolidin-1-yl)-2-oxoethyl)-2-methyl-1H-indol-3-yl)thio)benzoic acid Enantiomer A (1-74)[M+H]+ Found=541.5. The second compound eluted afforded 3-((6-chloro-7-fluoro-1-(2-(3-(4-fluorophenyl)pyrrolidin-1-yl)-2-oxoethyl)-2-methyl-1H-indol-3-yl)thio)benzoic acid Enantiomer B (1-75)[M+H]+ Found=515.5.

Example 68

6-((6-Chloro-7-fluoro-2-methyl-1-(2-oxo-2-(2-oxo-1-oxa-3,8-diazaspiro[4.5]decan-8-yl)ethyl)-1H-indol-3-yl)thio)picolinic acid (Compound 2-1)

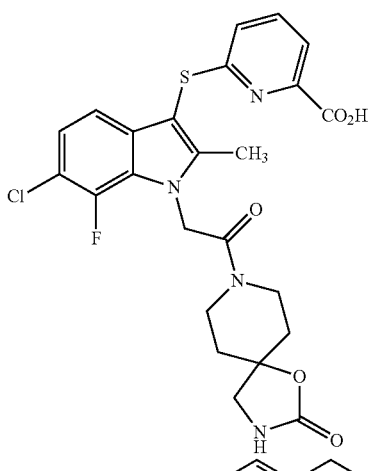

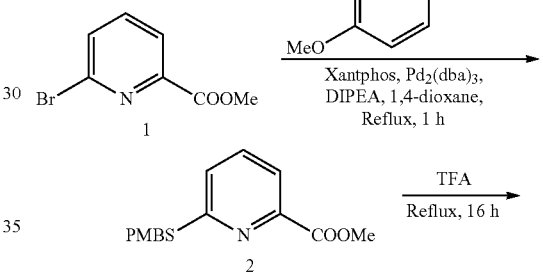

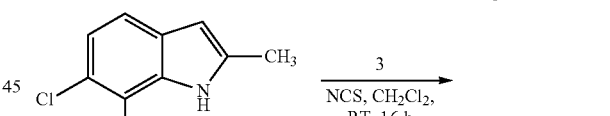

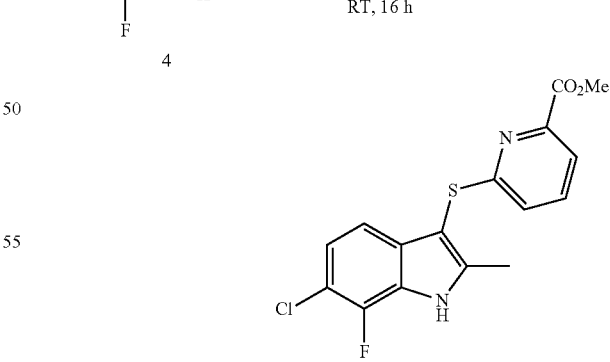

Step 1 Methyl 6-((4-methoxybenzyl)thio)picolinate (2)

To a stirred solution of methyl 6-bromopicolinate 1 (600 mg, 2.77 mmol) in 1,4-Dioxane (15 mL) under inert atmosphere were added (4-methoxyphenyl)methanethiol (427 mg, 2.77 mmol), xantphos (80 mg, 0.13 mmol), diisopropyl ethyl amine (714.6 mg, 5.54 mmol), $Pd_2(dba)_3$ (63 mg, 0.069 mmol) at RT, degassed under argon for 15 min; heated to reflux and stirred for 1 h. The reaction was monitored by TLC; after completion of the reaction, the reaction mixture was diluted with water (25 mL) and extracted with EtOAc (3×30 mL). The combined organic extracts were dried over $Na_2SO_4$, filtered and concentrated under reduced pressure to obtain the crude. The crude was purified through silica gel column chromatography using 7% EtOAc/Hexanes to afford compound 2 (700 mg, 87%) as a colorless syrup. $^1$H NMR (400 MHz, $CDCl_3$): δ 7.78 (d, J=7.6 Hz, 1H), 7.57 (t, J=8.0 Hz, 1H), 7.42-7.40 (m, 2H), 7.29-7.25 (m, 1H), 6.82 (d, J=8.4 Hz, 2H), 4.44 (s, 2H), 4.00 (s, 3H), 3.77 (s, 3H);

Step 2: Methyl 6-mercaptopicolinate (3)

A stirred solution of compound 2 (1 g, 3.46 mmol) in Trifluoro acetic acid (5 mL) under inert atmosphere was heated to reflux and stirred for 16 h. The reaction was monitored by TLC; after completion of the reaction, the volatiles were removed under reduced pressure. The residue was diluted with water (20 mL) and extracted with EtOAc (2×30 mL). The combined organic extracts were washed with aqueous $NaHCO_3$ solution (25 mL), aqueous NaCl solution (25 mL), dried over $Na_2SO_4$, filtered and concentrated under reduced pressure to obtain the compound 2 (900 mg, crude) as a pale brown solid. LC-MS: 61.1%; $(M+H)^+$ Found=170.

Step 3: Methyl 6-((6-chloro-7-fluoro-2-methyl-1H-indol-3-yl)thio)picolinate (5)

To a stirred solution of methyl 6-mercaptopicolinate 2 (900 mg, 5.42 mmol) in $CH_2Cl_2$ (10 mL) under inert atmosphere was added N-chloro succinimide (711 mg, 5.32 mmol) and stirred for 30 min. To this was added compound 6-chloro-7-fluoro-2-methyl-1H-indole 4 (973 mg, 5.32 mmol) and stirred for 16 h. The reaction was monitored by TLC; after completion of the reaction, the reaction mixture was diluted with water (30 mL) and extracted with $CH_2Cl_2$ (2×30 mL). The combined organic extracts were washed with water (25 mL), dried over $Na_2SO_4$, filtered and concentrated under reduced pressure to obtain the crude. The crude was purified through silica gel column chromatography using 20% EtOAc/n-hexane to afford compound 5 (500 mg, 30%) as a pink solid. $^1$H NMR (400 MHz, $CDCl_3$): δ 8.80 (br s, 1H), 7.78 (d, J=7.6 Hz, 1H), 7.46 (t, J=8.0 Hz, 1H), 7.19 (d, J=8.4 Hz, 1H), 7.11-7.07 (m, 1H), 6.72 (d, J=8.0 Hz, 1H), 4.00 (s, 3H), 2.54 (s, 3H); Mass: $(M+H)^+$ Found=351.4.

Step 4: 6-((6-Chloro-7-fluoro-2-methyl-1-(2-oxo-2-(2-oxo-1-oxa-3,8-diazaspiro[4.5]decan-8-yl)ethyl)-1H-indol-3-yl)thio)picolinic acid (Compound 2-1)

The title compound (2-1) was prepared using the procedure for Example 15, using methyl 6-((6-chloro-7-fluoro-2-methyl-1H-indol-3-yl)thio)picolinate 5 in Step 6. $^1$H NMR (400 MHz, CD3OD-$d_4$): δ 7.82 (d, J.=6.0 Hz, 1H), 7.75-7.54 (m, 1H), 7.34-7.30 (m, 1H), 7.21-7.19 (m, 1H), 6.98-6.85 (m, 1H), 5.55-544 (m, 2H), 4.44-4.43 (m, 1H), 4.01-3.98 (m, 1H), 3.54-3.53 (m, 2H), 3.43- 3.42 (m, 2H), 2.43 (s, 3H), 2.98-2.86 (m, 1H), 1.98-1.88 (m, 2H).; Mass: $(M+H)^+$ Found=534.1.

Example 69

Methyl 6-((6-chloro-7-fluoro-1-(2-(indolin-1-yl)-2-oxoethyl)-2-methyl-1H-indol-3-yl)thio)picolinate (Compound 2-3)

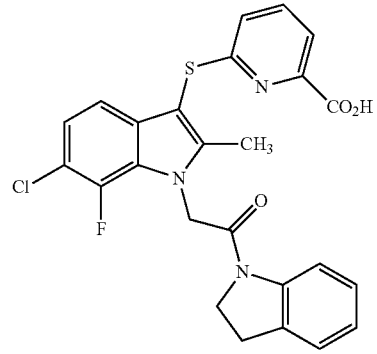 [SMILES: Cc1c(Sc2cccc(C(=O)O)n2)c2ccc(Cl)c(F)c2n1CC(=O)N1CCc2ccccc21]

The title compound (2-3) was prepared using the procedure for Example 17, using methyl 6-((6-chloro-7-fluoro-2-methyl-1H-indol-3-yl)thio)picolinate in Step 6. $^1$H NMR (400 MHz, $CD_3OD$-$d_4$): δ 8.04 (d, J=8.0 Hz, 1H), 7.76 (d, J=8.0 Hz, 1H), 7.63 (t, J=8.0 Hz, 1H), 7.30-7.23 (m, 2H), 7.18-7.05 (m, 3H), 6.87 (d, J=8.0 Hz, 1H), 5.43 (s, 2H), 4.35 (t, J=8.0 Hz, 2H), 3.37-3.35 (m, 2H), 2.49 (s, 3H); Mass: $(M+H)^+$ Found=496.6

Example 70

6-((6-Chloro-7-fluoro-2-methyl-1-(2-oxo-2-(spiro [cyclopropane-1,3'-indolin]-1'-yl)ethyl)-1H-indol-3-yl)thio)picolinic acid (Compound 2-54)

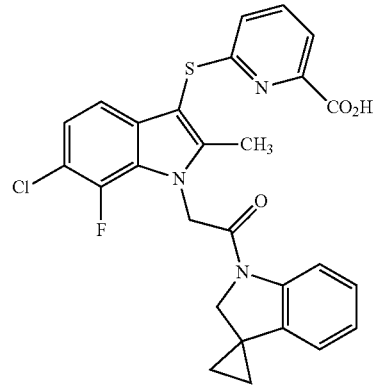 [SMILES: Cc1c(Sc2cccc(C(=O)O)n2)c2ccc(Cl)c(F)c2n1CC(=O)N1CC2(CC2)c2ccccc21]

The title compound (2-54) was prepared using the procedure for Example 14, using methyl 6-((6-chloro-7-fluoro-2-methyl-1H-indol-3-yl)thio)picolinate in Step 1 and spiro [cyclopropane-1,3'-indoline] in Step 3. $[M+Na]^+$ Found=543.9

Example 71

3-((6-Chloro-7-fluoro-2-methyl-1-(2-oxo-2-(spiro[cyclopropane-1,3'-indolin]-1'-yl)ethyl)-1H-indol-3-yl)thio)-2-fluorobenzoic acid (Compound 2-55)

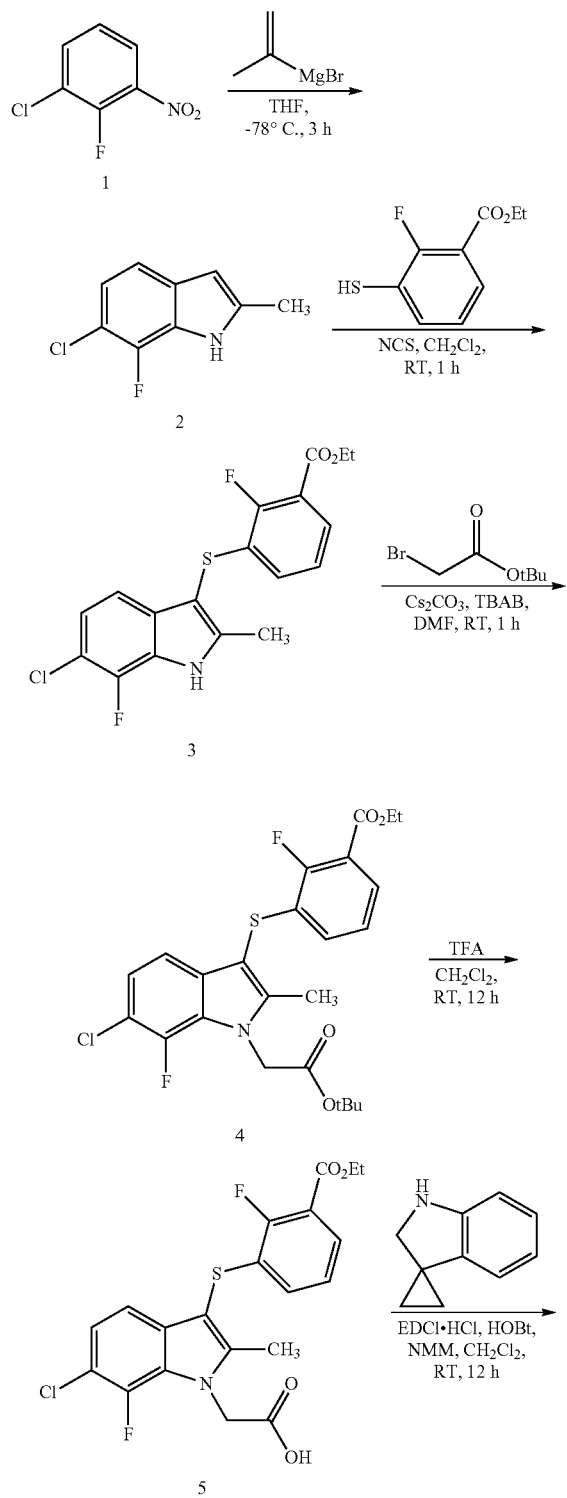

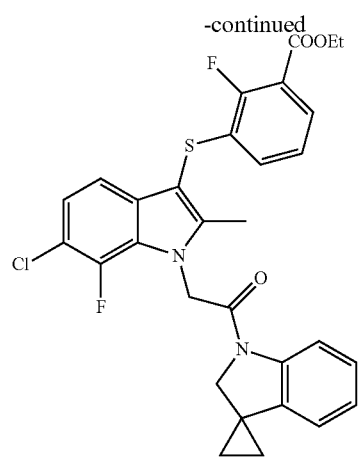

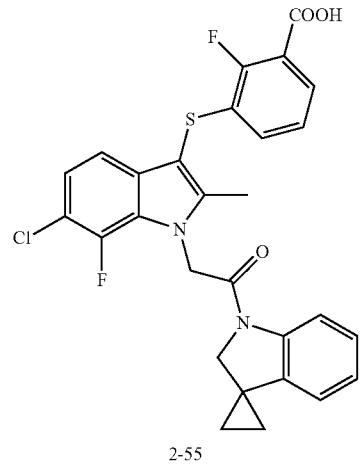 [SMILES: Cc1c(Sc2cccc(C(=O)O)c2F)c2ccc(Cl)c(F)c2n1CC(=O)N1CC2(CC2)c2ccccc21]

Step 1: 6-Chloro-7-fluoro-2-methyl-1H-indole (2)

To a stirred solution of isopropenyl magnesium bromide (200 mL, 99.99 mmol) in THF (50 mL) under inert atmosphere was added 1-chloro-2-fluoro-3-nitrobenzene 1 (5 g, 28.57 mmol) in THF (20 mL) at −78° C. and stirred for 3 h. The reaction was monitored by TLC; after completion of the reaction, the reaction mixture was quenched with saturated NH$_4$Cl solution (40 mL) and extracted with EtOAc (2×45 mL). The combined organic extracts were dried over Na$_2$SO$_4$, filtered and concentrated under reduced pressure to obtain the crude. The crude was purified through silica gel column chromatography using 1% EtOAc/Hexanes to afford compound 2 (1.5 g, 29%) as a brown oil. $^1$H NMR (500 MHz, DMSO-d$_6$): δ 11.57 (s, 1H), 7.21 (d, J=8.5 Hz, 1H), 6.99-6.96 (m, 1H), 6.22 (s, 1H), 2.35 (s, 3H); LC-MS: 87.8%; (M)$^+$ Found=182; (column: X Select CSH C-18, 50×3.0 mm, 3.5 μm); RT 3.98 min. 5 mM NH$_4$OAc: ACN; 0.8 mL/min).

Step 2: Ethyl 3-((6-chloro-7-fluoro-2-methyl-1H-indol-3-yl)thio)-2-fluorobenzoate (3)

To a stirred solution of compound ethyl 2-fluoro-3-mercaptobenzoate (2.3 g, 11.50 mmol) in CH$_2$Cl$_2$ (32 mL) under inert atmosphere was added N-chloro succinimide (1.69 g, 12.65 mmol) at RT and stirred for 1 h. To this was added 2 (2.10 g, 11.50 mmol) in CH$_2$Cl$_2$ (10 mL) and stirred for 12 h. The reaction was monitored by TLC; after completion of the reaction, the reaction mixture was diluted with water (20 mL) and extracted with $CH_2Cl_2$ (2×40 mL). The combined organic extracts were dried over $Na_2SO_4$, filtered and concentrated under reduced pressure to obtain the crude. The crude was purified through silica gel column chromatography using 2% EtOAc/Hexanes to afford compound 3 (2.5 g, 57%) as an off-white solid. $^1$H NMR (500 MHz, DMSO-$d_6$): δ 12.50 (s, 1H), 7.58 (t, J=7.0 Hz, 1H), 7.14 (s, 1H), 7.09 (t, J=8.0 Hz, 2H), 6.79 (t, J=8.0 Hz, 1H), 4.32 (q, 2H), 2.45 (s, 3H), 1.31 (t, J=7.5 Hz, 3H); Mass: (M+H)$^+$ Found=383.2.

Step 3: Ethyl 3-((1-(2-(tert-butoxy)-2-oxoethyl)-6-chloro-7-fluoro-2-methyl-1H-indol-3-yl)thio)-2-fluorobenzoate (4)

To a stirred solution of compound 3 (140 mg, 0.36 mmol) in DMF (3 mL) under inert atmosphere were added tert-butyl 2-bromoacetate (0.08 mL, 0.54 mmol), cesium carbonate (238 mg, 0.73 mmol), Bu$_4$NBr (5.9 mg, 0.018 mmol) at RT and stirred for 1 h. The reaction was monitored by TLC; after completion of the reaction, the reaction mixture was diluted with water (20 mL) and extracted with EtOAc (2×20 mL). The combined organic extracts were washed with water (15 mL) dried over $Na_2SO_4$, filtered and concentrated under reduced pressure to obtain the crude compound 4 (200 mg) as a pale green semisolid. $^1$H NMR (500 MHz, CDCl$_3$): δ 7.61 (t, J=7.0 Hz, 1H), 7.21 (d, J=8.0 Hz, 1H), 7.09 (t, J=8.5 Hz, 1H), 6.90 (t, J=8.5 Hz, 1H), 6.74 (t, J=6.5 Hz, 1H), 4.95 (s, 2H), 4.40 (q, 2H), 2.44 (s, 3H), 1.52 (s, 9H), 1.42 (t, J=7.5 Hz, 3H); LC-MS: 96.7%; 513.6 (M+H$_2$O)$^+$; (column: X Select CSH C-18, 50×3.0 mm, 3.5 μm); RT 4.72 min. 5 mM NH$_4$OAc: ACN; 0.8 mL/min).

Step 4: 2-(6-Chloro-3-((3-(ethoxycarbonyl)-2-fluorophenyl)thio)-7-fluoro-2-methyl-1H-indol-1-yl) acetic acid (5)

To a stirred solution of compound 4 (200 mg, 0.40 mmol) in $CH_2Cl_2$ (10 mL) under inert atmosphere was added Trifluoro acetic acid (0.8 mL) at 0° C.; warmed to RT and stirred for 12 h. The reaction was monitored by TLC; after completion of the reaction, the volatiles were removed under reduced pressure. The residue was diluted with water (20 mL) and extracted with $CH_2Cl_2$ (2×30 mL). The combined organic extracts were washed with water (15 mL), dried over $Na_2SO_4$, filtered and concentrated under reduced pressure to obtain the crude. The crude was triturated with n-pentane (2×5 mL) to afford compound 5 (149 mg, 81%) as an off-white solid. $^1$H NMR (400 MHz, DMSO-$d_6$): δ 7.59-7.55 (m, 1H), 7.19-7.06 (m, 3H), 6.79-6.75 (m, 1H), 4.93 (s, 2H), 4.32 (q, 2H), 2.40 (s, 3H), 1.31 (t, J=7.2 Hz, 3H); LC-MS: 98.7%; (M+H)$^+$ Found=440.3; (column: X Select CSH C-18, 50×3.0 mm, 3.5 μm); RT 2.90 min. 5 mM NH$_4$OAc: ACN; 0.8 mL/min).

Step 5: Ethyl 3-((6-chloro-7-fluoro-2-methyl-1-(2-oxo-2-(spiro[cyclopropane-1,3'-indolin]-1'-yl)ethyl)-1H-indol-3-yl)thio)-2-fluorobenzoate (6)

To a stirred solution of compound 5 (150 mg, 0.34 mmol) in $CH_2Cl_2$ (10 mL) under inert atmosphere were added EDCI. HCl (97.8 mg, 0.51 mmol), HOBt (69 mg, 0.51 mmol), spiro [cyclopropane-1,3'-indoline](99 mg, 0.68 mmol), N-methyl morpholine (0.11 mL, 1.02 mmol) at RT and stirred for 12 h. The reaction was monitored by TLC; after completion of the reaction, the reaction mixture was diluted with water (20 mL) and extracted with $CH_2Cl_2$ (2×30 mL). The combined organic extracts were washed with saturated NaHCO$_3$ solution (25 mL), dried over $Na_2SO_4$, filtered and concentrated under reduced pressure to obtain the crude. The crude was purified through silica gel column chromatography using 10% EtOAc/Hexanes to afford compound 6 (108 mg, 56%) as an off-white solid. $^1$H NMR (500 MHz, CDCl$_3$): δ 8.14 (d, J=7.5 Hz, 1H), 7.62 (t, J=7.0 Hz, 1H), 7.24 (d, J=8.5 Hz, 1H), 7.17 (t, J=8.0 Hz, 1H), 7.10-7.04 (m, 1H), 6.96 (t, J=8.0 Hz, 1H), 6.85 (t, J=7.5 Hz, 1H), 6.73 (d, J=8.0 Hz, 1H), 5.14 (s, 2H), 4.43-4.40 (m, 2H), 4.24 (s, 2H), 2.48 (s, 3H), 1.41 (t, J=7.0 Hz, 3H), 1.22-1.17 (m, 4H); LC-MS: 98.6%; (M+H)$^+$ Found=584.5; (column: X Select CSH C-18, 50×3.0 mm, 3.5 μm); RT 6.23 min. 5 mM NH$_4$OAc: ACN; 0.8 mL/min).

Step 6: 3-((6-Chloro-7-fluoro-2-methyl-1-(2-oxo-2-(spiro[cyclopropane-1,3'-indolin]-1'-yl)ethyl)-1H-indol-3-yl)thio)-2-fluorobenzoic acid (2-55)

To a stirred solution of compound 6 (100 mg, 0.17 mmol) in THF:H$_2$O (1:1, 4 mL) under inert atmosphere was added LiOH.H$_2$O (30 mg, 0.70 mmol) at RT and stirred for 12 h. The reaction was monitored by TLC; after completion of the reaction, the volatiles were removed under reduced pressure. The residue was diluted with water (20 mL), acidified with 1 N HCl and extracted with EtOAc (2×20 mL). The combined organic extracts were dried over $Na_2SO_4$, filtered and concentrated under reduced pressure to obtain the crude. The crude was triturated with n-pentane (2×5 mL) to afford the title compound 2-55 (65 mg, 68%) as an off-white solid. $^1$H NMR (400 MHz, DMSO-$d_6$): δ 13.31 (br s, 1H), 7.96 (d, J=8.0 Hz, 1H), 7.60 (t, J=6.4 Hz, 1H), 7.24-7.17 (m, 2H), 7.13-7.00 (m, 2H), 6.86 (t, J=7.6 Hz, 1H), 6.82-6.80 (m, 2H), 5.39 (s, 2H), 4.35 (s, 2H), 2.49 (s, 3H), 1.23-1.14 (m, 4H); Mass: [M+H]$^+$ Found=539.6.

Example 72

3-((6-Chloro-1-(2-(5-methoxyindolin-1-yl)-2-oxoethyl)-7-fluoro-2-methyl-1H-indol-3-yl)thio)benzoic acid (Compound 1-58)

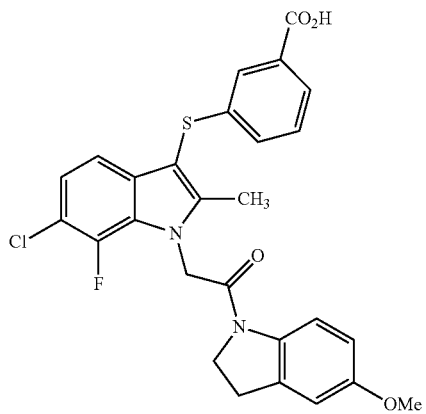 [SMILES: COc1ccc2c(c1)CCN2C(=O)Cn1c(C)c(Sc2cccc(C(=O)O)c2)c2ccc(Cl)c(F)c21]

The title compound (1-58) was prepared using the procedure for Example 14, using 5-methoxyindoline in Step 3. [M+Na]$^+$ Found=546.8

Example 73

3-[6-Chloro-7-fluoro-1-[2-(5'-fluorospiro[cyclopropane-1,3'-indoline]-1'-yl)-2-oxo-ethyl]-2-methyl-indol-3-yl]sulfanyl-2-fluoro-benzoic acid (Compound 3-23)

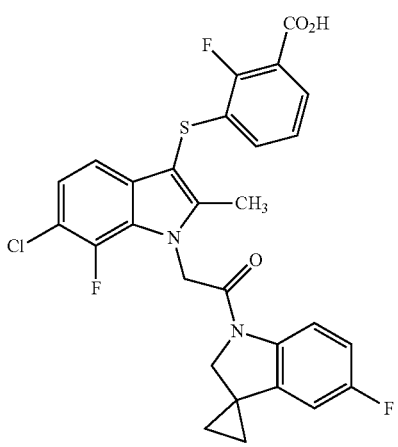 [SMILES: Cc1c(Sc2cccc(C(=O)O)c2F)c2ccc(Cl)c(F)c2n1CC(=O)N1CC2(CC2)c2cc(F)ccc21]

The title compound (3-23) was prepared using the procedure for Example 14, using methyl 3-[(6-chloro-7-fluoro-2-methyl-1H-indol-3-yl)sulfanyl]-2-fluoro-benzoic acid in Step 1 and 5'-fluorospiro[cyclopropane-1,3'-indoline] in Step 3. [M+Na]$^+$ Found=578.8

Example 74

6-((6-Chloro-7-fluoro-1-(2-(4'-fluorospiro[cyclobutane-1,3'-indolin]-1'-yl)-2-oxoethyl)-2-methyl-1H-indol-3-yl)thio)picolinic acid (Compound 3-104)

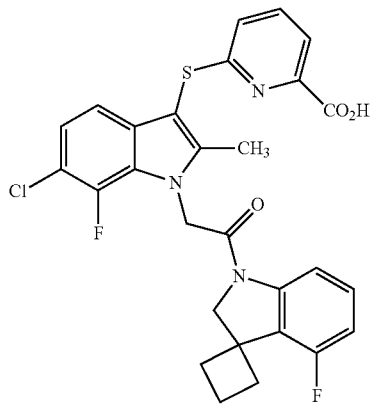 [SMILES: Cc1c(Sc2cccc(C(=O)O)n2)c2ccc(Cl)c(F)c2n1CC(=O)N1CC2(CCC2)c2c(F)cccc21]

The title compound (3-104) was prepared using the procedure for Example 14, using methyl3-[(6-chloro-7-fluoro-2-methyl-1H-indol-3-yl)sulfanyl]pyridine-2-carboxylic acid in Step 1 and 4'-fluorospiro[cyclobutane-1,3'-indoline] in Step 3. [M+Na]$^+$ Found=575.85

Example 75

3-((6-Chloro-7-fluoro-1-(2-(4'-fluorospiro[cyclobutane-1,3'-indolin]-1'-yl)-2-oxoethyl)-2-methyl-1H-indol-3-yl)thio)-2-fluorobenzoic acid (Compound 3-96)

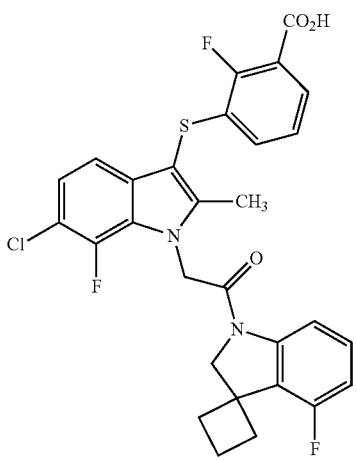 [SMILES: Cc1c(Sc2cccc(C(=O)O)c2F)c2ccc(Cl)c(F)c2n1CC(=O)N1CC2(CCC2)c2c(F)cccc21]

The title compound (3-96) was prepared using the procedure for Example 14, using methyl 3-[(6-chloro-7-fluoro-2-methyl-1H-indol-3-yl)sulfanyl]-2-fluoro-benzoic acid in Step 1 and 4'-fluorospiro[cyclobutane-1,3'-indoline] in Step 3. [M+Na]$^+$ Found=592.80

Example 76

3-((6-Chloro-7-fluoro-2-methyl-1-(2-oxo-2-(spiro[cyclopentane-1,3'-indolin]-1'-yl)ethyl)-1H-indol-3-yl)thio)-2-fluorobenzoic acid (Compound 3-221)

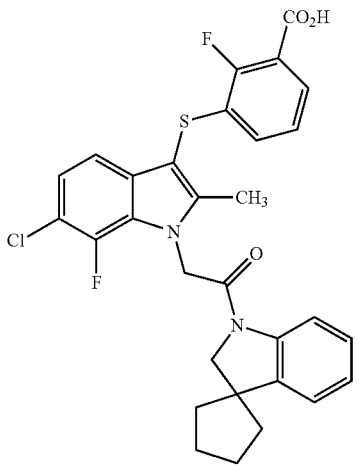 [SMILES: Cc1c(Sc2cccc(C(=O)O)c2F)c2ccc(Cl)c(F)c2n1CC(=O)N1CC2(CCCC2)c2ccccc21]

The title compound (3-221) was prepared using the procedure for Example 14, using methyl3-[(6-chloro-7-fluoro-2-methyl-1H-indol-3-yl)sulfanyl]-2-fluoro-benzoic acid in Step 1 and spiro[cyclopentane-1,3'-indoline] in Step 3. [M+Na]$^+$ Found=588.85

Example 77

3-((6-Chloro-7-fluoro-2-methyl-1-(2-oxo-2-(3-phenethylpyrrolidin-1-yl)ethyl)-1H-indol-3-yl)thio)benzoic acid (Compound 1-76)

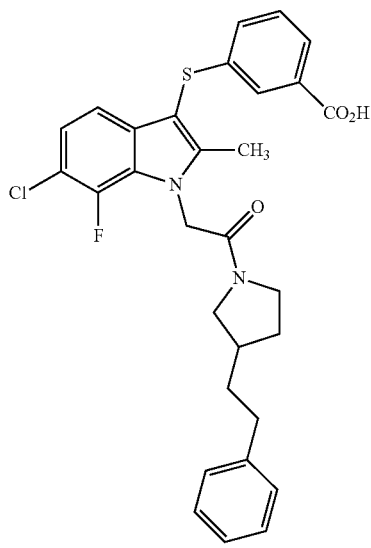 [SMILES: Cc1c(Sc2cccc(C(=O)O)c2)c2ccc(Cl)c(F)c2n1CC(=O)N1CCC(CCc2ccccc2)C1]

The title compound (1-76) was prepared using the procedure for Example 14, using methyl 3-[(6-chloro-7-fluoro-2-methyl-1H-indol-3-yl)sulfanyl]-2-fluoro-benzoic acid in Step 1 and 3-phenethylpyrrolidine in Step 3. $^1$H NMR (400 MHz, CD$_3$OD-d$_4$): δ 7.72 (s, 1H), 7.68 (d, J=8.0 Hz, 1H), 7.29-7.14 (m, 9H), 5.22 (q, 2H), 3.88-3.64 (m, 3H), 3.42-3.40 (m, 1H), 3.22-3.20 (m, 1H), 3.08 (t, J=9.2 Hz, 1H), 2.76-2.68 (m, 2H), 2.50 (s, 2H), 2.22-2.12 (m, 2H), 1.88-1.76 (m, 2H), 1.64-1.58 (m, 1H); Mass: (M−H)$^+$ Found 549.3.

Example 78

3-((6-Chloro-7-fluoro-2-methyl-1-(2-oxo-2-(3-propylpyrrolidin-1-yl)ethyl)-1H-indol-3-yl)thio)benzoic acid (Compound 1-77)

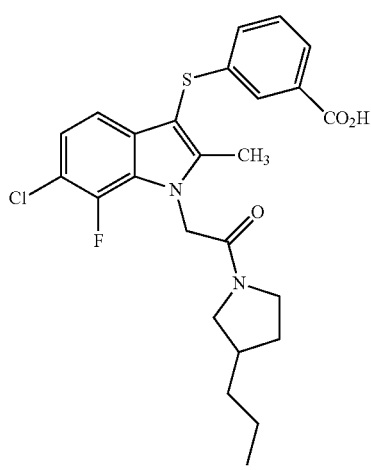 [SMILES: CCCC1CCN(C(=O)Cn2c(C)c(Sc3cccc(C(=O)O)c3)c3ccc(Cl)c(F)c32)C1]

The title compound (1-77) was prepared using the procedure for Example 14, using methyl 3-[(6-chloro-7-fluoro-2-methyl-1H-indol-3-yl)sulfanyl]-2-fluoro-benzoic acid in Step 1 and 3-propylpyrrolidine in Step 3. $^1$H NMR (400 MHz, CD$_3$OD-d$_4$): δ 7.74 (s, 1H), 7.70 (d, J=8.0 Hz, 1H), 7.28-7.20 (m, 2H), 7.14-7.06 (m, 2H), 5.20 (q, 2H), 3.90-3.64 (m, 3H), 3.40-3.38 (m, 1H), 3.22 (t, J=9.6 Hz, 1H), 3.01 (t, J=9.6 Hz, 1H), 2.50 (s, 3H), 2.41-2.39 (m, 1H), 2.28-2.25 (m, 1H), 2.12-2.09 (m, 1H), 1.84-1.82 (m, 1H), 1.60-1.42 (m, 3H), 1.02-0.96 (m, 1H); Mass: (M+H)$^+$ Found=489.4.

Example 79

3-((6-Chloro-7-fluoro-2-methyl-1-(2-oxo-2-(3-(4-(trifluoromethyl)benzyl)pyrrolidin-1-yl)ethyl)-1H-indol-3-yl)thio)benzoic acid (Compound 1-78)

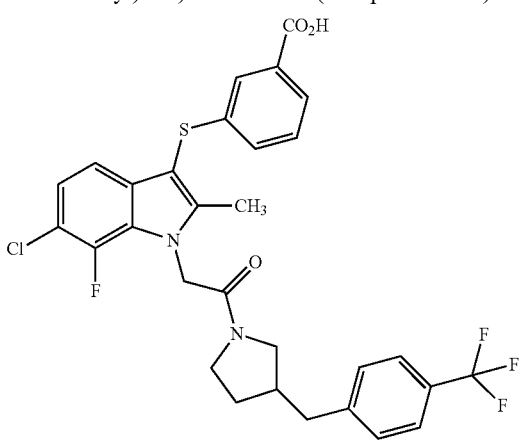

The title compound (1-78) was prepared using the procedure for Example 14, using methyl 3-[(6-chloro-7-fluoro-2-methyl-1H-indol-3-yl)sulfanyl]-2-fluoro-benzoic acid in Step 1 and 3-(4-(trifluoromethyl)benzyl)pyrrolidine in Step 3. $^1$H NMR (400 MHz, DMSO-d$_6$): δ 12.06 (br s, 1H), 7.68-7.64 (m, 2H), 7.58-7.52 (m, 4H), 7.22-7.14 (m, 3H), 7.00 (d, J=8.0 Hz, 1H), 5.22 (q, 2H), 3.78-3.74 (m, 1H), 3.60-3.56 (m, 3H), 3.06-3.04 (m, 1H), 2.88-2.78 (m, 2H), 2.64-2.62 (m, 1H), 2.44-2.42 (m, 4H), 2.18-1.88 (m, 1H), 1.78-1.58 (m, 1H); LC-MS: 95.4%; (M+H)$^+$ Found 605.7.

Example 80

3-((6-Chloro-1-(2-(3,4-dihydroisoquinolin-2(1H)-yl)-2-oxoethyl)-7-fluoro-2-methyl-1H-indol-3-yl)thio)benzoic acid (Compound 1-79)

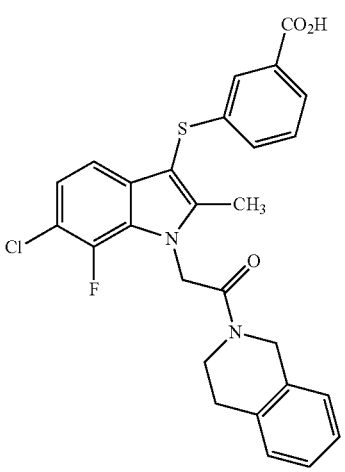 [SMILES: Cc1c(Sc2cccc(C(=O)O)c2)c2ccc(Cl)c(F)c2n1CC(=O)N1CCc2ccccc2C1]

The title compound (1-79) was prepared using the procedure for Example 14 using 1,2,3,4-Tetrahydroisoquinoline in Step 3. [M+H]+ Found=509.

Example 81

3-((6-Chloro-7-fluoro-2-methyl-1-(2-oxo-2-(6-(trifluoromethyl)indolin-1-yl)ethyl)-1H-indol-3-yl)thio)benzoic acid (Compound 1-80)

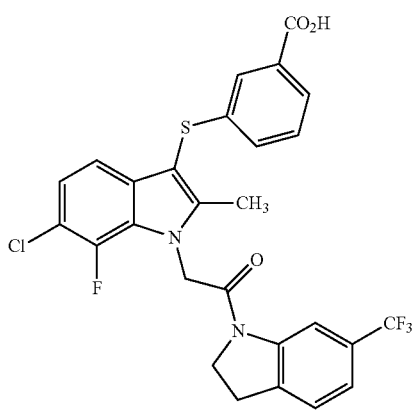 [SMILES: Cc1c(Sc2cccc(C(=O)O)c2)c2ccc(Cl)c(F)c2n1CC(=O)N1CCc2ccc(C(F)(F)F)cc21]

The title compound (1-80) was prepared using the procedure for Example 14 using 6-(trifluoromethyl)indoline in Step 3. [M+H]+ Found=589.

Example 82

3-((6-Chloro-7-fluoro-1-(2-(4-fluoroindolin-1-yl)-2-oxoethyl)-2-methyl-1H-indol-3-yl)thio)benzoic acid (Compound 1-81)

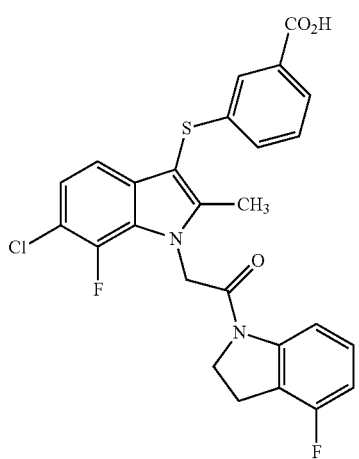 [SMILES: Cc1c(Sc2cccc(C(=O)O)c2)c2ccc(Cl)c(F)c2n1CC(=O)N1CCc2c(F)cccc21]

The title compound (1-81) was prepared using the procedure for Example 14 using 4-fluoroindoline instead of benzylamine in Step 3. [M+H]+ Found=553.

Example 83

3-((6-Chloro-1-(2-(3-cyclopropyl-3-hydroxyazetidin-1-yl)-2-oxoethyl)-7-fluoro-2-methyl-1H-indol-3-yl)thio)benzoic acid (Compound 1-82)

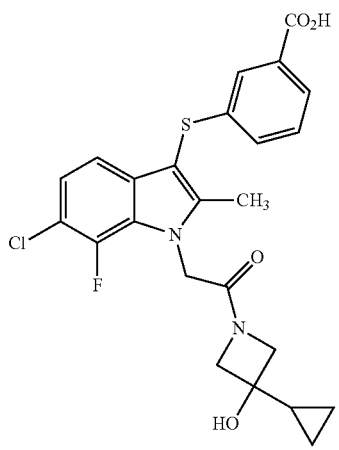 [SMILES: Cc1c(Sc2cccc(C(=O)O)c2)c2ccc(Cl)c(F)c2n1CC(=O)N1CC(O)(C2CC2)C1]

The title compound (1-82) was prepared using the procedure for Example 14 using 3-Cyclopropylazetidin-3-ol hydrochloride instead in Step 3. [M+H]+ Found=489.

Example 84

3-((6-Chloro-7-fluoro-1-(2-(3-hydroxy-3-(trifluoromethyl)piperidin-1-yl)-2-oxoethyl)-2-methyl-1H-indol-3-yl)thio)benzoic acid (Compound 1-83)

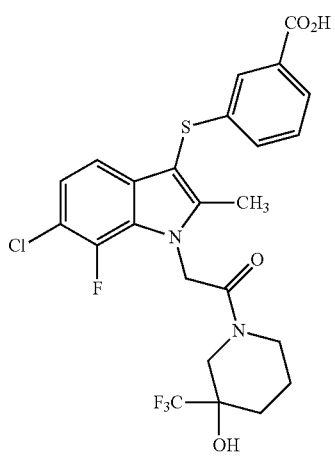 [SMILES: Cc1c(Sc2cccc(C(=O)O)c2)c2ccc(Cl)c(F)c2n1CC(=O)N1CCCC(O)(C(F)(F)F)C1]

The title compound (1-83) was prepared using the procedure for Example 14 using 3-(trifluoromethyl)piperidin-3-ol in Step 3. [M+H]+ Found=545.

Example 85

3-((6-Chloro-7-fluoro-1-(2-(3-hydroxy-3-(trifluoromethyl)azetidin-1-yl)-2-oxoethyl)-2-methyl-1H-indol-3-yl)thio)benzoic acid (Compound 1-84)

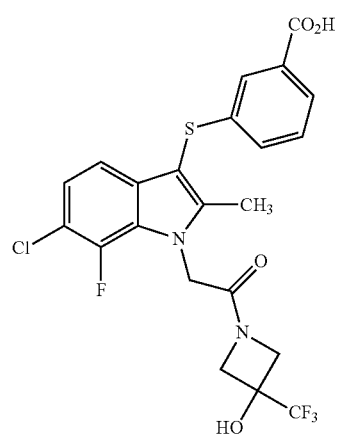 [SMILES: Cc1c(Sc2cccc(C(=O)O)c2)c2ccc(Cl)c(F)c2n1CC(=O)N1CC(O)(C(F)(F)F)C1]

The title compound (1-84) was prepared using the procedure for Example 14 using 3-(trifluoromethyl)azetidin-3-ol hydrochloride in Step 3 [M+Na]$^+$ Found=539.

Example 86

3-((6-Chloro-7-fluoro-2-methyl-1-(2-(2-(1-methyl-1H-pyrazol-4-yl)pyrrolidin-1-yl)-2-oxoethyl)-1H-indol-3-yl)thio)benzoic acid (Compound 1-85)

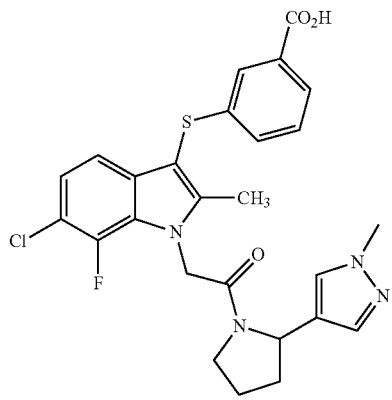 [SMILES: Cc1c(Sc2cccc(C(=O)O)c2)c2ccc(Cl)c(F)c2n1CC(=O)N1CCCC1c1cnn(C)c1]

The title compound (1-85) was prepared using the procedure for Example 14 using 1-methyl-4-(pyrrolidin-3-yl)-1H-pyrazole in Step 3. [M+Na]$^+$ Found=549.

Example 87

3-((1-(2-(3-(1H-Pyrazol-1-yl)azetidin-1-yl)-2-oxoethyl)-6-chloro-7-fluoro-2-methyl-1H-indol-3-yl)thio)benzoic acid (Compound 1-86)

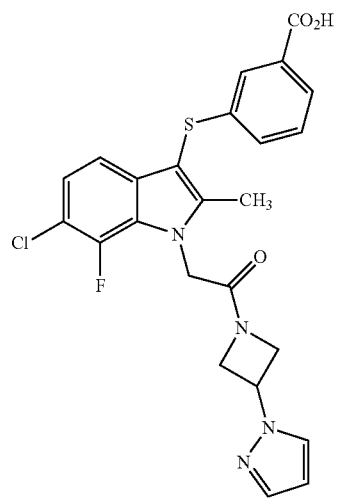 [SMILES: Cc1c(Sc2cccc(C(=O)O)c2)c2ccc(Cl)c(F)c2n1CC(=O)N1CC(n2cccn2)C1]

The title compound (1-86) was prepared using the procedure for Example 14 using 1-(azetidin-3-yl)-1H-pyrazole instead in Step 3. [M+Na]$^+$ Found=521.

Example 88

6-((6-Chloro-7-fluoro-1-(2-(3-hydroxy-3-(trifluoromethyl)pyrrolidin-1-yl)-2-oxoethyl)-2-methyl-1H-indol-3-yl)thio)picolinic acid (Compound 2-56)

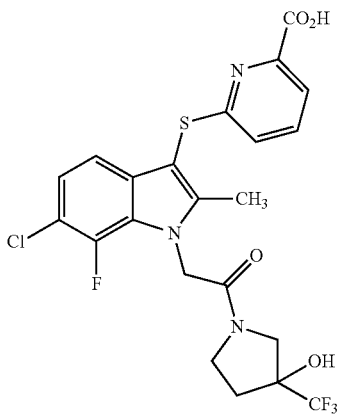 [SMILES: Cc1c(Sc2cccc(C(=O)O)n2)c2ccc(Cl)c(F)c2n1CC(=O)N1CCC(O)(C(F)(F)F)C1]

The title compound (2-56) was prepared using the procedure for Example 14, using methyl 3-[(6-chloro-7-fluoro-2-methyl-1H-indol-3-yl)sulfanyl]pyridine-2-carboxylic acid in Step 1 and 3-(trifluoromethyl)pyrrolidin-3-ol hydrochloride in Step 3. [M+Na]$^+$ Found=555.

Example 89

Sodium 3-((6-chloro-7-fluoro-1-(2-(3-hydroxy-3-(trifluoromethyl)pyrrolidin-1-yl)-2-oxoethyl)-2-methyl-1H-indol-3-yl)thio)-2-fluorobenzoate (Compound 2-57 Sodium Salt)

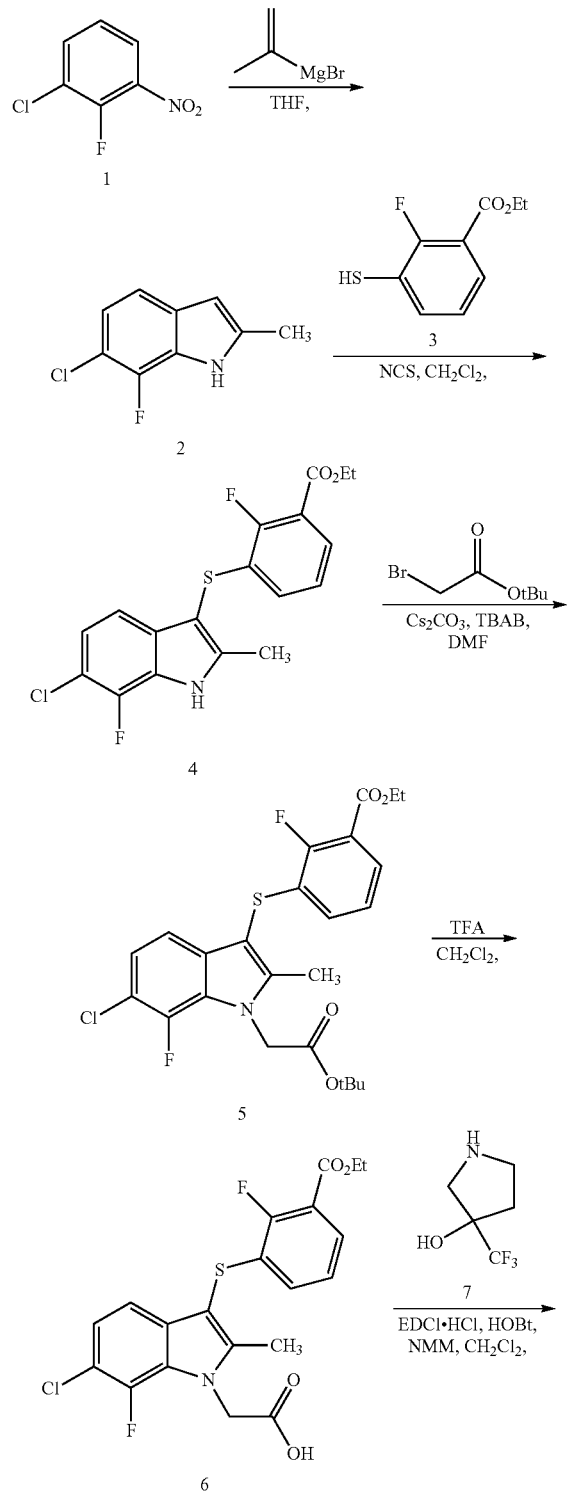

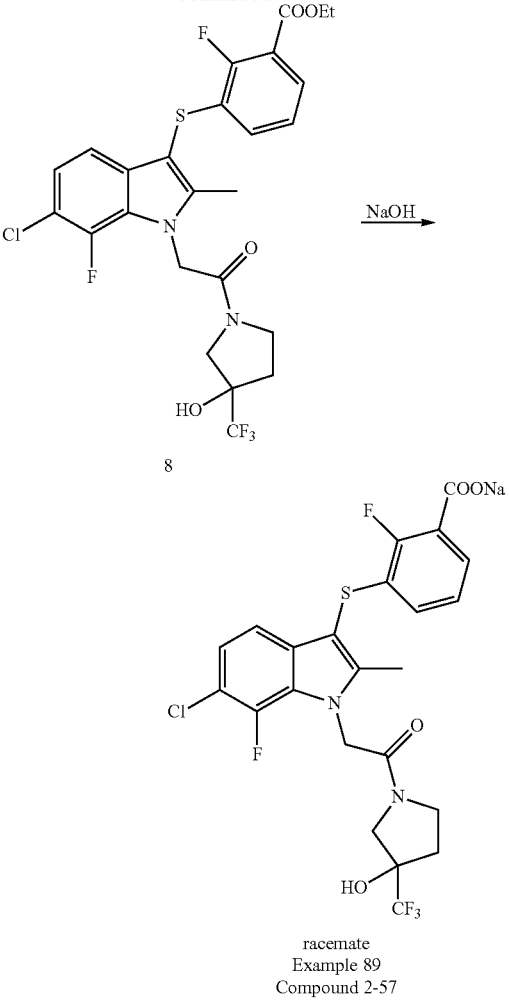

racemate
Example 89
Compound 2-57
Sodium Salt

Step 1: 6-Chloro-7-fluoro-2-methyl-1H-indole (2)

To a stirred solution of isopropenyl magnesium bromide (200 mL, 99.99 mmol) in THF (50 mL) under inert atmosphere was added 1-chloro-2-fluoro-3-nitrobenzene 1 (5 g, 28.57 mmol) in THF (20 mL) at −78° C. and stirred for 3 h. The reaction was monitored by TLC; after completion of the reaction, the reaction mixture was quenched with saturated NH$_4$Cl solution (40 mL) and extracted with EtOAc (2×45 mL). The combined organic extracts were dried over Na$_2$SO$_4$, filtered and concentrated under reduced pressure to obtain the crude. The crude was purified through silica gel column chromatography using 1% EtOAc/Hexanes to afford compound 2 (1.5 g, 29%) as a brown oil. $^1$H NMR (500 MHz, DMSO-d$_6$): δ 11.57 (s, 1H), 7.21 (d, J=8.5 Hz, 1H), 6.99-6.96 (m, 1H), 6.22 (s, 1H), 2.35 (s, 3H); LC-MS: 87.8%; (M+H)$^+$ Found=182; (column: X Select CSH C-18, 50×3.0 mm, 3.5 µm); RT 3.98 min. 5 mM NH$_4$OAc: ACN; 0.8 mL/min).

Step 2: Ethyl 3-((6-chloro-7-fluoro-2-methyl-1H-indol-3-yl)thio)-2-fluorobenzoate (4)

To a stirred solution of compound ethyl 2-fluoro-3-mercaptobenzoate 3 (Example 2, Step 7; 2.3 g, 11.50 mmol) in CH$_2$Cl$_2$ (32 mL) under inert atmosphere was added NCS (1.69 g, 12.65 mmol) at RT and stirred for 1 h. To this was added 2 (2.10 g, 11.50 mmol) in CH$_2$Cl$_2$ (10 mL) and stirred for 12 h. The reaction was monitored by TLC; after completion of the reaction, the reaction mixture was diluted with water (20 mL) and extracted with CH$_2$Cl$_2$ (2×40 mL). The combined organic extracts were dried over Na$_2$SO$_4$, filtered and concentrated under reduced pressure to obtain the crude. The crude was purified through silica gel column chromatography using 2% EtOAc/Hexanes to afford compound 4 (2.5 g, 57%) as an off-white solid. $^1$H NMR (500 MHz, DMSO-d$_6$): δ 12.50 (s, 1H), 7.58 (t, J=7.0 Hz, 1H), 7.14 (s, 1H), 7.09 (t, J=8.0 Hz, 2H), 6.79 (t, J=8.0 Hz, 1H), 4.32 (q, 2H), 2.45 (s, 3H), 1.31 (t, J=7.5 Hz, 3H); Mass: (M+H)$^+$ Found=383.2.

Step 3: Ethyl 3-((1-(2-(tert-butoxy)-2-oxoethyl)-6-chloro-7-fluoro-2-methyl-1H-indol-3-yl)thio)-2-fluorobenzoate (5)

To a stirred solution of compound 4 (140 mg, 0.36 mmol) in DMF (3 mL) under inert atmosphere were added tert-butyl 2-bromoacetate (0.08 mL, 0.54 mmol), Cs$_2$CO$_3$ (238 mg, 0.73 mmol), Bu$_4$NBr (5.9 mg, 0.018 mmol) at RT and stirred for 1 h. The reaction was monitored by TLC; after completion of the reaction, the reaction mixture was diluted with water (20 mL) and extracted with EtOAc (2×20 mL). The combined organic extracts were washed with water (15 mL) dried over Na$_2$SO$_4$, filtered and concentrated under reduced pressure to obtain the crude compound 5 (200 mg) as a pale green semisolid. $^1$H NMR (500 MHz, CDCl$_3$): δ 7.61 (t, J=7.0 Hz, 1H), 7.21 (d, J=8.0 Hz, 1H), 7.09 (t, J=8.5 Hz, 1H), 6.90 (t, J=8.5 Hz, 1H), 6.74 (t, J=6.5 Hz, 1H), 4.95 (s, 2H), 4.40 (q, 2H), 2.44 (s, 3H), 1.52 (s, 9H), 1.42 (t, J=7.5 Hz, 3H); LC-MS: 96.7%; (M+H$_2$O)$^+$ Found=513.6; (column: X Select CSH C-18, 50×3.0 mm, 3.5 μm); RT 4.72 min. 5 mM NH$_4$OAc: ACN; 0.8 mL/min).

Step 4: 2-(6-Chloro-3-((3-(ethoxycarbonyl)-2-fluorophenyl)thio)-7-fluoro-2-methyl-1H-indol-1-yl) acetic acid (6)

To a stirred solution of compound 5 (200 mg, 0.40 mmol) in CH$_2$Cl$_2$ (10 mL) under inert atmosphere was added TFA (0.8 mL) at 0° C.; warmed to RT and stirred for 12 h. The reaction was monitored by TLC; after completion of the reaction, the volatiles were removed under reduced pressure. The residue was diluted with water (20 mL) and extracted with CH$_2$Cl$_2$ (2×30 mL). The combined organic extracts were washed with water (15 mL), dried over Na$_2$SO$_4$, filtered and concentrated under reduced pressure to obtain the crude. The crude was triturated with n-pentane (2×5 mL) to afford compound 6 (149 mg, 81%) as an off-white solid. 1H NMR (400 MHz, DMSO-d$_6$): δ 7.59-7.55 (m, 1H), 7.19-7.06 (m, 3H), 6.79-6.75 (m, 1H), 4.93 (s, 2H), 4.32 (q, 2H), 2.40 (s, 3H), 1.31 (t, J=7.2 Hz, 3H); LC-MS: 98.7%; (M+H)$^+$ Found=440.3; (column: X Select CSH C-18, 50×3.0 mm, 3.5 μm); RT 2.90 min. 5 mM NH$_4$OAc: ACN; 0.8 mL/min).

Step 5: Ethyl 3-((6-chloro-7-fluoro-1-(2-(3-hydroxy-3-(trifluoromethyl)pyrrolidin-1-yl)-2-oxoethyl)-2-methyl-1H-indol-3-yl)thio)-2-fluorobenzoate (8)

To a stirred suspension of compound 6 (5.69 g, 12.9 mmol) in CH$_2$Cl$_2$ (65 mL) was added HATU (7.38 g, 19.4 mmol) and DIEA (2.25 mL, 12.9 mmol) at RT and stirred for 5 min. Then compound 7 (2.97 g, 15.5 mmol) and DIEA (7.85 mL, 38.7 mmol) was added and the reaction stirred at RT for 1 h. After the completion of the reaction, the mixture was washed with water. The aqueous layer was back extracted (2×DCM) and all the organic layers were combined. The combined organics was washed with brine, dried over Na$_2$SO$_4$, filtered, and concentrated under reduced pressure to obtain the crude material. The crude was purified through silica gel column chromatography using 0-50% EtOAc/DCM and then 0-50% EtOAc/Hexanes to afford the ester 8 as a racemate (6.6 g, 88%) as a tangerine solid. LC-MS: (M+H)$^+$ Found=577.

Step 6: Sodium 3-((6-chloro-7-fluoro-1-(2-(3-hydroxy-3-(trifluoromethyl)pyrrolidin-1-yl)-2-oxoethyl)-2-methyl-1H-indol-3-yl)thio)-2-fluorobenzoate (Compound 2-57 sodium salt; racemic Example 89)

To a solution of compound 8 (0.063 g, 0.10 mmole) in THF:water (3:1) (3.0 ml) was added 1M aq. NaOH solution (0.10 ml, 0.10 mmole) and the mixture was heated for 60° C. for 72 h. After the completion of the reaction, the solvent was removed to afford compound 2-57 sodium salt (0.060 g, 100%) as a white solid. LCMS: (M+H)$^+$ Found=549

Example 90

3-((6-Chloro-7-fluoro-2-methyl-1-(2-(7-methyl-1,7-diazaspiro[3.5]nonan-1-yl)-2-oxoethyl)-1H-indol-3-yl)thio)benzoic acid (Compound 1-87)

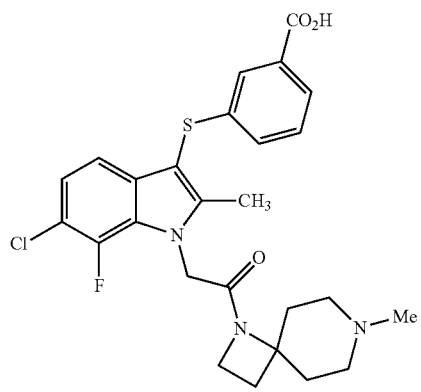 [SMILES: Cc1c(Sc2cccc(C(=O)O)c2)c2ccc(Cl)c(F)c2n1CC(=O)N1CCC12CCN(C)CC2]

The title compound (1-87) was prepared using the procedure for Example 14 using 7-methyl-1,7-diazaspiro[3.5]nonane dihydrochloride in Step 3. [M+H]+ Found=516

Example 91

3-((6-Chloro-7-fluoro-2-methyl-1-(2-oxo-2-(3-(pyridin-4-ylmethyl)pyrrolidin-1-yl)ethyl)-1H-indol-3-yl)thio)benzoic acid (Compound 1-88)

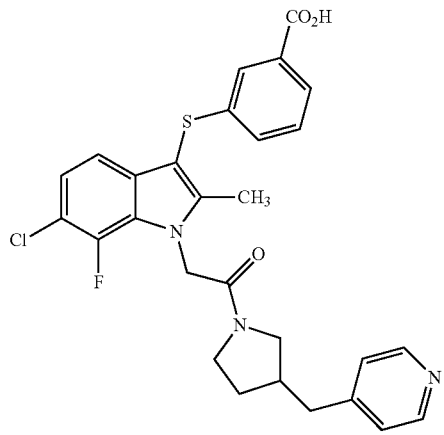 [SMILES: Cc1c(Sc2cccc(C(=O)O)c2)c2ccc(Cl)c(F)c2n1CC(=O)N1CCC(Cc2ccncc2)C1]

The title compound (1-88) was prepared using the procedure for Example 14 using 4-(pyrrolidin-3-ylmethyl)pyridine in Step 3. [M+H]+ Found=538.

Example 92

3-((6-Chloro-7-fluoro-2-methyl-1-(2-oxo-2-(3-(pyridin-4-yl)pyrrolidin-1-yl)ethyl)-1H-indol-3-yl)thio)benzoic acid (Compound 1-89)

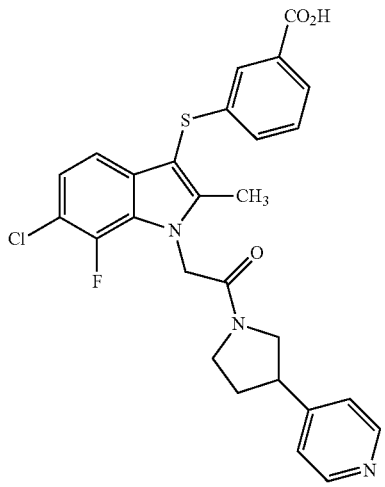 [SMILES: Cc1c(Sc2cccc(C(=O)O)c2)c2ccc(Cl)c(F)c2n1CC(=O)N1CCC(c2ccncc2)C1]

The title compound (1-89) was prepared using the procedure for Example 14 using 4-(pyrrolidin-3-yl)pyridine in Step 3. [M+H]+ Found=524.

Example 93

3-((6-Chloro-7-fluoro-1-(2-(3-hydroxypyrrolidin-1-yl)-2-oxoethyl)-2-methyl-1H-indol-3-yl)thio)benzoic acid (Compound 1-90)

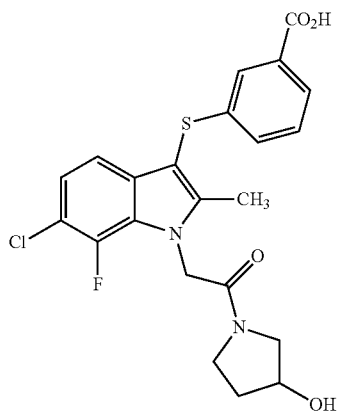 [SMILES: Cc1c(Sc2cccc(C(=O)O)c2)c2ccc(Cl)c(F)c2n1CC(=O)N1CCC(O)C1]

The title compound (1-90) was prepared using the procedure for Example 14 using hydroxypyrrolidine hydrochloride in Step 3. [M+H]+ Found=463.

Example 94

3-((6-Chloro-7-fluoro-1-(2-(isoindolin-2-yl)-2-oxoethyl)-2-methyl-1H-indol-3-yl)thio)benzoic acid (Compound 1-91)

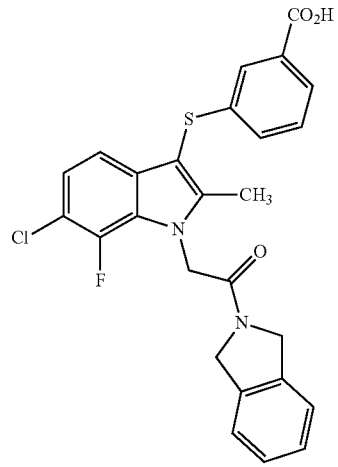 [SMILES: Cc1c(Sc2cccc(C(=O)O)c2)c2ccc(Cl)c(F)c2n1CC(=O)N1Cc2ccccc2C1]

The title compound (1-91) was prepared using the procedure for Example 14 using isoindoline in Step 3. [M+Na]+ Found=517.

Example 95

3-((6-Chloro-7-fluoro-2-methyl-1-(2-(5-methylindo-lin-1-yl)-2-oxoethyl)-1H-indol-3-yl)thio)benzoic acid (Compound 1-92)

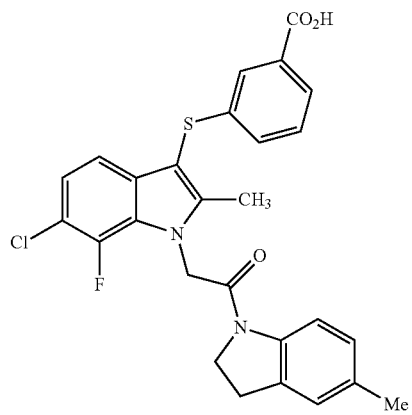 [SMILES: Cc1ccc2c(c1)CCN2C(=O)Cn1c(C)c(Sc2cccc(C(=O)O)c2)c2ccc(Cl)c(F)c21]

The title compound (1-92) was prepared using the procedure for Example 14 using 5-methylindoline in Step 3. [M+Na]$^+$ Found=531.

Example 96

3-((6-Chloro-7-fluoro-2-methyl-1-(2-(3-((1-methyl-1H-pyrazol-4-yl)methyl)pyrrolidin-1-yl)-2-oxo-ethyl)-1H-indol-3-yl)thio)benzoic acid (Compound 1-93)

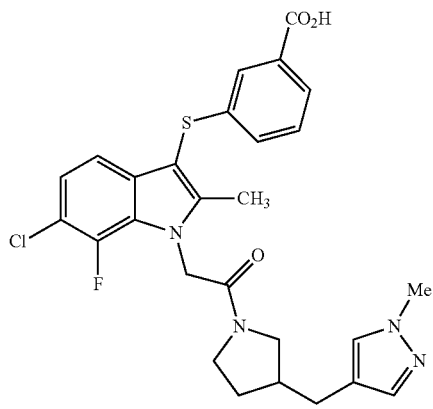 [SMILES: Cc1c(Sc2cccc(C(=O)O)c2)c2ccc(Cl)c(F)c2n1CC(=O)N1CCC(Cc2cnn(C)c2)C1]

The title compound (1-93) was prepared using the procedure for Example 14 using 1-methyl-4-(pyrrolidin-3-yl-methyl)-1H-pyrazole in Step 3. [M+Na]$^+$ Found=563.

Example 97

3-((1-(2-(2-(2-(1H-Pyrazol-1-yl)ethyl)piperidin-1-yl)-2-oxoethyl)-6-chloro-7-fluoro-2-methyl-1H-indol-3-yl)thio)benzoic acid (Compound 1-94)

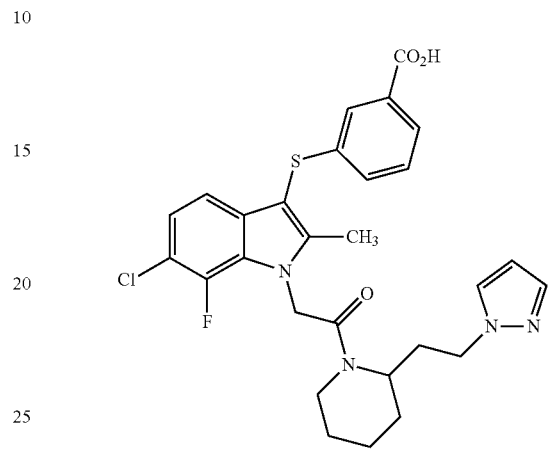

The title compound (1-94) was prepared using the procedure for Example 14 using 2-[2-(1H-pyrazol-1-yl)ethyl]piperidine in Step 3. [M+Na]$^+$ Found=555.

Example 98

3-((6-Chloro-7-fluoro-2-methyl-1-(2-oxo-2-(5-azaspiro[2.4]heptan-5-yl)ethyl)-1H-indol-3-yl)thio)benzoic acid (Compound 1-95)

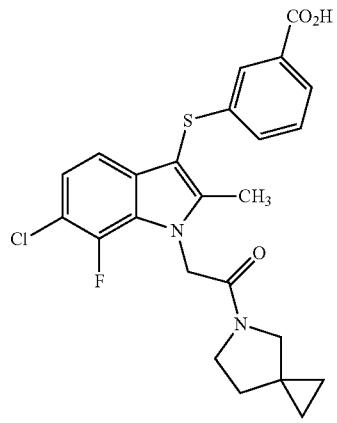 [SMILES: Cc1c(Sc2cccc(C(=O)O)c2)c2ccc(Cl)c(F)c2n1CC(=O)N1CCC2(CC2)C1]

The title compound (1-95) was prepared using the procedure for Example 14 using 5-Aza-spiro[2.4]heptane hydrochloride in Step 3. [M+H]$^+$ Found=473.

Example 99

3-((6-Chloro-7-fluoro-2-methyl-1-(2-(3-(1-methyl-1H-pyrazol-4-yl)pyrrolidin-1-yl)-2-oxoethyl)-1H-indol-3-yl)thio)benzoic acid (Compound 1-96)

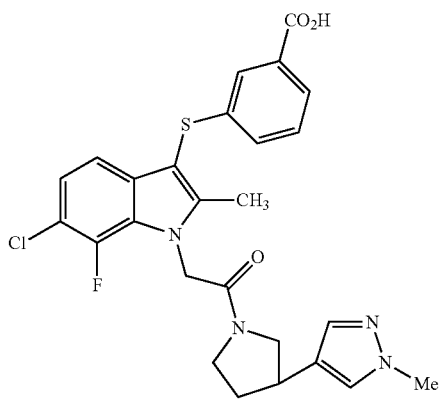 [SMILES: Cc1c(Sc2cccc(C(=O)O)c2)c2ccc(Cl)c(F)c2n1CC(=O)N1CCC(c2cnn(C)c2)C1]

The title compound (1-96) was prepared using the procedure for Example 14 using 1-methyl-4-(pyrrolidin-3-yl)-1H-pyrazole in Step 3. [M+Na]$^+$ Found=549.

Example 100

3-((6-Chloro-1-(2-(2,3-dihydro-1H-pyrrolo[2,3-c]pyridin-1-yl)-2-oxoethyl)-7-fluoro-2-methyl-1H-indol-3-yl)thio)benzoic acid (Compound 1-97)

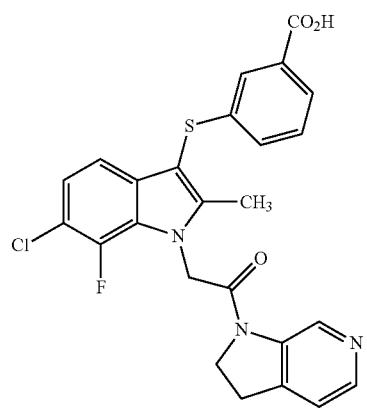 [SMILES: Cc1c(Sc2cccc(C(=O)O)c2)c2ccc(Cl)c(F)c2n1CC(=O)N1CCc2ccncc21]

The title compound (1-97) was prepared using the procedure for Example 14 using 1H,2H,3H-pyrrolo[2,3-c]pyridine dihydrochloride in Step 3. [M+H]$^+$ Found=496.

Example 101

3-((6-Chloro-7-fluoro-1-(2-(hexahydro-1H-isoindol-2(3H)-yl)-2-oxoethyl)-2-methyl-1H-indol-3-yl)thio)benzoic acid (Compound 1-98)

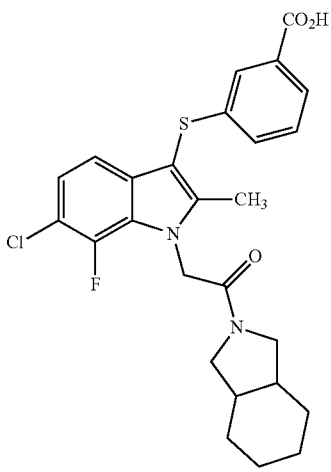 [SMILES: Cc1c(Sc2cccc(C(=O)O)c2)c2ccc(Cl)c(F)c2n1CC(=O)N1CC2CCCCC2C1]

The title compound (1-98) was prepared using the procedure for Example 14 using Octahydro-1H-isoindole in Step 3. [M+Na]$^+$ Found=523.

Example 102

Sodium 3-((6-chloro-7-fluoro-1-(2-(indolin-1-yl)ethyl)-2-methyl-1H-indol-3-yl)thio)-2-fluorobenzoate (Compound 2-73 Sodium Salt)

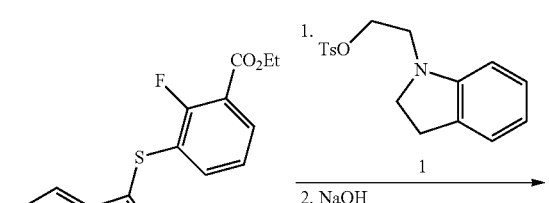

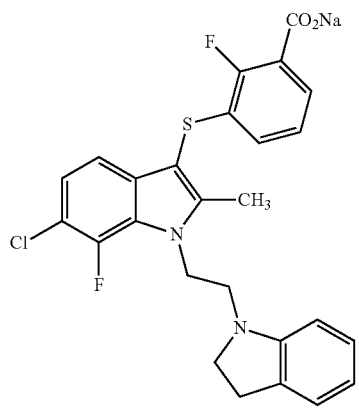

Step 1: 2-(Indolin-1-yl)ethanol

A solution of indoline (100 mg, 0.839 mmol), 2-bromoethanol (2.517 mmol), di-isopropyl ethylamine (2.517 mmol) and THF (4.0 mL) was heated at 60° C. for 48 hours. The organics were evaporated in vacuo. The residue was diluted with water and extracted with EtOAc (2×5 mL). The organic layer was dried over MgSO$_4$, filtered and concentrated. The crude product was purified by flash chromatography on silica gel eluting with EtOAc-hexane to afford the product as an amber oil (92 mg, 67%). [M+H]$^+$ Found=164

Step 2: 2-(Indolin-1-yl)ethyl 4-methylbenzenesulfonate (1)

A solution of product from Step 1 (166 mg, 1.02 mmol), 4-toluenesulfonyl chloride (1.23 mmol), Et$_3$N (2.04 mmol) and THF (8 mL) was stirred at room temperature for 16 h. The reaction mixture was concentrated in vacuo. The crude product was purified by flash chromatography on silica gel eluting with EtOAc-hexane to afford 1 as an oil (118 mg, 37%). [M+H]$^+$ Found=318]

Step 3: Ethyl 3-((6-chloro-7-fluoro-1-(2-(indolin-1-yl)ethyl)-2-methyl-1H-indol-3-yl)thio)-2-fluorobenzoate To a solution of the product from Step 2 (0.159 mmol), and the indole 2 (Example 71, Step 2; 55 mg, 0.0144 mmol) in THF (2.0 mL) was added K$_2$CO$_3$ (0.314 mmol). The reaction mixture was heated at 50° C. for 48 h, cooled down to ambient temperature, filtered and concentrated in vacuo. The crude product was purified by prep-HPLC to afford the product as a white solid (23 mg, 28%). [M+H]$^+$ Found=527.

Step 4: Sodium 3-((6-chloro-7-fluoro-1-(2-(indolin-1-yl)ethyl)-2-methyl-1H-indol-3-yl)thio)-2-fluorobenzoate (Compound 2-73 Sodium Salt)

To a solution of product from Step 3 (19 mg, 0.036 mmol) in THF/MeOH/H$_2$O (2:1:1, 1.5 mL) was added aqueous 1N NaOH (0.036 mmol) and the resulting solution was heated at 60° C. for 38 h. The reaction mixture was concentrated in vacuo to afford the title compound 2-73 sodium salt as a tan solid (18 mg, 96.7%) LCMS [M+H]$^+$ 499.

Example 103

3-((6-Chloro-1-(2-(2,3-dihydro-1H-pyrrolo[2,3-c]pyridin-1-yl)-2-oxoethyl)-7-fluoro-2-methyl-1H-indol-3-yl)thio)-2-fluorobenzoic acid (Compound 2-60)

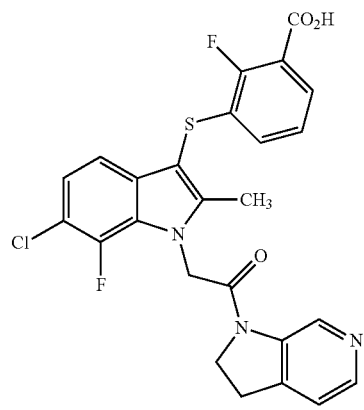 [SMILES: Cc1c(Sc2cccc(C(=O)O)c2F)c2ccc(Cl)c(F)c2n1CC(=O)N1CCc2ccncc21]

The title compound (2-60) was prepared using the procedure for Example 14, using methyl 3-[(6-chloro-7-fluoro-2-methyl-1H-indol-3-yl)sulfanyl]-2-fluoro-benzoic acid in Step 1 and 1H,2H,3H-pyrrolo[2,3-c]pyridine dihydrochloride in Step 3. [M+H]$^+$ Found=514.

Example 104

3-((6-Chloro-7-fluoro-1-(2-(3-hydroxy-3-methylpyrrolidin-1-yl)-2-oxoethyl)-2-methyl-1H-indol-3-yl)thio)-2-fluorobenzoic acid (Compound 2-61)

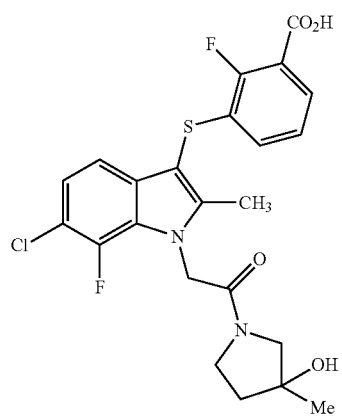 [SMILES: Cc1c(Sc2cccc(C(=O)O)c2F)c2ccc(Cl)c(F)c2n1CC(=O)N1CCC(C)(O)C1]

The title compound (2-61) was prepared using the procedure for Example 14, using methyl 3-[(6-chloro-7-fluoro-2-methyl-1H-indol-3-yl)sulfanyl]-2-fluoro-benzoic acid in Step 1 and 3-methylpyrrolidin-3-ol in Step 3. [M+H]$^+$ Found=495.

Example 105

3-((6-Chloro-7-fluoro-2-methyl-1-(2-oxo-2-(spiro[cyclobutane-1,3'-indolin]-1'-yl)ethyl)-1H-indol-3-yl)thio)-2-fluorobenzoic acid (Compound 3-220)

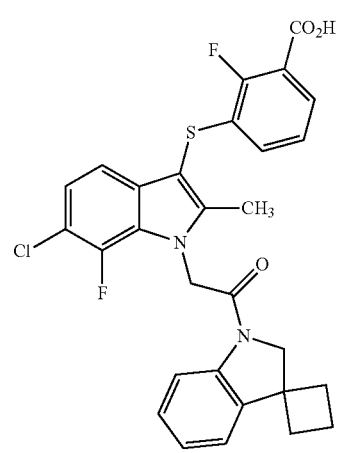 [SMILES: Cc1c(Sc2cccc(C(=O)O)c2F)c2ccc(Cl)c(F)c2n1CC(=O)N1CC2(CCC2)c2ccccc21]

The title compound (3-220) was prepared using the procedure for Example 14, using methyl3-[(6-chloro-7-fluoro-2-methyl-1H-indol-3-yl)sulfanyl]-2-fluoro-benzoic acid in Step 1 and 1',2'-dihydrospiro[cyclobutane-1,3'-indole]hydrochloride in Step 3. [M+Na]$^+$ Found=575.

Example 106

Sodium 3-((6-chloro-7-fluoro-2-methyl-1-(2-(spiro[cyclopropane-1,3'-indolin]-1'-yl)ethyl)-1H-indol-3-yl)thio)-2-fluorobenzoate (Compound 2-74 Sodium Salt)

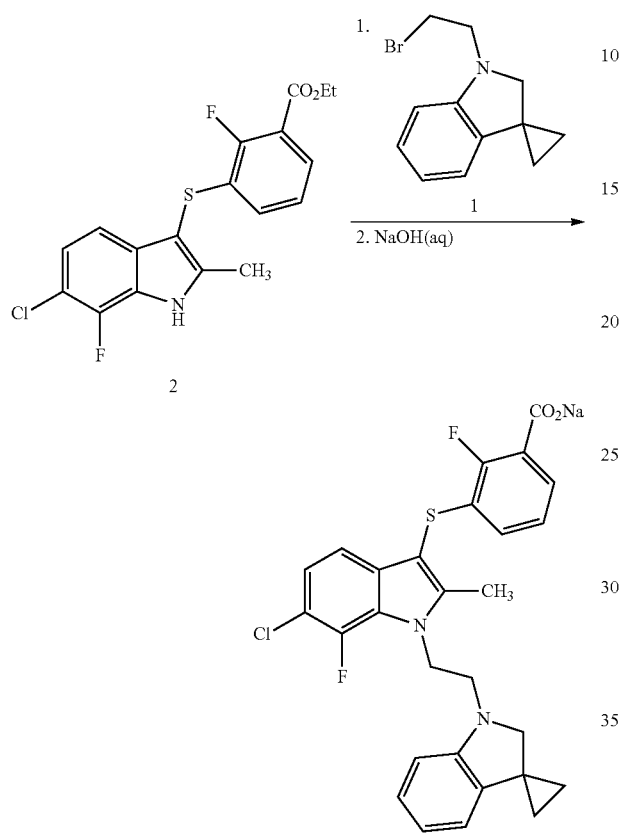

Step 1: 1'-(2-Bromoethyl)spiro[cyclopropane-1,3'-indoline](1)

A solution of 1'2'-dihydrospiro[cyclopropane-1,3'-indole (60 mg, 0.413 mmol), 1,2-Dibromoethane (1.85 mmol), potassium carbonate (1.24 mmol) and THF (3.0 mL) was heated at 70° C. for 72 hours. The organics were evaporated in vacuo. The residue was diluted with water. The aqueous phase was extracted with EtOAc (2×7 mL). The organic layer was dried over MgSO$_4$, filtered and concentrated. The crude product was purified by flash chromatography on silica gel eluting with EtOAc-hexane to afford 1 as an amber oil (75 mg, 72%). [M+H]$^+$ Found=252.

Step 2: Ethyl 3-((6-Chloro-7-fluoro-2-methyl-1-(2-(spiro[cyclopropane-1,3'-indolin]-1'-yl)ethyl)-1H-indol-3-yl)thio)-2-fluorobenzoate To a solution of product from Step 1 (0.139 mmol), and the indole 2 (Example 71, Step 2; 53 mg, 0.139 mmol) in THF (2.0 mL) was added NaI (0.139 mmol) and Cs$_2$CO$_3$ (0.416 mmol). The reaction mixture was heated at 75° C. for 60 h. The organics were evaporated in vacuo. The residue was diluted with water. The aqueous phase was extracted with EtOAc (2×10 mL). The organic layer was dried over MgSO$_4$, filtered and concentrated. The crude product was purified by flash chromatography on silica gel eluting with EtOAc-hexane to afford the product as white solid (52.5 mg, 68%). [M+H]$^+$ Found=553.

Step 3: Sodium 3-((6-chloro-7-fluoro-2-methyl-1-(2-(spiro[cyclopropane-1,3'-indolin]-1'-yl)ethyl)-1H-indol-3-yl)thio)-2-fluorobenzoate (Compound 2-74 Sodium Salt)

To a solution of product from Step 2 (32 mg, 0.058 mmol) in THF/MeOH/H$_2$O (3:1:1, 1.5 mL) was added aqueous 1N NaOH (0.058 mmol) and the resulting suspension was heated at 60° C. for 2 h. The reaction mixture was concentrated in vacuo to afford the title compound 2-74 sodium salt as an off white solid (31.3 mg, 99%). [M+H]$^+$ Found=525.

Example 107

3-((6-Chloro-7-fluoro-2-methyl-1-(2-(spiro[cyclobutane-1,3'-indolin]-1'-yl)ethyl)-1H-indol-3-yl)thio)-2-fluorobenzoic acid (Compound 2-75)

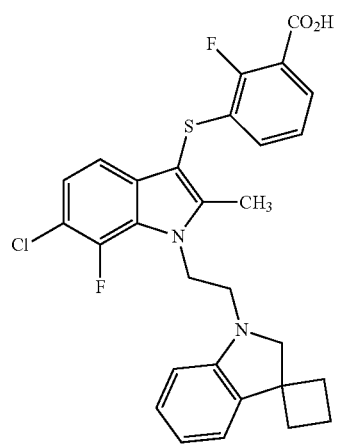 [SMILES: Cc1c(Sc2cccc(C(=O)O)c2F)c2ccc(Cl)c(F)c2n1CCN1CC2(CCC2)c2ccccc21]

The title compound (2-75) was prepared using the procedure for Example 106, using 1'2'-dihydrospiro[cyclobutane-1,3'-indole]hydrochloride instead in Step 1. [M+H]$^+$ Found=539.

Example 108

3-((6-Chloro-7-fluoro-2-methyl-1-(2-oxo-2-(spiro[cyclopentane-1,3'-indolin]-1'-yl)ethyl)-1H-indol-3-yl)thio)-2-fluoro-N-(phenylsulfonyl)benzamide

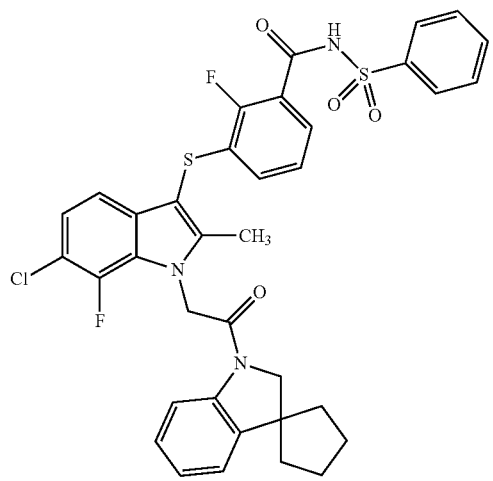 [SMILES: Cc1c(Sc2cccc(C(=O)NS(=O)(=O)c3ccccc3)c2F)c2ccc(Cl)c(F)c2n1CC(=O)N1CC2(CCCC2)c2ccccc21]

The title compound was prepared by dissolving Example 76 (Compound 3-221.17 mg; 0.029 mmole) in N,N-dimethylformamide (1 mL) followed by the addition of N,N-diisopropylethylamine (0.016 mL; 0.086 mmole), HATU (17 mg; 0.0432 mmole) and benzenesulphonamide (7.5 mg; 0.049 mmole). The mixture was stirred for 2 hr and purified by HPLC to give the title compound. [M+Na]+ Found=728.

Example 109

3-((6-Chloro-7-fluoro-1-(2-(3-(2-hydroxypropan-2-yl)pyrrolidin-1-yl)-2-oxoethyl)-2-methyl-1H-indol-3-yl)thio)-2-fluorobenzoic acid (Compound 2-62)

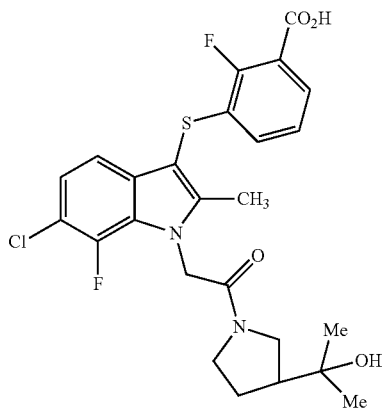 [SMILES: Cc1c(Sc2cccc(C(=O)O)c2F)c2ccc(Cl)c(F)c2n1CC(=O)N1CCC(C(C)(C)O)C1]

The title compound (2-62) was prepared using the procedure for Example 14, using methyl 3-[(6-chloro-7-fluoro-2-methyl-1H-indol-3-yl)sulfanyl]-2-fluoro-benzoic acid in Step 1 and (R,S)-2-(3-pyrrolidinyl)2-propanol hydrochloride in Step 3. $^1$H NMR (400 MHz, DMSO-d$_6$): δ 7.10-7.20 (m, 3H), 6.78 (t, 1H), 6.38 (dt, 1H), 3.70 (m, 1H), 3.40-3.60 (m, 2H), 3.31 (m, 1H), 3.16 (m, 1H), 2.38 (s, 3H), 2.37 (m, 1H), 2.15 (m, 1H), 1.70-2.00 (m, 2H), 1.09-1.14 (m, 6H); [M+H]+ Found=539.

Example 110

3-((6-Chloro-1-(2-(3-cyclopropyl-3-hydroxyazetidin-1-yl)-2-oxoethyl)-7-fluoro-2-methyl-1H-indol-3-yl)thio)-2-fluorobenzoic acid (Compound 2-63)

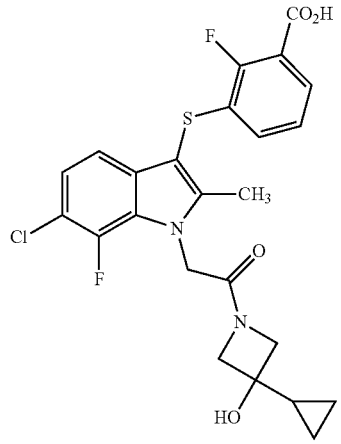 [SMILES: Cc1c(Sc2cccc(C(=O)O)c2F)c2ccc(Cl)c(F)c2n1CC(=O)N1CC(O)(C2CC2)C1]

The title compound (2-63) was prepared using the procedure for Example 14, using methyl 3-[(6-chloro-7-fluoro-2-methyl-1H-indol-3-yl)sulfanyl]-2-fluoro-benzoic acid in Step 1 and 3-cyclopropylazetidin-3-ol hydrochloride in Step 3. $^1$H NMR (400 MHz, DMSO-d$_6$): δ 7.12-7.21 (m, 3H), 6.78 (t, 1H), 6.39 (dt, 1H), 5.08 (m, 2H), 4.00 (s, 2H), 3.70 (dd, 2H), 2.40 (s, 3H), 1.20 (m, 1H), 0.25-0.45 (m, 4H); [M+H]+ Found=507.

Example 111

(R)-3-((6-Chloro-7-fluoro-1-(2-(3-(hydroxymethyl)pyrrolidin-1-yl)-2-oxoethyl)-2-methyl-1H-indol-3-yl)thio)-2-fluorobenzoic acid (Compound 2-64)

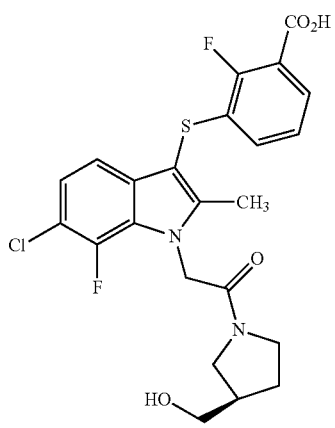 [SMILES: Cc1c(Sc2cccc(C(=O)O)c2F)c2ccc(Cl)c(F)c2n1CC(=O)N1CC[C@@H](CO)C1]

The title compound (2-64) was prepared using the procedure for Example 14, using methyl 3-[(6-chloro-7-fluoro-2-methyl-1H-indol-3-yl)sulfanyl]-2-fluoro-benzoic acid in Step 1 and D-β-prolinol in Step 3. $^1$H NMR (400 MHz, DMSO-d$_6$): δ 7.07-7.20 (m, 3H), 6.77 (t, 1H), 6.38 (m, 1H), 5.12-5.26 (m, 2H), 4.77 (m, 1H), 3.08-3.80 (m, 6H), 2.38 (s, 3H), 1.60-2.30 (m, 4H); [M−H]+ Found=493.

Example 112

3-((6-Chloro-7-fluoro-1-(2-((3S,4S)-3-hydroxy-4-morpholinopyrrolidin-1-yl)-2-oxoethyl)-2-methyl-1H-indol-3-yl)thio)-2-fluorobenzoic acid (Compound 2-65)

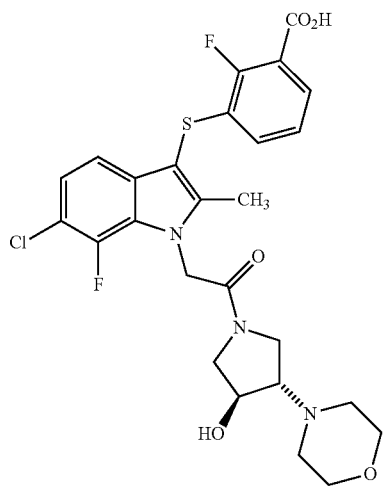 [SMILES: Cc1c(Sc2cccc(C(=O)O)c2F)c2ccc(Cl)c(F)c2n1CC(=O)N1C[C@H](O)[C@@H](N2CCOCC2)C1]

The title (2-65) compound was prepared using the procedure for Example 14, using methyl 3-[(6-chloro-7-fluoro-2-methyl-1H-indol-3-yl)sulfanyl]-2-fluoro-benzoic acid in Step 1 and (±)-trans-4-(4-morpholinyl)-3-pyrrolidinol dihydrochloride in Step 3. $^1$H NMR (400 MHz, DMSO-$d_6$): δ 7.10-7.19 (m, 3H), 6.78 (t, 1H), 6.38 (m, 1H), 5.46 (br s, 1H), 5.18-5.23 (m, 2H), 4.27 (m, 1H), 3.87 (m, 1H), 3.52-3.64 (m, 5H), 3.26-3.40 (m, 2H), 3.50 (m, 2H), 3.14 (m, 0.5H), 2.86 (m, 0.5H), 2.38-2.74 (m, 5H); [M−H]$^+$ Found=564.

Example 113

3-((6-Chloro-7-fluoro-1-(2-((3R,4R)-3-fluoro-4-hydroxypyrrolidin-1-yl)-2-oxoethyl)-2-methyl-1H-indol-3-yl)thio)-2-fluorobenzoic acid (Compound 2-66)

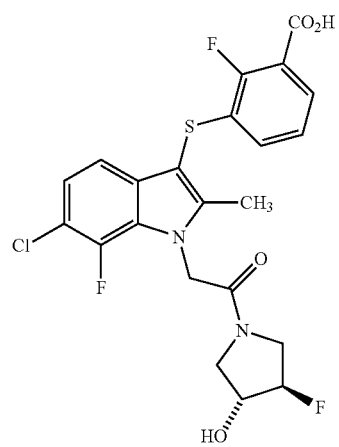 [SMILES: Cc1c(Sc2cccc(C(=O)O)c2F)c2ccc(Cl)c(F)c2n1CC(=O)N1C[C@@H](O)[C@H](F)C1]

The title compound (2-66) was prepared using the procedure for Example 14, using methyl 3-[(6-chloro-7-fluoro-2-methyl-1H-indol-3-yl)sulfanyl]-2-fluoro-benzoic acid in Step 1 and rac-(3R,4R)-4-fluoro-3-pyrrolidinol in Step 3. [M+Na]$^+$ Found=521.

Example 114

Sodium (S)-3-((6-chloro-7-fluoro-1-(2-(3-hydroxy-3-(trifluoromethyl)pyrrolidin-1-yl)-2-oxoethyl)-2-methyl-1H-indol-3-yl)thio)-2-fluorobenzoic acid Enantiomer A(Compound 2-58 Sodium Salt)

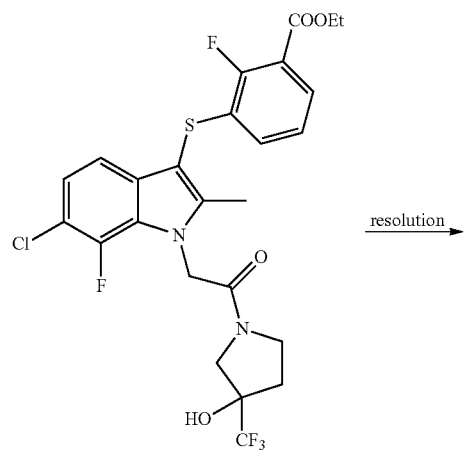

racemate 8
Example 89 resolution →

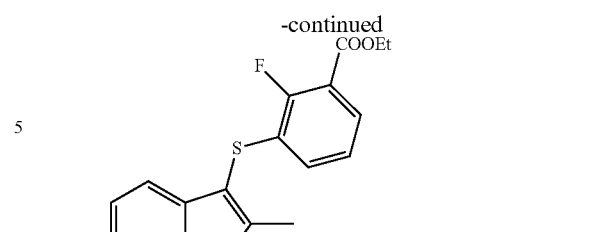

Enantiomer A and B

1N NaOH →

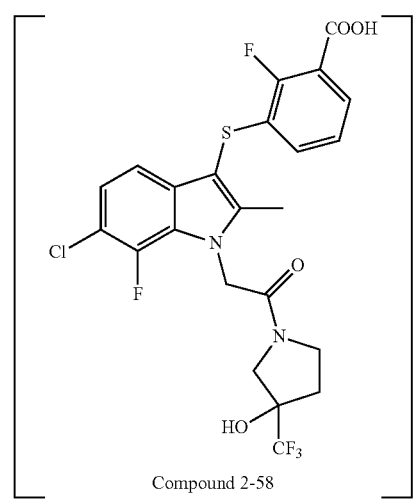

Compound 2-58

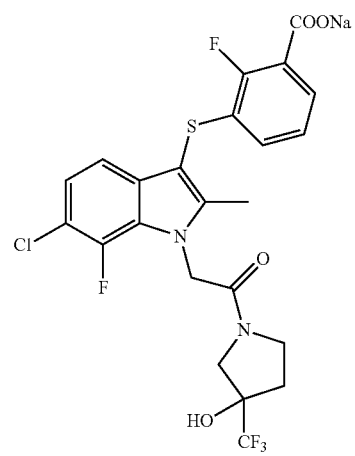

Compound 2-58 sodium salt

Resolution: Ethyl 3-((6-c-7-fluoro-1-(2-(3-hydroxy-3-(trifluoromethyl)pyrrolidin-1-yl)-2-oxoethyl)-2-methyl-1H-indol-3-yl)thio)-2-fluorobenzoate Enantiomer A Racemic compound 8 from Example 89 (11 g) was purified by chiral chromatography using Chiralpak-AD-H column eluting with 90:10 of Phase A (0.1% TFA in n-hexane): Phase B (EtOH:MeOH 50:50). The first eluted compound was collected to give Enantiomer A (4.3 g). HPLC: 98.6%; (column: Acquity BEH C-18 (50×2.1 mm, 1.7μ); RT 3.10 min. ACN: 0.025% TFA (aq); 0.5 mL/min. LC-MS: [M+H]$^+$ Found=577.5.

Sodium 3-((6-chloro-7-fluoro-1-(2-(3-hydroxy-3-(trifluoromethyl)pyrrolidin-1-yl)-2-oxoethyl)-2-methyl-1H-indol-3-yl)thio)-2-fluorobenzoate Enantiomer A (Compound 2-58 sodium salt)

To a solution of compound Enantiomer A (4.35 g, 7.54 mmol) in THF:water (3:1) (30 mL) was added 1M aq. NaOH solution (7.92 mL, 7.92 mmol) at RT and then heat at 60° C. overnight. The next day additional 1M aq. NaOH solution (0.23 mL, 0.23 mmol) was added to the reaction and heated at 60° C. for 5.5 h. After the completion of the reaction, solvent was removed to afford compound 2-58 sodium salt (4.30 g, 100%) as a beige solid. $^1$H NMR (300 MHz, DMSO-d$_6$): δ 7.20-7.10 (m, 3H), 6.77 (t, 1H), 6.40-6.35 (m, 1H), 5.31-5.16 (m, 2H), 3.91-3.69 (m, 5H), 2.36 (d, 3H), 2.17-1.97 (m, 2H); LC-MS: [M+H]$^+$ Found=549.

Example 115

Sodium (R)-3-((6-chloro-7-fluoro-1-(2-(3-hydroxy-3-(trifluoromethyl)pyrrolidin-1-yl)-2-oxoethyl)-2-methyl-1H-indol-3-yl)thio)-2-fluorobenzoate Enantiomer B (Compound 2-59 Sodium Salt)

Compound 2-59

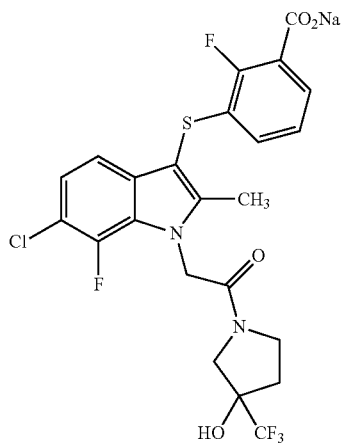

Enantiomer B

The title compound was prepared using the procedure for Example 114, except the second eluted compound from Step 1 was collected and hydrolysed to provide the title compound (2-59 sodium salt).

Example 116

3-((6-Chloro-1-(2-(3-cyanoazetidin-1-yl)-2-oxoethyl)-7-fluoro-2-methyl-1H-indol-3-yl)thio)-2-fluorobenzoic acid (Compound 2-67)

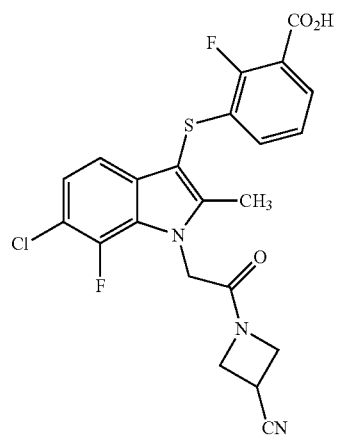 [SMILES: Cc1c(Sc2cccc(C(=O)O)c2F)c2ccc(Cl)c(F)c2n1CC(=O)N1CC(C#N)C1]

The title compound (2-67) was prepared using the procedure for Example 14, using methyl 3-[(6-chloro-7-fluoro-2-methyl-1H-indol-3-yl)sulfanyl]-2-fluoro-benzoic acid in Step 1 and 3-azetidinecarbonitrile hydrochloride in Step 3. [M+H]$^+$ Found=476.

Example 117

3-((6-Chloro-7-fluoro-1-(2-(3-hydroxy-3-phenylpyrrolidin-1-yl)-2-oxoethyl)-2-methyl-1H-indol-3-yl)thio)-2-fluorobenzoic acid (Compound 2-68)

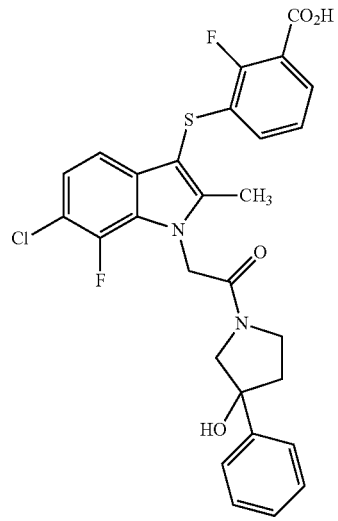 [SMILES: Cc1c(Sc2cccc(C(=O)O)c2F)c2ccc(Cl)c(F)c2n1CC(=O)N1CCC(O)(c2ccccc2)C1]

The title compound (2-68) was prepared using the procedure for Example 14, using methyl 3-[(6-chloro-7-fluoro-2-methyl-1H-indol-3-yl)sulfanyl]-2-fluoro-benzoic acid in Step 1 and (R,S)-3-phenyl-3-pyrrolidinol in Step 3. $^1$H NMR (400 MHz, DMSO-d$_6$): δ 7.47-7.61 (m, 2H), 7.12-7.42 (m, 6H), 6.78 (t, 1H), 6.39 (m, 1H), 5.60 (br s, 1H), 5.18-5.29 (m, 2H), 3.65-3.92 (m, 3H), 3.40-3.60 (m, 2H), 2.39 (s, 1.5H), 2.41 (s, 1.5H), 2.18 (m, 1H); [M+Na]$^+$ Found=579.

Example 118

3-((6-Chloro-1-(2-((3S,4S)-3-(dimethylamino)-4-hydroxypyrrolidin-1-yl)-2-oxoethyl)-7-fluoro-2-methyl-1H-indol-3-yl)thio)-2-fluorobenzoic acid (Compound 2-69)

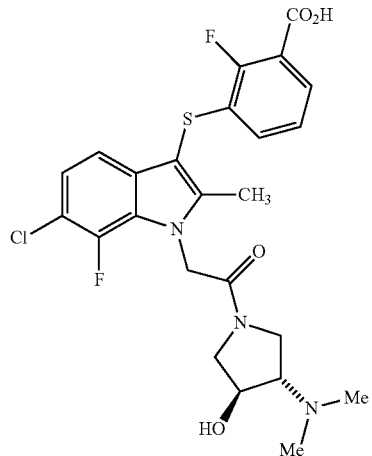 [SMILES: Cc1c(Sc2cccc(C(=O)O)c2F)c2ccc(Cl)c(F)c2n1CC(=O)N1C[C@H](O)[C@@H](N(C)C)C1]

The title compound (2-69) was prepared using the procedure for Example 14, using methyl 3-[(6-chloro-7-fluoro-2-methyl-1H-indol-3-yl)sulfanyl]-2-fluoro-benzoic acid in Step 1 and (±)-trans-4-(dimethylamino)-3-pyrrolidinol dihydrochloride in Step 3. 1H NMR (400 MHz, DMSO-$d_6$): δ 10.11 (br s, 1H), 7.57 (t, 1H), 7.14-7.19 (m, 2H), 7.05 (m, 1H), 6.74 (m, 1H), 5.20-5.30 (m, 2H), 4.90-4.53 (m, 2H), 4.14 (m, 1H), 3.65-4.00 (m, 2H), 3.48 (m, 1H), 2.84 (br m, 6H), 2.40 (s, 3H); [M+H]$^+$ Found=524.

Example 119

3-((6-Chloro-7-fluoro-1-(2-((3S,4S)-3-hydroxy-4-(4-methylpiperazin-1-yl)pyrrolidin-1-yl)-2-oxoethyl)-2-methyl-1H-indol-3-yl)thio)-2-fluorobenzoic acid (Compound 2-70)

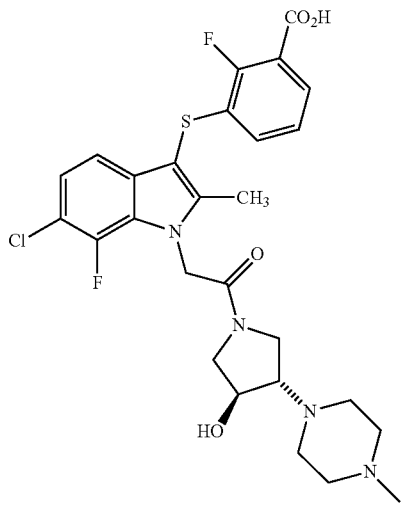 [SMILES: Cc1c(Sc2cccc(C(=O)O)c2F)c2ccc(Cl)c(F)c2n1CC(=O)N1C[C@H](O)[C@@H](N2CCN(C)CC2)C1]

The title compound (2-70) was prepared using the procedure for Example 14, using methyl 3-[(6-chloro-7-fluoro-2-methyl-1H-indol-3-yl)sulfanyl]-2-fluoro-benzoic acid in Step 1 and (±)-trans-4-(4-methyl-1-piperazinyl)-3-pyrrolidinol trihydrochloride in Step 3. $^1$H NMR (400 MHz, DMSO-$d_6$): δ 7.10-7.20 (m, 3H), 6.79 (t, 1H), 6.38 (m, 1H), 4.20 (m, 1H), 3.88 (m, 1H), 3.52-3.63 (m, 2H), 3.36 (m, 1H), 3.14 (m, 0.5H), 2.85 (m, 0.5H), 2.50-2.75 (m, 5H), 2.20-2.45 (m, 8H), 2.10-2.14 (m, 3H); [M+H]$^+$ Found=579.

Example 120

3-((6-Chloro-1-(2-(3-((dimethylamino)methyl)azetidin-1-yl)-2-oxoethyl)-7-fluoro-2-methyl-1H-indol-3-yl)thio)-2-fluorobenzoic acid (Compound 2-71)

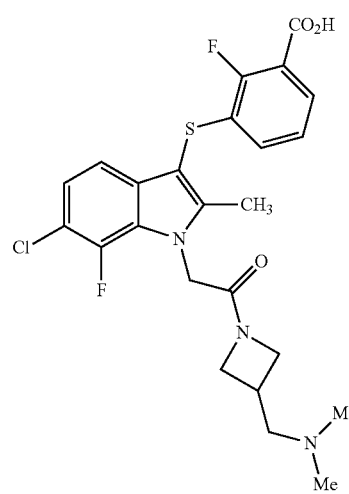

The title compound (2-71) was prepared using the procedure for Example 14, using methyl 3-[(6-chloro-7-fluoro-2-methyl-1H-indol-3-yl)sulfanyl]-2-fluoro-benzoic acid in Step 1 and azetidin-3-yl-N,N-dimethylmethanamine dihydrochloride in Step 3. $^1$H NMR (400 MHz, DMSO-$d_6$): δ 9.56 (br s, 1H), 7.57 (m, 1H), 7.14-7.22 (m, 2H), 7.06 (t, 1H), 6.75 (dt, 1H), 4.98-5.13 (m, 2H), 4.43 (t, 1H), 4.04-4.12 (m, 2H), 3.79 (m, 1H), 3.40-3.50 (m, 2H), 3.14 (m, 1H), 2.78 (s, 3H), 2.77 (s, 3H), 2.41 (s, 3H); [M+H]$^+$ Found=508.

Example 121

3-((6-Chloro-7-fluoro-2-methyl-1-(2-oxo-2-(1,4-dioxa-7-azaspiro[4.4]nonan-7-yl)ethyl)-1H-indol-3-yl)thio)-2-fluorobenzoic acid (Compound 2-72)

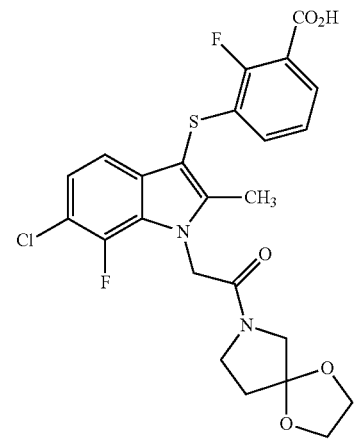 [SMILES: Cc1c(Sc2cccc(C(=O)O)c2F)c2ccc(Cl)c(F)c2n1CC(=O)N1CCC2(C1)OCCO2]

The title compound (2-72) was prepared using the procedure for Example 14, using methyl 3-[(6-chloro-7-fluoro-2-methyl-1H-indol-3-yl)sulfanyl]-2-fluoro-benzoic acid in Step 1 and 1,4-dioxa-7-azaspiro[4.4]nonane in Step 3. [M+Na]⁺ Found=545

Example 122

Sodium 3-((2,6-dichloro-7-fluoro-1-(2-oxo-2-(spiro[cyclobutane-1,3'-indolin]-1'-yl)ethyl)-1H-indol-3-yl)thio)-2-fluorobenzoate (Compound 4-121 Sodium Salt)

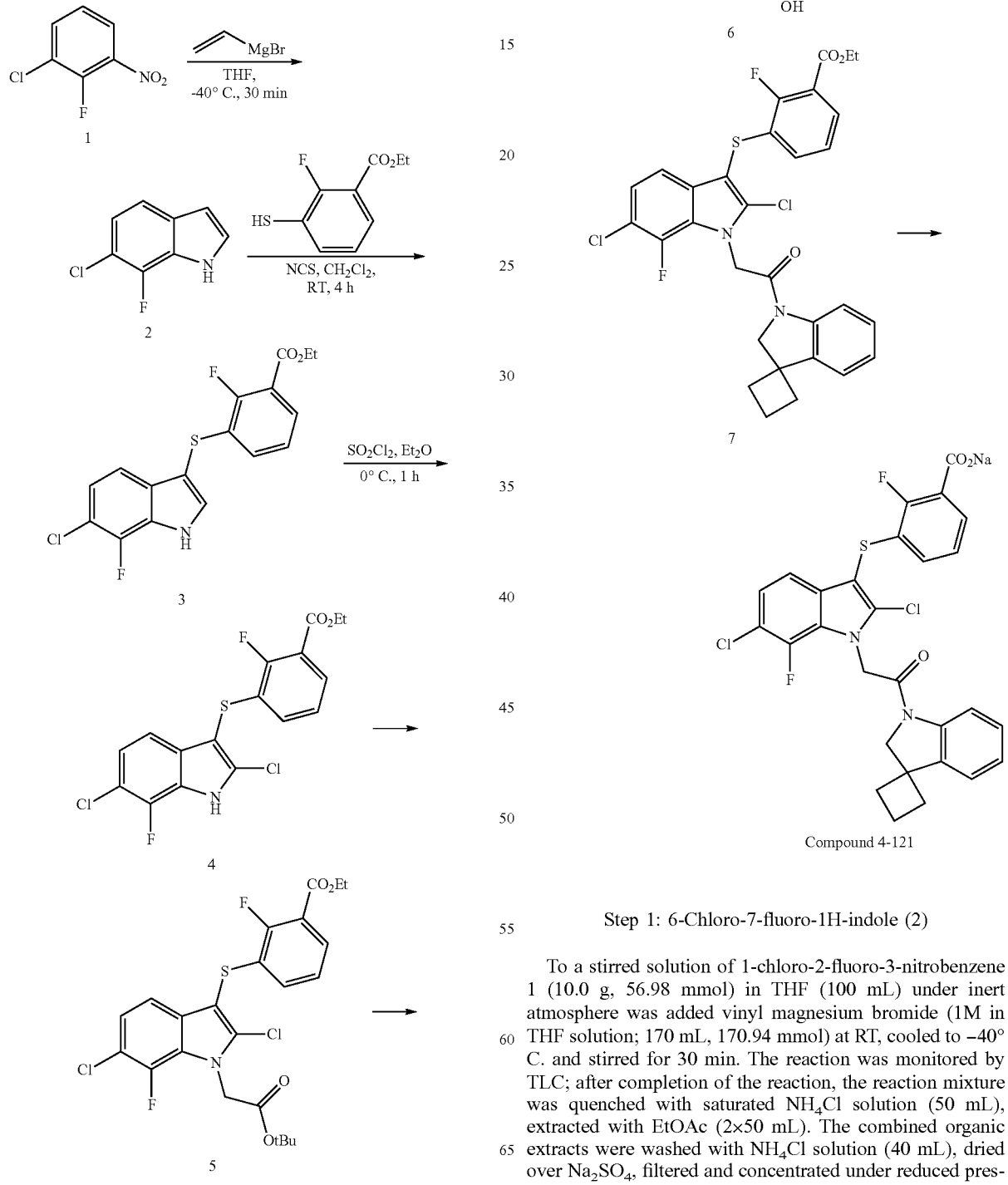

Compound 4-121

Step 1: 6-Chloro-7-fluoro-1H-indole (2)

To a stirred solution of 1-chloro-2-fluoro-3-nitrobenzene 1 (10.0 g, 56.98 mmol) in THF (100 mL) under inert atmosphere was added vinyl magnesium bromide (1M in THF solution; 170 mL, 170.94 mmol) at RT, cooled to −40° C. and stirred for 30 min. The reaction was monitored by TLC; after completion of the reaction, the reaction mixture was quenched with saturated NH₄Cl solution (50 mL), extracted with EtOAc (2×50 mL). The combined organic extracts were washed with NH₄Cl solution (40 mL), dried over Na₂SO₄, filtered and concentrated under reduced pressure to obtain the crude. This was purified by silica gel chromatography using 2% EtOAc/Hexanes to afford compound 2 (1.1 g, 11.4%) as a brown oil. $^1$H NMR (500 MHz, CDCl$_3$): δ 8.36 (br s, 1H), 7.31 (d, J=8.0 Hz, 1H), 7.25-7.22 (m, 1H), 7.08-7.05 (m, 1H), 6.56-6.54 (m, 1H).

Step 2: Ethyl 3-((6-Chloro-7-fluoro-1H-indol-3-yl)thio)-2-fluorobenzoate (3)

To a stirred solution of ethyl 2-fluoro-3-mercaptobenzoate (1.18 g, 5.91 mmol) in CH2Cl2 (30 mL) under inert atmosphere was added NCS (792 mg, 5.91 mmol) at RT and stirred for 1 h. To this, compound 2 (1.0 g, 5.91 mmol) in CH$_2$Cl$_2$ (20 mL) was added at RT and stirred for 4 h. The mixture was diluted with water (40 mL) and extracted with CH$_2$Cl$_2$ (2×60 mL). The combined organic extracts were washed with water (50 mL) and brine (50 mL), dried over Na$_2$SO$_4$, filtered and concentrated in vacuo to obtain the crude. The crude was purified (silica gel; 10% EtOAc/Hexanes) to afford compound 3 (1.2 g, 55%) as a pale brown solid. $^1$H NMR (500 MHz, DMSO-d$_6$): δ12.60 (br s, 1H), 8.00 (d, J=4.0 Hz, 1H), 7.61-7.57 (m, 1H), 7.24-7.17 (m, 2H), 7.09 (t, J=8.0 Hz, 1H), 6.90-6.86 (m, 1H), 4.34 (q, J=7.5 Hz, 2H), 1.32 (t, J=7.5 Hz, 3H); MS (ESI): m/z [M+H]$^+$ Found=368.6.

Step 3: Ethyl 3-((2,6-dichloro-7-fluoro-1H-indol-3-yl)thio)-2-fluorobenzoate (4)

To a stirred solution of compound 3 (750 mg, 2.04 mmol) in Et$_2$O (10 mL) was added sulfuryl chloride (0.18 mL, 2.25 mmol) in Et$_2$O (5 mL) at 0° C. under inert atmosphere and stirred for 1 h. The reaction was monitored by TLC; after completion of the reaction, the reaction mixture was diluted with ice cold water (30 mL) and extracted with EtOAc (3×30 mL). The combined organic extracts were washed with water (50 mL), dried over Na$_2$SO$_4$, filtered and concentrated under reduced pressure to obtain the crude. The crude was purified (silica gel; 3% EtOAc/hexanes) to afford compound 4 (314 mg, 38%) as pale brown solid. $^1$H NMR (500 MHz, DMSO-d$_6$): δ 13.54 (s, 1H), 7.65-7.61 (m, 1H), 7.28-7.20 (m, 2H), 7.17 (t, J=8.0 Hz, 1H), 6.96-6.92 (m, 1H), 4.33 (q, 2H), 1.34 (t, J=7.5 Hz, 3H); LC-MS (ESI): m/z [M−H]$^+$ Found=400.2.

Step 4: Ethyl 3-((1-(2-(tert-butoxy)-2-oxoethyl)-2,6-dichloro-7-fluoro-1H-indol-3-yl)thio)-2-fluorobenzoate (5)

To a stirred solution of indole 4 (100 mg, 0.25 mmol) in THF (2 mL) were added tert-butyl 2-bromoacetate (97 mg, 0.498 mmol), and K$_2$CO$_3$ (103 mg, 0.74 mmol). The reaction mixture was stirred at 65° C. for 16 h then the volatiles were evaporated under vacuum. The residue was diluted with water (3 mL) and extracted with EtOAc (3×10 mL). The combined organic extracts were dried over Na$_2$SO$_4$, filtered and concentrated under reduced pressure to obtain the crude. The crude was purified (silica gel; 10% EtOAc/hexanes) to afford compound 5 (115 mg, 89%) as an amber oil.

Step 5: 2-(2,6-Dichloro-3-((3-(ethoxycarbonyl)-2-fluorophenyl)thio)-7-fluoro-1H-indol-1-yl)acetic acid (6)

To a stirred solution of compound 5 (115 mg, 0.22 mmol) in CH$_2$Cl$_2$ (2 mL) was added TFA (0.3 mL) at 0° C. under inert atmosphere; warmed to RT and stirred for 16 h. The volatiles were removed in vacuo. The residue was triturated with diethyl ether to afford compound 6 (100 mg) as a tan solid.

Step 6: Ethyl 3-((2,6-dichloro-7-fluoro-1-(2-oxo-2-(spiro[cyclobutane-1,3'-indolin]-1'-yl)ethyl)-1H-indol-3-yl)thio)-2-fluorobenzoate (7)

To a stirred solution of compound 6 (35 mg, 0.076 mmol) in CH$_2$Cl$_2$ (1 mL) was added HATU (43.3 mg, 0.114 mmol), followed by spiro[cyclobutane-1,3'-indoline] (15.7 mg, 0.099 mmol) and DIEA (46 uL, 0.266 mmol). The reaction mixture was stirred at ambient temperature for 16 h. The volatiles were removed in vacuo, the residue was diluted with water (10 mL) and extracted with CH$_2$Cl$_2$ (3×7 mL). The combined organic extracts were dried over Na$_2$SO$_4$, filtered and concentrated under reduced pressure to obtain the crude. The crude was purified (silica gel, EtOAc/hexanes) to afford compound 7 (38.6 mg, 84%) as yellowish solid.

Step 7: Sodium 3-((2,6-dichloro-7-fluoro-1-(2-oxo-2-(spiro[cyclobutane-1,3'-indolin]-1'-yl)ethyl)-1H-indol-3-yl)thio)-2-fluorobenzoate (Compound 4-121 Sodium Salt)

To a solution of ester 7 (38.6 mg, 0.064 mmol) in THF/MeOH/H$_2$O (2:1:1, 1.5 mL) was added aqueous 1N NaOH (0.064 mmol) and the resulting solution was heated at 60° C. for 3 h. The reaction mixture was concentrated in vacuo. The residue was triturated with acetonitrile to afford the title compound (4-121 sodium salt) as a white solid (29.9 mg, 81.4%). LCMS [M+Na]$^+$ Found=595.

Example 123

Sodium 3-((2,6-dichloro-7-fluoro-1-(2-oxo-2-(spiro[cyclopropane-1,3'-indolin]-1'-yl)ethyl)-1H-indol-3-yl)thio)-2-fluorobenzoate (Compound 2-45 Sodium Salt)

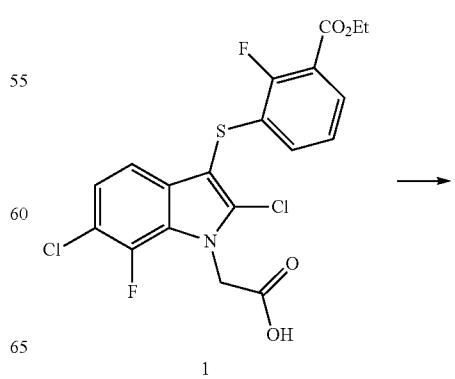

1

207
-continued
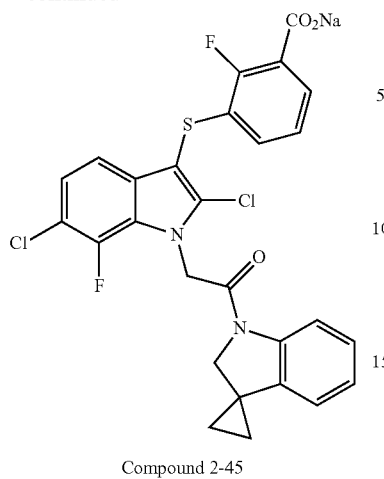
Compound 2-45
Following the procedure of Example 122 but using spiro[cyclopropane-1,3'-indoline] in place of spiro[cyclobutane-1,3'-indoline], the title compound (2-45) was obtained as a white solid. LCMS [M+Na]$^+$ Found=582].
Example 124
Sodium 3-((6-chloro-2-cyclopropyl-7-fluoro-1-(2-(indolin-1-yl)-2-oxoethyl)-1H-indol-3-yl)thio)-2-fluorobenzoate (Compound 4-29 Sodium Salt)
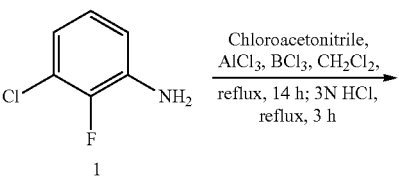
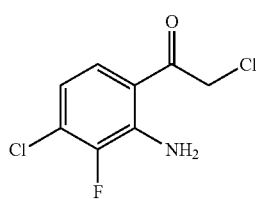
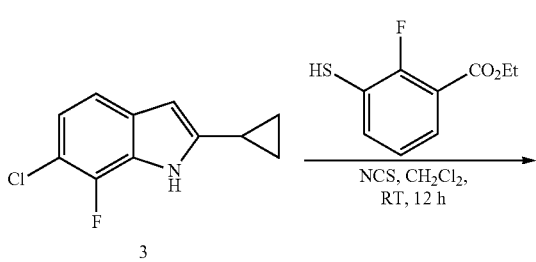
208
-continued
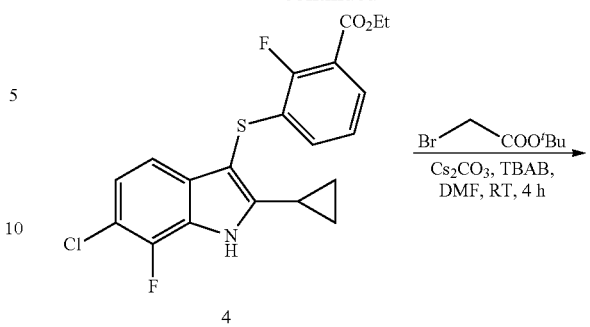
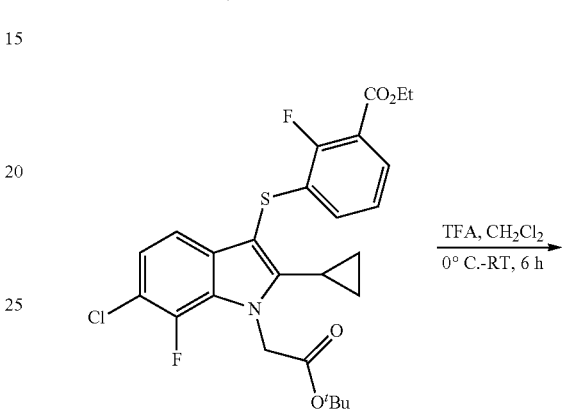
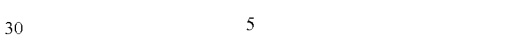
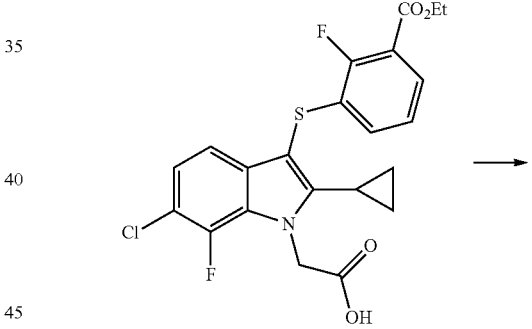
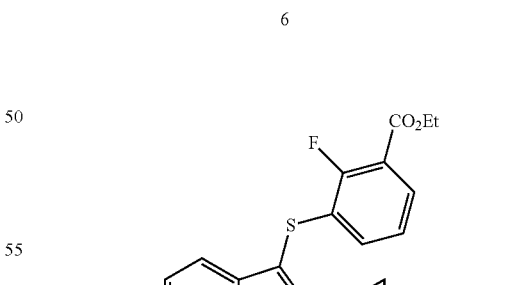
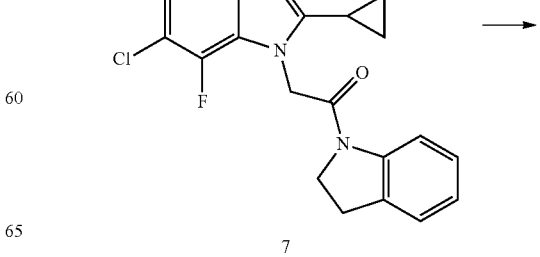

209
-continued

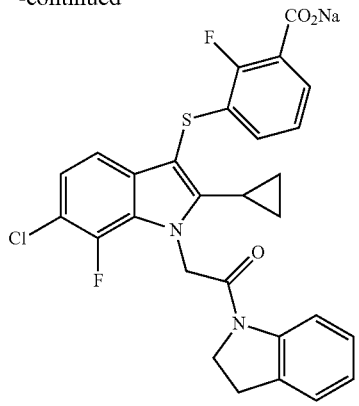

Compound 4-29

Step 1: 1-(2-Amino-4-chloro-3-fluorophenyl)-2-chloroethan-1-one (2)

To a stirred solution of AlCl₃ (10.0 g, 75.01 mmol) and BCl₃ (1M in n-hexane, 74 mL, 75.01 mmol) in CH₂Cl₂ (80 mL) was added 3-chloro-2-fluoroaniline 1 (9.0 g, 6.18 mmol) followed by a solution of chloroacetonitrile (11.6 g, 153.64 mmol) in CH₂Cl₂ (20 mL) at 0° C. under inert atmosphere. The reaction mixture was allowed to stir at RT for 30 minutes and heated to reflux for additional 14 h. The reaction mixture was then cooled to 0° C., added aqueous 3 N HCl (100 mL) and raised the temperature to reflux and stirred for 3 h. The mixture was cooled RT, diluted with water (50 mL) and extracted with CH₂Cl₂ (2×150 mL). The combined organic extracts were dried over Na₂SO₄, filtered and concentrated under reduced pressure to obtain the crude. The crude was purified by triturating with n-pentane to afford compound 2 (4.5 g, 33%) as an off-white solid. 1H NMR (500 MHz, DMSO-d₆): δ7.61 (d, J=9.0 Hz, 1H), 7.35 (br s, 2H), 6.72 (d, J=9.0 Hz, 1H), 5.06 (s, 2H).

Step 2: 6-Chloro-2-cyclopropyl-7-fluoro-1H-indole (3)

To a stirred solution of compound 2 (4.5 g, 20.3 mmol) in toluene (50 mL) was added cyclopropyl-MgBr (0.5 M in THF, 102.0 mL, 50.9 mmol) at 0° C. under inert atmosphere. The reaction mixture was stirred at 0° C. for 15 min and then warmed to RT for an additional 1 h. The mixture was quenched with sat. NH₄Cl (10 mL) and extracted with EtOAc (3×75 mL). The combined organic extracts were dried over Na₂SO₄, filtered and concentrated under reduced pressure to obtain the crude. The crude was purified (silica gel; 1% EtOAc/hexanes) to afford compound 3 (2.7 g, 63%) as an off-white solid. ¹H NMR (500 MHz, DMSO-d₆): δ 11.55 (s, 1H), 7.18 (d, J=8.5 Hz, 1H), 6.97 (dd, J=8.5, 6.5 Hz, 1H), 6.16 (s, 1H), 2.03-1.99 (m, 1H), 0.99-0.96 (m, 2H), 0.83-0.80 (m, 2H); LC-MS: m/z [M–H]⁺ Found=208.1.

Step 3:Ethyl 3-((6-chloro-2-cyclopropyl-7-fluoro-1H-indol-3-yl)thio)-2-fluorobenzoate (4)

To a stirred solution of ethyl 2-fluoro-3-mercaptobenzoate (190 mg, 0.95 mmol) in CH₂Cl₂ (10 mL) under inert atmosphere was added NCS (128 mg, 0.95 mmol) at RT and stirred for 1 h. To this, indole 3 (200 mg, 0.95 mmol) in CH₂Cl₂ (5 mL) was added at RT and stirred for 12 h. The mixture was diluted with water (50 mL) and extracted with CH₂Cl₂ (3×50 mL). The combined organic extracts were washed with brine (100 mL), dried over Na₂SO₄, filtered and concentrated under reduced pressure to obtain the crude. The crude was purified (silica gel; 5-10% EtOAc/hexanes) to obtain compound 4 (300 mg, 77%) as a pale pink solid. ¹H NMR (400 MHz, DMSO-d₆): δ 11.91 (s, 1H), 7.89-7.84 (m, 1H), 7.57 (t, J=8.0 Hz, 1H), 7.14-7.07 (m, 2H), 6.78 (t, J=8.0 Hz, 1H), 4.35-4.29 (m, 2H), 2.32-2.25 (m, 1H), 1.33-1.28 (m, 3H), 1.15-1.10 (m, 2H), 1.08-1.03 (m, 2H); LC-MS (ESI): m/z [M–H]⁺ Found=406.3.

Step 4: Ethyl 3-((1-(2-(tert-butoxy)-2-oxoethyl)-6-chloro-2-cyclopropyl-7-fluoro-1H-indol-3-yl)thio)-2-fluorobenzoate (5)

To a stirred solution of compound 4 (100 mg, 0.24 mmol) in DMF (5 mL) were added tert-butyl 2-bromoacetate (48 mg, 0.24 mmol), Cs₂CO₃ (160 mg, 0.49 mmol) followed by Bu₄NBr (cat.) at RT under inert atmosphere and stirred for 4 h. The mixture was diluted with water (20 mL) and extracted with EtOAc (3×20 mL). The combined organic extracts were dried over Na₂SO₄, filtered and concentrated under reduced pressure to obtain the crude. The crude was purified (silica gel; 3% EtOAc/hexanes) to afford compound 5 (120 mg, 93%) as an off-white solid. ¹H NMR (500 MHz, CDCl₃): δ 7.60 (t, J=6.5 Hz, 1H), 7.18 (d, J=7.5 Hz, 1H), 7.08-7.05 (m, 1H), 6.90 (t, J=8.0 Hz, 1H), 6.67-6.66 (m, 1H), 5.15 (s, 2H), 4.42 (q, 2H), 1.72-1.69 (m, 1H), 1.43 (s, 9H), 1.42-1.40 (m, 3H), 1.08-1.04 (m, 2H), 0.95-0.93 (m, 2H); LC-MS: m/z [M+H]⁺ Found=522.5.

Step 5: 2-(6-Chloro-2-cyclopropyl-3-((3-(ethoxycarbonyl)-2-fluorophenyl)thio)-7-fluoro-1H-indol-1-yl) acetic acid (6)

To a stirred solution of compound 5 (120 mg, 0.23 mmol) in CH₂Cl₂ (5 mL) was added TFA (0.5 mL) at 0° C. under inert atmosphere; warmed to RT and stirred for 6 h. The volatiles were removed in vacuo. The residue was diluted with water (10 mL), basified with aq. sat. NaHCO₃ (15 mL) and extracted with CH₂Cl₂ (3×20 mL). The combined organic extracts were dried over Na₂SO₄, filtered and concentrated under reduced pressure to afford compound 6 (100 mg) as an off-white solid which was used without purification. ¹H NMR (500 MHz, DMSO-d₆): δ13.20 (br s, 1H), 7.59-7.56 (m, 1H), 7.20-7.08 (m, 3H), 6.68-6.65 (m, 1H), 5.27 (s, 2H), 4.35-4.31 (m, 2H), 1.92-1.89 (m, 1H), 1.33-1.30 (m, 3H), 1.09-1.04 (m, 2H), 0.83-0.82 (m, 2H); LC-MS: m/z [M–H]⁺ Found=464.8.

Step 6: Ethyl 3-((6-chloro-2-cyclopropyl-7-fluoro-1-(2-(indolin-1-yl)-2-oxoethyl)-1H-indol-3-yl)thio)-2-fluorobenzoate (7)

To a stirred solution of compound 6 (25 mg, 0.053 mmol) in CH₂Cl₂ (1 mL) was added HATU (30 mg, 0.079 mmol), followed by indoline (9 mg, 0.074 mmol) and DIEA (27 uL, 0.159 mmol). The reaction mixture was stirred at ambient temperature for 16 h. The volatiles were removed in vacuo. The residue was diluted with water (10 mL) and extracted with CH$_2$Cl$_2$ (3×7 mL). The combined organic extracts were dried over Na$_2$SO$_4$, filtered and concentrated under reduced pressure to obtain the crude. The crude was purified (silica gel, EtOAc/hexanes) to afford compound 7 (23 mg, 77%) as an off-white solid.

Step 7: Sodium 3-((6-chloro-2-cyclopropyl-7-fluoro-1-(2-(indolin-1-yl)-2-oxoethyl)-1H-indol-3-yl)thio)-2-fluorobenzoate (Compound 4-29 Sodium Salt)

To a solution of compound 7 (23 mg, 0.040 mmol) in THF/MeOH/H$_2$O (2:1:1, 1.5 mL) was added aqueous 1N NaOH (0.040 mmol) and the resulting solution was heated at 60° C. for 3 h. The reaction mixture was concentrated in vacuo to afford the title compound (4-29 sodium salt) as a white solid (20 mg, 89%). LCMS [M+H]$^+$ Found=539.

Example 125

Sodium 3-((6-chloro-2-cyclopropyl-7-fluoro-1-(2-oxo-2-(spiro[cyclobutane-1,3'-indolin]-1'-yl)ethyl)-1H-indol-3-yl)thio)-2-fluorobenzoate (Compound 4-129 Sodium Salt)

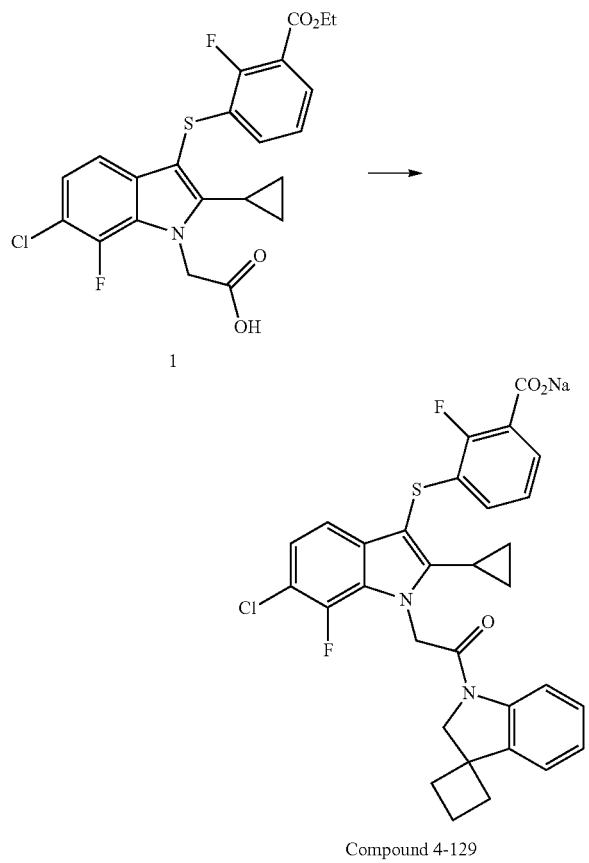

Compound 4-129

Following the procedure of Example 124 but using spiro[cyclobutane-1,3'-indoline] in place of indoline in Step 6, the title compound (4-129 Sodium Salt) was obtained as an off white solid. LCMS [M+H]$^+$ Found=580.

Example 126

Sodium 3-((6-chloro-2-cyclopropyl-7-fluoro-1-(2-oxo-2-(spiro[cyclopropane-1,3'-indolin]-1'-yl)ethyl)-1H-indol-3-yl)thio)-2-fluorobenzoate (Compound 4-85 Sodium Salt)

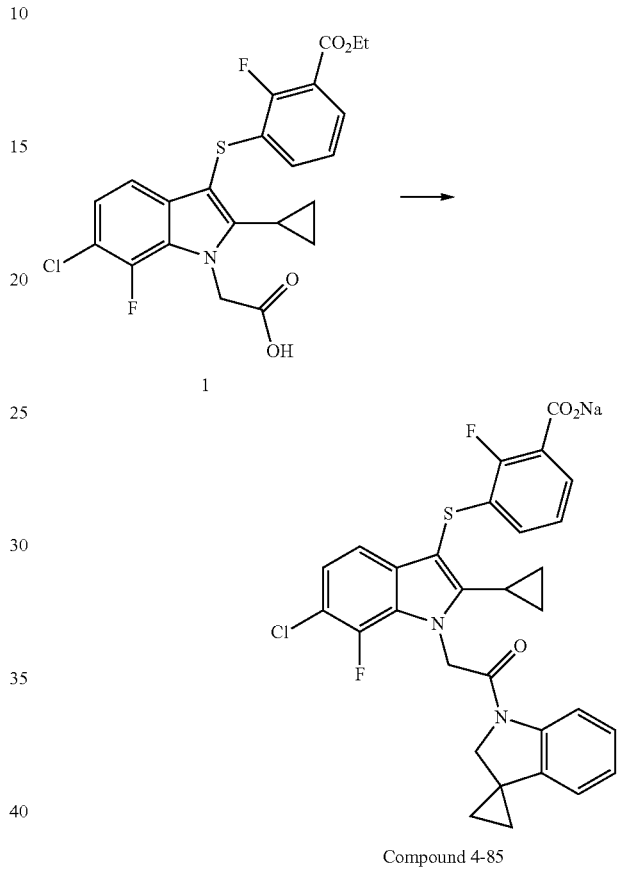

Compound 4-85

Following the procedure of Example 124 but using spiro[cyclopropyl-1,3'-indoline] in place of indoline in Step 6, the title compound (4-85 Sodium Salt) was obtained as an off white solid. LCMS [M+Na]$^+$ Found=587.

Example 127

Sodium 3-((2,6-dichloro-7-fluoro-1-(2-(spiro[cyclobutane-1,3'-indolin]-1'-yl)ethyl)-1H-indol-3-yl)thio)-2-fluorobenzoate (Compound 5-1 Sodium Salt)

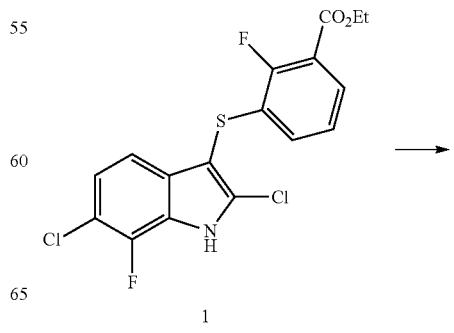

-continued

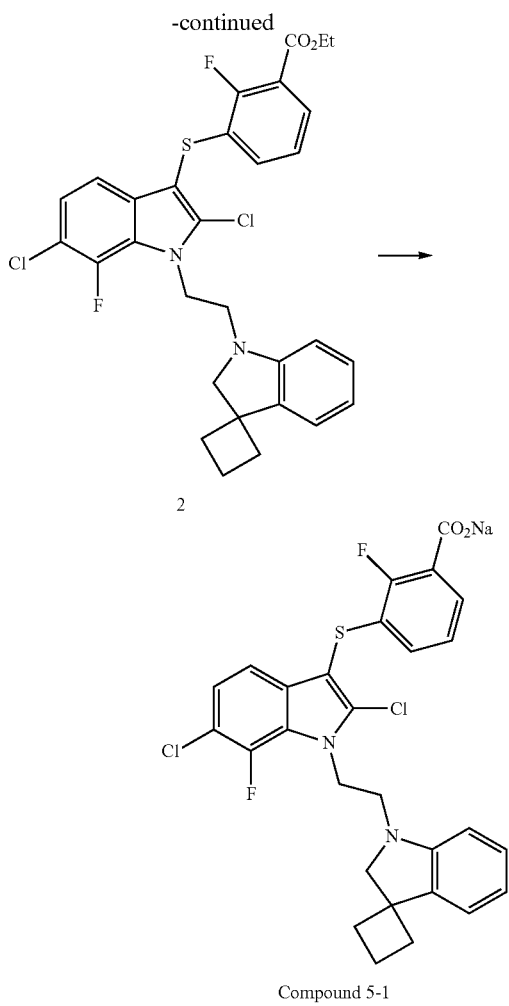

Compound 5-1

Step 1: Ethyl 3-((2,6-d-7-fluoro-1-(2-(spiro[cyclobutane-1,3'-indolin]-1'-yl)ethyl)-1H-indol-3-yl)thio)-2-fluorobenzoate (2)

To a solution of indole 1(Example 122 Step 3; 50 mg, 0.124 mmol), and bromoethyl-1'2-dihydrospiro[cyclobutane-1,3'-indole](0.161 mmol) in THF (2.0 mL) was added NaI (0.124 mmol) and Cs$_2$CO$_3$ (0.372 mmol). The reaction mixture was heated at 65° C. for 72 h. The organics were evaporated in vacuo. The residue was diluted with water. The aqueous phase was extracted with EtOAc (2×10 mL). The organic layer was dried over MgSO$_4$, filtered and concentrated. The crude product was purified by flash chromatography on silica gel eluting with EtOAc-hexane to afford the title compound as an off white solid (43 mg, 59%). LCMS [M+H]$^+$ Found=587.

Step 2: Sodium 3-((2,6-dichloro-7-fluoro-1-(2-(spiro[cyclobutane-1,3'-indolin]-1'-yl)ethyl)-1H-indol-3-yl)thio)-2-fluorobenzoate (Compound 5-1 Sodium Salt)

To a solution indole 2 (43 mg, 0.073 mmol) in THF/MeOH/H$_2$O (3:1:1, 1.5 mL) was added aqueous 1N NaOH (0.073 mmol) and the resulting suspension was heated at 60° C. for 16 h. The reaction mixture was concentrated in vacuo to afford the title compound (5-1 sodium salt) as an off white solid (35 mg, 83%). LCMS [M+H]$^+$ Found=559.

Example 128

Sodium 3-((2,6-dichloro-7-fluoro-1-(2-(spiro[cyclopropane-1,3'-indolin]-1'-yl)ethyl)-1H-indol-3-yl)thio)-2-fluorobenzoate (Compound 5-2 Sodium Salt)

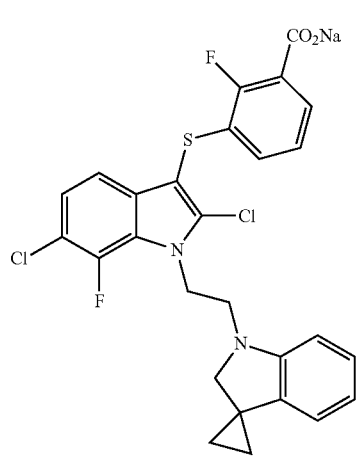

Compound 5-2

Following the procedure of Example 127 Steps 1 and 2 but using bromoethyl-1,2-dihydrospiro[cyclopropane-1,3-indole] in place of bromoethyl-1'2-dihydrospiro[cyclobutane-1,3'-indole], the title compound (5-2 sodium salt) was obtained as light yellow solid. LCMS [M+H]$^+$ Found=545.

Example 129

Sodium 3-((6-chloro-2-cyclopropyl-7-fluoro-1-(2-(spiro[cyclobutane-1,3'-indolin]-1'-yl)ethyl)-1H-indol-3-yl)thio)-2-fluorobenzoate (Compound 5-3 Sodium Salt)

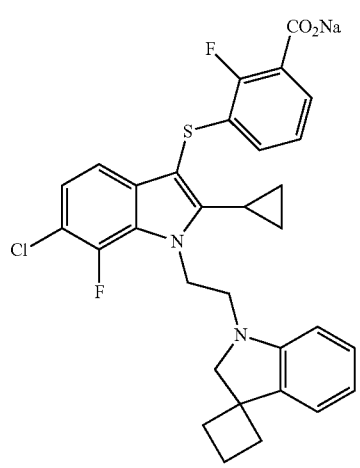

Compound 5-3

Following the procedure of Example 127 Steps 1 and 2 but using the ethyl 3-((6-chloro-2-cyclopropyl-7-fluoro-1H- indol-3-yl)thio)-2-fluorobenzoate (Example 124, Step 3) in place of ethyl 3-((2,6-dichloro-7-fluoro-1H-indol-3-yl) thio)-2-fluorobenzoate as starting material, the title compound (5-3 sodium salt) was obtained as an off white solid (30 mg, 90%). LCMS [M+H]+ Found=566.

Example 130

Sodium 3-((6-chloro-2-cyclopropyl-7-fluoro-1-(2-(indolin-1-yl)ethyl)-1H-indol-3-yl)thio)-2-fluorobenzoate (Compound 5-4 Sodium Salt)

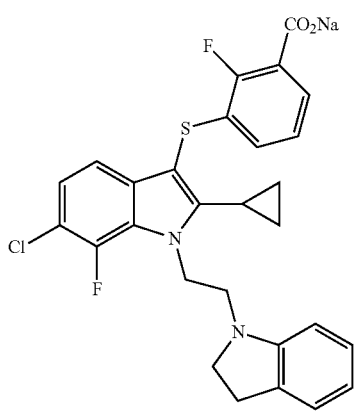

Compound 5-4

Following the procedure of Example 129 but using bromoethyl indoline in place of bromoethyl-1'2-dihydrospiro [cyclobutane-1,3'-indole], the title compound (5-4 sodium salt) was obtained as an off white solid. LCMS [M+H]+ Found=525.

Example 131

Sodium 3-((2,6-dichloro-7-fluoro-1-(2-(3-hydroxy-3-(trifluoromethyl)pyrrolidin-1-yl)-2-oxoethyl)-1H-indol-3-yl)thio)-2-fluorobenzoate (Compound 5-5 Sodium Salt)

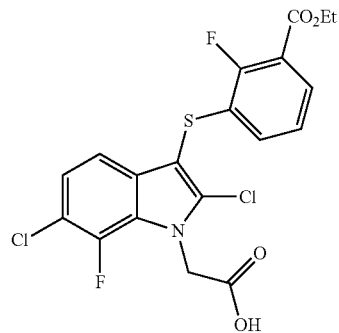

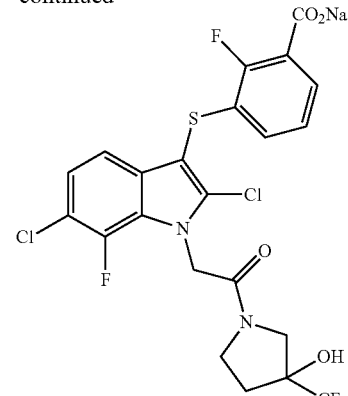

Compound 5-5

Following the procedure of Example 122 but using 3-(trifluoromethyl)pyrrolidin-3-ol hydrochloride in place of spiro [cyclobutane-1,3'-indoline] in Step 6, the title compound (5-5 sodium salt) was obtained. LCMS [M+Na]+ Found=591.

Example 132

Sodium 3-((6-chloro-2-cyclopropyl-7-fluoro-1-(2-(3-hydroxy-3-(trifluoromethyl)pyrrolidin-1-yl)-2-oxoethyl)-1H-indol-3-yl)thio)-2-fluorobenzoate (Compound 5-6 Sodium Salt)

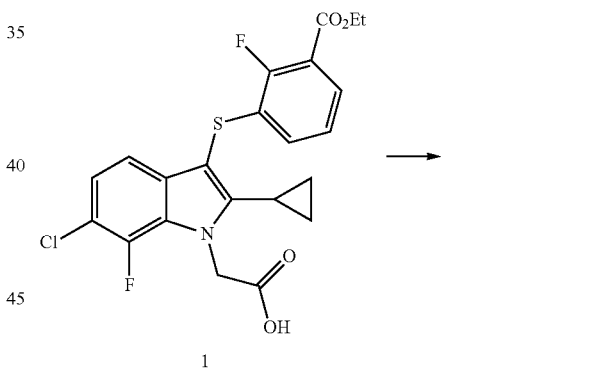

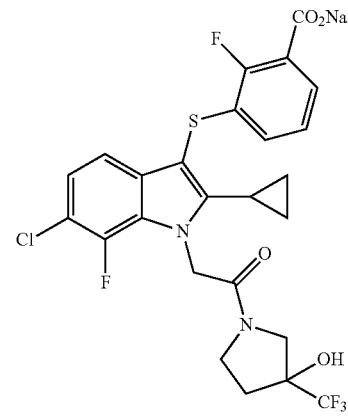

Compound 5-6

Following the procedure of Example 124 but using 3-hydroxypyrrolidine hydrochloride in place of spiro[cyclobu-

Example 133

Sodium 3-((6-chloro-2-cyclopropyl-7-fluoro-1-(2-(methoxy(methyl)amino)-2-oxoethyl)-1H-indol-3-yl)thio)-2-fluorobenzoate (Compound 5-7 Sodium Salt)

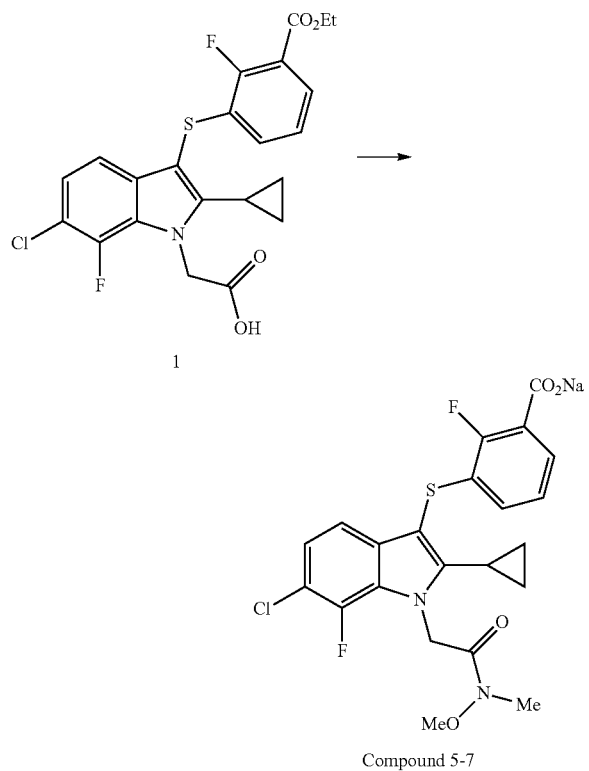

Compound 5-7

Following the procedure of Example 124 but using N,O-dimethylhydroxylamine.HCl in place of indoline in Step 6, the title compound (5-7 sodium salt) was obtained. LCMS [M+H]$^+$ Found=503.

All compounds can be isolated as the free acid or the corresponding sodium salt (following treatment with 1 equivalent of NaOH). The sodium salt was used for in vivo experiments.

Example 134

Parenteral Pharmaceutical Composition

To prepare a parenteral pharmaceutical composition suitable for administration by injection (subcutaneous, intravenous), 1-100 mg of a water-soluble salt of a compound described herein, or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection.

Example 135

Oral Solution

To prepare a pharmaceutical composition for oral delivery, a sufficient amount of a compound described herein, or a pharmaceutically acceptable salt thereof, is added to water (with optional solubilizer(s), optional buffer(s) and taste masking excipients) to provide a 20 mg/mL solution.

Example 136

Oral Tablet

A tablet is prepared by mixing 20-50% by weight of a compound described herein, or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example 137

Oral Capsule

To prepare a pharmaceutical composition for oral delivery, 10-500 mg of a compound described herein, or a pharmaceutically acceptable salt thereof, is mixed with starch or other suitable powder blend. The mixture is incorporated into an oral dosage unit such as a hard gelatin capsule, which is suitable for oral administration.

In another embodiment, 10-500 mg of a compound described herein, or a pharmaceutically acceptable salt thereof, is placed into Size 4 capsule, or size 1 capsule (hypromellose or hard gelatin) and the capsule is closed.

Example 138

Topical Gel Composition

To prepare a pharmaceutical topical gel composition, a compound described herein, or a pharmaceutically acceptable salt thereof, is mixed with hydroxypropyl celluose, propylene glycol, isopropyl myristate and purified alcohol USP. The resulting gel mixture is then incorporated into containers, such as tubes, which are suitable for topical administration.

Example 139

Human Autotaxin Assay

ATX activity is assayed in concentrated conditioned media from Hep3B human hepatocellular carcinoma cells by measuring the amount of choline released from the substrate, lysophosphatidylcholine (LPC) as it is cleaved to LPA. Conditioned media is collected from confluent Hep3B cells and concentrated 20-fold using Centriprep-30 filter devices (Millipore). To assay for autotaxin inhibition, 10-20 μL of the concentrated conditioned media is incubated with 2.5 μL of a test compound in DMSO and 72.5-82.5 μL lyso-PLD buffer (100 mM Tris pH 9, 500 mM NaCl, 5 mM MgCl$_2$, 5 mM CaCl$_2$, 0.05% Triton X-100 in the presence or absence of 0.2% fatty-acid-free human serum albumin) for 15 min at 37° C. After the 15 min incubation, 5 uL of 2 mM LPC (14:0; Avanti Polar Lipids Cat#855575C) diluted in lyso-PLD buffer is added for a final concentration of 100 uM and the incubation continues for 1.5-3 hours at 37° C. 100 µL of a color mix containing 4.5 mM 4-aminoantipyrine, 2.7 mM N-ethyl-N-(2-hydroxy-3-sulfopropyl)-m-toluidine, 21 units/ml horseradish peroxidase and 3 units/mL choline oxidase in 50 mM Tris, pH 8, 4.5 mM $MgCl_2$ is added and the incubation continued for 15 minutes at room temperature before reading the absorbance at 555 nm.

Illustrative biological activity of representative compounds in the human autotaxin assay described herein is presented in the following table:

| Compound number | $IC_{50}$ (µM) |
|---|---|
| 1-1 | A |
| 1-2 | B |
| 1-3 | B |
| 1-4 | C |
| 1-5 | A |
| 1-6 | A |
| 1-7 | A |
| 1-8 | B |
| 1-9 | A |
| 1-10 | A |
| 1-11 | B |
| 1-12 | A |
| 1-13 | A |
| 1-14 | A |
| 1-15 | B |
| 1-16 | A |
| 1-17 | C |
| 1-18 | A |
| 1-19 | A |
| 1-20 | A |
| 1-21 | A |
| 1-22 | A |
| 1-24 | A |
| 1-25 | A |
| 1-26 | A |
| 1-31 | A |
| 1-32 | A |
| 1-33 | A |
| 1-34 | A |
| 1-35 | A |
| 1-36 | A |
| 1-37 | A |
| 1-38 | A |
| 1-39 | A |
| 1-40 | B |
| 1-41 | A |
| 1-42 | A |
| 1-44 | A |
| 1-45 | A |
| 1-46 | A |
| 1-48 | A |
| 1-49 | A |
| 1-50 | A |
| 1-51 | A |
| 1-52 | A |
| 1-53 | A |
| 1-58 | A |
| 1-59 | B |
| 1-60 | B |
| 1-61 | A |
| 1-62 | B |
| 1-63 | A |
| 1-64 | A |
| 1-65 | A |
| 1-66 | B |
| 1-67 | B |
| 1-68 | A |
| 1-69 | A |
| 1-70 | A |
| 1-71 | A |
| 1-72 | B |
| 1-73 | A |
| 1-74 | B |
| 1-75 | A |
| 1-76 | B |
| 1-77 | A |
| 1-78 | B |
| 1-79 | A |
| 1-80 | A |
| 1-81 | A |
| 1-82 | A |
| 1-83 | A |
| 1-84 | A |
| 1-85 | A |
| 1-86 | A |
| 1-87 | A |
| 1-88 | A |
| 1-89 | A |
| 1-90 | A |
| 1-91 | A |
| 1-92 | A |
| 1-93 | A |
| 1-94 | A |
| 1-95 | A |
| 1-96 | A |
| 1-97 | A |
| 1-98 | A |
| 2-1 | A |
| 2-3 | A |
| 2-45 | A |
| 2-54 | A |
| 2-55 | A |
| 2-56 | A |
| 2-57 | A |
| 2-58 | A |
| 2-59 | A |
| 2-60 | A |
| 2-61 | A |
| 2-62 | A |
| 2-63 | A |
| 2-64 | A |
| 2-65 | A |
| 2-66 | A |
| 2-67 | A |
| 2-68 | A |
| 2-69 | A |
| 2-70 | A |
| 2-71 | A |
| 2-72 | A |
| 2-73 | A |
| 2-74 | A |
| 2-75 | A |
| 3-23 | A |
| 3-96 | A |
| 3-104 | A |
| 3-220 | A |
| 3-221 | A |
| 4-29 | A |
| 4-85 | A |
| 4-121 | A |
| 4-129 | A |
| 5-1 | A |
| 5-2 | A |
| 5-3 | A |
| 5-4 | A |
| 5-5 | A |
| 5-6 | A |
| 5-7 | B |

A is ≤0.5 µM; B is >0.5 µM but ≤3 µM; C >3 µM

Example 140

Human Whole Blood Autotaxin Assay

Inhibition of ATX activity in human whole blood is assayed by measuring the concentration of 20:4 LPA in plasma after a prolonged incubation at 37° C. Blood is drawn from consenting human volunteers into heparin vacutainer tubes and 200 µL aliquots are added to 2 µL test compound in DMSO or DMSO alone. Several of the vehicle tubes are centrifuged immediately at 800×g for 10 minutes at 4° C. and the plasma removed for processing to determine the baseline concentration of 20:4 LPA. The remaining blood samples containing vehicle or test compound are incubated at 37° C. for 4 hours before centrifuging at 800×g for 10 minutes at 4° C. to obtain plasma. Plasma is processed for LCMS as follows: 40 uL plasma is removed and 5 volumes of methanol containing 125 ng/mL 17:0 LPA as an internal standard are added and the mixture incubated at −20° C. for 10 min before centrifuging at 4000×g for 10 minutes at 4° C. 150 µL of the supernatant is transferred to a 96-well plate and diluted with 100 µL of an organic solution (90:10:0.1 of water/acetonitrile/ammonium hydroxide) for analysis of 20:4 LPA concentrations by LCMS. LPA 20:4 and the internal standard (LPA 17:0) were analyzed on a quadrupole mass spectrometer (ABI Sciex 4000QTrap) in the negative ion mode (ESI) by multiple reaction monitoring (MRM). The mobile phases contain 0.1% ammonium hydroxide in 90% water/10% acetonitrile (solvent A) and 0.1% ammonium hydroxide in 90% acetonitrile/10% water (solvent B). The flow rate was maintained at 0.8 mL/min and the total run time was 3 min. Analytes were separated using a linear gradient as follows: 1) mobile phase was held for 0.5 min at 10% B; 2) B was increased from 10% to 90% over the next 1 min; 3) B was held constant for 0.5 min at 90%; and 4) B was returned to the initial gradient conditions.

Example 141

Mouse Air Pouch Assay

LPA and ATX activity are induced by carrageenan injection into a mouse air pouch. A mouse air pouch assay was utilized to determine pharmacodynamic activity of autotaxin inhibitors in reducing carrageenan-induced ATX activity and LPA biosynthesis. An air pouch was formed in female balb/c mice by instilling 5 mL of 0.2 µm filtered air into the subcutaneous space in the scapular region on Day 1. On Day 3, 3 mL of air was instilled into the pouch and on Day 6, another 3 ml air was instilled into the pouch. On Day 7, test compounds were administered by oral gavage. At the appropriate time (0-24 hr) after compound administration, carrageenan dissolved in sterile saline was injected into the air pouch. Two hours following carrageenan challenge, mice were sacrificed and blood obtained via cardiac puncture. A 0.5-1 mL bolus of bolus of ice-cold phosphate buffered saline solution was instilled into the air pouch and after 20 seconds of gentle massaging, the pouch was opened and the fluid removed. An aliquot of the air pouch fluid was analyzed for LPA concentrations by LC-MS as described in the Human Whole Blood Autotaxin Assay (Example 86). A separate aliquot of the air pouch fluid was taken, centrifuged (800×g, 10 min) and assayed for choline content using a TOOS method or for drug concentrations by LCMS. Plasma prepared from blood was assayed for drug concentrations by LCMS. Drug concentrations to achieve 50% inhibition of ATX activity or carrageenan-induced pouch LPA could be calculated by nonlinear regression (Graphpad Prism) of % inhibition versus log drug concentration.

Example 142

MDA-MB-435 Melanoma Cell Migration Assay

Cells from the MDA-MB-435S human melanoma line are maintained in subconfluent culture in media containing FBS and penicillin/streptomycin. The day before the assay, cells are serum-starved overnight in media containing 0.1-0.2% fatty-acid-free BSA. On the day of the assay, the conditioned media is removed from the cells and set aside. The cells are then harvested by scraping, counted, and pelleted by centrifugation. The cells are resuspended at 1.05× the final desired density in the conditioned media. The assays are performed in duplicate using the Neuroprobe 96-well chemotaxis system with 8 µm pore size and fibronectin-coated filters. 152 µL cells are added to 8 µL test compound and incubated for 15 min at 37° C. The lower chamber is loaded with 2-10 M LPC and then 50 µL of the cell/test compound suspension is added to the top of each filter well site. The filters are incubated at 37° C. for 1-24 hours and non-migrated cells removed from the top of the filter by rinsing with PBS and scraping. The filter is air dried then stained before reading the absorbance at 580 nm.

Example 143

Spontaneous Metastasis Mouse Model

A syngeneic mouse model is used to test efficacy of compounds in inhibiting tumor metastases. 4T1 cells are in injected into the #7 mammary fat pad of female Balb/c mice while the mice are anesthetized. The primary tumors are measured by caliper twice weekly until they are resected under isofluorane anesthesia (between days 10-14). Test compound is administered orally daily at various times after the injection of the 4T1 cells. At 8-11 weeks after the 4T1 injection, lymph nodes, lungs, liver and any other organs suspected of harboring metastases are collected for histological analysis.

Example 144

Lung Metastases Model

An experimental lung metastasis model is used to test efficacy of compounds in reducing the number of metastases of injected B16-F 10 mouse melanoma cells to the lung. Briefly, female C57BL/6J mice, female (BALB/cByJ× C57BL/6J)Fi, mice (CByB6Fi/J), athymic nude female and male CByB6Fi/J mice (nu/nu), and control littermates (nu/nu) are used at ages 7-18 weeks, when they weighed between 18 and 28 g. A single-cell suspension of B16F10 cells, harvested in log phase (approx. 5-10×10$^4$ cells) in 0.2 mL of Hanks' balanced salt solution are injected intravenously into the lateral tail vein of the mice. Test compound or vehicle is delivered daily. After 21 days, the mice are sacrificed, and the lungs are removed. Lungs are fixed in 10% buffered formalin overnight and weighed, and tumor colonies at the surface are scored with the aid of a dissecting microscope.

Example 145

Mouse Carbon Tetrachloride ($CCl_4$)-Induced Liver Fibrosis Model

Female balb/c mice receive $CCl_4$ (1.0 ml/kg body weight) diluted in olive oil via intraperitoneal injection twice a week for 8 weeks. (Higazi, A. A. et al, Clin Exp Immunol. 2008 April; 152(1):163-73). Control mice receive an equivalent volume of olive oil only. Test compound or vehicle is delivered orally daily. At the end of the study (8 weeks after first i.p. injection of $CCl_4$), mice are sacrificed using inhaled isoflurane and blood is drawn via cardiac puncture for subsequent analysis of ALT/AST levels. The liver is harvested and frozen at −80° C. for the biochemical analysis of liver fibrosis or fixed in 10% neutral buffered formalin for histological assessment of liver fibrosis. For the biochemical assessment of liver fibrosis, liver tissue homogenates are analyzed for collagen concentration using a hydroxyproline assay. For the histological assessment of liver fibrosis, fixed liver tissue is Masson's trichrome stained and liver fibrosis is determined by quantitative, computer-assisted densitometry using light microscopy.

Example 146

Rat Diethylnitrosamine (DEN)-Induced Liver Fibrosis and Hepatocellular Carcinoma Male Wistar rats receive weekly intraperitoneal injections of 35-100 mg/kg diethylnitrosamine (DEN) for 5-18 weeks in a total volume of 1.5 ml phosphate-buffered saline (PBS) to induce cirrhosis and hepatocellular carcinoma (HCC). Control rats receive weekly injections of an equivalent volume of PBS. Test compound or vehicle is delivered orally daily. At the end of the study, rats are sacrificed using inhaled isoflurane and blood is drawn via cardiac puncture for subsequent analysis of ALT/AST levels and drug concentrations. The liver is harvested and frozen at −80° C. for biochemical analysis of fibrosis or fixed in 10% neutral buffered formalin for histological assessment of liver fibrosis. For biochemical assessment of fibrosis, liver tissue homogenates are analyzed for collagen concentration using a hydroxyproline assay. For histological assessment of liver fibrosis and HCC, fixed liver tissue is hematoxylin and eosin stained and Masson's trichrome stained and liver fibrosis and HCC is determined by quantitative, computer-assisted densitometry using light microscopy.

Example 147

Clinical Trial for Pulmonary Fibrosis

A non-limiting example of a pulmonary fibrosis clinical trial in humans is described below.
Purpose:
The purposes of this study are to assess the efficacy of a compound described herein, or a pharmaceutically acceptable salt thereof, as single agent or in combination, in the treatment of patients with pulmonary fibrosis, collect information on any side effects the compound may cause as single agent or in combination, and evaluate the pharmacokinetic properties of the compound as single agent or in combination.
Intervention:
Patients are administered 1-100 mg/kg of a compound described herein, or a pharmaceutically acceptable salt thereof, per day as single agent or in combination.
Detailed Description:
Patients will be given a compound described herein, or a pharmaceutically acceptable salt thereof, orally once or twice a day as single agent or in combination. Prior to each dosing cycle, a physical exam, blood work and assessment of any side effects will be performed.
Primary Outcome Measures:
Progression-free survival, defined as free of death or a decrease from baseline in the FVC of at least 10%.

Secondary Outcome Measures:
Number of Acute Exacerbations of IPF; health related quality of life; $PO_2$ at rest and at exercise from baseline; $P(A-a)O_2$ at rest and at exercise from baseline; Predicted FEV1 from baseline; forced expiratory volume in one second (FEV1) to FVC from baseline; plethysmographic lung volumes from baseline; diffusion capacity for carbon monoxide (DLco) from baseline; Six-Minute Walk test, from baseline: resting and 6 minute $SpO^2$, presence or absence of desaturation to 88% or lower at the end of the six minute walk, walked distance; Pre and post modified Borg dyspnea scores; scoring of extent of lung fibrosis on HRCT, according to two independent chest radiologists, form baseline; number and severity of adverse effects.
Eligibility:
Male and female subjects that are 40 years to 80 years.
Inclusion Criteria:
Clinical symptoms of IPF for at least 3 months; forced vital capacity (FVC) between 50 to 90% of the predicted value; DLco at least 35% of the predicted value; PaO2>55 mm Hg while breathing ambient air at rest; High-resolution computed tomography (HRCT) showing definite or probable criteria of IPF.
Exclusion Criteria:
Clinically significant exposure to known fibrogenic agents (birds, molds, asbestos, radiation and drugs known to cause pulmonary fibrosis (amiodarone, nitrofurantoin, bleomicin, etc)); history of neurofibromatosis, Hermansky-Pudlak syndrome, metabolic storage disorders, etc.; history of fever, weight loss, myalgias, arthralgias, skin rash, arthritis; active infection within one week before enrollment; alternative cause of interstitial lung disease; ratio of the forced expiratory volume in one second (VEF1) to FVC of less than 0.6 after the use of a bronchodilator; residual volume more than 120% of the predicted value (when available); more than 20% of lymphocytes or eosinophils in bronchoalveolar lavage (BAL) (when available); granulomas, infection or malignancy in the transbronchial or surgical biopsy (when available); previous therapy with azathioprine, prednisolone (>0.5 mg/kg/day or more for at least 3 months), cyclophosphamide or novel biotech drugs; unstable cardiovascular or neurologic disease; uncontrolled diabetes; pregnancy; lactation; likelihood of death, as predicted by the investigator, within the next year; white cell blood count <4000/mm3; platelet count <100000/mm3; Hematocrit <30% or >59%; liver enzymes more than 3 times the upper limit of the normal range; creatinine level >1.5 mg/dL; albumin level <3 g/dL; refusal to sign informed consent by patient or guardian.

Example 148

Clinical Trial for Liver Fibrosis

A non-limiting example of a liver fibrosis clinical trial in humans is described below.
Purpose:
The purposes of this study are to assess the efficacy of a compound described herein, or a pharmaceutically acceptable salt thereof, as single agent or in combination, in the treatment of patients with liver fibrosis, collect information on any side effects the compound may cause as single agent or in combination, and evaluate the pharmacokinetic properties of the compound as single agent or in combination.

Intervention:

Patients are administered 1-100 mg/kg of a compound described herein, or a pharmaceutically acceptable salt thereof, per day as single agent or in combination.

Detailed Description:

Patients will be given a compound described herein, or a pharmaceutically acceptable salt thereof, orally once or twice a day as single agent or in combination. Prior to each dosing cycle, a physical exam, blood work and assessment of any side effects will be performed.

Primary Outcome Measures:

Liver enzymes (ALT, AST, ALP), liver biopsy

Secondary Outcome Measures:

Pharmacodynamic markers may include: Tissue PD markers through mRNA expression, ATX, LOXL2, LOX, Other LOXL proteins, αSMA, Collagen 1A1, NF-κB1, Caspase 1, SMAD, and NOD; Serum and plasma PD markers include: AST-to-platelet ratio index (APRI), ATX activity, LOXL2, Osteopontin, Hyaluronic Acid, CXCL 9, 10 and 11, MMP1, MMP3, MMP9, TIMP1, CD40L, TGF-β1, ET-1, VEGF, GAL3, IL-6/IL-8/TNFα/IFNγ, α2-macroglobulin, Apolipoprotein A1, PINP, PIIINP, PVCP-1230, PDGF; Assessing the effects of chronic dosing on liver structure and fibrotic markers; incidence of adverse events resulting from the administration of multiple doses of compound.

Eligibility:

Male and female subjects that are 18 to 60 years old.

Inclusion Criteria:

Stage 1-3 fibrosis by Metavir score on a liver biopsy; Body mass index <36 kg/m2.

Exclusion Criteria:

Any evidence of hepatic decompensation past or present; subjects currently abusing amphetamines, cocaine, opiates, or alcohol; clinically significant cardiac disease; history of cancer, other than non-melanomatous skin cancer, within 5 years prior to screening; systemic fungal, bacterial, viral, or other infection that is not controlled; use of systemic immunosuppressants within 28 days of the Pre-treatment Phase; use of approved therapy for hepatitis C or hepatitis B virus within 28 days of the Pre-treatment Phase; pregnant or lactating; history of bleeding diathesis within the last 6 months of study Day 1.

Example 149

Clinical Trial for Cholestatic Pruritus

A non-limiting example of a cholestatic pruritus clinical trial in humans is described below.

Purpose:

The purposes of this study are to assess the efficacy of a compound described herein, or a pharmaceutically acceptable salt thereof in the treatment of patients with cholestatic pruritus, collect information on any side effects the compound may cause and evaluate the pharmacokinetic properties of the compound as single agent or in combination.

Intervention:

Patients are administered 1-100 mg/kg of a compound described herein, or a pharmaceutically acceptable salt thereof, per day.

Detailed Description:

Patients will be given a compound described herein, or a pharmaceutically acceptable salt thereof, orally once or twice a day. Prior to each dosing cycle, a physical exam, blood work and assessment of any side effects will be performed.

Eligibility:

Male and female subjects that are 21 to 80 years old.

Inclusion Criteria:

Patients with pruritus as a result of a cholestatic disorder.

Exclusion Criteria:

Use of cholestyramine; pregnancy; malignancy/life expectancy <6 months.

Primary Outcome Measures:

Normalization of liver enzymes (ALT, AST, ALP), Reduction of pruritus according to visual analogue scores.

Secondary Outcome Measures:

Improvement in quality of life scores; reduction in pruritus score/scratch lesions.

Example 150

Clinical Trial for Pancreatic Cancer

A non-limiting example of a pancreatic cancer clinical trial in humans is described below.

Purpose:

The purposes of this study are to assess the efficacy of a compound described herein, or a pharmaceutically acceptable salt thereof, as single agent or in combination, in the treatment of patients with pancreatic cancer, collect information on any side effects the compound may cause as single agent or in combination, and evaluate the pharmacokinetic properties of the compound as single agent or in combination.

Intervention:

Patients are administered 1-100 mg/kg of a compound described herein, or a pharmaceutically acceptable salt thereof, per day as single agent or in combination.

Detailed Description:

Patients will be given a compound described herein, or a pharmaceutically acceptable salt thereof, orally once or twice a day as single agent or in combination. Prior to each dosing cycle, a physical exam, blood work and assessment of any side effects will be performed.

Eligibility:

Male and female subjects that are 21 to 80 years old with advanced pancreatic cancer.

Inclusion Criteria:

Radiographic or clinical evidence of measurable advanced pancreatic carcinoma (Stage II, II, IV). Subjects must have measurable disease at least 2 cm in diameter. ECOG performance status of 0 or 1

Exclusion Criteria:

Prior history of malignancy (except basal cell or squamous cell carcinoma or carcinoma in situ of the breast) unless the subject has been free of disease for > or = to 1 year. Moderate or severe cardiac disease; Active infection; Not pregnant or nursing; Negative pregnancy test; Fertile patients must use effective contraception during and for ≥3 months after completion of study treatment; Able to swallow oral medication; No other malignancy within the past 5 years except for in situ cancers or basal cell or squamous cell carcinoma of the skin; No hypersensitivity or intolerance to statins; no other non-malignant systemic disease that would preclude rosuvastatin administration or prolonged follow-up.

Primary Outcome Measures:

Progression free survival, overall survival, worsening of pain, onset of pain

Secondary Outcome Measures:

tumor size/response (RECIST)

Example 151

Clinical Trial for Hepatocellular Carcinoma (HCC)

A non-limiting example of a hepatocellular carcinoma clinical trial in humans is described below.

Purpose:

The purposes of this study are to assess the efficacy of a compound described herein, or a pharmaceutically acceptable salt thereof, as single agent or in combination, in the treatment of patients with hepatocellular carcinoma, collect information on any side effects the compound may cause as single agent or in combination, and evaluate the pharmacokinetic properties of the compound as single agent or in combination.

Intervention:

Patients are administered 1-100 mg/kg of a compound described herein, or a pharmaceutically acceptable salt thereof, per day as single agent or in combination.

Detailed Description:

Patients will be given a compound described herein, or a pharmaceutically acceptable salt thereof, orally once or twice a day as single agent or in combination. Prior to each dosing cycle, a physical exam, blood work and assessment of any side effects will be performed.

Eligibility:

Male and female subjects that are 21 to 80 years old.

Inclusion Criteria:

Patients with histopathologically or clinically confirmed diagnosis of hepatocellular carcinoma; unresponsive to standard therapy or for whom standard therapy is intolerable, or for whom there is no appropriate therapy; ECOG performance status score of 0-2.

Exclusion Criteria:

Patients with a primary malignant tumor; history of liver transplant; brain metastases; psychiatric disorder that might cause difficulty in obtaining informed consent or in conducting the trial; Not pregnant or nursing; Fertile patients must use effective contraception during and for ≥3 months after completion of study treatment; No other malignancy within the past 5 years except for in situ cancers or basal cell or squamous cell carcinoma of the skin; No hypersensitivity or intolerance to statins; no other non-malignant systemic disease that would preclude rosuvastatin administration or prolonged follow-up.

Primary Outcome Measures:

time to progression, progression free survival, overall response (RECIST)

Secondary Outcome Measures:

liver function tests, tumor biomarkers

Example 152

Clinical Trial for Fatty Liver Disease/Steatosis (NAFLD, NASH)

A non-limiting example of a fatty liver disease/steatosis clinical trial in humans is described below.

Purpose:

The purposes of this study are to assess the efficacy of a compound described herein, or a pharmaceutically acceptable salt thereof, as single agent or in combination, in the treatment of patients with hepatocellular carcinoma, collect information on any side effects the compound may cause as single agent or in combination, and evaluate the pharmacokinetic properties of the compound as single agent or in combination.

Intervention:

Patients are administered 1-100 mg/kg of a compound described herein, or a pharmaceutically acceptable salt thereof, per day as single agent or in combination.

Detailed Description:

Patients will be given a compound described herein, or a pharmaceutically acceptable salt thereof, orally once or twice a day as single agent or in combination. Prior to each dosing cycle, a physical exam, blood work and assessment of any side effects will be performed.

Eligibility:

Male and female subjects that are 21 to 80 years old.

Inclusion Criteria:

Patients with clinically confirmed diagnosis of non-alcohol fatty liver disease or non-alcohol steatohepatitis; histologic evidence of definite or probable nonalcoholic steatohepatitis (NASH) based upon a liver biopsy obtained no more than 90 days prior to randomization and a nonalcoholic fatty liver disease activity score (NAS) of 4 or greater.

Exclusion Criteria:

Current or history of significant alcohol consumption, use of drugs historically associated with nonalcoholic fatty liver disease (NAFLD) (amiodarone, methotrexate, systemic glucocorticoids, tetracyclines, tamoxifen, estrogens at doses greater than those used for hormone replacement, anabolic steroids, valproic acid, and other known hepatotoxins) for more than 2 weeks in the year prior to randomization, prior or planned (during the study period) bariatric surgery (eg, gastroplasty, roux-en-Y gastric bypass), uncontrolled diabetes defined as Hemoglobin A1e 9.5% or higher within 60 days prior to enrollment, presence of cirrhosis on liver biopsy, platelet count below 100,000/mm3; Clinical evidence of hepatic decompensation as defined by the presence of any of the following abnormalities: serum albumin less than 3.2 grams/deciliter (g/dL), INR (international normalized ratio) greater than 1.3, direct bilirubin greater than 1.3 milligrams per deciliter (mg/dL), history of esophageal varices, ascites or hepatic encephalopathy; Evidence of other forms of chronic liver disease: hepatitis B as defined by presence of hepatitis B surface antigen (HBsAg), hepatitis C as defined by presence of hepatitis C virus (HCV) ribonucleic acid (RNA) or positive hepatitis C antibody (anti-HCV), evidence of ongoing autoimmune liver disease as defined by compatible liver histology, primary biliary cirrhosis, primary sclerosing cholangitis, Wilson's disease, Alpha-1-antitrypsin(A1 AT) deficiency, history of hemochromatosis or iron overload, drug-induced liver disease as defined on the basis of typical exposure and history, known bile duct obstruction, suspected or proven liver cancer, any other type of liver disease other than nonalcoholic stcatohcpatitis (NASH); serum alanine aminotransfcrase (ALT) greater than 300 units per liter (U/L); serum creatinine of 2.0 mg/dL or greater; use of ursodeoxycholic acid (Ursodiol, Urso) within 90 days prior to enrollment; inability to safely obtain a liver biopsy, history of biliary diversion, known positivity for Human Immunodeficiency Virus (HIV) infection; pregnancy, planned pregnancy, potential for pregnancy and unwillingness to use effective birth control during the trial, breast feeding Primary Outcome Measures:

liver function tests, liver biopsy, NAS score

Secondary Outcome Measures:

fibrotic biomarkers, liver imaging (ultrasound, MRI), insulin resistance as measure by HOMA-IR, lipid panel.

The examples and embodiments described herein are for illustrative purposes only and various modifications or changes suggested to persons skilled in the art are to be included within the spirit and purview of this application and scope of the appended claims.

What is claimed is:

1. A compound of Formula (I), or a pharmaceutically acceptable salt, or solvate thereof:

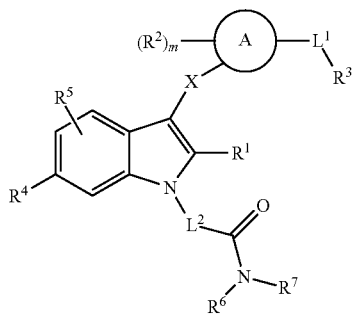

Formula (I)

wherein, $R^1$ is H, D, halogen, —CN, —C(=O)H, —NH$_2$, $C_1$-$C_4$alkyl, $C_3$-$C_6$cycloalkyl, $C_1$-$C_4$fluoroalkyl, —O $C_1$-$C_4$alkyl or $C_1$-$C_4$deuteroalkyl;

X is —O—, —S—, —S(=O)—, or —S(=O)$_2$—;

Ring A is a monocyclic aryl, bicyclic aryl, monocyclic heterocycloalkyl, monocyclic heteroaryl or bicyclic heteroaryl;

each $R^2$ is independently selected from H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, or substituted or unsubstituted monocyclic heteroaryl;

m is 0, 1, or 2;

$L^1$ is absent, $C_1$-$C_6$alkylene, $C_1$-$C_6$fluoroalkylene, or $C_3$-$C_6$cycloalkylene;

$R^3$ is —CO$_2$H, —CO$_2$($C_1$-$C_6$alkyl), —OH, —B(OH)$_2$, —C(=O)NHSO$_2$R$^9$, —C(=O)N(R$^{10}$)$_2$, —C(=O)NH—OH, —C(=O)NH—CN, —SO$_2$NHC(=O)R$^9$, —OP(=O)(OH)$_2$, —P(=O)(OH)$_2$, tetrazolyl, or carboxylic acid bioisostere;

$R^4$ is H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, $C_1$-$C_4$alkyl, $C_1$-$C_4$fluoroalkyl, $C_1$-$C_4$deuteroalkyl, $C_1$-$C_4$hydroxyalkyl, $C_1$-$C_4$heteroalkyl, $C_3$-$C_6$cycloalkyl, substituted or unsubstituted phenyl, substituted or unsubstituted monocyclic heteroaryl;

$R^5$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, or $C_1$-$C_4$fluoroalkoxy;

$L^2$ is absent or $C_1$-$C_6$ alkylene;

$R^6$ is H, $C_1$-$C_6$alkyl, $C_1$-$C_6$fluoroalkyl, $C_1$-$C_6$deuteroalkyl, or $C_3$-$C_8$cycloalkyl;

$R^7$ is $C_1$-$C_6$alkyl, $C_1$-$C_6$fluoroalkyl, $C_1$-$C_6$deuteroalkyl, substituted or unsubstituted cycloalkyl, substituted or unsubstituted heterocycloalkyl, substituted or unsubstituted aryl, substituted or unsubstituted heteroaryl, —C(=O)R$^9$, or —S(=O)$_2$R$^9$, wherein if $R^7$ is substituted, then $R^7$ is substituted with 1 to 4 $R^8$ groups;

or $R^6$ and $R^7$ are taken together with the nitrogen atom to which they are attached to form an unsubstituted N-containing heterocycle or a substituted N-containing heterocycle that is substituted with 1-4 $R^8$ and 0 or 1 $R^{12}$ groups;

each $R^8$ and $R^{12}$ substituent is independently selected from the group consisting of H, halogen, OH, —CN, —NO$_2$, $C_1$-$C_6$alkyl, $C_1$-$C_6$fluoroalkyl, $C_1$-$C_6$deuteroalkyl, $C_1$-$C_6$heteroalkyl, $C_3$-$C_8$cycloalkyl, $C_1$-$C_6$alkoxy, $C_2$-$C_{10}$heterocycloalkyl, —C(=O)R$^9$, —S(=O)$_2$R$^9$, S(=O)R$^9$, SR$^9$, —S(=O)$_2$N(R$^{10}$)$_2$, —NR$^{10}$S(=O)$_2$R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, substituted or unsubstituted aryl, $C_1$-$C_6$alkylene-substituted or unsubstituted aryl, —Y—$C_1$-$C_6$alkylene-substituted or unsubstituted aryl, substituted or unsubstituted heteroaryl, $C_1$-$C_6$alkylene-substituted or unsubstituted heteroaryl, and —Y—$C_1$-$C_6$alkylene-substituted or unsubstituted heteroaryl; Y is O or S;

or two $R^8$ substituents on the same carbon atom are taken together to form =O, or two $R^8$ substituents on the same or different carbon atoms are taken together to form to form a substituted or unsubstituted ring containing 0, 1, 2, or 3 heteroatoms in the ring selected from —NR$^{11}$—, —S(=O)$_n$—, and —O—; n is 0, 1, or 2;

$R^9$ is $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, $C_1$-$C_4$alkylene-substituted or unsubstituted phenyl, a substituted or unsubstituted monocyclic heteroaryl, $C_1$-$C_4$alkylene-substituted or unsubstituted monocyclic heteroaryl, a substituted or unsubstituted bicyclic heteroaryl, or a $C_1$-$C_4$alkylene-substituted or unsubstituted bicyclic heteroaryl;

each $R^{10}$ is independently selected from H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, $C_1$-$C_4$alkylene-substituted or unsubstituted phenyl, a substituted or unsubstituted monocyclic heteroaryl, $C_1$-$C_4$alkylene-substituted or unsubstituted monocyclic heteroaryl, a substituted or unsubstituted bicyclic heteroaryl, or a $C_1$-$C_4$alkylene-substituted or unsubstituted bicyclic heteroaryl; or two $R^{10}$ groups attached to the same N atom are taken together with the N atom to which they are attached to form a substituted or unsubstituted heterocycle; and $R^{11}$ is H, $C_1$-$C_6$alkyl, $C_1$-$C_6$fluoroalkyl, $C_1$-$C_6$deuteroalkyl, $C_3$-$C_8$cycloalkyl, —C(=O)R$^9$, —S(=O)$_2$R$^9$, —CO$_2$R$^9$, —C(=O)N(R$^{10}$)$_2$, substituted or unsubstituted aryl, $C_1$-$C_4$alkylene-substituted or unsubstituted aryl, substituted or unsubstituted heteroaryl, or $C_1$-$C_4$alkylene-substituted or unsubstituted heteroaryl.

2. The compound of claim 1, or a pharmaceutically acceptable salt, or solvate thereof, wherein:

R[6] and R[7] are taken together with the nitrogen atom to which they are attached to form a ring B as shown in Formula (II):

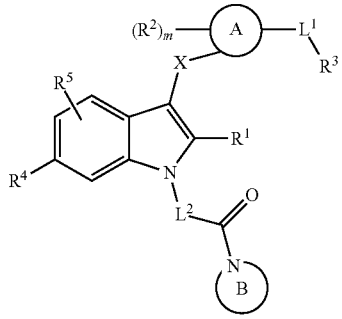

Formula (II)

wherein,
Ring B is an N-containing monocyclic or bicyclic heterocycle that is unsubstituted or substituted with 1-4 R[8] and 0 or 1 R[12] groups;
each R[8] and R[12] substituent is independently selected from the group consisting of H, halogen, OH, —CN, —NO$_2$, C$_1$-C$_6$alkyl, C$_1$-C$_6$fluoroalkyl, C$_1$-C$_6$deuteroalkyl, C$_1$-C$_6$heteroalkyl, C$_3$-C$_8$cycloalkyl, C$_1$-C$_6$alkoxy, C$_2$-C$_{10}$heterocycloalkyl, —C(=O)R[9], —S(=O)$_2$R[9], S(=O)R[9], SR[9], —S(=O)$_2$N(R[10])$_2$, —NR[10] S(=O)$_2$R[9], —OC(=O)R[9], —CO$_2$R[10], —OCO$_2$R[9], —N(R[10])$_2$, —C(=O)N(R[10])$_2$, —OC(=O)N(R[10])$_2$, —NHC(=O)R[9], —NHC(=O)OR[9], substituted or unsubstituted aryl, C$_1$-C$_6$alkylene-substituted or unsubstituted aryl, —Y—C$_1$-C$_6$alkylene-substituted or unsubstituted aryl, substituted or unsubstituted heteroaryl, C$_1$-C$_6$alkylene-substituted or unsubstituted heteroaryl, or —Y—C$_1$-C$_6$alkylene-substituted or unsubstituted heteroaryl; Y is O or S;
or two R[8] substituents on the same carbon atom are taken together to form =O, or two R[8] substituents on the same or different carbon atoms are taken together to form a substituted or unsubstituted ring containing 0, 1, 2, or 3 heteroatoms in the ring selected from —NR[11]—, —S(=O)$_n$—, and —O—; n is 0, 1, or 2.

3. The compound of claim 2, or a pharmaceutically acceptable salt, or solvate thereof, wherein:

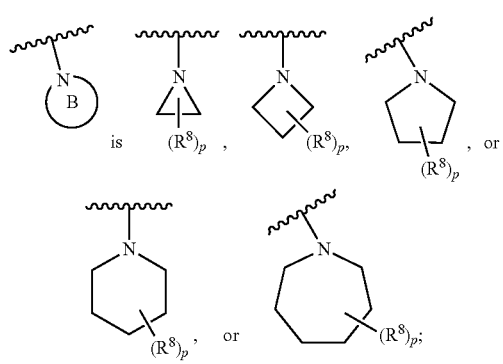

p is 1, 2, 3, or 4.

4. The compound of claim 2, or a pharmaceutically acceptable salt, or solvate thereof, wherein the compound has the structure of Formula (III):

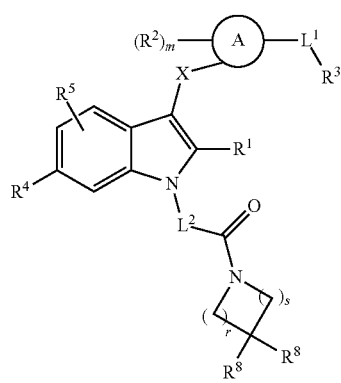

Formula (III)

wherein,
Ring A is phenyl, pyridinyl, pyrimidinyl, pyrazinyl, pyridazinyl, or triazinyl;
X is —S—;
r is 1, 2, 3, or 4;
s is 0, 1, or 2.

5. The compound of claim 4, wherein the compound has the following structure of Formula (IV):

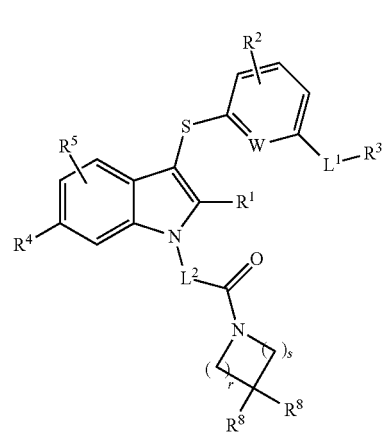

Formula (IV)

wherein,
W is CH, CF or N;
or a pharmaceutically acceptable salt, or solvate thereof.

6. The compound of claim 5, wherein the compound has the following structure of Formula (V):

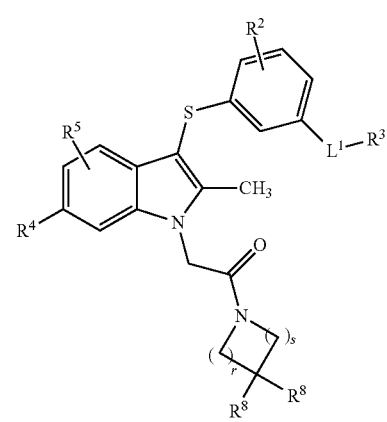

Formula (V)

or a pharmaceutically acceptable salt, or solvate thereof.

7. The compound of claim 5, or a pharmaceutically acceptable salt, or solvate thereof, wherein:

each R⁸ substituent is independently H, halogen, OH, —CN, C₁-C₆alkyl, C₁-C₆fluoroalkyl, C₁-C₆heteroalkyl, C₃-C₈cycloalkyl, or C₁-C₆alkoxy;

or the two R⁸ substituents are joined together to form a substituted or unsubstituted C₃-C₈cycloalkyl or substituted or unsubstituted C₂-C₈ heterocycloalkyl containing 1, 2, or 3 heteroatoms selected from —NR¹¹— or —O—.

8. The compound of claim 2, or a pharmaceutically acceptable salt, or solvate thereof, wherein:

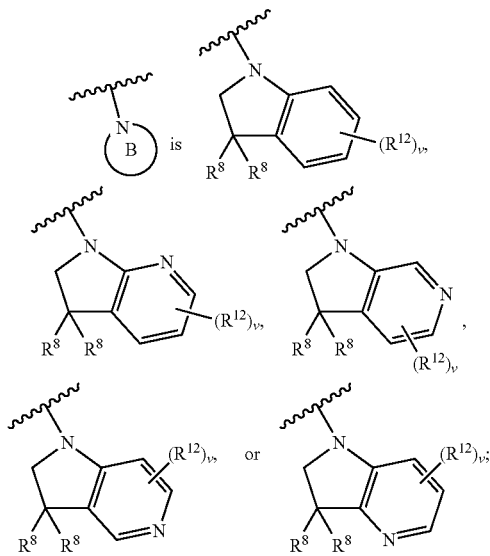

and v is 0 or 1.

9. The compound of claim 2, or a pharmaceutically acceptable salt, or solvate thereof, wherein the compound has the following structure of Formula (VI):

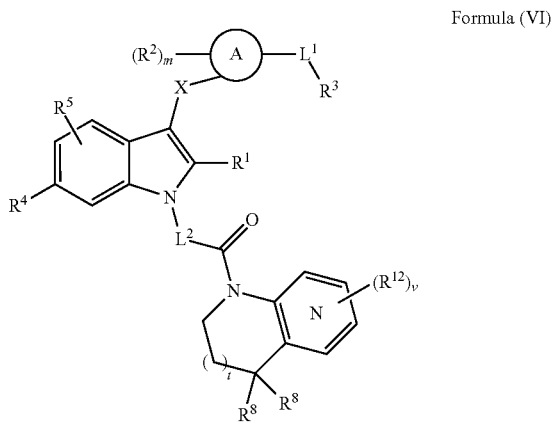

Formula (VI)

wherein, ring N is phenyl or a 6-membered heteroaryl containing 1 or 2 nitrogen atoms;

each R⁸ substituent is independently H, halogen, OH, —CN, —NO₂, C₁-C₆alkyl, C₁-C₆fluoroalkyl, C₁-C₆deuteroalkyl, C₁-C₆heteroalkyl, C₃-C₈cycloalkyl, C₁-C₆alkoxy, C₂-C₁₀heterocycloalkyl, —C(=O)R⁹, —S(=O)₂R⁹, —S(=O)R⁹, —SR⁹, —S(=O)₂N(R¹⁰)₂, —NR¹⁰S(=O)₂R⁹, —OC(=O)R⁹, —CO₂R¹⁰, —OCO₂R⁹, —N(R¹⁰)₂, —C(=O)N(R¹⁰)₂, —OC(=O)N(R¹⁰)₂, —NHC(=O)R⁹, —NHC(=O)OR⁹, substituted or unsubstituted aryl, C₁-C₆alkylene-substituted or unsubstituted aryl, —Y—C₁-C₆alkylene-substituted or unsubstituted aryl, substituted or unsubstituted heteroaryl, C₁-C₆alkylene-substituted or unsubstituted heteroaryl, or —Y—C₁-C₆alkylene-substituted or unsubstituted heteroaryl;

Y is O or S;

or two R⁸ substituents are taken together to form a substituted or unsubstituted ring containing 0, 1, 2, or 3 heteroatoms in the ring selected from —NR¹¹—, —S(=O)ₙ—, and —O—;

n is 0, 1, or 2;

t is 0 or 1;

each R¹² is independently selected from H, halogen, —CN, —NO₂, —OH, C₁-C₆alkoxy, —SR⁹, —S(=O)R⁹, —S(=O)₂R⁹, —S(=O)₂N(R¹⁰)₂, —NR¹⁰S(=O)₂R⁹, —C(=O)R⁹, —OC(=O)R⁹, —CO₂R¹⁰, —OCO₂R⁹, —N(R¹⁰)₂, —C(=O)N(R¹⁰)₂, —OC(=O)N(R¹⁰)₂, —NHC(=O)R⁹, —NHC(=O)OR⁹, C₁-C₆alkyl, C₁-C₆fluoroalkyl, C₁-C₆deuteroalkyl, C₁-C₆heteroalkyl, C₃-C₈cycloalkyl, C₂-C₁₀heterocycloalkyl, substituted or unsubstituted phenyl, or substituted or unsubstituted monocyclic heteroaryl; and v is 0 or 1.

10. The compound of claim 9, or a pharmaceutically acceptable salt, or solvate thereof, wherein:

Ring A is phenyl, pyridinyl, pyrimidinyl, pyrazinyl, pyridazinyl, or triazinyl;

X is —S—.

11. The compound of claim 10, wherein the compound has the following structure of Formula (VII):

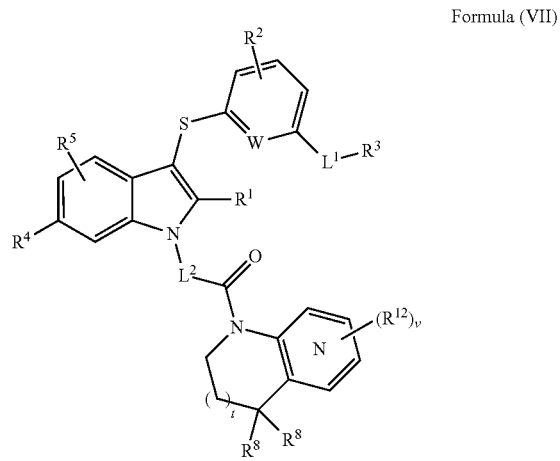

Formula (VII)

wherein,

W is CH, CF or N;

R¹ is H, halogen, —CN, —C(=O)H, C₁-C₄alkyl, C₃-C₆cycloalkyl, or C₁-C₄fluoroalkyl;

L² is absent, C₁-C₄ alkylene;

or a pharmaceutically acceptable salt, or solvate thereof.

12. The compound of claim 11, or a pharmaceutically acceptable salt, or solvate thereof, wherein:
$R^1$ Cl, —$CH_3$, —$CH_2CH_3$, cyclopropyl, or —$CF_3$;
$L^2$ is absent, —$CH_2$—, —$CH(CH_3)$—, —$C(CH_3)_2$—, or —$(CH_2)_2$—.

13. The compound of claim 12, wherein the compound has the following structure of Formula (VIII):

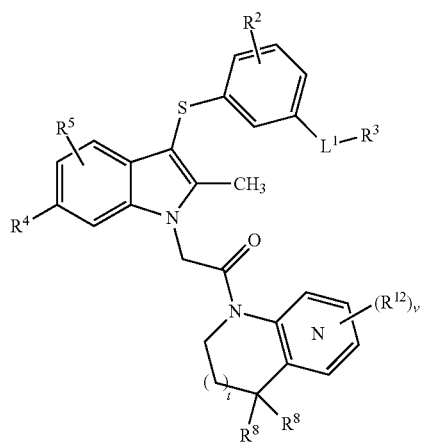

Formula (VIII)

or a pharmaceutically acceptable salt, or solvate thereof.

14. The compound of claim 12, or a pharmaceutically acceptable salt, or solvate thereof, wherein:
each $R^8$ substituent is independently H, halogen, OH, —CN, $C_1$-$C_6$alkyl, $C_1$-$C_6$fluoroalkyl, $C_1$-$C_6$heteroalkyl, $C_3$-$C_8$cycloalkyl, or $C_1$-$C_6$alkoxy;
or the two $R^8$ substituents are joined together to form a substituted or unsubstituted $C_3$-$C_8$cycloalkyl.

15. The compound of claim 13, or a pharmaceutically acceptable salt, or solvate thereof, wherein:
$R^2$ is H, F, Cl, —CN, —OH, —$CH_3$, —$OCH_3$, —$CF_3$, or —$OCF_3$;
$L^1$ is absent, $C_1$-$C_6$alkylene, or $C_3$-$C_6$cycloalkylene;
$R^3$ is —$CO_2H$, —$CO_2(C_1$-$C_6$alkyl), —$B(OH)_2$, or $C(=O)NHSO_2R^9$;
$R^4$ is F, Cl, Br, I, —CN, —OH, —$CH_3$, —$CH_2CH_3$, —$CH(CH_3)_2$, —$OCH_3$, —$OCH_2CH_3$, —$CF_3$, —$OCF_3$, —S—$CH_3$, or —$S(O)_2$—$CH_3$; and
$R^5$ is H, F, Cl, —CN, —OH, —$CH_3$, —$OCH_3$, —$CF_3$, or —$OCF_3$.

16. The compound of claim 7, or a pharmaceutically acceptable salt, or solvate thereof, wherein:
$R^2$ is H, F, Cl, —CN, —OH, —$CH_3$, —$OCH_3$, —$CF_3$, or —$OCF_3$;
$L^1$ is absent, —$CH_2$—, —$CH(CH_3)$—, or —$CH_2CH_2$—;
$R^3$ is —$CO_2H$ or —$CO_2(C_1$-$C_6$alkyl);
$R^4$ is F, Cl, Br, —CN, —$OCH_3$, or —$CF_3$; and
$R^5$ is H, F, Cl, —CN, —$CH_3$, —$OCH_3$, —$CF_3$, or —$OCF_3$.

17. The compound of claim 14, or a pharmaceutically acceptable salt, or solvate thereof, wherein:
$R^2$ is H, F, Cl, —$CH_3$, —$OCH_3$, —$CF_3$, or —$OCF_3$;
$L^1$ is absent;
$R^3$ is —$CO_2H$;
$R^4$ is F or Cl; and
$R^5$ is H, F, or Cl.

18. A compound that is:
3-((6-Chloro-1-(2-((3,5-dichlorophenyl)amino)-2-oxoethyl)-7-fluoro-2-methyl-1H-indol-3-yl)thio)benzoic acid;

3-((6-Chloro-7-fluoro-2-methyl-1-(2-oxo-2-(phenylamino)ethyl)-1H-indol-3-yl)thio)benzoic acid;
3-((6-Chloro-7-fluoro-2-methyl-1-(2-((1-methyl-1H-pyrazol-4-yl)amino)-2-oxoethyl)-1H-indol-3-yl)thio) benzoic acid;
3-((6-Chloro-7-fluoro-1-(2-(isoxazol-4-ylamino)-2-oxoethyl)-2-methyl-1H-indol-3-yl)thio)benzoic acid;
3-((6-Chloro-7-fluoro-2-methyl-1-(2-oxo-2-((2,2,2-trifluoroethyl)amino)ethyl)-1H-indol-3-yl)thio)benzoic acid;
3-((6-Chloro-7-fluoro-2-methyl-1-(2-oxo-2-(pyrrolidin-1-yl)ethyl)-1H-indol-3-yl)thio)benzoic acid;
3-((6-Chloro-7-fluoro-2-methyl-1-(2-(methyl(phenyl)amino)-2-oxoethyl)-1H-indol-3-yl)thio)benzoic acid;
3-((6-Chloro-1-(2-(cyclohexylamino)-2-oxoethyl)-7-fluoro-2-methyl-1H-indol-3-yl)thio)benzoic acid;
3-((6-Chloro-7-fluoro-1-(2-(isopropylamino)-2-oxoethyl)-2-methyl-1H-indol-3-yl)thio)benzoic acid;
3-((6-Chloro-1-(2-(dimethylamino)-2-oxoethyl)-7-fluoro-2-methyl-1H-indol-3-yl)thio)benzoic acid;
3-((1-(Benzylcarbamoyl)-6-chloro-2-methyl-1H-indol-3-yl)thio)benzoic acid;
3-((6-Chloro-7-fluoro-2-methyl-1-(2-oxo-2-(piperidin-1-yl)ethyl)-1H-indol-3-yl)thio)benzoic acid;
3-((6-Chloro-1-(2-(4-((3,4-difluorobenzyl)oxy)piperidin-1-yl)-2-oxoethyl)-7-fluoro-2-methyl-1H-indol-3-yl) thio)benzoic acid;
3-((6-Chloro-7-fluoro-1-(2-(3-(4-fluorobenzyl)piperidin-1-yl)-2-oxoethyl)-2-methyl-1H-indol-3-yl)thio)benzoic acid;
3-((6-Chloro-7-fluoro-2-methyl-1-(2-(2-oxo-1-oxa-3,8-diazaspiro[4.5]decan-8-yl)acetyl)-1H-indol-3-yl)thio) benzoic acid;
3-((6-Chloro-7-fluoro-2-methyl-1-(3-oxo-3-(phenylamino)propyl)-1H-indol-3-yl)thio)benzoic acid;
3-((6-Chloro-7-fluoro-1-(2-(indolin-1-yl)-2-oxoethyl)-2-methyl-1H-indol-3-yl)thio)benzoic acid;
3-(6-Chloro-7-fluoro-2-methyl-1-(2-oxo-2-(2-oxo-7-azaspiro[3.5]nonan-7-yl)ethyl)-1H-indol-3-yl)thio) benzoic acid;
3-((6-Chloro-1-(2-(2-cyano-7-azaspiro[3.5]nonan-7-yl)-2-oxoethyl)-7-fluoro-2-methyl-1H-indol-3-yl)thio) benzoic acid;
3-((6-Chloro-7-fluoro-1-(2-(3-(4-fluorophenyl)pyrrolidin-1-yl)-2-oxoethyl)-2-methyl-1H-indol-3-yl)thio) benzoic acid;
3-((6-Chloro-7-fluoro-1-(2-(3-(4-fluorobenzyl)pyrrolidin-1-yl)-2-oxoethyl)-2-methyl-1H-indol-3-yl)thio) benzoic acid;
3-((6-Chloro-7-fluoro-1-(2-(3-((4-fluorobenzyl)oxy)pyrrolidin-1-yl)-2-oxoethyl)-2-methyl-1H-indol-3-yl)thio) benzoic acid;
3-((6-Chloro-7-fluoro-1-(2-(3-(4-trifluoromethylbenzyl) pyrrolidin-1-yl)-2-oxoethyl)-2-methyl-1H-indol-3-yl) thio)benzoic acid;
3-((6-Chloro-7-fluoro-1-(2-(3-cyanopyrrolidin-1-yl)-2-oxoethyl)-2-methyl-1H-indol-3-yl)thio)benzoic acid;
3-((6-Chloro-7-fluoro-2-methyl-1-(3-oxo-3-(pyrrolidin-1-yl)propyl)-1H-indol-3-yl)thio)benzoic acid;
3-((6-Chloro-7-fluoro-1-(3-(indolin-1-yl)-3-oxopropyl)-2-methyl-1H-indol-3-yl)thio)benzoic acid;
3-((6-Chloro-7-fluoro-2-methyl-1-(3-oxo-3-(spiro[cyclopropane-1,3'-indolin]-1'-yl)propyl)-1H-indol-3-yl)thio) benzoic acid;
3-((6-Chloro-7-fluoro-2-methyl-1-(2-oxo-2-(spiro[cyclopropane-1,3'-indolin]-1'-yl)ethyl)-1H-indol-3-yl)thio) benzoic acid;

3-((6-Chloro-7-fluoro-1-(2-(5'-fluorospiro[cyclopropane-1,3'-indolin]-1'-yl)-2-oxoethyl)-2-methyl-1H-indol-3-yl)thio)benzoic acid;
3-((6-Chloro-7-fluoro-1-(2-(4'-fluorospiro[cyclobutane-1,3'-indolin]-1'-yl)-2-oxoethyl)-2-methyl-1H-indol-3-yl)thio)benzoic acid;
3-((6-Chloro-7-fluoro-1-(2-(6-fluoro-3,3-dimethylindolin-1-yl)-2-oxoethyl)-2-methyl-1H-indol-3-yl)thio)benzoic acid;
3-((6-Chloro-7-fluoro-2-methyl-1-(2-oxo-2-(3-oxo-2,7-diazaspiro[4.5]decan-7-yl)ethyl)-1H-indol-3-yl)thio)benzoic acid;
3-((6-Chloro-1-(2-(3,4-dihydroquinolin-1(2H)-yl)-2-oxoethyl)-7-fluoro-2-methyl-1H-indol-3-yl)thio)benzoic acid;
3-((6-Chloro-7-fluoro-1-(2-(3-hydroxy-3-(trifluoromethyl)pyrrolidin-1-yl)-2-oxoethyl)-2-methyl-1H-indol-3-yl)thio)benzoic acid;
3-((6-Chloro-7-fluoro-2-methyl-1-(2-(1'-methylspiro[indoline-3,4'-piperidin]-1'-yl)-2-oxoethyl)-1H-indol-3-yl)thio)benzoic acid;
3-((6-Chloro-7-fluoro-2-methyl-1-(2-oxo-2-(spiro[cyclopentane-1,3'-indolin]-1'-yl)ethyl)-1H-indol-3-yl)thio)benzoic acid;
3-((6-Chloro-7-fluoro-2-methyl-1-(2-oxo-2-(1-(pyrrolidine-1-carbonyl)-6-azaspiro[2.5]octan-6-yl)ethyl)-1H-indol-3-yl)thio)benzoic acid;
3-((6-Chloro-7-fluoro-2-methyl-1-(2-oxo-2-(2-oxo-1,7-diazaspiro[3.5]nonan-7-yl)ethyl)-1H-indol-3-yl)thio)benzoic acid;
3-((6-Chloro-1-(2-(3-(3,3-difluoropyrrolidin-1-yl)azetidin-1-yl)-2-oxoethyl)-7-fluoro-2-methyl-1H-indol-3-yl)thio)benzoic acid;
3-((6-Chloro-1-(2-(2,4-dioxo-1,3,7-triazaspiro[4.4]nonan-7-yl)-2-oxoethyl)-7-fluoro-2-methyl-1H-indol-3-yl)thio)benzoic acid;
3-((6-Chloro-1-(2-(4,4-dimethylpiperidin-1-yl)-2-oxoethyl)-7-fluoro-2-methyl-1H-indol-3-yl)thio)benzoic acid;
3-((6-Chloro-7-fluoro-2-methyl-1-(2-oxo-2-(3-oxo-2,8-diazaspiro[4.5]decan-8-yl)ethyl)-1H-indol-3-yl)thio)benzoic acid;
3-((6-Chloro-7-fluoro-2-methyl-1-(2-oxo-2-(8-oxa-2-azaspiro[4.5]decan-2-yl)ethyl)-1H-indol-3-yl)thio)benzoic acid;
3-((6-Chloro-7-fluoro-2-methyl-1-(2-oxo-2-(2-oxa-6-azaspiro[3.3]heptan-6-yl)ethyl)-1H-indol-3-yl)thio)benzoic acid;
3-((6-Chloro-1-(2-(3-(1,1-dioxidothiomorpholino)azetidin-1-yl)-2-oxoethyl)-7-fluoro-2-methyl-1H-indol-3-yl)thio)benzoic acid;
3-((6-Chloro-7-fluoro-2-methyl-1-(2-oxo-2-(7-oxo-2,6-diazaspiro[3.4]octan-2-yl)ethyl)-1H-indol-3-yl)thio)benzoic acid;
3-((6-Chloro-7-fluoro-2-methyl-1-(2-oxo-2-(2-oxa-6-azaspiro[3.4]octan-6-yl)ethyl)-1H-indol-3-yl)thio)benzoic acid;
3-((1-(2-((1R,5S,6R)-6-Carbamoyl-3-azabicyclo[3.1.0]hexan-3-yl)-2-oxoethyl)-6-chloro-7-fluoro-2-methyl-1H-indol-3-yl)thio)benzoic acid;
3-((6-Chloro-7-fluoro-1-(2-(3-hydroxy-3-methylazetidin-1-yl)-2-oxoethyl)-2-methyl-1H-indol-3-yl)thio)benzoic acid;
3-((6-Chloro-7-fluoro-2-methyl-1-(2-oxo-2-(10-oxo-3,9-diazaspiro[5.6]dodecan-3-yl)ethyl)-1H-indol-3-yl)thio)benzoic acid;
3-((6-Chloro-7-fluoro-2-methyl-1-(2-oxo-2-(2-oxopyrrolidin-1-yl)ethyl)-1H-indol-3-yl)thio)benzoic acid;
3-((6-Chloro-7-fluoro-1-(2-(4-(4-fluorobenzyl)piperidin-1-yl)-2-oxoethyl)-2-methyl-1H-indol-3-yl)thio)benzoic acid;
3-((1-(2-(4-(2-(1H-Pyrazol-1-yl)ethyl)piperidin-1-yl)-2-oxoethyl)-6-chloro-7-fluoro-2-methyl-1H-indol-3-yl)thio)benzoic acid;
3-((6-Chloro-7-fluoro-2-methyl-1-(2-oxo-2-(4-phenethylpiperidin-1-yl)ethyl)-1H-indol-3-yl)thio)benzoic acid;
3-((6-Chloro-7-fluoro-2-methyl-1-(2-oxo-2-(4-(pyridin-4-ylmethyl)piperidin-1-yl)ethyl)-1H-indol-3-yl)thio)benzoic acid;
3-((6-Chloro-7-fluoro-2-methyl-1-(2-(4-(1-methyl-1H-pyrazol-4-yl)piperidin-1-yl)-2-oxoethyl)-1H-indol-3-yl)thio)benzoic acid;
3-((6-Chloro-7-fluoro-1-(2-(3-(4-fluorobenzyl)pyrrolidin-1-yl)-2-oxoethyl)-2-methyl-1H-indol-3-yl)thio)benzoic acid Enantiomer A;
3-((6-Chloro-7-fluoro-1-(2-(3-(4-fluorobenzyl)pyrrolidin-1-yl)-2-oxoethyl)-2-methyl-1H-indol-3-yl)thio)benzoic acid Enantiomer B;
3-((1-(2-(8-Benzyl-2,8-diazaspiro[4.5]decan-2-yl)-2-oxoethyl)-6-chloro-7-fluoro-2-methyl-1H-indol-3-yl)thio)benzoic acid;
3-((6-Chloro-7-fluoro-2-methyl-1-(2-(7-methyl-2,7-diazaspiro[3.5]nonan-2-yl)-2-oxoethyl)-1H-indol-3-yl)thio)benzoic acid;
3-((6-Chloro-7-fluoro-2-methyl-1-(2-oxo-2-(2-oxo-1-oxa-3,7-diazaspiro[4.5]decan-7-yl)ethyl)-1H-indol-3-yl)thio)benzoic acid;
3-((6-Chloro-1-(2-(4,6-difluoroindolin-1-yl)-2-oxoethyl)-7-fluoro-2-methyl-1H-indol-3-yl)thio)benzoic acid;
3-((6-Chloro-1-(2-(5-chloroindolin-1-yl)-2-oxoethyl)-7-fluoro-2-methyl-1H-indol-3-yl)thio)benzoic acid;
3-((6-Chloro-1-(2-(6-chloroindolin-1-yl)-2-oxoethyl)-7-fluoro-2-methyl-1H-indol-3-yl)thio)benzoic acid;
3-((6-Chloro-1-(2-(2,3-dihydro-1H-pyrrolo[2,3-b]pyridin-1-yl)-2-oxoethyl)-7-fluoro-2-methyl-1H-indol-3-yl)thio)benzoic acid;
3-((6-Chloro-7-fluoro-1-(2-(3-(4-fluorophenyl)pyrrolidin-1-yl)-2-oxoethyl)-2-methyl-1H-indol-3-yl)thio)benzoic acid Enantiomer A;
3-((6-Chloro-7-fluoro-1-(2-(3-(4-fluorophenyl)pyrrolidin-1-yl)-2-oxoethyl)-2-methyl-1H-indol-3-yl)thio)benzoic acid Enantiomer B;
6-((6-Chloro-7-fluoro-2-methyl-1-(2-oxo-2-(2-oxo-1-oxa-3,8-diazaspiro[4.5]decan-8-yl)ethyl)-1H-indol-3-yl)thio)picolinic acid;
Methyl 6-((6-chloro-7-fluoro-1-(2-(indolin-1-yl)-2-oxoethyl)-2-methyl-1H-indol-3-yl)thio)picolinate;
6-((6-Chloro-7-fluoro-2-methyl-1-(2-oxo-2-(spiro[cyclopropane-1,3'-indolin]-1'-yl)ethyl)-1H-indol-3-yl)thio)picolinic acid;
3-((6-Chloro-7-fluoro-2-methyl-1-(2-oxo-2-(spiro[cyclopropane-1,3'-indolin]-1'-yl)ethyl)-1H-indol-3-yl)thio)-2-fluorobenzoic acid;
3-((6-Chloro-1-(2-(5-methoxyindolin-1-yl)-2-oxoethyl)-7-fluoro-2-methyl-1H-indol-3-yl)thio)benzoic acid;
3-[6-Chloro-7-fluoro-1-[2-(5'-fluorospiro[cyclopropane-1,3'-indoline]-1'-yl)-2-oxo-ethyl]-2-methyl-indol-3-yl]sulfanyl-2-fluoro-benzoic acid;
6-((6-Chloro-7-fluoro-1-(2-(4'-fluorospiro[cyclobutane-1,3'-indolin]-1'-yl)-2-oxoethyl)-2-methyl-1H-indol-3-yl)thio)picolinic acid;

3-((6-Chloro-7-fluoro-1-(2-(4'-fluorospiro[cyclobutane-1,3'-indolin]-1'-yl)-2-oxoethyl)-2-methyl-1H-indol-3-yl)thio)-2-fluorobenzoic acid;

3-((6-Chloro-7-fluoro-2-methyl-1-(2-oxo-2-(spiro[cyclopentane-1,3'-indolin]-1'-yl)ethyl)-1H-indol-3-yl)thio)-2-fluorobenzoic acid;

3-((6-Chloro-7-fluoro-2-methyl-1-(2-oxo-2-(3-phenethylpyrrolidin-1-yl)ethyl)-1H-indol-3-yl)thio)benzoic acid;

3-((6-Chloro-7-fluoro-2-methyl-1-(2-oxo-2-(3-propylpyrrolidin-1-yl)ethyl)-1H-indol-3-yl)thio)benzoic acid;

3-((6-Chloro-1-(2-(3,4-dihydroisoquinolin-2(1H)-yl)-2-oxoethyl)-7-fluoro-2-methyl-1H-indol-3-yl)thio)benzoic acid;

3-((6-Chloro-7-fluoro-2-methyl-1-(2-oxo-2-(6-(trifluoromethyl)indolin-1-yl)ethyl)-1H-indol-3-yl)thio)benzoic acid;

3-((6-Chloro-7-fluoro-1-(2-(4-fluoroindolin-1-yl)-2-oxoethyl)-2-methyl-1H-indol-3-yl)thio)benzoic acid;

3-((6-Chloro-1-(2-(3-cyclopropyl-3-hydroxyazetidin-1-yl)-2-oxoethyl)-7-fluoro-2-methyl-1H-indol-3-yl)thio)benzoic acid;

3-((6-Chloro-7-fluoro-1-(2-(3-hydroxy-3-(trifluoromethyl)piperidin-1-yl)-2-oxoethyl)-2-methyl-1H-indol-3-yl)thio)benzoic acid;

3-((6-Chloro-7-fluoro-1-(2-(3-hydroxy-3-(trifluoromethyl)azetidin-1-yl)-2-oxoethyl)-2-methyl-1H-indol-3-yl)thio)benzoic acid;

3-((6-Chloro-7-fluoro-2-methyl-1-(2-(2-(1-methyl-1H-pyrazol-4-yl)pyrrolidin-1-yl)-2-oxoethyl)-1H-indol-3-yl)thio)benzoic acid;

3-((1-(2-(3-(1H-Pyrazol-1-yl)azetidin-1-yl)-2-oxoethyl)-6-chloro-7-fluoro-2-methyl-1H-indol-3-yl)thio)benzoic acid;

6-((6-Chloro-7-fluoro-1-(2-(3-hydroxy-3-(trifluoromethyl)pyrrolidin-1-yl)-2-oxoethyl)-2-methyl-1H-indol-3-yl)thio)picolinic acid;

3-((6-chloro-7-fluoro-1-(2-(3-hydroxy-3-(trifluoromethyl)pyrrolidin-1-yl)-2-oxoethyl)-2-methyl-1H-indol-3-yl)thio)-2-fluorobenzoic acid;

3-((6-Chloro-7-fluoro-2-methyl-1-(2-(7-methyl-1,7-diazaspiro[3.5]nonan-1-yl)-2-oxoethyl)-1H-indol-3-yl)thio)benzoic acid;

3-((6-Chloro-7-fluoro-2-methyl-1-(2-oxo-2-(3-(pyridin-4-ylmethyl)pyrrolidin-1-yl)ethyl)-1H-indol-3-yl)thio)benzoic acid;

3-((6-Chloro-7-fluoro-2-methyl-1-(2-oxo-2-(3-(pyridin-4-yl)pyrrolidin-1-yl)ethyl)-1H-indol-3-yl)thio)benzoic acid;

3-((6-Chloro-7-fluoro-1-(2-(3-hydroxypyrrolidin-1-yl)-2-oxoethyl)-2-methyl-1H-indol-3-yl)thio)benzoic acid;

3-((6-Chloro-7-fluoro-1-(2-(isoindolin-2-yl)-2-oxoethyl)-2-methyl-1H-indol-3-yl)thio)benzoic acid;

3-((6-Chloro-7-fluoro-2-methyl-1-(2-(5-methylindolin-1-yl)-2-oxoethyl)-1H-indol-3-yl)thio)benzoic acid;

3-((6-Chloro-7-fluoro-2-methyl-1-(2-(3-((1-methyl-1H-pyrazol-4-yl)methyl)pyrrolidin-1-yl)-2-oxoethyl)-1H-indol-3-yl)thio)benzoic acid;

3-((1-(2-(2-(2-(1H-Pyrazol-1-yl)ethyl)piperidin-1-yl)-2-oxoethyl)-6-chloro-7-fluoro-2-methyl-1H-indol-3-yl)thio)benzoic acid;

3-((6-Chloro-7-fluoro-2-methyl-1-(2-oxo-2-(5-azaspiro[2.4]heptan-5-yl)ethyl)-1H-indol-3-yl)thio)benzoic acid;

3-((6-Chloro-7-fluoro-2-methyl-1-(2-(3-(1-methyl-1H-pyrazol-4-yl)pyrrolidin-1-yl)-2-oxoethyl)-1H-indol-3-yl)thio)benzoic acid;

3-((6-Chloro-1-(2-(2,3-dihydro-1H-pyrrolo[2,3-c]pyridin-1-yl)-2-oxoethyl)-7-fluoro-2-methyl-1H-indol-3-yl)thio)benzoic acid;

3-((6-Chloro-7-fluoro-1-(2-(hexahydro-1H-isoindol-2(3H)-yl)-2-oxoethyl)-2-methyl-1H-indol-3-yl)thio)benzoic acid;

3-((6-chloro-7-fluoro-1-(2-(indolin-1-yl)ethyl)-2-methyl-1H-indol-3-yl)thio)-2-fluorobenzoic acid;

3-((6-Chloro-1-(2-(2,3-dihydro-1H-pyrrolo[2,3-c]pyridin-1-yl)-2-oxoethyl)-7-fluoro-2-methyl-1H-indol-3-yl)thio)-2-fluorobenzoic acid;

3-((6-Chloro-7-fluoro-1-(2-(3-hydroxy-3-methylpyrrolidin-1-yl)-2-oxoethyl)-2-methyl-1H-indol-3-yl)thio)-2-fluorobenzoic acid;

3-((6-Chloro-7-fluoro-2-methyl-1-(2-oxo-2-(spiro[cyclobutane-1,3'-indolin]-1'-yl)ethyl)-1H-indol-3-yl)thio)-2-fluorobenzoic acid;

3-((6-chloro-7-fluoro-2-methyl-1-(2-(spiro[cyclopropane-1,3'-indolin]-1'-yl)ethyl)-1H-indol-3-yl)thio)-2-fluorobenzoic acid;

3-((6-Chloro-7-fluoro-2-methyl-1-(2-(spiro[cyclobutane-1,3'-indolin]-1'-yl)ethyl)-1H-indol-3-yl)thio)-2-fluorobenzoic acid;

3-((6-Chloro-7-fluoro-2-methyl-1-(2-oxo-2-(spiro[cyclopentane-1,3'-indolin]-1'-yl)ethyl)-1H-indol-3-yl)thio)-2-fluoro-N-(phenylsulfonyl)benzamide;

3-((6-Chloro-7-fluoro-1-(2-(3-(2-hydroxypropan-2-yl)pyrrolidin-1-yl)-2-oxoethyl)-2-methyl-1H-indol-3-yl)thio)-2-fluorobenzoic acid;

3-((6-Chloro-1-(2-(3-cyclopropyl-3-hydroxyazetidin-1-yl)-2-oxoethyl)-7-fluoro-2-methyl-1H-indol-3-yl)thio)-2-fluorobenzoic acid;

(R)-3-((6-Chloro-7-fluoro-1-(2-(3-(hydroxymethyl)pyrrolidin-1-yl)-2-oxoethyl)-2-methyl-1H-indol-3-yl)thio)-2-fluorobenzoic acid;

3-((6-Chloro-7-fluoro-1-(2-((3S,4S)-3-hydroxy-4-morpholinopyrrolidin-1-yl)-2-oxoethyl)-2-methyl-1H-indol-3-yl)thio)-2-fluorobenzoic acid;

3-((6-Chloro-7-fluoro-1-(2-((3R,4R)-3-fluoro-4-hydroxypyrrolidin-1-yl)-2-oxoethyl)-2-methyl-1H-indol-3-yl)thio)-2-fluorobenzoic acid;

(S)-3-((6-chloro-7-fluoro-1-(2-(3-hydroxy-3-(trifluoromethyl)pyrrolidin-1-yl)-2-oxoethyl)-2-methyl-1H-indol-3-yl)thio)-2-fluorobenzoic acid Enantiomer A;

(R)-3-((6-chloro-7-fluoro-1-(2-(3-hydroxy-3-(trifluoromethyl)pyrrolidin-1-yl)-2-oxoethyl)-2-methyl-1H-indol-3-yl)thio)-2-fluorobenzoic acid Enantiomer B;

3-((6-Chloro-1-(2-(3-cyanoazetidin-1-yl)-2-oxoethyl)-7-fluoro-2-methyl-1H-indol-3-yl)thio)-2-fluorobenzoic acid;

3-((6-Chloro-7-fluoro-1-(2-(3-hydroxy-3-phenylpyrrolidin-1-yl)-2-oxoethyl)-2-methyl-1H-indol-3-yl)thio)-2-fluorobenzoic acid;

3-((6-Chloro-1-(2-((3S,4S)-3-(dimethylamino)-4-hydroxypyrrolidin-1-yl)-2-oxoethyl)-7-fluoro-2-methyl-1H-indol-3-yl)thio)-2-fluorobenzoic acid;

3-((6-Chloro-7-fluoro-1-(2-((3S,4S)-3-hydroxy-4-(4-methylpiperazin-1-yl)pyrrolidin-1-yl)-2-oxoethyl)-2-methyl-1H-indol-3-yl)thio)-2-fluorobenzoic acid;

3-((6-Chloro-1-(2-(3-((dimethylamino)methyl)azetidin-1-yl)-2-oxoethyl)-7-fluoro-2-methyl-1H-indol-3-yl)thio)-2-fluorobenzoic acid;

3-((6-Chloro-7-fluoro-2-methyl-1-(2-oxo-2-(1,4-dioxa-7-azaspiro[4.4]nonan-7-yl)ethyl)-1H-indol-3-yl)thio)-2-fluorobenzoic acid;

3-((2,6-dichloro-7-fluoro-1-(2-oxo-2-(spiro[cyclobutane-1,3'-indolin]-1'-yl)ethyl)-1H-indol-3-yl)thio)-2-fluorobenzoic acid;

3-((2,6-dichloro-7-fluoro-1-(2-oxo-2-(spiro[cyclopropane-1,3'-indolin]-1'-yl)ethyl)-1H-indol-3-yl)thio)-2-fluorobenzoic acid;

3-((6-chloro-2-cyclopropyl-7-fluoro-1-(2-(indolin-1-yl)-2-oxoethyl)-1H-indol-3-yl)thio)-2-fluorobenzoic acid;

3-((6-chloro-2-cyclopropyl-7-fluoro-1-(2-oxo-2-(spiro[cyclobutane-1,3'-indolin]-1'-yl)ethyl)-1H-indol-3-yl)thio)-2-fluorobenzoic acid;

3-((6-chloro-2-cyclopropyl-7-fluoro-1-(2-oxo-2-(spiro[cyclopropane-1,3'-indolin]-1'-yl)ethyl)-1H-indol-3-yl)thio)-2-fluorobenzoic acid;

3-((2,6-dichloro-7-fluoro-1-(2-(3-hydroxy-3-(trifluoromethyl)pyrrolidin-1-yl)-2-oxoethyl)-1H-indol-3-yl)thio)-2-fluorobenzoic acid;

3-((6-chloro-2-cyclopropyl-7-fluoro-1-(2-(3-hydroxy-3-(trifluoromethyl)pyrrolidin-1-yl)-2-oxoethyl)-1H-indol-3-yl)thio)-2-fluorobenzoic acid;

3-((6-chloro-2-cyclopropyl-7-fluoro-1-(2-(methoxy(methyl)amino)-2-oxoethyl)-1H-indol-3-yl)thio)-2-fluorobenzoic acid;

or a pharmaceutically acceptable salt, or solvate thereof.

19. A pharmaceutical composition comprising a compound of claim 1, or a pharmaceutically acceptable salt, or solvate thereof, and at least one pharmaceutically acceptable excipient.

20. A method of treating fibrosis, pruritis, or combination thereof in a mammal comprising administering a compound of claim 1, or a pharmaceutically acceptable salt, or solvate thereof, to the mammal in need thereof.

* * * * *